(12) United States Patent
Brooks et al.

(10) Patent No.: US 8,048,274 B2
(45) Date of Patent: *Nov. 1, 2011

(54) ELECTROCHEMISTRY TECHNICAL FIELD

(75) Inventors: Juliana H. J. Brooks, North East, MD (US); Mark G. Mortenson, North East, MD (US); Bentley J. Blum, Fisher Island, FL (US)

(73) Assignee: GR Intellectual Reserve, LLC, Havre de Grace, MD (US)

( * ) Notice: Subject to any disclaimer, the term of this patent is extended or adjusted under 35 U.S.C. 154(b) by 806 days.

This patent is subject to a terminal disclaimer.

(21) Appl. No.: 10/507,659

(22) PCT Filed: Mar. 11, 2003

(86) PCT No.: PCT/US03/08241
§ 371 (c)(1),
(2), (4) Date: Mar. 10, 2005

(87) PCT Pub. No.: WO03/078362
PCT Pub. Date: Sep. 25, 2003

(65) Prior Publication Data
US 2005/0139484 A1 Jun. 30, 2005

(51) Int. Cl.
*C07C 1/00* (2006.01)
*C25B 5/00* (2006.01)
*H01M 2/00* (2006.01)
*C25B 1/00* (2006.01)

(52) U.S. Cl. ............... 204/157.15; 204/155; 429/10; 205/340; 205/343

(58) Field of Classification Search ............. 204/157.15, 204/155, 450; 429/13, 10; 205/67, 80, 333, 205/340, 343, 464, 560, 655, 775
See application file for complete search history.

(56) References Cited

U.S. PATENT DOCUMENTS

| | | | | | |
|---|---|---|---|---|---|
| 3,847,670 | A | * | 11/1974 | Johnsen | 429/408 |
| H675 | H | * | 9/1989 | Wortman et al. | 436/152 |
| 6,033,531 | A | * | 3/2000 | Brooks et al. | 204/157.15 |
| 6,217,712 | B1 | * | 4/2001 | Mohr | 204/157.15 |
| 7,482,072 | B2 | * | 1/2009 | Brooks et al. | 429/10 |
| 2002/0031814 | A1 | * | 3/2002 | Brooks et al. | 435/173.1 |
| 2003/0027021 | A1 | * | 2/2003 | Sharivker et al. | 429/13 |
| 2004/0089532 | A1 | * | 5/2004 | Brooks et al. | 204/157.15 |
| 2005/0139485 | A1 | * | 6/2005 | Brooks et al. | 205/687 |
| 2006/0037177 | A1 | * | 2/2006 | Blum et al. | 23/296 |

* cited by examiner

*Primary Examiner* — Edna Wong
(74) *Attorney, Agent, or Firm* — Mark G. Mortenson

(57) ABSTRACT

The invention relates to novel methods for affecting, controlling and/or directing various reactions and/or reaction pathways or systems by exposing one or more components in a holoreaction system to at least one spectral energy pattern. In a first aspect of the invention, at least one spectral energy pattern can be applied to a reaction system. In a second aspect of the invention, at least one spectral energy conditioning pattern can be applied to a conditioning reaction system. The spectral energy conditioning pattern can, for example, be applied at a separate location from the reaction vessel (e.g., in a conditioning reaction vessel) or can be applied in (or to) the reaction vessel, but prior to other reaction system participants being introduced into the reaction vessel.

16 Claims, 65 Drawing Sheets

| Initial Frequencies (Hz) | | |
|---|---|---|
| 400 | and | 100 |
| 400 + 100 = 500 | and | 400 - 100 = 300 |
| 500 + 300 = 800 | and | 500 - 300 = 200 |
| 800 + 200 = 1000 | and | 800 - 200 = 600 |
| 1000 + 600 = 1600 | and | 1000 - 600 = 400 |

| Sum (Added) Frequencies (Hz) | Difference (Subtracted) Frequencies (Hz) |
|---|---|
| 400 | 100 |
| 500 | 300 |
| 800 | 200 |
| 1000 | 600 |
| 1600 | 400 |
| 2000 | 1200 |
| 3200 | 800 |

Fig. 6d
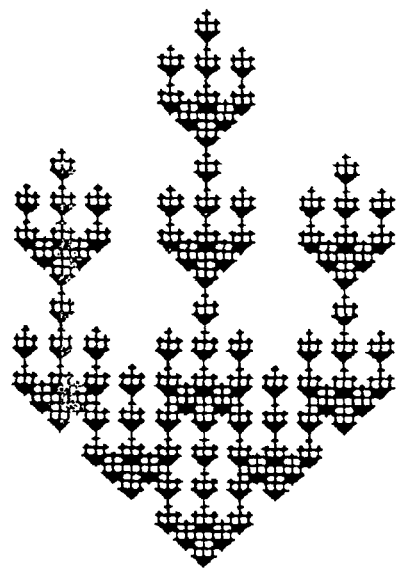
Fig. 6c
Fig. 6b
Fig. 6a
Fig. 7a
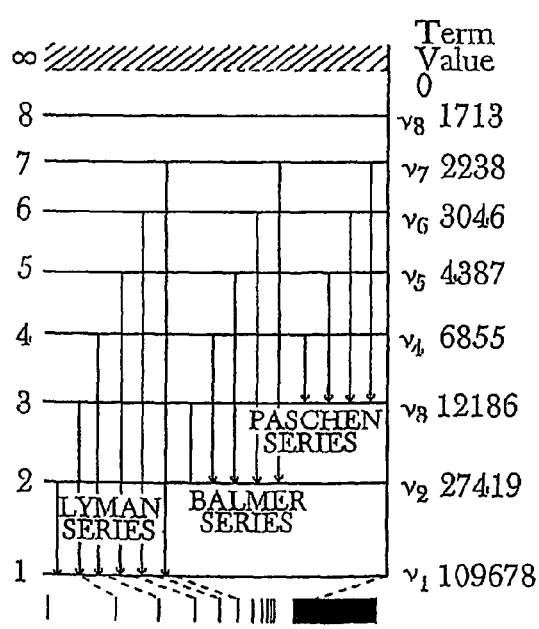
Fig. 7b
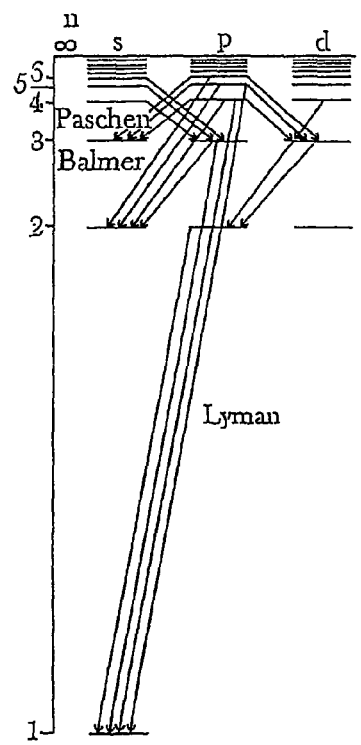

Frequency Curves - THz (relative intensity)

| V | IV | III | II | I |
|---|---|---|---|---|
| 40 (6) | 74 (15) | 160 (40) | 456 (300) | 2466 (1000) |
| 64 (4) | 114 (8) | 234 (20) | 616 (80) | 2923 (300) |
|  | 138 (5) | 274 (12) | 690 (30) | 3082 (100) |
|  |  | 298 (7) | 731 (15) | 3156 (50) |
|  |  | 314 (5) | 755 (8) | 3196 (30) |
|  |  |  | 770 (6) | 3220 (20) |
|  |  |  | 781 (5) | 3236 (15) |

Resonance curve with high Q

Resonance curve with low Q

Spectral pattern at low temperature

Spectral pattern at moderate temperature

Spectral pattern at high temperature

Separate and distinct spectral curves at low temperature

Overlapping spectral curves at higher temperature, allowing resonant energy transfer Emission spectrum
T = 50K High resolution spectrum Rotational and Vibrational Frequencies for LiF

| Rotational Transition | | | | |
|---|---|---|---|---|
| 0→1 | 89,740.46 | 88,319.18 | 86,921.20 | |
| 1→2 | 179,470.35 | 176,627.91 | 173,832.04 | 171,082.27 |
| 2→3 | 269,179.18 | 264,915.79 | 260,722.24 | 256,597.84 |
| 3→4 | 358,856.19 | 353,172.23 | 347,583.39 | 342,082.66 |
| 4→5 | 448,491.07 | | | |
| Vibrational Level | 0 | 1 | 2 | 3 |

Fig. 43a

Rotational and Vibrational Frequencies for LiF

Differences Between Rotational And Vibrational Frequencies (MHz) For LiF

| Rotational Transition | | | |
|---|---|---|---|
| 0→1 | 1,421.28 | 1,397.98 | |
| 1→2 | 2,842.44 | 2,795.87 | 2,749.77 |
| 2→3 | 4,263.39 | 4,193.55 | 4,124.40 |
| 3→4 | 5,683.96 | 5,590.84 | 5,498.73 |
| 4→5 | 7,104.24 | | |
| Vibrational Level | 0 | 1 | 2 | 3 |

Fig. 43b

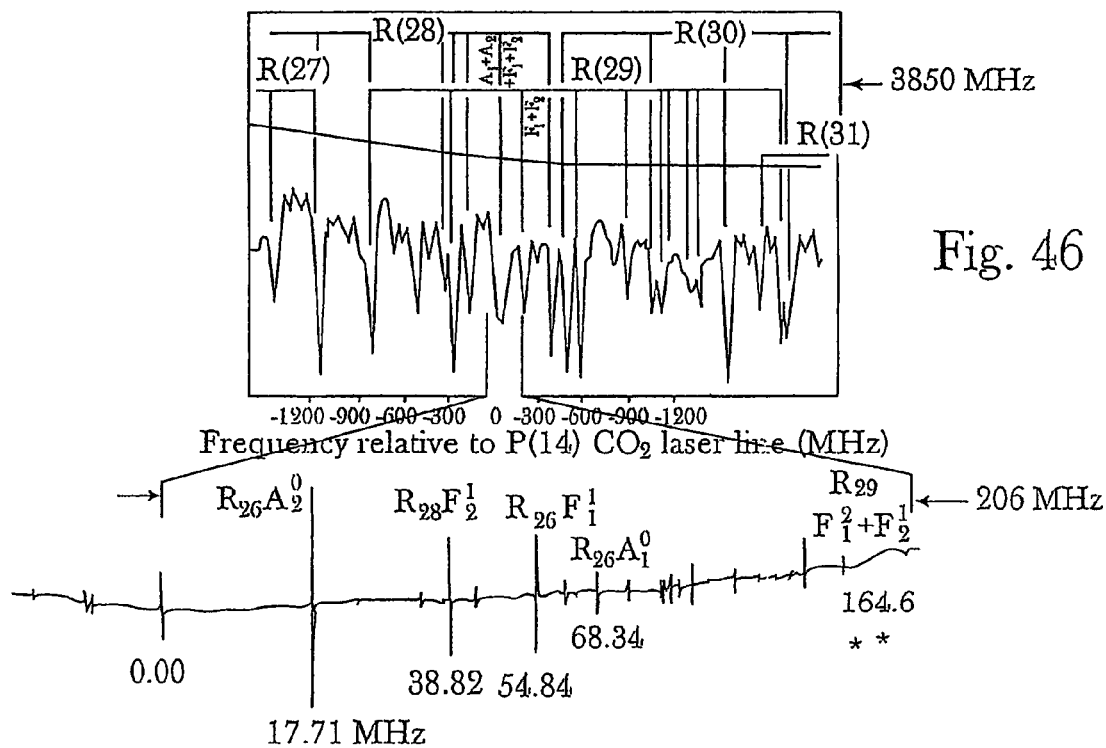
Fig. 46
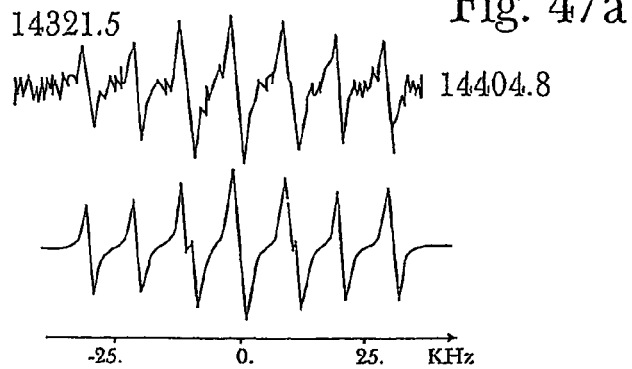
Fig. 47a
Fig. 47b
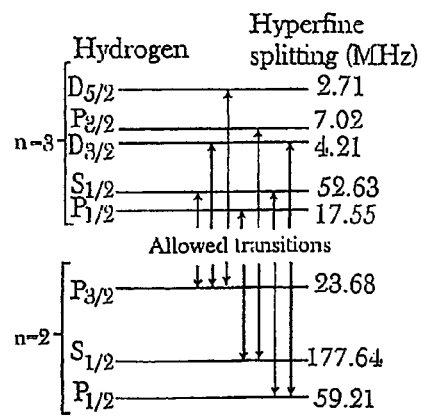
Fig. 48

Fig. 49
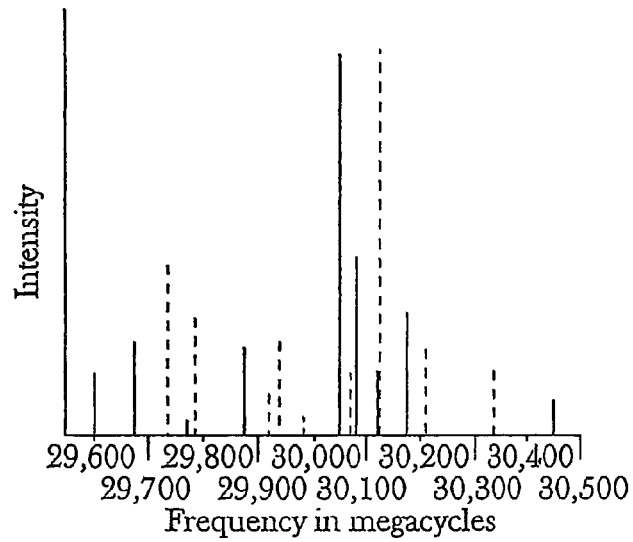
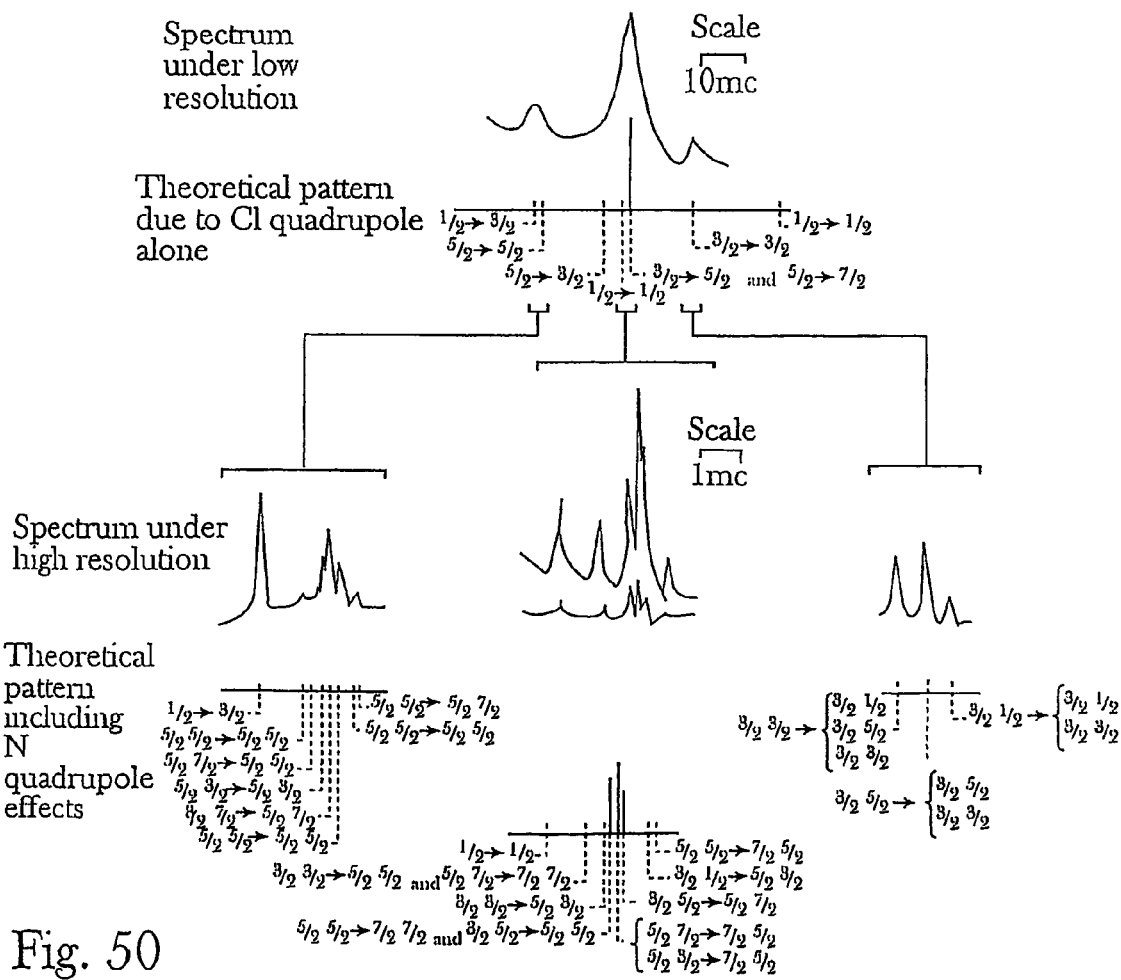
Fig. 50

| | Field
| | No field
Fig. 62a
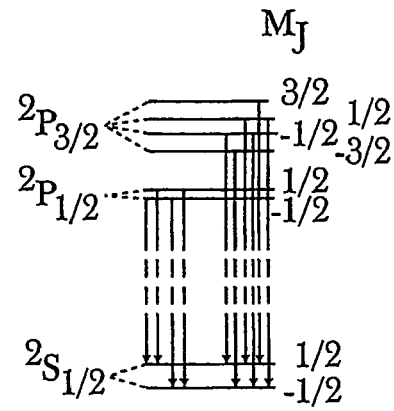
Fig. 62b
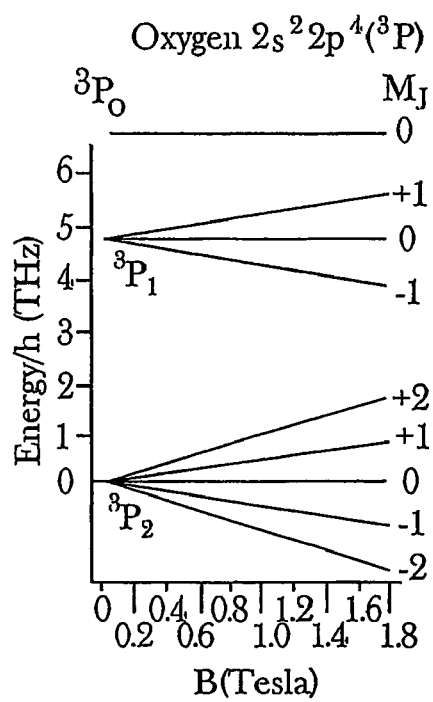
Fig. 63
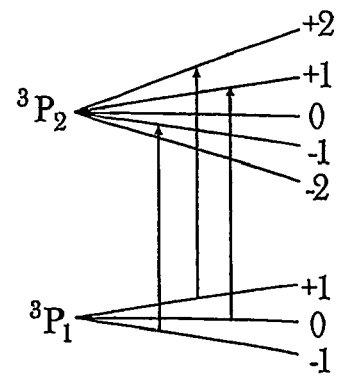
Fig. 64

| 100 | 7.7144 | 10.786 | 15.732 | 24.2382 | 40.1985 | 54.4367 | 74.0016 | 114.2 | 139.428 | 159.881 | 233.832 | 274.081 | 298.319 | 314.051 | 456.811 |
|---|---|---|---|---|---|---|---|---|---|---|---|---|---|---|---|
| 354.501 | 0 | 0 | 0 | 0 | 0 | 0 | 0 | 0 | 0 | 0 | 0 | 0 | 0 | 0 | 0 |
| 421.428 | 0 | 0 | 0 | 0 | 0 | 0 | 0 | 0 | 0 | 0 | 0 | 0 | 0 | 0 | 0 |
| 438.121 | 0 | 0 | 0 | 0 | 0 | 0 | 0 | 0 | 0 | 0 | 0 | 0 | 0 | 0 | 0 |
| 443.127 | 0 | 0 | 0 | 0 | 0 | 0 | 0 | 0 | 0 | 0 | 0 | 0 | 0 | 0 | 0 |
| 443.479 | 0 | 0 | 0 | 0 | 0 | 0 | 5.99283 | 0 | 0 | 0 | 0 | 0 | 0 | 0 | 0 |
| 449.757 | 0 | 0 | 0 | 0 | 0 | 0 | 0 | 0 | 0 | 0 | 0 | 0 | 0 | 0 | 0 |
| 459.561 | 0 | 0 | 0 | 0 | 0 | 0 | 0 | 0 | 0 | 0 | 0 | 0 | 0 | 0 | 1.00602 |
| 473.862 | 0 | 0 | 0 | 0 | 0 | 0 | 0 | 0 | 0 | 0 | 0 | 0 | 0 | 0 | 0 |
| 474.476 | 0 | 43.9902 | 0 | 0 | 0 | 0 | 0 | 0 | 0 | 0 | 0 | 0 | 0 | 0 | 0 |
| 497.485 | 0 | 0 | 0 | 0 | 0 | 0 | 0 | 0 | 0 | 0 | 0 | 0 | 0 | 0 | 0 |
| 512.918 | 0 | 0 | 0 | 0 | 0 | 0 | 0 | 0 | 0 | 0 | 0 | 0 | 0 | 0 | 0 |
| 513.333 | 0 | 0 | 0 | 0 | 0 | 0 | 0 | 0 | 0 | 0 | 0 | 0 | 0 | 0 | 0 |
| 520.151 | 0 | 0 | 0 | 0 | 0 | 0 | 0 | 0 | 0 | 0 | 0 | 0 | 0 | 0 | 0 |
| 547.216 | 0 | 0 | 0 | 0 | 0 | 0 | 0 | 0 | 0 | 0 | 0 | 1.99555 | 0 | 0 | 0 |
| 547.469 | 0 | 0 | 0 | 0 | 0 | 0 | 0 | 0 | 0 | 0 | 0 | 1.99754 | 0 | 0 | 0 |
| 556.12 | 0 | 0 | 0 | 0 | 0 | 0 | 0 | 0 | 0 | 0 | 0 | 0 | 0 | 0 | 0 |
| 558.378 | 0 | 0 | 0 | 0 | 0 | 0 | 0 | 0 | 0 | 0 | 0 | 0 | 0 | 0 | 0 |
| 565.537 | 0 | 0 | 0 | 0 | 0 | 0 | 0 | 0 | 0 | 0 | 0 | 0 | 0 | 0 | 0 |
| 573.474 | 0 | 0 | 0 | 0 | 0 | 0 | 0 | 0 | 0 | 0 | 0 | 0 | 0 | 0 | 0 |
| 592.536 | 0 | 0 | 0 | 0 | 0 | 8.00707 | 0 | 0 | 0 | 0 | 0 | 0 | 0 | 0 | 0 |
| 594.35 | 0 | 0 | 0 | 0 | 0 | 0 | 0 | 0 | 0 | 0 | 0 | 0 | 1.99233 | 0 | 0 |
| 614.388 | 0 | 0 | 0 | 0 | 0 | 0 | 0 | 0 | 0 | 0 | 0 | 0 | 0 | 0 | 0 |
| 658.534 | 0 | 0 | 0 | 0 | 0 | 0 | 0 | 0 | 0 | 0 | 0 | 0 | 0 | 0 | 0 |
| 663.126 | 0 | 0 | 0 | 0 | 0 | 0 | 0 | 0 | 0 | 0 | 0 | 0 | 0 | 0 | 0 |
| 666.389 | 0 | 0 | 0 | 0 | 0 | 0 | 9.00506 | 0 | 0 | 0 | 0 | 0 | 0 | 0 | 0 |
| 674.365 | 0 | 0 | 0 | 0 | 0 | 0 | 0 | 0 | 0 | 0 | 0 | 0 | 0 | 0 | 0 |
| 674.821 | 0 | 0 | 0 | 0 | 0 | 0 | 0 | 0 | 0 | 0 | 0 | 0 | 0 | 0 | 0 |
| 692.614 | 0 | 0 | 0 | 0 | 0 | 0 | 0 | 0 | 0 | 0 | 0 | 0 | 0 | 0 | 0 |
| 692.832 | 0 | 0 | 0 | 0 | 0 | 0 | 0 | 0 | 5.00464 | 0 | 0 | 0 | 0 | 0 | 0 |
| 715.091 | 0 | 0 | 0 | 0 | 0 | 0 | 0 | 0 | 0 | 0 | 0 | 0 | 0 | 0 | 0 |
| 719.866 | 0 | 0 | 0 | 0 | 0 | 0 | 0 | 0 | 0 | 0 | 0 | 0 | 0 | 0 | 0 |
| 727.883 | 0 | 0 | 0 | 0 | 0 | 0 | 0 | 0 | 0 | 0 | 0 | 0 | 0 | 0 | 0 |
| 750.124 | 0 | 0 | 0 | 0 | 0 | 0 | 0 | 0 | 0 | 0 | 0 | 0 | 0 | 0 | 0 |
| 755.838 | 0 | 0 | 0 | 0 | 0 | 0 | 0 | 0 | 0 | 0 | 0 | 0 | 0 | 0 | 0 |
| 759.276 | 0 | 0 | 0 | 0 | 0 | 0 | 0 | 0 | 0 | 0 | 0 | 0 | 0 | 0 | 0 |
| 764.2 | 0 | 0 | 0 | 0 | 0 | 0 | 0 | 0 | 0 | 0 | 0 | 0 | 0 | 0 | 0 |
| 768.555 | 0 | 0 | 0 | 0 | 0 | 0 | 0 | 0 | 0 | 0 | 0 | 0 | 0 | 0 | 0 |
| 785.066 | 0 | 0 | 0 | 0 | 0 | 0 | 0 | 0 | 0 | 0 | 0 | 0 | 0 | 0 | 0 |
| 808.823 | 0 | 0 | 0 | 0 | 0 | 0 | 0 | 0 | 0 | 0 | 0 | 0 | 0 | 0 | 0 |
| 810.27 | 0 | 0 | 0 | 0 | 0 | 0 | 0 | 0 | 0 | 0 | 0 | 0 | 0 | 0 | 0 |
| 815.975 | 0 | 0 | 0 | 0 | 0 | 0 | 0 | 0 | 0 | 0 | 0 | 0 | 0 | 0 | 0 |
| 816.431 | 0 | 0 | 0 | 0 | 0 | 0 | 0 | 0 | 0 | 0 | 0 | 0 | 0 | 0 | 0 |
| 818.412 | 0 | 0 | 0 | 0 | 0 | 0 | 0 | 0 | 0 | 0 | 0 | 0 | 0 | 0 | 0 |
| 822.883 | 0 | 0 | 0 | 0 | 0 | 0 | 0 | 0 | 0 | 0 | 0 | 3.00236 | 0 | 0 | 0 |
| 823.38 | 0 | 0 | 0 | 0 | 0 | 0 | 0 | 0 | 0 | 0 | 0 | 3.00597 | 0 | 0 | 0 |
| 826.305 | 0 | 0 | 0 | 33.991 | 0 | 0 | 0 | 0 | 0 | 0 | 0 | 0 | 0 | 0 | 0 |
| 860.17 | 0 | 0 | 0 | 0 | 0 | 0 | 0 | 0 | 0 | 0 | 0 | 0 | 0 | 0 | 0 |
| 860.624 | 0 | 0 | 0 | 0 | 0 | 0 | 0 | 0 | 0 | 0 | 0 | 0 | 0 | 0 | 0 |
| 874.558 | 0 | 0 | 0 | 0 | 0 | 0 | 0 | 0 | 0 | 0 | 0 | 0 | 0 | 0 | 0 |
| 879.639 | 0 | 0 | 0 | 0 | 0 | 0 | 0 | 0 | 0 | 0 | 0 | 0 | 0 | 0 | 0 |
| 901.957 | 0 | 0 | 0 | 0 | 0 | 13.9976 | 0 | 0 | 0 | 0 | 0 | 0 | 0 | 0 | 0 |
| 904.338 | 0 | 0 | 0 | 0 | 0 | 0 | 0 | 0 | 0 | 0 | 0 | 0 | 0 | 0 | 0 |
| 907.95 | 0 | 0 | 0 | 0 | 0 | 0 | 0 | 0 | 0 | 0 | 0 | 0 | 0 | 0 | 0 |
| 911.162 | 0 | 0 | 0 | 0 | 0 | 0 | 0 | 0 | 0 | 0 | 0 | 0 | 0 | 0 | 1.99461 |
| 913.453 | 0 | 0 | 0 | 0 | 0 | 0 | 0 | 7.99871 | 0 | 0 | 0 | 0 | 0 | 0 | 1.99963 |
| 917.24 | 0 | 0 | 0 | 0 | 0 | 0 | 0 | 0 | 0 | 0 | 0 | 0 | 0 | 0 | 2.00792 |
| 920.761 | 0 | 0 | 0 | 0 | 0 | 0 | 0 | 0 | 0 | 0 | 0 | 0 | 0 | 0 | 0 |
| 921.877 | 0 | 0 | 0 | 0 | 0 | 0 | 0 | 0 | 0 | 0 | 0 | 0 | 0 | 0 | 0 |
| 922.336 | 0 | 0 | 0 | 0 | 0 | 0 | 0 | 0 | 0 | 0 | 0 | 0 | 0 | 0 | 0 |
| 927.168 | 0 | 0 | 0 | 0 | 0 | 0 | 0 | 0 | 0 | 0 | 0 | 0 | 0 | 0 | 0 |
| 928.067 | 0 | 58.9923 | 0 | 0 | 0 | 0 | 0 | 0 | 0 | 0 | 0 | 0 | 0 | 0 | 0 |
| 935.67 | 0 | 0 | 0 | 0 | 0 | 0 | 0 | 0 | 0 | 0 | 4.00061 | 0 | 0 | 0 | 0 |
| 936.644 | 0 | 0 | 0 | 0 | 0 | 0 | 0 | 0 | 0 | 0 | 4.00477 | 0 | 0 | 0 | 0 |
| 949.744 | 0 | 0 | 0 | 0 | 0 | 0 | 0 | 0 | 0 | 0 | 0 | 0 | 0 | 0 | 0 |
| 954.939 | 0 | 0 | 0 | 0 | 0 | 0 | 0 | 0 | 0 | 0 | 0 | 0 | 0 | 0 | 0 |
| 967.06 | 0 | 0 | 0 | 0 | 15.0079 | 0 | 0 | 0 | 0 | 0 | 0 | 0 | 0 | 0 | 0 |
| 975.506 | 0 | 0 | 0 | 0 | 0 | 0 | 0 | 0 | 0 | 0 | 0 | 0 | 0 | 0 | 0 |
| 978.208 | 0 | 0 | 0 | 0 | 0 | 0 | 0 | 0 | 0 | 0 | 0 | 0 | 0 | 0 | 0 |
| 985.304 | 0 | 0 | 0 | 0 | 0 | 0 | 0 | 0 | 0 | 0 | 0 | 0 | 0 | 0 | 0 |
| 987.312 | 0 | 0 | 0 | 0 | 0 | 0 | 0 | 0 | 0 | 0 | 0 | 0 | 0 | 0 | 0 |
| 993.388 | 0 | 0 | 0 | 0 | 0 | 0 | 0 | 0 | 0 | 0 | 0 | 0 | 0 | 0 | 0 |
| 998.553 | 0 | 0 | 0 | 0 | 0 | 0 | 0 | 0 | 0 | 0 | 0 | 0 | 0 | 0 | 0 |
| 999.985 | 0 | 0 | 0 | 0 | 0 | 0 | 0 | 0 | 0 | 0 | 0 | 0 | 0 | 0 | 0 |
| 1012.56 | 0 | 0 | 0 | 0 | 0 | 0 | 0 | 0 | 0 | 0 | 0 | 0 | 0 | 0 | 0 |
| 1013.12 | 0 | 0 | 0 | 0 | 0 | 0 | 0 | 0 | 0 | 0 | 0 | 0 | 0 | 0 | 0 |
| 1018.06 | 0 | 0 | 0 | 42.0023 | 0 | 0 | 0 | 0 | 0 | 0 | 0 | 0 | 0 | 0 | 0 |

Fig. 69a

| 100 | 7.7144 | 10.796 | 15.732 | 24.2392 | 40.1985 | 64.4367 | 74.9016 | 114.2 | 138.478 | 159.681 | 233.882 | 274.091 | 293.319 | 314.051 | 455.811 |
|---|---|---|---|---|---|---|---|---|---|---|---|---|---|---|---|
| 1018.75 | 0 | 0 | 0 | 0 | 0 | 0 | 0 | 0 | 0 | 0 | 0 | 0 | 0 | 0 | 0 |
| 1023.26 | 0 | 0 | 0 | 0 | 0 | 0 | 0 | 0 | 0 | 0 | 0 | 0 | 0 | 0 | 0 |
| 1026.2 | 0 | 0 | 0 | 0 | 0 | 0 | 0 | 0 | 0 | 0 | 0 | 0 | 0 | 0 | 0 |
| 1026.92 | 0 | 0 | 0 | 0 | 0 | 0 | 0 | 8.99229 | 0 | 0 | 0 | 0 | 0 | 0 | 0 |
| 1028.96 | 0 | 0 | 0 | 0 | 0 | 0 | 0 | 0 | 0 | 0 | 0 | 0 | 0 | 0 | 0 |
| 1029.42 | 0 | 0 | 0 | 0 | 0 | 0 | 0 | 0 | 0 | 0 | 0 | 0 | 0 | 0 | 0 |
| 1031.67 | 0 | 0 | 0 | 0 | 0 | 0 | 0 | 0 | 0 | 0 | 0 | 0 | 0 | 0 | 0 |
| 1034.53 | 0 | 0 | 0 | 0 | 0 | 0 | 0 | 0 | 0 | 0 | 0 | 0 | 0 | 0 | 0 |
| 1035.95 | 0 | 0 | 0 | 0 | 0 | 0 | 13.9992 | 0 | 0 | 0 | 0 | 0 | 0 | 0 | 0 |
| 1036.19 | 0 | 0 | 0 | 0 | 0 | 0 | 14.0023 | 0 | 0 | 0 | 0 | 0 | 0 | 0 | 0 |
| 1037.93 | 0 | 0 | 0 | 0 | 0 | 0 | 0 | 0 | 0 | 0 | 0 | 0 | 0 | 0 | 0 |
| 1050.76 | 0 | 0 | 0 | 0 | 0 | 0 | 0 | 0 | 0 | 0 | 0 | 0 | 0 | 0 | 0 |
| 1057.58 | 0 | 0 | 0 | 0 | 0 | 0 | 0 | 0 | 0 | 0 | 0 | 0 | 0 | 0 | 0 |
| 1059.23 | 0 | 0 | 0 | 0 | 0 | 0 | 0 | 0 | 0 | 0 | 0 | 0 | 0 | 0 | 0 |
| 1063.75 | 0 | 0 | 0 | 0 | 0 | 0 | 0 | 0 | 0 | 0 | 0 | 0 | 0 | 0 | 0 |
| 1067.44 | 0 | 0 | 0 | 0 | 0 | 0 | 0 | 0 | 0 | 0 | 0 | 0 | 0 | 0 | 0 |
| 1069.45 | 0 | 0 | 0 | 0 | 0 | 0 | 0 | 0 | 0 | 0 | 0 | 0 | 0 | 0 | 0 |
| 1073.27 | 0 | 0 | 0 | 0 | 0 | 0 | 0 | 0 | 0 | 0 | 0 | 0 | 0 | 0 | 0 |
| 1080.72 | 0 | 0 | 0 | 0 | 0 | 0 | 0 | 0 | 0 | 0 | 0 | 0 | 0 | 0 | 0 |
| 1081.02 | 0 | 0 | 0 | 0 | 0 | 0 | 0 | 0 | 0 | 0 | 0 | 0 | 0 | 0 | 0 |
| 1081.63 | 0 | 0 | 0 | 0 | 0 | 0 | 0 | 0 | 0 | 0 | 0 | 0 | 0 | 0 | 0 |
| 1082.35 | 0 | 0 | 0 | 0 | 0 | 0 | 0 | 0 | 0 | 0 | 0 | 0 | 0 | 0 | 0 |
| 1088.21 | 0 | 0 | 0 | 0 | 0 | 0 | 0 | 0 | 0 | 0 | 0 | 0 | 0 | 0 | 0 |
| 1088.63 | 0 | 0 | 0 | 0 | 0 | 0 | 0 | 0 | 0 | 0 | 0 | 0 | 0 | 0 | 0 |
| 1091.1 | 0 | 0 | 0 | 0 | 0 | 0 | 0 | 0 | 0 | 0 | 0 | 0 | 0 | 0 | 0 |
| 1094.74 | 0 | 0 | 0 | 0 | 0 | 0 | 0 | 0 | 0 | 0 | 0 | 3.99422 | 0 | 0 | 0 |
| 1096.55 | 0 | 0 | 0 | 0 | 0 | 0 | 0 | 0 | 0 | 0 | 0 | 4.00082 | 0 | 0 | 0 |
| 1098.17 | 0 | 0 | 0 | 0 | 0 | 0 | 0 | 0 | 0 | 0 | 0 | 4.00674 | 0 | 0 | 0 |
| 1102.57 | 0 | 0 | 0 | 0 | 0 | 0 | 0 | 0 | 0 | 0 | 0 | 0 | 0 | 0 | 0 |
| 1104.97 | 0 | 0 | 0 | 0 | 0 | 0 | 0 | 0 | 0 | 0 | 0 | 0 | 0 | 0 | 0 |
| 1107.93 | 0 | 0 | 0 | 0 | 0 | 0 | 0 | 0 | 8.0303 | 0 | 0 | 0 | 0 | 0 | 0 |
| 1109.36 | 0 | 0 | 0 | 0 | 0 | 0 | 14.991 | 0 | 0 | 0 | 0 | 0 | 0 | 0 | 0 |
| 1110.99 | 0 | 0 | 0 | 0 | 0 | 0 | 0 | 0 | 0 | 0 | 0 | 0 | 0 | 0 | 0 |
| 1119.82 | 0 | 103.003 | 0 | 0 | 0 | 0 | 0 | 0 | 0 | 7.00408 | 0 | 0 | 0 | 0 | 0 |
| 1120.9 | 0 | 0 | 0 | 0 | 0 | 0 | 0 | 0 | 0 | 0 | 0 | 0 | 0 | 0 | 0 |
| 1127.27 | 0 | 0 | 0 | 0 | 0 | 0 | 0 | 0 | 0 | 0 | 0 | 0 | 0 | 0 | 0 |
| 1127.82 | 0 | 0 | 0 | 0 | 0 | 0 | 0 | 0 | 0 | 0 | 0 | 0 | 0 | 0 | 0 |
| 1130.93 | 0 | 0 | 0 | 0 | 0 | 0 | 0 | 0 | 0 | 0 | 0 | 0 | 0 | 0 | 0 |
| 1132.62 | 0 | 105.008 | 71.9947 | 0 | 0 | 0 | 0 | 0 | 0 | 0 | 0 | 0 | 0 | 0 | 0 |
| 1135.86 | 0 | 0 | 0 | 0 | 0 | 0 | 0 | 0 | 0 | 0 | 0 | 0 | 0 | 0 | 0 |
| 1140.75 | 0 | 0 | 0 | 0 | 0 | 0 | 0 | 0 | 0 | 0 | 0 | 0 | 0 | 0 | 0 |
| 1144.43 | 0 | 0 | 0 | 0 | 0 | 0 | 0 | 0 | 0 | 0 | 0 | 0 | 0 | 0 | 0 |
| 1151.66 | 0 | 0 | 0 | 0 | 0 | 0 | 0 | 0 | 0 | 0 | 0 | 0 | 0 | 0 | 0 |
| 1154.82 | 0 | 0 | 0 | 0 | 0 | 0 | 0 | 0 | 0 | 0 | 0 | 0 | 0 | 0 | 0 |
| 1174.62 | 0 | 0 | 0 | 0 | 0 | 0 | 0 | 0 | 0 | 0 | 0 | 0 | 0 | 0 | 0 |
| 1175.91 | 0 | 0 | 0 | 0 | 0 | 0 | 0 | 0 | 0 | 0 | 0 | 0 | 0 | 0 | 0 |
| 1180.66 | 0 | 0 | 0 | 0 | 0 | 0 | 0 | 0 | 0 | 0 | 0 | 0 | 0 | 0 | 0 |
| 1181.82 | 0 | 0 | 0 | 0 | 0 | 0 | 0 | 0 | 0 | 0 | 0 | 0 | 0 | 0 | 0 |
| 1185.23 | 0 | 0 | 0 | 0 | 0 | 0 | 0 | 0 | 0 | 0 | 0 | 0 | 0 | 0 | 0 |
| 1187.63 | 0 | 0 | 0 | 46.9983 | 0 | 0 | 0 | 0 | 0 | 0 | 0 | 0 | 0 | 0 | 0 |
| 1191.74 | 0 | 0 | 0 | 0 | 0 | 0 | 0 | 0 | 0 | 0 | 0 | 0 | 3.99485 | 0 | 0 |
| 1192 | 0 | 0 | 0 | 0 | 0 | 0 | 0 | 0 | 0 | 0 | 0 | 0 | 3.99572 | 0 | 0 |
| 1192.46 | 0 | 0 | 0 | 0 | 0 | 0 | 0 | 0 | 0 | 0 | 0 | 0 | 3.99726 | 0 | 0 |
| 1195.11 | 0 | 0 | 0 | 0 | 0 | 0 | 0 | 0 | 0 | 0 | 0 | 0 | 4.00615 | 0 | 0 |
| 1196.33 | 0 | 0 | 0 | 0 | 0 | 0 | 0 | 0 | 0 | 0 | 0 | 0 | 0 | 0 | 0 |
| 1199.89 | 0 | 0 | 0 | 0 | 0 | 0 | 0 | 0 | 0 | 0 | 0 | 0 | 0 | 0 | 0 |
| 1201.18 | 0 | 0 | 0 | 0 | 0 | 0 | 0 | 0 | 0 | 0 | 0 | 0 | 0 | 0 | 0 |
| 1203.93 | 0 | 0 | 0 | 0 | 0 | 0 | 0 | 0 | 0 | 0 | 0 | 0 | 0 | 0 | 0 |
| 1205.36 | 0 | 0 | 0 | 0 | 0 | 0 | 0 | 0 | 0 | 0 | 0 | 0 | 0 | 0 | 0 |
| 1213.24 | 0 | 0 | 0 | 0 | 0 | 0 | 0 | 0 | 0 | 0 | 0 | 0 | 0 | 0 | 0 |
| 1214.99 | 0 | 0 | 0 | 0 | 0 | 0 | 0 | 0 | 0 | 0 | 0 | 0 | 0 | 0 | 0 |
| 1223.16 | 0 | 0 | 0 | 0 | 0 | 0 | 0 | 0 | 0 | 0 | 0 | 0 | 0 | 0 | 0 |
| 1228.63 | 0 | 0 | 0 | 0 | 0 | 0 | 0 | 0 | 0 | 0 | 0 | 0 | 0 | 0 | 0 |
| 1230.33 | 0 | 0 | 0 | 0 | 0 | 0 | 0 | 0 | 0 | 0 | 0 | 0 | 0 | 0 | 0 |
| 1234.17 | 0 | 0 | 0 | 0 | 0 | 0 | 0 | 0 | 0 | 0 | 0 | 0 | 0 | 0 | 0 |
| 1234.63 | 0 | 0 | 0 | 0 | 0 | 0 | 0 | 0 | 0 | 0 | 0 | 0 | 0 | 0 | 0 |
| 1234.71 | 0 | 0 | 0 | 0 | 0 | 0 | 0 | 0 | 0 | 0 | 0 | 0 | 0 | 0 | 0 |
| 1239.81 | 0 | 0 | 0 | 0 | 0 | 0 | 0 | 0 | 0 | 0 | 0 | 0 | 0 | 0 | 0 |
| 1247.53 | 0 | 0 | 0 | 0 | 0 | 0 | 0 | 0 | 0 | 0 | 0 | 0 | 0 | 0 | 0 |
| 1248.16 | 0 | 0 | 0 | 0 | 0 | 0 | 0 | 0 | 0 | 0 | 0 | 0 | 0 | 0 | 0 |
| 1251.13 | 0 | 115.9360 | 0 | 0 | 0 | 0 | 0 | 0 | 0 | 0 | 0 | 0 | 0 | 0 | 0 |
| 1254.61 | 0 | 0 | 0 | 0 | 0 | 0 | 0 | 0 | 0 | 0 | 0 | 0 | 0 | 3.99492 | 0 |
| 1256.04 | 0 | 0 | 0 | 0 | 0 | 0 | 10.9336 | 0 | 0 | 0 | 0 | 0 | 0 | 3.99948 | 0 |
| 1257.71 | 0 | 0 | 0 | 0 | 0 | 0 | 16.9957 | 0 | 0 | 0 | 0 | 0 | 0 | 4.0048 | 0 |
| 1265.87 | 0 | 0 | 0 | 0 | 0 | 0 | 0 | 0 | 0 | 0 | 0 | 0 | 0 | 0 | 0 |
| 1271.87 | 0 | 0 | 0 | 0 | 0 | 0 | 0 | 0 | 0 | 0 | 0 | 0 | 0 | 0 | 0 |

Fig. 69b

| 180 | 7.7144 | 10.786 | 15.732 | 24.2392 | 40.1985 | 64.4367 | 74.0016 | 114.2 | 138.438 | 159.881 | 233.882 | 274.081 | .298.319 | 314.051 | 456.811 |
|---|---|---|---|---|---|---|---|---|---|---|---|---|---|---|---|
| 1281.07 | 0 | 0 | 0 | 0 | 0 | 0 | 0 | 0 | 0 | 0 | 0 | 0 | 0 | 0 | 0 |
| 1288.82 | 0 | 0 | 0 | 0 | 0 | 20.0013 | 0 | 0 | 0 | 0 | 0 | 0 | 0 | 0 | 0 |
| 1293.16 | 0 | 0 | 0 | 0 | 0 | 0 | 0 | 0 | 0 | 0 | 0 | 0 | 0 | 0 | 0 |
| 1294.72 | 0 | 0 | 0 | 0 | 0 | 0 | 0 | 0 | 0 | 0 | 0 | 0 | 0 | 0 | 0 |
| 1298.91 | 0 | 0 | 0 | 0 | 0 | 0 | 0 | 0 | 0 | 0 | 0 | 0 | 0 | 0 | 0 |
| 1307.77 | 0 | 0 | 0 | 0 | 0 | 0 | 0 | 0 | 0 | 0 | 0 | 0 | 0 | 0 | 0 |
| 1308.56 | 0 | 0 | 0 | 0 | 0 | 0 | 0 | 0 | 0 | 0 | 0 | 0 | 0 | 0 | 0 |
| 1318.13 | 0 | 0 | 0 | 0 | 0 | 0 | 0 | 0 | 0 | 0 | 0 | 0 | 0 | 0 | 0 |
| 1321.35 | 0 | 0 | 83.9912 | 0 | 0 | 0 | 0 | 0 | 0 | 0 | 0 | 0 | 0 | 0 | 0 |
| 1332.83 | 0 | 0 | 0 | 0 | 0 | 0 | 0 | 0 | 0 | 0 | 0 | 0 | 0 | 0 | 0 |
| 1346.83 | 0 | 0 | 0 | 0 | 0 | 0 | 0 | 0 | 0 | 0 | 0 | 0 | 0 | 0 | 0 |
| 1361.32 | 0 | 0 | 0 | 0 | 0 | 0 | 0 | 0 | 0 | 0 | 0 | 0 | 0 | 0 | 0 |
| 1378.57 | 0 | 0 | 0 | 0 | 0 | 0 | 0 | 0 | 0 | 0 | 0 | 0 | 0 | 0 | 0 |
| 1384.61 | 0 | 0 | 0 | 0 | 0 | 0 | 0 | 0 | 100.017 | 0 | 0 | 0 | 0 | 0 | 0 |
| 1398.14 | 0 | 0 | 0 | 0 | 0 | 0 | 0 | 0 | 0 | 0 | 0 | 0 | 0 | 0 | 0 |
| 1408.04 | 0 | 0 | 0 | 0 | 0 | 0 | 0 | 0 | 0 | 0 | 0 | 0 | 0 | 0 | 0 |
| 1425.32 | 0 | 0 | 0 | 0 | 0 | 0 | 0 | 0 | 0 | 0 | 0 | 0 | 0 | 0 | 0 |
| 1438.14 | 0 | 0 | 0 | 0 | 0 | 0 | 0 | 0 | 0 | 8.99507 | 0 | 0 | 0 | 0 | 0 |
| 1450.02 | 0 | 0 | 0 | 0 | 0 | 0 | 0 | 0 | 0 | 0 | 0 | 0 | 0 | 0 | 0 |
| 1462.85 | 0 | 0 | 0 | 0 | 0 | 0 | 0 | 0 | 0 | 0 | 0 | 0 | 0 | 0 | 0 |
| 1475.06 | 0 | 0 | 0 | 0 | 0 | 0 | 0 | 0 | 0 | 0 | 0 | 0 | 0 | 0 | 0 |
| 1476.35 | 0 | 0 | 0 | 0 | 0 | 0 | 0 | 0 | 0 | 0 | 0 | 0 | 0 | 0 | 0 |

| 100 | 456.816 | 616.688 | 690.691 | 730.891 | 755.131 | 770.063 | 781.649 | 2466 | 2923 | 3083 | 3157 | 3197 | 3221 | 3236.7 |
|---|---|---|---|---|---|---|---|---|---|---|---|---|---|---|
| 1018.75 | 0 | 0 | 0 | 0 | 0 | 0 | 0 | 0 | 0 | 0 | 0 | 0 | 0 | 0 |
| 1023.26 | 0 | 0 | 0 | 0 | 0 | 0 | 0 | 0 | 0 | 0 | 0 | 0 | 0 | 0 |
| 1026.2 | 0 | 0 | 0 | 0 | 0 | 0 | 0 | 0 | 0 | 0 | 0 | 0 | 0 | 0 |
| 1026.92 | 0 | 0 | 0 | 0 | 0 | 0 | 0 | 0 | 0 | 0 | 0 | 0 | 0 | 0 |
| 1028.95 | 0 | 0 | 0 | 0 | 0 | 0 | 0 | 0 | 0 | 0 | 0 | 0 | 0 | 0 |
| 1029.42 | 0 | 0 | 0 | 0 | 0 | 0 | 0 | 0 | 0 | 0 | 0 | 0 | 0 | 0 |
| 1031.6 | 0 | 0 | 0 | 0 | 0 | 0 | 0 | 0 | 0 | 0 | 0 | 0 | 0 | 0 |
| 1034.53 | 0 | 0 | 0 | 0 | 0 | 0 | 0 | 0 | 0 | 0 | 0 | 0 | 0 | 0 |
| 1035.96 | 0 | 0 | 0 | 0 | 0 | 0 | 0 | 0 | 0 | 0 | 0 | 0 | 0 | 0 |
| 1036.19 | 0 | 0 | 0 | 0 | 0 | 0 | 0 | 0 | 0 | 0 | 0 | 0 | 0 | 0 |
| 1037.99 | 0 | 0 | 0 | 0 | 0 | 0 | 0 | 0 | 0 | 0 | 0 | 0 | 0 | 0 |
| 1050.76 | 0 | 0 | 0 | 0 | 0 | 0 | 0 | 0 | 0 | 0 | 0 | 0 | 0 | 0 |
| 1057.56 | 0 | 0 | 0 | 0 | 0 | 0 | 0 | 0 | 0 | 0 | 0 | 0 | 0 | 0 |
| 1059.23 | 0 | 0 | 0 | 0 | 0 | 0 | 0 | 0 | 0 | 0 | 0 | 0 | 0 | 0 |
| 1063.75 | 0 | 0 | 0 | 0 | 0 | 0 | 0 | 0 | 0 | 0 | 0 | 0 | 0 | 0 |
| 1067.44 | 0 | 0 | 0 | 0 | 0 | 0 | 0 | 0 | 0 | 0 | 0 | 0 | 0 | 0 |
| 1069.45 | 0 | 0 | 0 | 0 | 0 | 0 | 0 | 0 | 0 | 0 | 0 | 0 | 0 | 0 |
| 1073.27 | 0 | 0 | 0 | 0 | 0 | 0 | 0 | 0 | 0 | 0 | 0 | 0 | 0 | 0 |
| 1080.72 | 0 | 0 | 0 | 0 | 0 | 0 | 0 | 0 | 0 | 0 | 0 | 0 | 0 | 0 |
| 1081.02 | 0 | 0 | 0 | 0 | 0 | 0 | 0 | 0 | 0 | 0 | 0 | 0 | 0 | 0 |
| 1081.63 | 0 | 0 | 0 | 0 | 0 | 0 | 0 | 0 | 0 | 0 | 0 | 0 | 0 | 0 |
| 1082.35 | 0 | 0 | 0 | 0 | 0 | 0 | 0 | 0 | 0 | 0 | 0 | 0 | 0 | 0 |
| 1088.21 | 0 | 0 | 0 | 0 | 0 | 0 | 0 | 0 | 0 | 0 | 0 | 0 | 0 | 0 |
| 1088.63 | 0 | 0 | 0 | 0 | 0 | 0 | 0 | 0 | 0 | 0 | 0 | 0 | 0 | 0 |
| 1091.1 | 0 | 0 | 0 | 0 | 0 | 0 | 0 | 0 | 0 | 0 | 0 | 0 | 0 | 0 |
| 1094.74 | 0 | 0 | 0 | 0 | 0 | 0 | 0 | 0 | 0 | 0 | 0 | 0 | 0 | 0 |
| 1096.55 | 0 | 0 | 0 | 0 | 0 | 0 | 0 | 0 | 0 | 0 | 0 | 0 | 0 | 0 |
| 1098.17 | 0 | 0 | 0 | 0 | 0 | 0 | 0 | 0 | 0 | 0 | 0 | 0 | 0 | 0 |
| 1102.57 | 0 | 0 | 0 | 0 | 0 | 0 | 0 | 0 | 0 | 0 | 0 | 0 | 0 | 0 |
| 1104.97 | 0 | 0 | 0 | 0 | 0 | 0 | 0 | 0 | 0 | 0 | 0 | 0 | 0 | 0 |
| 1107.93 | 0 | 0 | 0 | 0 | 0 | 0 | 0 | 0 | 0 | 0 | 0 | 0 | 0 | 0 |
| 1109.36 | 0 | 0 | 0 | 0 | 0 | 0 | 0 | 0 | 0 | 0 | 0 | 0 | 0 | 0 |
| 1110.99 | 0 | 0 | 0 | 0 | 0 | 0 | 0 | 0 | 0 | 0 | 0 | 0 | 0 | 0 |
| 1119.82 | 0 | 0 | 0 | 0 | 0 | 0 | 0 | 0 | 0 | 0 | 0 | 0 | 0 | 0 |
| 1120.9 | 0 | 0 | 0 | 0 | 0 | 0 | 0 | 0 | 0 | 0 | 0 | 0 | 0 | 0 |
| 1127.27 | 0 | 0 | 0 | 0 | 0 | 0 | 0 | 0 | 0 | 0 | 0 | 0 | 0 | 0 |
| 1127.82 | 0 | 0 | 0 | 0 | 0 | 0 | 0 | 0 | 0 | 0 | 0 | 0 | 0 | 0 |
| 1130.93 | 0 | 0 | 0 | 0 | 0 | 0 | 0 | 0 | 0 | 0 | 0 | 0 | 0 | 0 |
| 1132.62 | 0 | 0 | 0 | 0 | 0 | 0 | 0 | 0 | 0 | 0 | 0 | 0 | 0 | 0 |
| 1135.95 | 0 | 0 | 0 | 0 | 0 | 0 | 0 | 0 | 0 | 0 | 0 | 0 | 0 | 0 |
| 1140.75 | 0 | 0 | 0 | 0 | 0 | 0 | 0 | 0 | 0 | 0 | 0 | 0 | 0 | 0 |
| 1144.43 | 0 | 0 | 0 | 0 | 0 | 0 | 0 | 0 | 0 | 0 | 0 | 0 | 0 | 0 |
| 1151.66 | 0 | 0 | 0 | 0 | 0 | 0 | 0 | 0 | 0 | 0 | 0 | 0 | 0 | 0 |
| 1154.82 | 0 | 0 | 0 | 0 | 0 | 0 | 0 | 0 | 0 | 0 | 0 | 0 | 0 | 0 |
| 1174.62 | 0 | 0 | 0 | 0 | 0 | 0 | 0 | 0 | 0 | 0 | 0 | 0 | 0 | 0 |
| 1175.91 | 0 | 0 | 0 | 0 | 0 | 0 | 0 | 0 | 0 | 0 | 0 | 0 | 0 | 0 |
| 1180.66 | 0 | 0 | 0 | 0 | 0 | 0 | 0 | 0 | 0 | 0 | 0 | 0 | 0 | 0 |
| 1181.92 | 0 | 0 | 0 | 0 | 0 | 0 | 0 | 0 | 0 | 0 | 0 | 0 | 0 | 0 |
| 1185.23 | 0 | 0 | 0 | 0 | 0 | 0 | 0 | 0 | 0 | 0 | 0 | 0 | 0 | 0 |
| 1187.63 | 0 | 0 | 0 | 0 | 0 | 0 | 0 | 0 | 0 | 0 | 0 | 0 | 0 | 0 |
| 1191.74 | 0 | 0 | 0 | 0 | 0 | 0 | 0 | 0 | 0 | 0 | 0 | 0 | 0 | 0 |
| 1192 | 0 | 0 | 0 | 0 | 0 | 0 | 0 | 0 | 0 | 0 | 0 | 0 | 0 | 0 |
| 1192.46 | 0 | 0 | 0 | 0 | 0 | 0 | 0 | 0 | 0 | 0 | 0 | 0 | 0 | 0 |
| 1195.11 | 0 | 0 | 0 | 0 | 0 | 0 | 0 | 0 | 0 | 0 | 0 | 0 | 0 | 0 |
| 1196.33 | 0 | 0 | 0 | 0 | 0 | 0 | 0 | 0 | 0 | 0 | 0 | 0 | 0 | 0 |
| 1199.89 | 0 | 0 | 0 | 0 | 0 | 0 | 0 | 0 | 0 | 0 | 0 | 0 | 0 | 0 |
| 1201.18 | 0 | 0 | 0 | 0 | 0 | 0 | 0 | 0 | 0 | 0 | 0 | 0 | 0 | 0 |
| 1203.93 | 0 | 0 | 0 | 0 | 0 | 0 | 0 | 0 | 0 | 0 | 0 | 0 | 0 | 0 |
| 1205.36 | 0 | 0 | 0 | 0 | 0 | 0 | 0 | 0 | 0 | 0 | 0 | 0 | 0 | 0 |
| 1213.24 | 0 | 0 | 0 | 0 | 0 | 0 | 0 | 0 | 0 | 0 | 0 | 0 | 0 | 0 |
| 1214.99 | 0 | 0 | 0 | 0 | 0 | 0 | 0 | 0 | 0 | 0 | 0 | 0 | 0 | 0 |
| 1223.16 | 0 | 0 | 0 | 0 | 0 | 0 | 0 | 0 | 0 | 0 | 0 | 0 | 0 | 0 |
| 1228.63 | 0 | 1992.3 | 0 | 0 | 0 | 0 | 0 | 0 | 0 | 0 | 0 | 0 | 0 | 0 |
| 1230.33 | 0 | 1995.06 | 0 | 0 | 0 | 0 | 0 | 0 | 0 | 0 | 0 | 0 | 0 | 0 |
| 1234.17 | 0 | 2001.29 | 0 | 0 | 0 | 0 | 0 | 0 | 0 | 0 | 0 | 0 | 0 | 0 |
| 1234.63 | 0 | 2002.13 | 0 | 0 | 0 | 0 | 0 | 0 | 0 | 0 | 0 | 0 | 0 | 0 |
| 1234.71 | 0 | 2002.16 | 0 | 0 | 0 | 0 | 0 | 0 | 0 | 0 | 0 | 0 | 0 | 0 |
| 1239.81 | 0 | 0 | 0 | 0 | 0 | 0 | 0 | 0 | 0 | 0 | 0 | 0 | 0 | 0 |
| 1247.53 | 0 | 0 | 0 | 0 | 0 | 0 | 0 | 0 | 0 | 0 | 0 | 0 | 0 | 0 |
| 1248.16 | 0 | 0 | 0 | 0 | 0 | 0 | 0 | 0 | 0 | 0 | 0 | 0 | 0 | 0 |
| 1251.13 | 0 | 0 | 0 | 0 | 0 | 0 | 0 | 0 | 0 | 0 | 0 | 0 | 0 | 0 |
| 1254.61 | 0 | 0 | 0 | 0 | 0 | 0 | 0 | 0 | 0 | 0 | 0 | 0 | 0 | 0 |
| 1256.04 | 0 | 0 | 0 | 0 | 0 | 0 | 0 | 0 | 0 | 0 | 0 | 0 | 0 | 0 |
| 1257.71 | 0 | 0 | 0 | 0 | 0 | 0 | 0 | 0 | 0 | 0 | 0 | 0 | 0 | 0 |
| 1265.87 | 0 | 0 | 0 | 0 | 0 | 0 | 0 | 0 | 0 | 0 | 0 | 0 | 0 | 0 |
| 1271.87 | 0 | 0 | 0 | 0 | 0 | 0 | 0 | 0 | 0 | 0 | 0 | 0 | 0 | 0 |

Fig. 69e

| 100 | 456.816 | 616.608 | 690.691 | 730.091 | 755.131 | 778.803 | 781.649 | 2456 | 2923 | 3093 | 3157 | 3197 | 3221 | 3236.7 |
|---|---|---|---|---|---|---|---|---|---|---|---|---|---|---|
| 1281.07 | 0 | 0 | 0 | 0 | 0 | 0 | 0 | 0 | 0 | 0 | 0 | 0 | 0 | 0 |
| 1289.82 | 0 | 0 | 0 | 0 | 0 | 0 | 0 | 0 | 0 | 0 | 0 | 0 | 0 | 0 |
| 1293.16 | 0 | 0 | 0 | 0 | 0 | 0 | 0 | 0 | 0 | 0 | 0 | 0 | 0 | 0 |
| 1294.72 | 0 | 0 | 0 | 0 | 0 | 0 | 0 | 0 | 0 | 0 | 0 | 0 | 0 | 0 |
| 1298.91 | 0 | 0 | 0 | 0 | 0 | 0 | 0 | 0 | 0 | 0 | 0 | 0 | 0 | 0 |
| 1300.77 | 0 | 0 | 0 | 0 | 0 | 0 | 0 | 0 | 0 | 0 | 0 | 0 | 0 | 0 |
| 1309.56 | 0 | 0 | 0 | 0 | 0 | 0 | 0 | 0 | 0 | 0 | 0 | 0 | 0 | 0 |
| 1318.13 | 0 | 0 | 0 | 0 | 0 | 0 | 0 | 0 | 0 | 0 | 0 | 0 | 0 | 0 |
| 1321.35 | 0 | 0 | 0 | 0 | 0 | 0 | 0 | 0 | 0 | 0 | 0 | 0 | 0 | 0 |
| 1332.83 | 0 | 0 | 0 | 0 | 0 | 0 | 0 | 0 | 0 | 0 | 0 | 0 | 0 | 0 |
| 1348.83 | 0 | 0 | 0 | 0 | 0 | 0 | 0 | 0 | 0 | 0 | 0 | 0 | 0 | 0 |
| 1361.32 | 0 | 0 | 0 | 0 | 0 | 0 | 0 | 0 | 0 | 0 | 0 | 0 | 0 | 0 |
| 1378.57 | 0 | 0 | 1995.93 | 0 | 0 | 0 | 0 | 0 | 0 | 0 | 0 | 0 | 0 | 0 |
| 1384.61 | 0 | 0 | 2004.67 | 0 | 0 | 0 | 0 | 0 | 0 | 0 | 0 | 0 | 0 | 0 |
| 1398.14 | 0 | 0 | 0 | 0 | 0 | 0 | 0 | 0 | 0 | 0 | 0 | 0 | 0 | 0 |
| 1409.04 | 0 | 0 | 0 | 0 | 0 | 0 | 0 | 0 | 0 | 0 | 0 | 0 | 0 | 0 |
| 1425.32 | 0 | 0 | 0 | 0 | 0 | 0 | 0 | 0 | 0 | 0 | 0 | 0 | 0 | 0 |
| 1438.14 | 0 | 0 | 0 | 0 | 0 | 0 | 0 | 0 | 0 | 0 | 0 | 0 | 0 | 0 |
| 1450.02 | 0 | 0 | 0 | 0 | 0 | 0 | 0 | 0 | 0 | 0 | 0 | 0 | 0 | 0 |
| 1462.85 | 0 | 0 | 0 | 2001.46 | 0 | 0 | 0 | 0 | 0 | 0 | 0 | 0 | 0 | 0 |
| 1475.06 | 0 | 0 | 0 | 0 | 0 | 0 | 0 | 0 | 0 | 0 | 0 | 0 | 0 | 0 |
| 1476.35 | 0 | 0 | 0 | 0 | 0 | 0 | 0 | 0 | 0 | 0 | 0 | 0 | 0 | 0 |

Fig. 69f

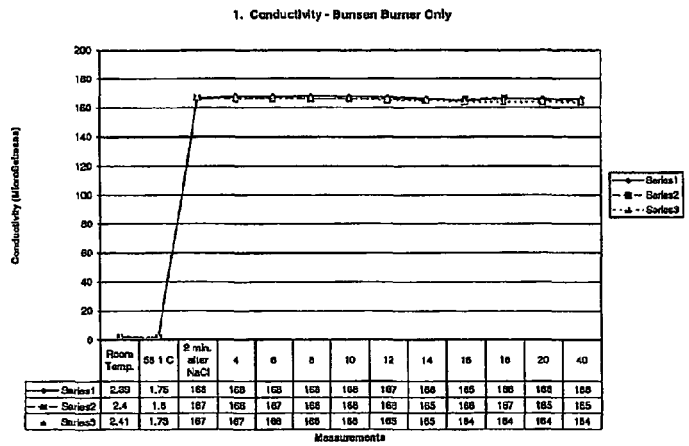
FIG. 75a
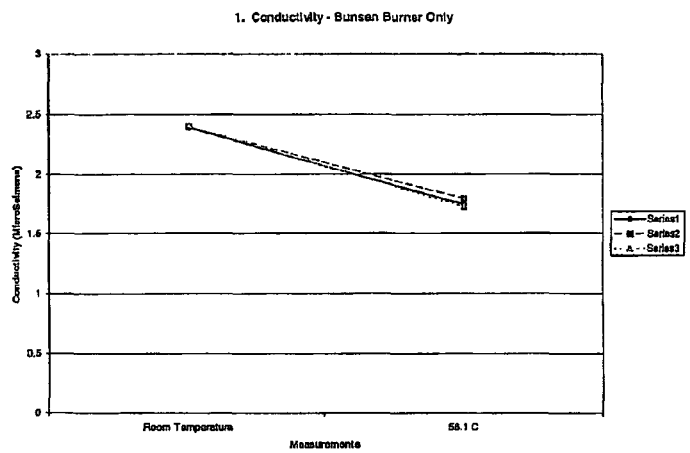
FIG. 75b
FIG. 75c
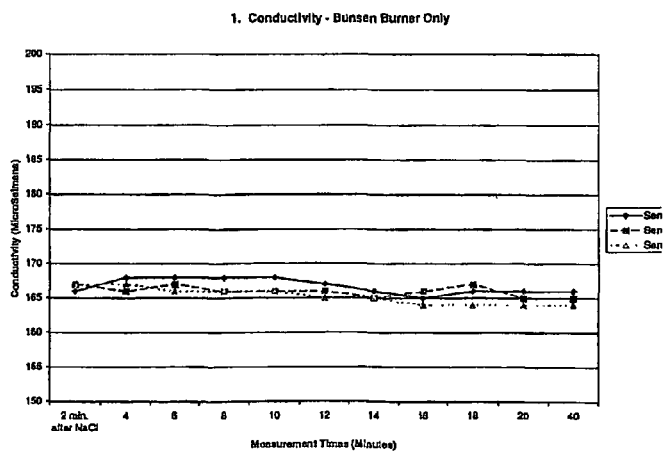

ELECTROCHEMISTRY TECHNICAL FIELD

TECHNICAL FIELD

This invention relates to novel methods for affecting, controlling and/or directing various reactions and/or reaction pathways or systems by exposing one or more components in a holoreaction system to at least one spectral energy pattern. In a first aspect of the invention, at least one spectral energy pattern can be applied to a reaction system. In a second aspect of the invention, at least one spectral energy conditioning pattern can be applied to a conditioning reaction system. The spectral energy conditioning pattern can, for example, be applied at a separate location from the reaction vessel (e.g., in a conditioning reaction vessel) or can be applied in (or to) the reaction vessel, but prior to other reaction system participants being introduced into the reaction vessel.

The techniques of the present invention are applicable to certain reactions in various cell reaction systems, including but not limited to, the following known cells: galvanic cells, electrochemical cells, electrolytic cells, fuel cells, batteries, photoelectrochemical cells, photogalvanic cells, photoelectrolytic cells, capacitors. Cell reaction systems can be organic, biologic and/or inorganic. The invention also relates to mimicking various mechanisms of action of various catalysts in cell reaction systems under various environmental reaction conditions. The invention specifically discloses different means for achieving the control of energy dynamics (e.g., matching or non-matching) between, for example, applied energy and matter (e.g., solids, liquids, gases, plasmas and/or combinations or portions thereof), to achieve (or to prevent) and/or increase energy transfer to, for example, at least one participant (or at least one conditionable participant) in a holoreaction system by taking into account various energy considerations in the holoreaction system. The invention further discloses different techniques and different means for delivery of at least one spectral energy pattern (or at least one spectral energy conditioning pattern) to at least a portion of a cell reaction system. The invention also discloses an approach for designing or determining appropriate physical catalyst(s) and/or conditioned participants to be used in a cell reaction system.

DISCUSSION OF RELATED AND COMMONLY OWNED PATENT APPLICATIONS

The subject matter of the present invention is related to the subject matter contained in U.S. Provisional Application Ser. No. 60/363,152, entitled "Improvements in Electrochemistry", which was filed on Mar. 11, 2002.

The subject matter of the present invention is also related to the subject matter contained in co-pending U.S. Provisional Application Ser. No. 60/403,251, entitled "Spectral Chemistry", which was filed on Aug. 13, 2002.

The subject matter of the present invention is also related to the subject matter contained in co-pending U.S. Provisional Application Ser. No. 60/439,223, entitled "Spectral Conditioning", which was filed on Jan. 10, 2003.

The subject matter of the present invention is related to the subject matter contained in co-pending U.S. application Ser. No. 10/203,797, entitled "Spectral Chemistry", which entered the National Phase on Aug. 12, 2002.

Further, the subject matter of the present invention is also related to the subject matter contained in two (2) co-pending U.S. Provisional Application Ser. Nos. 60/366,755 and 60/403,225, both entitled, "Methods for Controlling Crystal Growth, Crystallization and Phases in Biologic, Organic and Inorganic Systems", the first being filed on Mar. 21, 2002, and the second being filed on Aug. 13, 2002.

The subject matter of each of the aforementioned Patent Applications is herein expressly incorporated by reference.

BACKGROUND OF THE INVENTION

Electrochemistry can be summarized as two simple and mirrored concepts: (1) the passage of an electrical current to cause chemical transformation of matter; and (2) the chemical transformation of matter to cause the passage of an electrical current.

Electrochemistry involves numerous oxidation and reduction reactions at or near anodes, cathodes and electrolytes in various electrochemical and electrolytic cells. The specific reactions can occur by applying a current to various chemical reactants contained in a system to achieve a desired chemical species (e.g., electrolysis) or conversely, chemical reactions can result in the production of electricity (e.g., electrochemical reactions). In certain systems both electrolytic and electrochemical reactions occur (e.g., rechargeable cells or rechargeable batteries). Oxidation reactions are those reactions which lose electrons, whereas reduction reactions are those reactions which gain electrons. Oxidation and reduction reactions occur in many chemical systems. For example, the rusting of metals, photosynthesis in the leaves of green plants, the conversion of foods to energy in the body, the generation of current from batteries and fuel cells, etc., are all examples of chemical changes that involve the transfer of electrons from one chemical species to another. When such reactions result in electrons flowing through a wire or when the flow of electrons causes a particular reduction reaction to occur, the processes are generally referred to as electrochemical reactions. Whereas the study and/or application of these electrochemical reactions is often referred to as electrochemistry.

The applications of electrochemistry are widespread, as discussed above. Additionally, electrical measurements are used to monitor chemical reactions in a wide variety of reactions, including those reactions occurring in an element as small as a living cell. Further, numerous important chemicals are manufactured by electrochemical means. In addition, electrochemistry is used to form a variety of important metals (e.g., aluminum and magnesium). Still further, electrochemistry is used in corrosion protection, brine electrolysis, electrocrystallization, electroforming, electrolyte pickling, electrometallurgy, electroplating, electrorefining, electrowinning, galvanizing, photoelectrochemistry; photoelectrosynthesis and sonoelectrochemistry.

Many reactions that occur in the aforementioned systems appear to involve a shifting of electron density from one atom to another. Collectively, this shifting of electron density is referred to as oxidation/reduction reactions or more simply, redox reactions. The term "oxidation" refers to the loss of electrons by one reactant and the term "reduction" refers to the gain of electrons by another. Oxidation and reduction typically occur together. In particular, if one substance is oxidized, another substance is typically reduced. Otherwise, electrons would be a product of a reaction, and this has not been observed in these reactions. During a redox reaction the substance that accepts the electrons that another substance loses is known as an "oxidizing agent", because it helps something else to be oxidized. Moreover, the substance that supplies electrons is termed the "reducing agent" because it helps something else to be reduced.

The various reactions that occur in the aforementioned electrochemical systems are driven by energy. The energy comes primarily in two different forms: chemical and electrical. There are many other forms of energy that drive chemical transformation, however, including thermal, mechanical, acoustic, and electromagnetic. Various features of each type of energy are thought to contribute in different ways to the driving of chemical reactions. Irrespective of the type of energy involved, chemical reactions and transformations are undeniably and inextricably intertwined with the transfer and combination of energy. An understanding of energy is, therefore, vital to an understanding of chemical reactions, including electrochemical reactions.

A chemical reaction can be controlled and/or directed either by the addition of energy to the reaction medium in the form of thermal, mechanical, acoustic, electrical, magnetic, and/or electromagnetic energy or by means of transferring energy through a physical catalyst. These methods are traditionally not that energy efficient and can produce, for example, either unwanted by-products, decomposition of required transients, and/or intermediates and/or activated complexes and/or insufficient quantities of preferred products of a reaction.

It has been generally believed that chemical reactions occur as a result of collisions between reacting molecules. In terms of the collision theory of chemical kinetics, it has been expected that the rate of a reaction is directly proportional to the number of the molecular collisions per second:

$$\text{rate } \alpha \text{ number of collisions/sec}$$

This simple relationship has been used to explain the dependence of reaction rates on concentration. Additionally, with few exceptions, reaction rates have been believed to increase with increasing temperature because of increased collisions.

The dependence of the rate constant k of a reaction can be expressed by the following equation, known as the Arrhenius equation:

$$k = Ae^{-Ea/RT}$$

where $E_\alpha$ is the activation energy of the reaction which is the minimum amount of energy required to initiate a chemical reaction, R is the gas constant, T is the absolute temperature and e is the base of the natural logarithm scale. The quantity A represents the collision rate and shows that the rate constant is directly proportional to A and, therefore, to the collision rate. Furthermore, because of the minus sign associated with the exponent $E_\alpha/RT$, the rate constant decreases with increasing activation energy and increases with increasing temperature.

Normally, only a small fraction of the colliding molecules, typically the fastest-moving ones, have enough kinetic energy to exceed the activation energy, therefore, the increase in the rate constant k has been explained with the temperature increase. Since more high-energy molecules are present at a higher temperature, the rate of product formation is also greater at the higher temperature. But, with increased temperatures there are a number of problems which can be introduced into the cell reaction system. With thermal excitation other competing processes, such as bond rupture, may occur before the desired energy state can be reached. Also, there are a number of decomposition products which often produce fragments that are extremely reactive, but they can be so short-lived because of their thermodynamic instability, that a preferred reaction may be dampened.

In electrochemical reactions, it is generally believed that chemical transformations occur as the result of the passage of an electrical current, or conversely that a chemical reaction produces an electrical current. In this regard, electrochemistry involves the science of ionically conducting solutions, as well as the science of electrically charged interfaces. There are four important aspects of ionically conducting solutions: (1) ion interactions with the solvent; (2) ion interactions with other ions (either of the same or different species); (3) movement of ions in solutions; and (4) ionic liquids or "pure electrolytes"

Electrodics, the same science of electrically charged interfaces, involves the transfer of charge across solid-solution interfaces and interfacial regions. Electrodics thus involves the transfer of electrical charge between two phases of matter. These phases can exist on surfaces of materials not customarily thought of as solid-solution interfaces. Corrosion is a good example of this, wherein a material is covered by a thick invisible film of moisture. Atoms on the surface of the material leave the material and dissolve into the ion-containing film of moisture. Thus, in electrochemistry, the familiar kinetic catalysts of chemical reactions by molecules and atoms colliding with each other is replaced by species colliding with electrodes. In this regard, the electrodes can be thought of as separate "charge-transfer catalysts".

Radiant or light energy is another form of energy that may be added to the reaction medium that also may have negative side effects but which may be different from (or the same as) those side effects from thermal energy. Addition of radiant energy to a system produces electronically excited molecules that are capable of undergoing chemical reactions.

A molecule in which all the electrons are in stable orbitals is said to be in the ground electronic state. These orbitals may be either bonding or non-bonding. If a photon of the proper energy collides with the molecule the photon may be absorbed and one of the electrons may be promoted to an unoccupied orbital of higher energy. Electronic excitation results in spatial redistribution of the valence electrons with concomitant changes in internuclear configurations. Since chemical reactions are controlled to a great extent by these factors, an electronically excited molecule undergoes a chemical reaction that may be distinctly different from those of its ground-state counterpart.

The energy of a photon is defined in terms of its frequency or wavelength, $$E = h\nu = hc/\lambda$$

where E is energy; h is Plank's constant, $6.6 \times 10^{-34}$ J·sec; $\nu$ is the frequency of the radiation, $\text{sec}^{-1}$; c is the speed of light; and $\lambda$ is the wavelength of the radiation. When a photon is absorbed, all of its energy is typically imparted to the absorbing species. The primary act following absorption depends on the wavelength of the incident light. Photochemistry studies photons whose energies lie in the ultraviolet region (e.g., 100 Å-4000 Å) and in the visible region (e.g., 4000 Å-7000 Å) of the electromagnetic spectrum. Such photons are primarily a cause of electronically excited molecules.

Since the molecules are imbued with electronic energy upon absorption of light, reactions occur from different potential-energy surfaces from those encountered in thermally excited systems. However, there are several drawbacks of using the known techniques of photochemistry, that being, utilizing a broad band of frequencies thereby causing unwanted side reactions, undue experimentation, and poor quantum yield. Some good examples of photochemistry are shown in the following patents.

In particular, U.S. Pat. No. 5,174,877 issued to Cooper, et al. al., (1992) discloses an apparatus for the photocatalytic treatment of liquids. In particular, it is disclosed that ultraviolet light irradiates the surface of a prepared slurry to activate the photocatalytic properties of the particles contained in the slurry. The transparency of the slurry affects, for example, absorption of radiation. Moreover, discussions of different frequencies suitable for achieving desirable photocatalytic activity are disclosed.

Further, U.S. Pat. No. 4,755,269 issued to Brumer, et al. al., (1998) discloses a photodisassociation process for disassociating various molecules in a known energy level. In particular, it is disclosed that different disassociation pathways are possible and the different pathways can be followed due to selecting different frequencies of certain electromagnetic radiation. It is further disclosed that the amplitude of electromagnetic radiation applied corresponds to amounts of product produced.

Selective excitation of different species is shown in the following three (3) patents. Specifically, U.S. Pat. No. 4,012,301 to Rich, et al. al., (1977) discloses vapor phase chemical reactions that are selectively excited by using vibrational modes corresponding to the continuously flowing reactant species. Particularly, a continuous wave laser emits radiation that is absorbed by the vibrational mode of the reactant species.

U.S. Pat. No. 5,215,634 issued to Wan, et al., (1993) discloses a process of selectively converting methane to a desired oxygenate. In particular, methane is irradiated in the presence of a catalyst with pulsed microwave radiation to convert reactants to desirable products. The physical catalyst disclosed comprises nickel and the microwave radiation is applied in the range of about 1.5 to 3.0 GHz.

U.S. Pat. No. 5,015,349 issued to Suib, et al. al., (1991) discloses a method for cracking a hydrocarbon to create cracked reaction products. It is disclosed that a stream of hydrocarbon is exposed to a microwave energy which creates a low power density microwave discharge plasma, wherein the microwave energy is adjusted to achieve desired results. A particular frequency desired of microwave energy is disclosed as being 2.45 GHz.

Photoelectrochemistry has focussed on three main areas. In the first, light is shone on a metal electrode, but metals absorb broadband light very poorly and so this method is not greatly effective. The second area of photoelectric chemistry involves the passage of electrons in a solution by absorption of light by photoactive species resulting in electron generation. Again, these techniques use broadband methods and have drawbacks. The third area of photoelectricalchemistry considered by many to be the most promising involves the absorption of light by semiconductors in cell reaction systems, elevating electrons from valence bands to conduction bands. The semiconductors in electrodes function as photo-induced charge transfer catalysts.

Physical catalysts are well known in the art. Specifically, a physical catalyst is a substance which alters the reaction rate of a chemical reaction without appearing in the end product. It is known that some reactions can be speeded up or controlled by the presence of substances which themselves appear to remain unchanged after the reaction has ended. By increasing the velocity of a desired reaction relative to unwanted reactions, the formation of a desired product can be maximized compared with unwanted by-products. Often only a trace of physical catalyst is necessary to accelerate the reaction. Also, it has been observed that some substances, which if added in trace amounts, can slow down the rate of a reaction. This looks like the reverse of catalysis, and, in fact, substances which slow down a reaction rate have been called negative catalysts or poisons. Known physical catalysts go through a cycle in which they are used and regenerated so that they can be used again and again. A physical catalyst operates by providing another path for the reaction which can have a higher reaction rate or slower rate than available in the absence of the physical catalyst. At the end of the reaction, because the physical catalyst can be recovered, it appears the physical catalyst is not involved in the reaction. But, the physical catalyst must somehow take part in the reaction, or else the rate of the reaction would not change. The catalytic act has historically been represented by five essential steps originally postulated by Ostwald around the late 1800's:

1. Diffusion to the catalytic site (reactant);
2. Bond formation at the catalytic site (reactant);
3. Reaction of the catalyst-reactant complex;
4. Bond rupture at the catalytic site (product); and
5. Diffusion away from the catalytic site (product).

The exact mechanisms of catalytic actions are unknown in the art but it is known that physical catalysts can speed up a reaction that otherwise would take place too slowly to be practical.

There are a number of problems involved with known industrial catalysts: firstly, physical catalysts can not only lose their efficiency but also their selectivity, which can occur due to, for example, overheating or contamination of the catalyst; secondly, many physical catalysts include costly metals such as platinum or silver and have only a limited life span, some are difficult to rejuvenate, and the precious metals may not be easily reclaimed. There are numerous physical limitations associated with physical catalysts which render them less than ideal participants in many reactions.

Accordingly, what is needed is an understanding of the catalytic process so that biological processing, chemical processing, industrial processing, etc., can be engineered by more precisely controlling the multitude of reaction processes that currently exist, as well as developing completely new reaction pathways and/or reaction products. Examples of such understandings include methods to catalyze reactions without the drawbacks of: (1) known physical catalysts; and (2) utilizing energy with much greater specificity than the prior art teachings which utilize less than ideal thermal and electromagnetic radiation methods and which result in numerous inefficiencies.

Accordingly, what is also needed are techniques for electrochemistry which improve the functioning of electrodes as charge-transfer catalysts. Further, improvements are required in the transport of ions and charges through electrolyte solutions. Passage of electrons through metals and semiconductors is not rate-limiting, rather it is the passage of ions and charged species through solutions that is slow.

DEFINITIONS

For the purposes of this invention, the terms and expressions below, appearing in the Specification and claims, are intended to have the following meanings:

"Activated complex", as used herein, means the assembly of atom(s) (charged or neutral) which corresponds to the maximum in the reaction profile describing the transformation of reactant(s) into reaction product(s). Either the reactant or reaction product in this definition could be an intermediate in an overall transformation involving more than one step.

"Alkaline battery" or "alkaline cell", as used herein, means a cell which utilizes an aqueous solution of alkaline potassium hydroxide as the electrolyte. One electrode comprises zinc and the other electrode comprises manganese dioxide. In batteries, the zinc is typically present as a high surface area powder and the electrolyte is typically gelled. The typical half-reactions are:

$$Zn+2OH^-=Zn(OH)_2+2e^-; \text{ and}$$

$$2MnO_2+H_2O+2e^-=Mn_3O_2+2OH^-$$

"Anode", as used herein, means the electrode where oxidation occurs in an electrochemical cell. It is the positive electrode in an electrolytic cell, while it is the negative electrode in a galvanic cell.

"Anode effect", as used herein, means a particular condition in an electrolytic cell that produces a quick increase in cell voltage and a corresponding decrease in current flow. This effect is usually caused by the temporary formation of an insulating layer on the anode surface. It occurs almost exclusively in molten salt electrolysis (e.g., aluminum production).

"Anodic protection" or "corrosion protection", as used herein, means a process for corrosion protection of a metal or an alloy achieved by causing an anodic current of appropriate magnitude to form a passive film on the material used as the anode in an electrolytic cell. Anodic protection is utilized for metals such as stainless steel and titanium.

"Anodizing", as used herein means, the process of producing an oxide film or coating on metals or alloys by the process of electrolysis. The metal which is coated functions as an anode in an electrolytic cell and the surface of the anode (i.e., metal) is electrochemically oxidized. Anodization improves certain properties including, for example, corrosion resistance, abrasion resistance, and hardness.

"Applied spectral energy conditioning pattern", as used herein, means the totality of: (a) all spectral energy conditioning patterns that are externally applied to a conditionable participant; and/or (b) spectral conditioning environmental reaction conditions that are used to condition one or more conditionable participants to form a conditioned participant in a conditioning reaction system.

"Applied spectral energy pattern", as used herein, means the totality of: (a) all spectral energy patterns that are externally applied; and/or (b) spectral environmental reaction conditions input into a cell reaction system.

"Backing layers", as used herein, means a portion of some fuel cells which is/are located adjacent to each electrode that provide for partial support of such electrode(s) and for diffusion (e.g., interconnected porosity may be provided) of, for example, reactants toward an electrode and/or reaction products away from an electrode.

"Battery", as used herein, means a device which stores an electrical energy using electrochemical cells. Chemical reactions occur spontaneously at the electrodes when the electrodes are connected by an external circuit producing an electric current. Batteries are typically comprised of several, internally connected, electrochemical cells (i.e., batteries often contain several cells). However, the term "battery" and "cell" are often interchangeably used.

"Bioelectrochemistry", as used herein, means the electrochemical reactions that occur in biological systems and/or biological compounds.

"Bi-polar electrode", as used herein, means an electrode that is shared by two-series coupled electrochemical cells such that one side of the electrode acts as an anode in a first cell and the other side of the electrode acts as a cathode in an adjacent cell. These electrodes are often used in storage batteries and fuel cell stacks that connect many cells internally.

"Brine electrolysis", as used herein, means electrolysis of an aqueous solution of sodium chloride, also known as "brine", which results in the production of chlorine gas at the anode and hydrogen gas at the cathode. The overall cell reaction is:

$$2NaCl+2H_2O=Cl_2+H_2+2NaOH.$$

"Capacitance", as used herein, means the ability of a capacitor to store electrical charge. The unit of capacitance is the Farad.

"Capacitive current" or "current density", as used herein, means the current, or current density flowing through an electrochemical cell that is charging/discharging an electrical double-layer capacitance. This current does not involve chemical reactions, rather, the current results in accumulation (or removal) of electrical charges on the electrode and in the electrolyte solution near the electrode.

"Capacitor" or "capacitor cells", as used herein, means an electrical device which stores electricity or electrical energy. It includes three essential parts, two electrodes, (e.g., metal plates) which are physically separated from each other and are, typically, substantially parallel to each; and located therebetween is a third part known as a dielectric. The electrodes are charged with a substantially equal amount of positive and negative electrical charges, respectively. Capacitors result in a physical storage of electricity rather than a chemical storage of electricity.

"Catalytic spectral conditioning pattern", as here herein, means at least a portion of a spectral conditioning pattern of a physical catalyst which when applied to a conditionable participant can condition the conditionable participant to catalyze and/or assist in catalyzing the cell reaction system by the following:

completely replacing a physical chemical catalyst;
  acting in unison with a physical chemical catalyst to increase the rate of reaction;
  reducing the rate of reaction by acting as a negative catalyst; or
  altering the reaction pathway for formation of a specific reaction product.

"Catalytic spectral energy conditioning pattern", as used herein, means at least a portion of a spectral energy conditioning pattern which when applied to a conditionable participant in the form of a beam or field can condition the conditionable participant to form a conditioned participant having a spectral energy pattern corresponding to at least a portion of a spectral pattern of a physical catalyst which catalyzes and/or assists in catalyzing the cell reaction system when the conditioned participant is placed into, or becomes involved with, the cell reaction system.

"Catalytic spectral energy pattern", as used herein, means at least a portion of a spectral energy pattern of a physical catalyst which when applied to a cell reaction system in the form of a beam or field can catalyze a particular reaction in the cell reaction system.

"Catalytic spectral pattern", as used herein, means at least a portion of a spectral pattern of a physical catalyst which when applied to a cell reaction system can catalyze a particular reaction by the following:

a) completely replacing a physical chemical catalyst;
  b) acting in unison with a physical chemical catalyst to increase the rate of reaction;
  c) reducing the rate of reaction by acting as a negative catalyst; or
  d) altering the reaction pathway for formation of a specific reaction product.

"Cell", as used herein, means a fundamental unit comprising at least two material(s) functioning as electrodes and at least one substance or material (e.g., at least a portion of which is an electrolyte or a dielectric) located between the electrodes. These fundamental units can be organic, biologic and/or inorganic.

"Cell reaction system", as used herein, means all the constituents in a cell (e.g., galvanic cell, battery, fuel cell, electrochemical cell, electrolytic cell, photoelectrochemical cell, photogalvanic cell, photoelectrolytic cell, capacitor, electrochemical processes, etc.), including, but not limited to, reactants, intermediates, transients, activated complexes, physical catalysts, poisons, promoters, solvents, physical catalyst support materials, spectral catalysts, spectral energy catalysts, reaction products, environmental reaction conditions, spectral environmental reaction conditions, applied spectral energy pattern, reaction vessels, containers, electrolytes, electrodes, backing layers, flow fields, housings, etc., that are involved in any reaction pathway.

"Concentration", as used herein, means a measure of the amount of a dissolved material (i.e., solute) in a solution.

"Concentration cell", as used herein, means a galvanic cell in which the chemical energy converted into electrical energy comes from a concentration difference of a species at the two electrodes in the cell.

"Condition" or "conditioning", as used herein, means the application or exposure of a conditioning energy or combination of conditioning energies to at least one conditionable participant prior to the conditionable participant becoming involved (e.g., being placed into a cell reaction system and/or prior to being activated) in the cell reaction system.

"Conditionable participant", as used herein, means reactant, physical catalyst, solvent, physical catalyst support material, reaction vessel, conditioning reaction vessel, promoter and/or poison comprised of molecules, macromolecules, ions and/or atoms (or components thereof) in any form of matter (e.g., solid, liquid, gas, plasma) that can be conditioned by an applied spectral energy conditioning pattern.

"Conditioned participant", as used herein, means reactant, physical catalyst, solvent, physical catalyst support material, reaction vessel, conditioning reaction vessel, physical promoter and/or poison comprised of molecules, ions and/or atoms (or components thereof) in any form of matter (e.g., solid, liquid, gas, plasma) that has been conditioned by an applied spectral energy conditioning pattern.

"Conditioning energy", as used herein means at least one of the following spectral energy conditioning providers: spectral energy conditioning catalyst; spectral conditioning catalyst; spectral energy conditioning pattern; spectral conditioning pattern; catalytic spectral energy conditioning pattern; catalytic spectral conditioning pattern; applied spectral energy conditioning pattern and spectral conditioning environmental reaction conditions.

"Conditioning environmental reaction condition", as used herein, means and includes traditional reaction variables such as temperature, pressure, surface area of catalysts, physical catalyst size and shape, concentrations, electromagnetic radiation, electric fields, magnetic fields, mechanical forces, acoustic fields, reaction vessel size, shape and composition and combinations thereof, etc., which may be present and are capable of influencing, positively or negatively, the conditioning of at least one conditionable participant.

"Conditioning reaction system", as used herein, means the combination of reactants, physical catalysts, poisons, promoters, solvents, physical catalyst support materials, conditioning reaction vessel, reaction vessel, spectral conditioning catalysts, spectral energy conditioning catalysts, conditioned participants, environmental conditioning reaction conditions, spectral environmental conditioning reaction conditions, applied spectral energy conditioning pattern, etc., that are involved in any reaction pathway to form a conditioned participant.

"Conditioning reaction vessel", as used herein, means the physical vessel(s) or containment system(s) which contains or houses all components of the conditioning reaction system, including any physical structure or media which are contained within the vessel or system.

"Conditioning targeting", as used herein, means the application of conditioning energy to a conditionable participant to condition the conditionable participant prior to the conditionable participant being involved, and/or activated, in a holoreaction system, said conditioning energy being provided by at least one of the following spectral energy conditioning providers: spectral energy conditioning catalyst; spectral conditioning catalyst; spectral energy conditioning pattern; spectral conditioning pattern; catalytic spectral energy conditioning pattern; catalytic spectral conditioning pattern; applied spectral energy conditioning pattern; and spectral environmental conditioning reaction conditions, to achieve (1) direct resonance; and/or (2) harmonic resonance; and/or (3) non-harmonic heterodyne-resonance with at least a portion of at least one of the following conditionable participants: reactants; physical catalysts; promoters; poisons; solvents; physical catalyst support materials; reaction vessels; conditioning reaction vessels; conditioning reaction vessels and/or mixtures or components thereof (in any form of matter), said spectral energy conditioning provider providing conditioning energy to condition at least one conditionable participant by interacting with at least one frequency thereof, to form at least one conditioned participant which assists in producing at least one desired reaction product and/or at least one desired reaction product at a desired reaction rate, when the conditioned participant becomes involved with, and/or activated in, a reaction system.

"Corrosion", as used herein, means chemical processes, as well as electrochemical processes, that destroy structural materials. Typically, it refers to corrosions of metals, but other materials (e.g., plastics or semiconductors) also exhibit corrosion. Metallic corrosion is most always an electrochemical process when the metal is immersed in a solution. However, certain atmospheric conditions which result in, for example, thin-films of moisture often result in similar electrochemical processes occurring on at least a portion of a metal. Metal in the corrosive solution functions as a short-circuited galvanic cell. In particular, a first portion of a surface of the metal acts as an anode and another portion acts as a cathode. Oxidation occurs at the anodic areas, whereas at the cathodic areas dissolved oxygen is reduced. Accordingly, the spontaneous complimentary redox reaction of rusting causes electrical current to be flowing into/from two different parts in a metal.

"Current", as used herein, means the movement of electrical charges in a conductor (e.g., electrons moving in an electronic conductor and ions moving in an ionic conductor). Electrochemistry uses almost exclusively direct current. Accordingly, unless mentioned in context of the disclosure herein, the use of the term "current" is typically in connection with direct currents. The typical unit of a current is an ampere.

"Current collector", as used herein, means a plate or device which can conduct electrons produced by, for example, an oxidation reaction at an anode. These devices are typically plates that also may incorporate a flow field and are thus made from materials that are typically relatively impervious to reactants and/or reaction products under the process conditions of the cell reaction system.

"Cycle life", as used herein, means the number of times a rechargeable battery can be cycled (i.e., charged and discharged) before the battery or cell loses its ability to accept charge.

"Dielectric", as used herein, means a material present between electrodes in a capacitor.

"Dielectric constant", as used herein, means the relative permittivity of a material compared to the permittivity of a vacuum. Different materials have different dielectric constants which are determined by the following equation:

$$E_{actual} = E_r E_o,$$

where $E_{actual}$ is the actual permittivity; $E_r$ is the dielectric constant and $E_o$ is the permittivity of a vacuum.

"Diffusion layer", as used herein, means a thin-liquid boundary layer at the surface of an electrode that is immobile. This immobile layer is part of a model which is often referred to as the "Nernstian Hypothesis". In this approach, the electrolyte solution is divided into three distinct parts, the bulk solution and two diffusion layers located at or near the surfaces of the electrodes. The bulk solution is assumed to be homogenous. Thus, mass transport occurs primarily through convection. However, in the diffusion layers, mass transport occurs primarily through diffusion. Charge transport occurs by an electric migration approach everywhere within a cell. However, the thickness of the diffusion layer typically varies between about 0.01 cm to about 0.0001 cm. Diffusion layers can affect the functioning of cells.

"Direct resonance conditioning targeting", as used herein, means the application of conditioning energy to a conditionable participant to condition the conditionable participant prior to the conditionable participant being involved, and/or activated, in a cell reaction system, said conditioning energy being provided by at least one of the following spectral energy conditioning providers: spectral energy conditioning catalyst; spectral conditioning catalyst; spectral energy conditioning pattern; spectral conditioning pattern; catalytic spectral energy conditioning pattern; catalytic spectral conditioning pattern; applied spectral energy conditioning pattern and spectral conditioning environmental reaction conditions, to achieve direct resonance with at least a portion of at least one conditionable participant (e.g.; reactants; physical catalysts; promoters; poisons; solvents; physical catalyst support materials; reaction vessels; conditioning reaction vessels and/or mixtures or components thereof in any form of matter), said spectral energy conditioning providers providing conditioning energy to condition at least one conditionable participant(s) by interacting with at least one frequency thereof to form at least one conditioned participant, which assists in producing at least one desired reaction product and/or at least one desired reaction product at a desired reaction rate, when the conditioned participant becomes involved with, and/or activated in, a cell reaction system.

"Direct resonance targeting", as used herein, means the application of energy to a cell reaction system by at least one of the following spectral energy providers: spectral energy catalyst; spectral catalyst; spectral energy pattern; spectral pattern; catalytic spectral energy pattern; catalytic spectral pattern; applied spectral energy pattern and spectral environmental reaction conditions, to achieve direct resonance with at least one of the following forms of matter: reactants; transients; intermediates; activated complexes; physical catalysts; reaction products; promoters; poisons; solvents; physical catalyst support materials; reaction vessels; and/or mixtures or components thereof, said spectral energy providers providing energy to at least one of said forms of matter by interacting with at least one frequency thereof, to produce at least one desired reaction product and/or at least one desired reaction product at a desired reaction rate.

"Dry cell", as used herein, means a non-rechargeable battery wherein the electrolyte is immobilized by a gelling agent. The whole cell is typically sealed.

"Electrical double layer", as used herein, means the structure of charge accumulation and charge separation that occurs at the interface between an electrode and an electrolyte when an electrode is, for example, immersed in an electrolyte solution.

"Electrical potential", as used herein, means the difference in potential between two points in a circuit.

"Electrical power", as used herein, means the rate at which an electrical source can supply electrical energy. Electrical power is often expressed in the units of watts. Watts relate to the rate at which energy can be delivered.

"Electroacoustics or "electroacoustic effect", as used herein, means electrokinetic effects arising when sound waves cause certain oscillations of one or more parts in a cell.

"Electroanalytical chemistry", as used herein, means the application of electrochemical cells and electrochemical techniques for electrochemical analysis. The material to be analyzed is dissolved in the electrolyte of a cell.

"Electrochemical cell", as used herein, means a device that converts chemical energy into electrical energy. It includes two electrodes which are separated by an electrolyte. The electrodes may comprise any electrically conducting material (e.g., solid or liquid metals, semiconductors, etc.) which can communicate with each other through an electrolyte. These cells experience separate oxidation and reduction reactions at each electrode.

"Electrocrystallization", as used herein, means an electroplating technique that results in a crystalline metal deposit on one electrode (e.g., typically the cathode in an electrolytic cell).

"Electrode", as used herein, means one of the two electronically conducting parts in an electrochemical cell, galvanic cell, electrolytic cell and/or capacitor, through which electrons are transported and/or exchanged with chemical reactants in a cell.

"Electroforming", as used herein, means a process to produce metallic objects by an electroplating technique. The metal is deposited onto a forming object (e.g., mandrel) of suitable shape and to a desired thickness, followed by the removal of the forming object to result in a freestanding metal object.

"Electrokinetic effects" or "electrokinetics", as used herein, means a process that arises due to a charge separation caused by the relative motion of a solid and liquid phase. A portion of the so-called "Gouy-Chapman diffuse layer" is sheared as the two phases move relative to each other, resulting in a charge separation.

"Electrolysis", as used herein, means a process that decomposes a chemical compound into its constituent elements and/or a process which produces a new compound by the action of an electrical current. Redox reactions typically occur at the electrode (e.g., water is decomposed to hydrogen and oxygen by this process).

"Electrolyte", as used herein, means a substance located between at least a portion of an anode and a cathode and which is composed of at least some positive and negative ions and which is capable of transporting at least one ionic species therethrough.

"Electrolytic capacitor", as used herein, means a storage device similar to other types of electrical capacitors, however, one of the conducting phases in this material is a metallic plate, and the other conducting phase is an electrolyte solution. The dielectric is typically a thin oxide film on the surface of the metal (e.g., aluminum or tantalum) that comprises one conducting phase of the capacitor.

"Electrolytic cell", as used herein, means an electrochemical cell that converts electrical energy into chemical energy. The chemical reactions typically do not occur spontaneously at the electrodes when the electrodes are connected through an external circuit. The chemical reaction is typically forced by applying an external electric current to the electrodes. This cell is used to store electrical energy in chemical form such as in, for example, a secondary or rechargeable battery. The process of water being decomposed into hydrogen gas and oxygen is termed electrolysis and such electrolysis is performed in an electrolytic cell.

"Electrolytic pickling", as used herein, means a process for removing oxide scales from metal surfaces in preparation for electroplating. The metal for which oxide scales are to be removed from is the cathode in an electrolytic cell and the electrolyte contains a strong acidic solution that dissolves oxide scales.

"Electrometallurgy", as used herein, means a branch of metallurgy which utilizes electrochemical processes known as electrowinning.

"Electromigration", as used herein, means the movement of ions under the influence of electrical potential difference.

"Electrophoresis", as used herein, means the movement of small-suspended particles or large molecules in a liquid, such movement being driven by an electrical potential difference.

"Electroplating", as used herein, means a process that produces a thin, metallic coating on the surface of another material (e.g., a metal or another electrically conducting material such as graphite). The substrate to be coated is situated to be the cathode in an electrolytic cell, where the cations of the electrolyte becomes the positive ions of the metal to be coated on the surface of the cathode. When a current is applied, the electrode reaction occurring on the cathode is a reduction reaction causing the metal ions to become metal on the surface of the cathode.

"Electrorefining", as used herein, means a process that produces a purified metal from a less pure metal. The metal to be purified is situated to be the anode in an electrolytic cell and the anode is dissolved by the application of a current into a usually acidic aqueous electrolyte or a molten salt solution. At the same time, the pure metal is electroplated on the cathode. Examples of electrorefining include copper that is electrorefined in aqueous solutions; and aluminum that is electrorefined using a molten salt electrolyte.

"Electrowinning", as used herein, means an electrochemical process that produces metals from their ores. In particular, metal oxides typically occur in nature and electrochemical reduction is one of the most economic methods for producing metals from these ores. In particular, the ore is dissolved in an acidic aqueous solution or molten salt and the resulting electrolyte solution is electrolyzed. The metal is electroplated on the cathode (e.g., either in a solid or liquid form) while oxygen is involved in the reaction at the anode. Copper, zinc, aluminum, magnesium and sodium are manufactured by this technique.

"Energy density", as used herein, means the amount of electrical energy stored per unit weight or volume in a cell or battery.

"Energy efficiency", as used herein, in reference to a rechargeable battery is expressed as a percentage of charge that is recoverable during discharging.

"Environmental reaction condition", as used herein, means and includes traditional reaction variables such as temperature, pressure, surface area of catalysts, physical catalyst size and shape, concentrations, electromagnetic radiation, electric fields, magnetic fields, mechanical forces, acoustic fields, reaction vessel size, shape and composition and combinations thereof, etc., which may be present and are capable of influencing, positively or negatively, reaction pathways in a cell reaction system.

"Faraday's laws", as used herein, means: (1) in any electrolytic process the amount of chemical change produced is proportional to the total amount of electrical charge passed through the cell; and (2) the mass of the chemicals changed is proportional to the equivalent weight of the chemicals involved. The proportionality constant is referred to as the "Faraday Number".

"Flow fields", as used herein, are present in some cells (e.g., fuel cells) and are typically, located adjacent to backing plates. Flow field plates or devices often serve a dual function as current collectors. The flow fields are typically plates made of lightweight but strong and gas-impermeable electron-conducting materials. Typical materials include graphites or metals. These plates are typically located adjacent to backing layers and include at least one channel which is utilized to carry, for example, reactant gases to an active area of a membrane/electrode assembly. These plates also conduct electrons produced by oxidation of the anode.

"Frequency", as used herein, means the number of times which a physical event (e.g., wave, field and/or motion) varies from the equilibrium value through a complete cycle in a unit of time (e.g., one second; and one cycle/sec=1 Hz). The variation from equilibrium can be positive and/or negative, and can be, for example, symmetrical, asymmetrical and/or proportional with regard to the equilibrium value.

"Fuel cell", as used herein, means an electrochemical device that continuously converts the chemical energy of at least one externally supplied fuel and at least one oxidant directly to electrical energy.

"Galvanic cell", as used herein, means an electrochemical cell that converts chemical energy into electrical energy. Chemical reactions, in this cell occur spontaneously at the electrodes when the electrodes are connected by an external circuit, producing an electrical current. Examples of these cells include fuel cells and batteries.

"Galvanizing", as used herein, means a process for coating iron or steel with a thin layer of zinc for corrosion protection. Galvanizing is performed electrochemically by an electroplating process or by a hot-dip galvanizing process which consists of immersing the metal into a molten zinc.

"Gas electrode", as used herein, means any electrode in gaseous phase.

"Harmonic conditioning targeting", as used herein, means the application of conditioning energy to a conditionable participant to condition the conditionable participant prior to the conditionable participant becoming involved, and/or activated, in a cell reaction system, said conditioning energy being provided by at least one of the following spectral energy conditioning providers: spectral energy conditioning catalyst; spectral conditioning catalyst; spectral energy conditioning pattern; spectral conditioning pattern; catalytic spectral energy conditioning pattern; catalytic spectral conditioning pattern; applied spectral energy conditioning pattern and spectral conditioning environmental reaction conditions, to achieve harmonic resonance with at least a portion of at least one conditionable participant (e.g.; reactants; physical catalysts; promoters, poisons; solvents; physical catalyst support materials; reaction vessels; conditioning reaction vessels; and/or mixtures or components thereof in any form of matter), said spectral energy conditioning provider providing conditioning energy to condition at least one conditionable participant(s) by interacting with at least one frequency thereof, to form at least one conditioned participant which assists in producing at least one desired reaction product and/or at least one desired reaction product at a desired reaction rate when the conditioned participant becomes involved with, and/or activated in, a cell reaction system.

"Harmonic targeting", as used herein, means the application of energy to a cell reaction system by at least one of the following spectral energy providers: spectral energy catalyst; spectral catalyst; spectral energy pattern; spectral pattern; catalytic spectral energy pattern; catalytic spectral pattern; applied spectral energy pattern and spectral environmental reaction conditions, to achieve harmonic resonance with at least one of the following forms of matter: reactants; transients; intermediates; activated complexes; physical catalysts; reaction products; promoters; poisons; solvents; physical catalyst support materials; reaction vessels; and/or mixtures or components thereof, said spectral energy providers providing energy to at least one of said forms of matter by interacting with at least one frequency thereof, to produce at least one desired reaction product and/or at least one desired reaction product at a desired reaction rate.

"Holoreaction system", as used herein, means all components of the cell reaction system and the conditioning reaction system.

"Hydrolysis", as used herein, means a chemical reaction in which water reacts with another substance and causes decomposition of other products, often including the reaction of water with a salt to create an acid or a base.

"Indirect electrolysis", as used herein, means the production of chemicals in an electrolytic cell through intermediate electrolysis products. In particular, an intermediate oxidizing/reducing agent is produced at an electrode surface and the produced material can react with another material in the bulk solution.

"Intermediate", as used herein, means a molecule, ion and/or atom which is present between a reactant and a reaction product in a reaction pathway or reaction profile. It corresponds to a minimum in the reaction profile of the reaction between reactant and reaction product. A reaction which involves an intermediate is typically a stepwise reaction.

"Ion-exchange membrane", as used herein, means a sheet formed from an ion exchange resin. These membranes typically allow only either positive ions (i.e., cation-exchange membranes) or negative ions (i.e., anion-exchange membranes) to be transmitted.

"Ion-exchange resin", as used herein, means a polymeric resin that contains electrically charged fragments (i.e., fixed ions) permanently attached to the polymer backbone; and wherein electrical neutrality is achieved by attached mobile "counter-ions" in the solution phase into which the resin is immersed.

"Laclanch-type cell", as used herein, means a cell which utilizes a zinc anode and a manganese dioxide cathode with ammonium chloride or zinc chloride solution as an electrolyte. The electrolyte may be immobilized permitting the cell to be a dry cell. The overall cell reaction is:

$$Zn+2MnO_2+2H_2O+ZnCl_2=2MnOOH+2\ Zn(OH)Cl.$$

"Lead-acid cell" or "Pb/acid battery", as used herein, means a cell or battery which utilizes a rechargeable acidic electrolyte and electrodes of lead and lead-oxide. The cathode is typically lead-oxide, the anode is typically lead and the electrolyte is typically sulfuric acid. The typical half-reactions are:

$$Pb+SO_4^{2-}=PbSO_4^{2-}(sol)+2e^-;\ and$$

$$PbO_2+4E^++2e^-+SO_4^{2-}(sol)=PbSO_4^{2-}(sol).$$

"Lithium cell" or "Lithium battery", as used herein, means a cell which utilizes lithium as an anode and various materials as cathodes including CF, $MnO_2$, $FeS_2$ and $I_2$. Various non-aqueous electrolytes comprised of polar-organic liquids (e.g., dimethyl ether, propylene carbonate, etc.) containing a dissolved lithium salt are used. Additionally, various polymer-based electrolytes such as polyethylene oxide/salt complexes have also been used. Typical half-reactions include the following:

$$Zn=Zn^{2+}+2e^-$$

$$Cd=Cd^{2+}+2e^-$$

$$Li=Li^++e^-.$$

Examples of overall cell reactions include:

$$Li(CF)_n=LiF+C;$$

$$Li+MnO_2=LiMnO_2;$$

$$Li+FeS_2=Li_2S+Fe;\ and$$

$$Li+½I_2=LiI.$$

"Lithium ion battery" or "Lithium ion cell", as used herein, means a rechargeable cell which functions in a somewhat similar manner to the lithium cell. These batteries have very good power to weight ratios.

"Magnetoelectrochemistry", as used herein, means electrochemical phenomena occurring under the influence of magnetic field(s).

"Mass transport", as used herein means the movement or transportation of mass (e.g., chemical compounds, ions, etc.) from one part of a system to another. This phenomena is typically associated with diffusion and convection, but can also occur through electromigration.

"Membrane/Electrode assembly" or "MEA", as used herein, means the combination of the anode/membrane/cathode in a fuel cell. The assembly also often includes a catalyst on, in and/or around at least a portion of the electrodes.

"Nernst equation", as used herein, means an equation which defines the equilibrium potential of an electrode. The potential is the sum of the standard electrode potential and a correction term for the deviation from unit concentrations of reactant and product from the electrode reaction.

"NiCd battery" or "NiCd cell", as used herein, means a cell which utilizes $Ni(OH)_2$ as the cathode, a Cd anode and an aqueous potassium hydroxide (KOH) electrolyte. The overall cell reaction is:

$$2\ NiOOH+2H_2O+Cd=2Ni(OH)_2+Cd(OH)_2.$$

These cells have high cycle life (i.e., into the thousands) and long shelf lives without significant self-discharge. However, these cells have somewhat lower power densities.

"NiMH battery" or Nickel Metal Hydride Cell", as used herein means, an anode comprising a metal hydride electrode that serves as a solid source of hydrogen. Classical examples of anodes used in these cells include alloys of V, Ti, Zr, Ni, Cr, Co and Fe. The cathode comprises nickel and the electrolyte comprises aqueous KOH.

"Non-harmonic heterodyne conditioning targeting", as used herein, means the application of conditioning energy to a conditionable participant to condition the conditionable participant prior to the conditionable participant being involved, and/or activated, in a cell reaction system, said conditioning energy being provided by at least one of the following spectral energy conditioning providers: spectral energy conditioning catalyst; spectral conditioning catalyst; spectral energy conditioning pattern; spectral conditioning pattern; catalytic spectral energy conditioning pattern; catalytic spectral conditioning pattern; applied spectral energy conditioning pattern and spectral conditioning environmental reaction conditions, to achieve non-harmonic heterodyne resonance with at least a portion of at least one conditionable participant (e.g.; reactants; physical catalysts; promoters; poisons; solvents; physical catalyst support materials; reaction vessels; conditioning reaction vessels and/or mixtures or components thereof in any form of matter), said spectral energy conditioning provider providing conditioning energy to condition at least one conditionable participant by interacting with at least one frequency thereof, to form at least one conditioned participant which assists in producing at least one desired reaction product and/or at least one desired reaction product at a desired reaction rate when the conditioned participant becomes involved with, and/or activated in, a cell reaction system.

"Non-harmonic heterodyne targeting", as used herein, means the application of energy to a cell reaction system by at least one of the following spectral energy providers: spectral energy catalyst; spectral catalyst; spectral energy pattern; spectral pattern; catalytic spectral energy pattern; catalytic spectral pattern; applied spectral energy pattern and spectral environmental reaction condition to achieve non-harmonic heterodyne resonance with at least one of the following forms of matter: reactants; transients; intermediates; activated complexes; physical catalysts; reaction products; promoters; poisons; solvents; physical catalyst support materials; reaction vessels; and/or mixtures or components thereof, said spectral energy provider providing energy to at least one of said forms of matter by interacting with at least one frequency thereof, to produce at least one desired reaction product and/or at least one desired reaction product at a desired reaction rate.

"Overpotential", as used herein, means a difference in the electrode potential of an electrode between its equilibrium potential and its operating potential when a current is flowing.

"Overvoltage", as used herein, means the difference between cell voltage with a current flowing and an open-circuit voltage.

"Participant", as used herein, means reactant, current, transient, intermediate, activated complex, physical catalyst, promoter, poison and/or reaction product comprised of molecules, macromolecules, ions and/or atoms (or components thereof).

"Photoelectrochemical cell" or "photogalvanic cell" or "solar cell", as used herein, means a galvanic cell wherein usable current and voltage are simultaneously produced upon absorption of light by at least one of the electrodes.

"Photoelectrochemistry", as used herein, means the interaction of light with electrochemical systems.

"Photoelectrolytic cell", as used herein, means an electrolytic cell wherein the production of chemicals is caused, or influenced, by the absorption of light by at least one of the electrodes. The process occurring in such a cell is termed photoelectrosynthesis.

"Photoelectrosynthesis", as used herein, means the production of chemicals in a photoelectrolytic cell, where the production is caused, or influenced, by the absorption of light by at least one of the electrodes.

"Plasma", as used herein means, an approximately electrically neutral (quasineutral) collection of electrically activated atoms or molecules, or ions (positive and/or negative) and electrons which may or may not contain a background neutral gas, and at least a portion of which is capable of responding to at least electric and/or magnetic fields.

"Power density", as used herein, means a parameter in a battery indicating the electrical power per unit weight or per unit volume.

"Primary cell" or "primary battery" or "non-rechargeable battery", as used herein, means a cell or battery in which the chemical reaction system providing the electrical current is not readily reversible by a chemical process. This cell provides current until substantially all of the chemicals inside it are utilized. The cell or battery is typically discarded after a single discharge. This cell or battery always operates as a galvanic cell in which the anode is the negative electrode and the cathode is the positive electrode.

"Reactant", as used herein, means a starting material or starting component in a cell reaction system. A reactant can be any inorganic, organic and/or biologic atom, molecule, macromolecule, ion, compound, substance, and/or the like.

"Reaction coordinate", as used herein, means an intra- or inter-molecular/atom configurational variable whose change corresponds to the conversion of reactant into reaction product.

"Reaction pathway", as used herein, means those steps which lead to the formation of reaction product(s). A reaction pathway may include intermediates and/or transients and/or activated complexes. A reaction pathway may include some or all of a reaction profile.

"Reaction product", as used herein, means any product of a reaction involving a reactant. A reaction product may have a different chemical composition from a reactant or a substantially similar (or exactly the same) chemical composition but exhibit a different physical or crystalline structure and/or phase and/or properties. A reaction product may also be a current.

"Reaction profile", as used herein means a plot of energy (e.g., molecular potential energy, molar enthalpy, or free energy) against reaction coordinate for the conversion of reactant(s) into reaction product(s).

"Residual current" or "residual current density", as used herein, means a small faradic current density flowing through an electrode under conditions where zero faradic current is expected (e.g., within an electrical double-layer range). This type of current is typically caused by traces of impurities present in the electrolyte.

"Resultant energy conditioning pattern", as used herein, means the totality of energy interactions between the applied spectral energy conditioning pattern with at least one conditionable participant before said conditionable participant becomes involved, and/or activated, in a cell reaction system as a conditioned participant.

"Resultant energy pattern", as used herein, means the totality of energy interactions between the applied spectral energy pattern with all participants and/or components in the cell reaction system.

"Secondary cell" or "secondary battery" or "rechargeable battery", as used herein, means a cell or battery in which the chemical reaction system providing electrical current is readily reversible chemically. Specifically, after discharging, this cell or battery can be recharged by applying an electrical current to its terminals. Certain of these batteries or cells can be recharged hundreds or thousands of times such as, for example, a lead-acid battery. These batteries or cells operate as a galvanic cell during discharge and as an electrolytic cell during charge. Accordingly, the anode is the negative electrode during discharging, while the anode becomes the positive electrode during charging.

"Self discharge", as used herein, means a slow discharging of a battery without being connected to an external load. These types of reactions are typically caused by impurities and/or side reactions (i.e., reactions occurring other than the primary reaction) within a cell.

"Shelf life", as used herein, means a time period for non-rechargeable batteries storage whereby electrochemical reactions of suitable magnitude are still capable of occurring.

"Sodium/Sulfur battery" or "Sodium/Sulfur cell", as used herein, means cells that utilize molten sodium metal as the anode, molten sulfur as the cathode and a solid aluminum oxide electrolyte. The overall cell reaction is $$2Na+xS=NaS_x.$$

"Sonoelectrochemistry", as used herein, means electrochemical phenomena and processes occurring under the influence of sound waves.

"Spectral catalyst", as used herein, means electromagnetic energy which acts as a catalyst in a cell reaction system, for example, electromagnetic energy having a spectral pattern which affects, controls, or directs a reaction pathway.

"Spectral conditioning catalyst", as used herein, means electromagnetic energy which, when applied to a conditionable participant to form a conditioned participant, assists the conditioned participant to act as a catalyst in a cell reaction system, for example, electromagnetic energy having a spectral conditioning pattern which causes the conditioned participant to affect, control, or direct a reaction pathway in a cell reaction system when the conditioned participant becomes involved with, and/or activated in, the cell reaction system.

"Spectral conditioning environmental reaction condition", as used herein, means at least one frequency and/or field which simulates at least a portion of at least one conditioning environmental reaction condition.

"Spectral conditioning pattern", as used herein, means a pattern formed by one or more electromagnetic frequencies emitted or absorbed after excitation of an atom or molecule. A spectral conditioning pattern may be formed by any known spectroscopic technique.

"Spectral energy catalyst", as used herein, means energy which acts as a catalyst in a cell reaction system having a spectral energy pattern which affects, controls, and/or directs a reaction pathway.

"Spectral energy conditioning catalyst", as used herein, means conditioning energy which, when applied to a conditionable participant, assists a conditionable participant, once conditioned, to act as a catalyst in a cell reaction system, the conditioned participant having a spectral energy pattern which affects, controls and/or directs a reaction pathway when the conditioned participant becomes involved with, and/or activated in, the cell reaction system.

"Spectral energy conditioning pattern", as used herein, means a pattern formed by one or more conditioning energies and/or components emitted or absorbed by a molecule, ion, atom and/or component(s) thereof and/or which is present by and/or within a molecule, ion, atom and/or component(s) thereof.

"Spectral energy pattern", as used herein, means a pattern formed by one or more energies and/or components emitted or absorbed by a molecule, ion, atom and/or component(s) thereof and/or which is present by and/or within a molecule, ion, atom and/or component(s) thereof. For example, the spectral energy pattern could be a series of electromagnetic frequencies designed to heterodyne with reaction intermediates, or the spectral energy pattern could be the portion of the actual spectrum emitted by a reaction intermediate.

"Spectral environmental reaction condition", as used herein, means at least one frequency and/or field which simulates at least a portion of at least one environmental reaction condition in a cell reaction system.

"Spectral pattern", as used herein, means a pattern formed by one or more electromagnetic frequencies emitted or absorbed after excitation of an atom or molecule. A spectral pattern may be formed by any known spectroscopic technique.

"Targeting", as used herein, means the application of energy to a cell reaction system by at least one of the following spectral energy providers: spectral energy catalyst; spectral catalyst; spectral energy pattern; spectral pattern; catalytic spectral energy pattern; catalytic spectral pattern; applied spectral energy pattern; and spectral environmental reaction conditions, to achieve direct resonance and/or harmonic resonance and/or non-harmonic heterodyne-resonance with at least one of the following forms of matter: reactants; transients; intermediates; activated complexes; physical catalysts; reaction products; promoters; poisons; solvents; physical catalyst support materials; reaction vessels; and/or mixtures or components thereof, said spectral energy provider providing energy to at least one of said forms of matter by interacting with at least one frequency thereof, to produce at least one desired reaction product and/or at least one desired reaction product at a desired reaction rate.

"Throwing power", as used herein, means the ability of an electroplating system to produce a uniformly thick deposit on a substrate surface.

"Transient", as used herein, means any chemical and/or physical state that exists between reactant(s) and reaction product(s) in a reaction pathway or reaction profile.

"Zinc air cell", as used herein, means a cell which uses a gas diffusion electrode, a zinc anode separated by an electrolyte and some form of mechanical separators. The gas diffusion electrode permits atmospheric oxygen to pass through. The oxygen is converted into hydroxyl ions and water and the hydroxyl ions travel through an electrolyte to the zinc anode. The hydroxyl ions react with zinc and zinc oxide is formed. The formation of zinc oxide creates an electrical potential.

"Zinc-carbon battery" or "Zinc-carbon cell", as used herein, means a battery or cell wherein the electrodes are comprised of zinc and carbon, respectively, with an acidic paste serving as the electrolyte.

SUMMARY OF THE INVENTION

This invention overcomes many of the deficiencies associated with various electrochemical reactions occurring in a variety of different environments. More importantly, this invention discloses a variety of novel spectral energy techniques, referred to sometimes herein as spectral electrochemistry, that can be utilized in a number of reactions in a cell reaction system, including very basic reactions, which may be desirable to achieve or to permit to occur in many of the chemical/electrochemical reactions utilized in various cell reaction systems. These spectral energy techniques can be used to improve, for example, (1) the supply of fuel to the cell reaction systems; (2) assisting in one or both of the half-reactions occurring at the electrodes, to, for example, increase the rate of the reaction(s) and/or decrease the amount of physical catalyst required; (3) assisting in the transport of one or more ionic species into/through various electrolyte materials; and/or (4) assisting in the movement, into and/or from, of various reactants and/or reaction products through at least a portion of a cell reaction system.

Further, the invention discloses a variety of novel spectral energy conditioning techniques, referred to sometimes herein as spectral conditioning electrochemistry, or conditioning electrochemistry energies, that can be utilized to condition a conditionable participant. Once a conditionable participant has been conditioned, the conditioned participant can be used in a cell reaction system. These spectral energy conditioning techniques can be used to condition at least one conditionable participant which can thereafter be used in, for example, any type of organic or inorganic cell reaction system, biological cell reaction system (e.g., plant and animal), industrial cell reaction system, etc. Further, the conditioned participant may itself comprise both a reactant and a reaction product, whereby, for example, the chemical composition of the conditioned participant does not substantially change (if at all) but one or more physical properties or structures and/or phases is changed once the conditioned participant is involved with, and/or activated by, the cell reaction system.

These novel spectral energy techniques (now referred to as spectral electrochemistry) and novel spectral energy conditioning techniques (now referred to as spectral electrochemistry conditioning) are possible to achieve due to the fundamental discoveries contained herein that disclose various means for achieving the transfer of energy (or preventing the transfer of energy) and/or controlling the energy dynamics and controlling the resonant exchange of energy between, for example, at least two entities. The invention teaches that the key for transferring energy between two entities (e.g., one entity sharing energy with another entity) is that when frequencies match, energy transfers. For example: (1) matching of frequencies of spectral energy patterns of two different forms of matter or matching of frequencies of a spectral energy pattern of matter with energy in the form of a spectral energy catalyst; and/or (2) matching of frequencies of spectral energy conditioning patterns of two different forms of matter or matching of frequencies of a spectral energy pattern of matter with energy in the form of a spectral conditioning catalyst. In the case of achieving the transfer of energy between, for example, a spectral energy conditioning pattern and a conditionable participant, once conditioning energy has been transferred, the conditioned participant can thereafter favorably utilize its conditioned energy pattern in a cell reaction system. The aforementioned entities may both be comprised of matter (solids, liquids, gases and/or plasmas and/or mixtures and/or components thereof), both comprised of various form(s) of energy, or one comprised of various form(s) of energy and the other comprised of matter (solids, liquids, gases and/or plasmas and/or mixtures and/or components thereof).

More specifically, all matter can be represented by spectral energy patterns, which can be quite simple to very complex in appearance, depending on, for example, the complexity of the matter. One example of a spectral energy pattern is a spectral pattern (or a spectral conditioning pattern) which likewise can be quite simple to quite complex in appearance, depending on, for example, the complexity of the matter. In the case of matter represented by spectral patterns (or spectral conditioning patterns), matter can exchange energy with other matter if, for example, the spectral patterns of the two forms of matter match, at least partially, or can be made to match or overlap, at least partially (e.g., spectral curves or spectral patterns (or spectral conditioning patterns) comprising one or more electromagnetic frequencies may overlap with each other). In general, but not in all cases, the greater the overlap in spectral patterns (and thus, the greater the overlap of frequencies comprising the spectral patterns or spectral conditioning patterns), the greater the amount of energy transferred. Likewise, for example, if the spectral pattern (or spectral conditioning pattern) of at least one form of energy can be caused to match or overlap, at least partially, with the spectral pattern of matter, (e.g., a participant or a conditionable participant) energy will also transfer to the matter. Thus, energy can be transferred to matter by causing frequencies to match.

As discussed elsewhere herein, energy (E), frequency (v) and wavelength ($\lambda$) and the speed of light (c) in a vacuum are interrelated through, for example, the following equation:

$$E = hv = hc/\lambda$$

When a frequency or set of frequencies corresponding to at least a first form of matter can be caused to match with a frequency or set of frequencies corresponding to at least a second form of matter, energy can transfer between the different forms of matter and permit at least some interaction and/or reaction to occur involving at least one of the two different forms of matter. For example, solid, liquid, gas and/or plasma (and/or mixtures and/or portions thereof) forms of matter can interact and/or react and form a desirable reaction product or result. Any combination(s) of the above forms of matter (e.g., solid/solid, solid/liquid, solid/gas, solid/plasma, solid/gas/plasma, solid/liquid/gas, etc., and/or mixtures and/or portions thereof) are possible to achieve for desirable interactions and/or reactions to occur in various cell reaction systems in biologic, organic and/or inorganic systems.

For example, the techniques of the present invention can be utilized to help in the formation of desirable fuels to be input and/or stored in various cell reaction systems. For example, if hydrogen gas ($H_2$) was a desired fuel to be used/stored, a precursor to hydrogen may be provided/stored as a source of hydrogen. Specifically, hydrogen could be stored in a solid state. In this regard, if hydrogen can be readily stored and released, the amount of hydrogen that is capable of being stored in the same volume as a highly compressed gas is about 5-10 times the amount. The techniques of the present invention can be used to assist in the storage and/or release of hydrogen that is absorbed into, for example, a metal or metal alloy such as palladium, lithium, beryllium, titanium, aluminum, (e.g., $Pd_2H$, $TiFeH_2$ etc.), by inputting a spectral energy to the metallic material that reacts with the material in such a way as to produce electromagnetic emissions from the materials that are resonant with hydrogen's electronic frequencies. For example, a spectral energy pattern could heterodyne with an inherent frequency of the metallic material to produce a hydrogen electronic frequency, or electromagnetic radiation of one frequency could be absorbed by a color center of the material, which in turn emits at a frequency resonant with hydrogen.

The techniques of the present invention can also assist with either of the electrochemical half-reactions which occur at the anode or cathode in a variety of cell reaction systems. For example, in certain cell reaction systems, catalysts are utilized to assist in increasing the reaction rates of the electrochemical reaction. As a specific example, the polymer electrolyte membrane fuel cells ("PEM fuel cell") that utilize hydrogen as a fuel experience an oxidation reaction at the anode where hydrogen gas molecules are converted into hydrogen ions (i.e., protons) with the assistance of platinum. The platinum is typically provided on at least a portion of a porous electrode. In most cases, the platinum is actually mixed with an appropriate powder electrode material and the two powdered materials are together applied by printing the powders onto each side of a polymer membrane. As disclosed elsewhere herein, the various frequencies of platinum resonate with various hydrogen frequencies as well as various frequencies which are intermediate in the formation of water. Accordingly, the use of a spectral energy provider, such as a spectral catalyst or a spectral energy catalyst, irradiated onto, into and/or around at least a portion of an electrode, which may or may not contain a physical catalyst (e.g., the spectral energy catalyst may augment a physical catalyst or may be supplied instead of a physical catalyst) can result in effective catalyzation of the desired oxidation reaction.) Similarly, the use of a spectral energy conditioning provider, such as a spectral conditioning catalyst or a spectral energy conditioning catalyst, irradiates or interacts with a conditionable participant to condition the conditionable participant and form a conditioned participant (e.g., transport ion) which can be located on, in and/or around at least a portion of an electrode. The electrode may or may not contain a physical catalyst and/or a conditioned participant (e.g., the spectral conditioning energy may form a conditioned participant that may augment a physical catalyst or be supplied instead of a physical catalyst) and may result in effective catalyzation of the desired oxidation reaction. Moreover, combinations of spectral energy providers, spectral energy conditioning providers, conditionable participants and/or physical catalysts could also be utilized in a holoreaction system.

As discussed elsewhere herein, the composition, size and/or shape of any material(s) combined with and/or contacting or even simply juxtaposed to a catalyst (i.e., traditional or electrodic) can have positive or negative catalyzing effects. In particular, for example, the spectral patterns of one or more materials combined, contacting and/or juxtaposed to a catalyst can result in desirable or undesirable changes to the spectral pattern of the catalyst. Further, by understanding that physical materials that are combined, contacting and/or juxtaposed to a physical catalyst can result in a desirable influence on a physical catalyst, specific materials can be chosen for such purposes and/or additional materials (or additional conditioned materials) and/or spectral energy providers (and/or spectral energy conditioning providers) used to condition conditionable participants can be utilized to obtain enhanced performance of the physical catalyst including charge-transfer catalysts. These mechanisms are discussed in much greater detail later herein. Accordingly, the techniques of the present invention assist in controlling the various reactions that occur in many cell reaction systems.

Moreover, the techniques of the present invention can be used in a similar manner at the cathode where, for example, a reduction reaction or charge-transfer catalysis occurs. In the case of the aforementioned PEM fuel cell, for example, oxygen is caused to flow near the cathode and oxygen reacts with hydrogen ions (i.e., protons) which have migrated through the polymer membrane and combines with electrons to form water molecules. Once again, platinum can be utilized as a physical catalyst to catalyze the reaction of oxygen and hydrogen to form water. As stated elsewhere herein, various intermediates are formed in this process (e.g., hydroxy ions and hydrogen atoms) and numerous platinum energy frequencies resonate with many of these intermediates, as well as reactants, in the water formation reaction. Accordingly, similar to the above discussion regarding the anode, if a spectral energy provider, such as a spectral catalyst or a spectral energy catalyst, were provided alone or in combination with a physical catalyst, (e.g., as the only source of catalyst or augmenting an existing physical catalyst, respectively) then the applied spectral energy provider will assist in the rate of the reduction reaction. Likewise, if a spectral energy conditioning provider, such as a spectral conditioning catalyst or a spectral energy conditioning catalyst, were provided to a conditionable participant to form a conditioned participant, and the conditioned participant was present, alone or in combination with a physical catalysts (e.g., as the only source of catalyst or augmenting an existing physical catalysts, respectively) then the conditioned participant could assist in the rate of the reduction reaction. Moreover, combinations of spectral energy providers, spectral energy conditioning providers, conditioned participants and/or physical catalysts, etc., could also be utilized.

Still further, the techniques of the present invention can assist in the transport of ions into, through and/or from the electrolyte, one of the slowest processes in electrochemical reactions. For example, by understanding the particular ionic transfer mechanism which occurs in the different electrolytes, the present invention can apply a suitable spectral energy provider, such as a spectral catalyst or spectral energy catalyst and/or a suitable spectral energy conditioning provider, (e.g., a spectral conditioning environmental reaction condition) which can enhance the dissolution of ionic species into the electrolyte by affecting the dynamic equilibrium between bound and dissociated ions. (For an example, see a discussion of $H_2 \rightarrow 2H$, discussed later herein). Further, conduction of ions through the electrolyte can be enhanced using spectral electromagnetic frequencies such as rotational frequencies. In this regard, depending upon the particular electrolyte and the particular ionic species which needs to be transported, various environmental conditions can be simulated by an appropriate spectral environmental conditioning reaction condition. Likewise, other techniques which could be utilized to enhance ion transport include: (1) inputting, for example, a resonant or harmonic frequency corresponding to the wavelength between the bonding sites for the ionic species which is being transported through the electrolyte; (2) utilizing ion cyclotron resonance, for example, by inputting the naturally occurring frequency of gyration radius to the ions in the electrolyte, or by applying magnetic field lines to the electrolyte thereby modifying the spiral trajections of the ions and inputting the modified frequency of the gyration radius; (3) applying at least one spectral environmental reaction condition which imitates, for example, at least one temperature, concentration and/or pressure gradient within at least a portion of the electrolyte which causes ions to migrate from these higher temperatures, concentrations and/or pressure areas to the lower corresponding region; and/or (4) by exposing the electrolyte to a spectral frequency that is resonant with the migrating ions in the electrolyte; and (5) by spectrally conditioning an electrolyte solution thereby altering its material properties as a solvent and hence transport medium.

Also, the rate of ionic species transfer to an electrolyte in a chemical transformation can be enhanced with spectral energy providers. For example, a receiving electrode can project an electromagnetic scaffolding that resonates with and attracts an ionic species, such as its electronic spectral pattern.

In each of the above-discussed instances, the applications of: (1) a spectral energy provider (e.g., in the form of, for example, a catalytic spectral energy pattern, a catalytic spectral pattern, a spectral energy pattern, a spectral energy catalyst, a spectral pattern, a spectral catalyst, a spectral environmental reaction condition and/or combinations thereof, which can collectively result in an applied spectral energy pattern being applied in at least a portion of a cell reaction system); and/or (2) a spectral energy conditioning provider (e.g., in the form of, for example, a catalytic spectral energy conditioning pattern, a catalytic spectral conditioning pattern, a spectral energy conditioning pattern, a spectral energy conditioning catalyst, a spectral conditioning pattern, a spectral conditioning catalyst, a spectral environmental conditioning reaction condition and/or combinations thereof, which can collectively result in an applied spectral energy conditioning pattern being applied to a conditionable participant in a conditioning reaction system) can occur by one or more of the following techniques including:

(1) use of suitable directors of energy such as fiberoptic cables, waveguides, transducers, transmission elements etc., which can be directed to provide energy to at least a portion of the cell reaction system where a desirable reaction is to occur;

(2) providing energy to at least a portion of, or a side of, for example, an electrolyte, whereby the electrolyte is capable of transmitting (e.g., through one or more faces or portions thereof) the applied energy to at least another portion of a cell reaction system (e.g., a portion of a catalyst located on an adjacent anode and/or cathode). The energy can be targeted to the ions, solution, or an ion solution interaction;

(3) including one or more suitable members (e.g., membrane capable of transmitting energy) within at least a portion of an electrode and/or in at least a portion of electrolyte which permits energy to be introduced to at least a portion of an electrode where a reaction is to occur and/or in the case of augmenting to at least a portion of an electrode or portion of a cell reaction system where a physical catalyst is located;

(4) providing conditioning energy to one or more reactants prior to its (their) arrival and reaction in the cell reaction system at, and/or near the anode and/or cathode to augment physical catalyst activity;

(5) applying a spectral energy pattern (or a spectral energy conditioning pattern) in a reformer reaction used to provide fuel for a cell reaction system whereby, for example, reactions in the reformer are controlled and/or directed and/or products leaving the reformer are affected prior to their arrival in the cell reaction system;

(6) controlling cell reaction system parameters such that the current and/or electrical field strength generated are optimized to produce desirable Stark frequencies and optimal reaction rates;

(7) controlling inherent fuel reaction system parameters, or applying external magnetic fields such that desired Zeeman frequencies are produced in the cell reaction system, thereby optimizing at least one reaction rate;

(8) applying at least one form of energy to increase the flow of reactants in the cell reaction system; and/or (9) applying at least one form of energy directly to at least a portion of a cell reaction system to cause and/or influence at least one reaction therein.

In all such cases, the goal of providing energy in an appropriate amount and to the appropriate location would be the primary impetus for deciding what techniques, or combinations of techniques, would be most desirable. In this regard, so long as an appropriate energy pattern for a cell reaction (and/or conditioning energy pattern in a conditioning reaction system), as discussed above, is delivered to, at least a portion of the cell reaction system (or conditioning reaction system) where a desirable reaction is to occur, then the delivered energy pattern (and/or conditioning energy pattern) can ultimately serve to enhance desired chemical reactions (e.g., electrochemical and/or electrolytic) within the cell reaction system (e.g., either directly or through a conditioned participant).

The techniques of the present invention are suitable to each of the known cell reaction systems. In this regard, in each of the cell reaction systems that involve oxidation reactions and reduction reactions, the techniques of the present invention can be utilized to enhance one or more of such reactions, depending upon for example, the particular rates of reaction that are desired to be achieved. In this regard, matter (e.g., solids, liquids, gases and/or plasmas and/or mixtures and/or portions thereof) can be caused, or influenced, to interact and/or react with other matter and/or portions thereof in, for example, a desired reaction in a cell reaction system along a desired reaction pathway by applying energy, in the form of, for example, a catalytic spectral energy pattern, a catalytic spectral pattern, a spectral energy pattern, a spectral energy catalyst, a spectral pattern, a spectral catalyst, a spectral environmental reaction condition, and/or combinations thereof, which can collectively result in an applied spectral energy pattern being applied in at least a portion of the cell reaction system.

Further, the conditioning techniques of the present invention are suitable to each of the known cell reaction systems. In this regard, in each of the cell reaction systems that involve oxidation reactions and reduction reactions, the conditioning techniques of the present invention can be utilized to enhance one or more of such reactions by forming a conditioned participant in a conditioning reaction system depending upon, for example, the particular rates of reaction that are desired to be achieved in a cell reaction system. In this regard, conditionable matter (e.g., solids, liquids, gases and/or plasmas and/or mixtures and/or portions thereof) can be conditioned and then introduced into a cell reaction system to cause, or influence or interact and/or react with other matter and/or portions in a cell reaction system along a desired reaction pathway. A conditioned participant can be formed by applying conditioning energy in the form of, for example, a catalytic spectral energy conditioning pattern, a catalytic spectral conditioning pattern, a spectral energy conditioning pattern, a spectral energy conditioning catalyst, a spectral conditioning pattern, a spectral conditioning catalyst, a spectral environmental conditioning reaction condition, and/or combinations thereof, which can collectively result in an applied spectral energy conditioning pattern being applied in at least a portion of a conditioning reaction system. The conditioned participant can thereafter favorably influence a cell reaction system.

The techniques of the present invention are applicable to the following non-inclusive list of cell reaction systems: alkaline batteries or alkaline cells; anodic protection or corrosion protection systems; anodizing cells; batteries; bioelectrochemical cell reaction systems; brine electrolysis processes; corrosion cell reaction systems; dry cells; electroacoustic cells; electroanalytical chemistry techniques; electrochemical cells; electrocrystallization cells; electroforming cells; electrokinetic cells; electrolysis reactions; electrolyte reactions; electrode reactions; electrolytic cells; electrolytic pickling reactions; electrometallurgical reactions; electromigration reactions; electrophoresis reactions; electroplating cells; electrorefining cells; electrowinning cells; fuel cells; galvanic cells; galvanizing reactions; hydrolysis reactions; ion exchange membrane reactions; ion-resin systems; Laclanch-type cells; lithium cells or lithium batteries; lithium ion batteries or lithium ion cells; magnetoelectrochemical reactions; mass transport reactions; reactions in membrane/electrode assemblies; NiCd batteries or NiCd cells; NiMH batteries or nickel-metal hydride cells; photoelectrochemical or photogalvanic or solar cells; photoelectrochemistry reactions; photoelectrolytic cells; photoelectrosynthesis reactions; plasma reactions; secondary cells or secondary batteries or rechargeable batteries; sodium/sulfur batteries or sodium/sulfur cells; sonoelectrochemistry reactions; zinc air cells; and zinc-carbon batteries or zinc-carbon cells.

In addition to the redox reactions which occur in the various techniques, processes, systems, cells and/or cell reaction systems listed immediately above, the techniques of the present invention are also applicable in capacitor cell reaction systems. In this regard, the techniques of the present invention are more broadly applicable to techniques other than simple redox reactions which involve, typically, electrolytes. Specifically, the techniques of the present invention (and the conditioning techniques of the present invention) are also applicable to capacitor cell reaction systems which utilize dielectrics rather than electrolytes. However, certain capacitors also utilize electrolyte-like materials, for example, as at least one electrode.

Electrical capacitors, or electrical condensers, are electrical devices which store up electricity or electrical energy. The action of storing this electrical energy can be viewed as being analogous to a gas tank used for the storage of gas. The amount of electricity which a capacitor can hold depends upon the electrical pressure or voltage applied to the capacitor, just as the amount of gas that tank can hold depends upon the pressure of the gas in the tank. For example, if the pressure is doubled on a tank of gas, twice the amount of gas can be forced into the tank; likewise, if the electrical pressure or voltage applied to a capacitor is doubled, twice the amount of electricity can be forced into the capacitor. Thus, in capacitors, the "electrical size" is designated as a form of capacity. The capacity of an electrical capacitor is the ratio of the quantity of electricity and the electrical pressure or voltage. The ratio is expressed as follows:

$$Q=CV$$

wherein, Q=quantity of electricity, C=capacity of the capacitor and V=electrical pressure or voltage. Thus, the capacity of the capacitor can be expressed as follows:

$$C=Q/V.$$

Thus, the capacity is equal to the quantity of electricity divided by the electrical pressure or voltage. The capacity of a capacitor is dependent upon the size and spacing of the conducting plates and the type of insulating and dielectric medium between the plates.

The dielectric material of a capacitor is one of the essential parts of the capacitor. The dielectric material may be a solid, a liquid, a gas or even be in the form of a plasma or vacuum. The simplest form of capacitors comprise two electrodes or conducting plates which are separated by air. In this case, the capacitor includes a gaseous dielectric. It is common practice to identify capacitors in accordance with the type of dielectric employed in their structure. Accordingly, terms such as mica capacitors, air capacitors, oil capacitors and paper capacitors are commonly used. However, according to the present invention, electrochemical capacitors and electrolytic capacitors are of particular interest. In particular, for example, an electrolytic capacitor uses a metallic plate for one of its conducting surfaces, whereas the other conducting surface is typically a chemical compound or electrolyte. The dielectric employed is typically a thin film of an oxide of the metal which constitutes the one metallic plate used in the structure. Electrolytic capacitors are divided into two general types, namely, wet electrolytic capacitors and dry electrolytic capacitors.

In order to practice the techniques of the present invention, it has been discovered that matter (e.g., solids, liquids, gases and/or plasmas and/or mixtures and/or portions thereof) can be caused, or influenced, to interact and/or react (or be prevented from reacting and/or interacting) with other matter and/or portions thereof in, a cell reaction system along a desired reaction pathway by applying energy, in the form of, for example, a spectral energy provider such as a catalytic spectral energy pattern, a catalytic spectral pattern, a spectral energy pattern, a spectral energy catalyst, a spectral pattern, a spectral catalyst, a spectral environmental reaction condition and/or combinations thereof, which can collectively result in an applied spectral energy pattern being applied or provided in at least a portion of the cell reaction system. One example of this phenomenon, discussed in greater detail in the "Examples" section later herein, utilizes a sodium vapor light as a spectral energy pattern which results in enhanced conductivity in an aqueous solution.

Likewise, matter (e.g., solids, liquids, gases and/or plasmas and/or mixtures and/or portions thereof) can be caused, or influenced, to interact and/or react with other matter and/or portions thereof in, for example, a conditioning reaction system along a desired reaction pathway by applying conditioning energy to a conditionable participant, in the form of, for example, a catalytic spectral energy conditioning pattern, a catalytic spectral conditioning pattern, a spectral energy conditioning pattern, a spectral energy conditioning catalyst, a spectral conditioning pattern, a spectral conditioning catalyst, a spectral conditioning environmental reaction condition and/ or combinations thereof, which can collectively result in an applied spectral energy conditioning pattern being applied to a conditionable participant. Specifically, the applied conditioning energy results in a conditioned participant which, when exposed to, and/or activated by, a cell reaction system, can cause the cell reaction system to behave in a desirable manner (e.g., the conditioned energy pattern of the conditioned participant favorably interacts with at least one participant in a cell reaction system). One example of this phenomenon, discussed in grater detail in the "Examples" section later herein, utilizes a sodium vapor light as a spectral energy conditioning pattern for conditioning water prior to sodium chloride being dissolved therein which also resulted in enhanced conductivity.

In these cases, interactions and/or reactions may be caused to occur when the applied spectral energy pattern (or the applied spectral energy conditioning pattern) results in, for example, some type of modification to the spectral energy pattern of one or more of the forms of matter in the cell reaction system. The various forms of matter include reactants; transients; intermediates; activated complexes; physical catalysts; reaction products; promoters; poisons; solvents; physical catalyst support materials; reaction vessels; and/or mixtures of components thereof. For example, the applied spectral energy provider (i.e., at least one of spectral energy catalyst; spectral catalyst; spectral energy pattern; spectral pattern; catalytic spectral energy pattern; catalytic spectral pattern; applied spectral energy pattern and spectral environmental reaction conditions) when targeted appropriately to, for example, a participant and/or component in the cell reaction system, can result in the generation of, and/or desirable interaction with one or more participants. Specifically, the applied spectral energy provider can be targeted to achieve very specific desirable results and/or reaction product and/or reaction product at a desired rate and/or along a desired reaction pathway).

The targeting can occur by a direct resonance approach, (i.e., direct resonance targeting), a harmonic resonance approach (i.e., harmonic targeting) and/or a non-harmonic heterodyne resonance approach (i.e., non-harmonic heterodyne targeting). The spectral energy provider can be targeted to, for example, interact with at least one frequency of an atom or molecule, including, but not limited to, electronic frequencies, vibrational frequencies, rotational frequencies, rotational-vibrational frequencies, librational frequencies, translational frequencies, gyrational frequencies, fine splitting frequencies, hyperfine splitting frequencies, magnetic field induced frequencies, electric field induced frequencies, natural oscillating frequencies, and all components and/or portions thereof (discussed in greater detail later herein; and specific examples being given in Table D). These approaches may result in, for example, the mimicking of at least one mechanism of action of a physical catalyst in a cell reaction system.

Similar concepts also apply to utilizing an applied spectral energy conditioning pattern in a conditioning reaction system. In the case where one applied spectral energy conditioning pattern is utilized, interactions and/or reactions may be caused to occur in the conditioning reaction system when the applied spectral energy conditioning pattern results in, for example, some type of modification to the spectral energy pattern of one or more conditionable participants prior to such participant(s) being involved in, and/or activated by, the cell reaction system. The various forms of matter that can be used as a conditionable participant include: reactants; physical catalysts; reaction products; promoters; poisons; solvents; physical catalyst support materials; reaction vessels; conditioning reaction vessels and/or mixtures of components thereof. For example, the applied spectral energy conditioning provider (e.g., at least one of a: spectral energy conditioning catalyst; spectral conditioning catalyst; spectral energy conditioning pattern; spectral conditioning pattern; catalytic spectral energy conditioning pattern; catalytic spectral conditioning pattern; applied spectral energy conditioning pattern and spectral conditioning environmental reaction conditions) when targeted appropriately to, for example, a conditionable participant and/or component thereof prior to the conditionable participant, and/or component thereof, becoming involved in, and/or activated by, the cell reaction system, can result in the generation of a desirable reaction product, and/or desirable interaction with one or more participants in the cell reaction system. Specifically, the applied spectral energy conditioning provider can be targeted to a conditionable participant to achieve very specific desirable results (e.g., a very specific conditioned energy pattern). The desirable conditioned energy pattern can thereafter result in a desirable reaction pathway, a desirable reaction product and/or a desired rate in a cell reaction system, when the conditioned participant becomes involved in the cell reaction system. Further, the conditioned participant may itself comprise both a reactant and a reaction product, whereby, for example, the chemical composition of the conditioned participant does not substantially change (if at all) but one or more physical properties or structures or phases or relationship(s) in one or more of its energy structure(s) is changed once the conditioned participant is involved with, and/or activated by, the cell reaction system.

The conditioning targeting can occur by a direct resonance conditioning approach, (i.e., direct resonance conditioning targeting), a harmonic resonance conditioning approach (i.e., harmonic conditioning targeting), non-harmonic heterodyne conditioning resonance approach (i.e., non-harmonic heterodyne conditioning targeting). The spectral energy conditioning provider can be targeted to, for example, interact with the conditionable participant by interacting with at least one frequency of an atom or molecule, including, but not limited to, electronic frequencies, vibrational frequencies, rotational frequencies, rotational-vibrational frequencies, fine splitting frequencies, hyperfine splitting frequencies, magnetic field induced frequencies, electric field induced frequencies, natural oscillating frequencies, and all components and/or portions thereof (discussed in greater detail later herein). Some examples of known sources of spectral energy conditioning providers include, but are not limited to, ELF sources, VLF sources, radio sources, microwave sources, infrared sources, visible light sources, ultraviolet sources, x-ray sources and gamma ray sources.

The following Table D lists examples of various possible sources of spectral energy patterns and of spectral energy conditioning patterns.

TABLE D

| ELF, VLF, and Radio Sources |
|---|
| Electron tubes |
|   (e.g. oscillators such as regenerative, Meissner, Harley, Colpitts, Ultraudion, Tuned-Grid Tuned Plate, Crystal, Dynatron, Transitron, Beat-requency, R-C Transitron, Phase-Shift, Multivibrator, Inverse-Feedback, Sweep-Circuit, Thyratron Sweep) |
| Glow tube |
| Thyratron |
| Electron-ray tube |
| Cathode-ray tube |
| Phototube |
| Ballast tube |
| Hot body |
| Magnetron |
| Klystron |
| Crystals |
|   (e.g. microprocessor, piezoelectric, quartz, quartz strip, SAW resonator, semiconductor) |
| Oscillators |
|   (e.g. crystal, digitally compensated crystal, hybrid, IC, microcomputer compensated crystal, oven controlled crystal OCXO, positive emitter-coupled logic, pulse, RC, RF, RFXO, SAW, sinusoidal, square wave, temperature compensated TCXO, trigger coherent, VHF/UHF, voltage controlled crystal VCXO, voltage controlled VCO, dielectric resonator DRO) |
| Microwave Sources |
| Hot body |
|   Spark discharge |
|   Electronic tubes (e.g. triode) |
|   Klystrons |
|   Klystron plus multipliers |

TABLE D-continued

Magnetrons
Magnetron harmonics
Traveling-wave and backward wave tubes
Spark oscillator
Mass oscillator
Vacuum tube
Multipliers
   Microwave tube
   Microwave solid-state device
      (e.g. transistors, bipolar transistors, field-effect transistors,
      transferred electron (Gunn) devices, avalanche diodes, tunnel diodes)
   Maser
   Oscillators
      (e.g. crystal, digitally compensated crystal, hybrid, IC, microcomputer
      compensated crystal, oven controlled crystal OCXO, positive emitter-
      coupled logic, pulse, RC, RF, RFXO, SAW, sinusoidal, square wave,
      temperature compensated TCXO, trigger coherent, VHF/UHF, voltage
      controlled crystal VCXO, voltage controlled VCO, dielectric resonator
      DRO)

Infrared Sources

Filaments (e.g. Nernst, refractory, Globar)
Gas mantle
Lamp (e.g. mercury, neon)
Hot body
Infrared light emitting diode ILED, arrays

Visible Light Sources

Flame
Electric arc
Spark electrode
Gaseous discharge (e.g. sodium, mercury)
Planar Gas discharge
Plasma
Hot body
Filament, Incandescence
Laser, laser diodes (e.g. multiple quantum well types, double heterostructured)
Lamps
   (e.g. arc, cold cathode, fluorescent, electroluminescent, fluorescent,
   high intensity discharge, hot cathode, incandescent, mercury, neon,
   tungsten-halogen, deuterium, tritium, hollow cathode, xenon, high
   pressure, photoionization, zinc)
Light-emitting diode LED, LED arrays
Organic Light-emitting diode OLED (e.g. small molecule, polymer)
Luminescence (e.g. electro-, chemi-)
Charge coupled devices CCD
Cathode ray tube CRT
Cold cathode
Field emission
Liquid crystal LCD
Liquid crystal on silicon LcoS
Low Temperature polycrystalline silicon LTPS
Metal-Insulated-Metal (MIM) Active Matrix
Active Matrix Liquid Crystal
Chip on Glass COG
Twist Nematic TN
Super Twist Nematic STN
Thin film transistor TNT
Fluorescence (e.g. vacuum, chemi-)

Ultraviolet Sources

Spark discharge
Arc discharge
Hot body
Lamps (e.g. gaseous discharge, mercury vapor, neon, fluorescence, mercury-
xenon)
Light emiting diode LED, LED arrays
Laser

X-ray Sources

Atomic inner shell
Positron-electron annihilation
Electron impact on a solid
Spark discharge
Hot body
Tubes (e.g. gas, high vacuum)

TABLE D-continued

γ-ray Sources

Radioactive nuclei
Hot body

In some cases, desirable results in a cell reaction system may be achieved by utilizing a single applied spectral energy pattern targeted to a single participant; while in other cases, more than one applied spectral energy pattern may be targeted to a single participant or multiple participants, by, for example, multiple approaches in a single cell reaction system. Specifically, combinations of direct resonance targeting, harmonic targeting and non-harmonic heterodyne targeting, which can be made to interact with one or more frequencies occurring in atoms and/or molecules, could be used sequentially or substantially continuously. Further, in certain cases, the spectral energy provider targeting may result in various interactions at predominantly the upper energy levels of one or more of the various forms of matter present in a cell reaction system.

Further, desirable results may be achieved once a conditioned participant is exposed to (e.g., activated in) a cell reaction system and/or the conditioned participant may enhance certain reaction pathways and/or reaction rates (e.g., kinetics of a reaction may be increased or decreased; or reaction products may be altered, increased or decreased). For example, in some cases, desirable results may be achieved by utilizing a single applied spectral energy conditioning pattern targeted to a single conditionable participant; while in other cases, more than one applied spectral energy conditioning pattern may be targeted to a single conditionable participant or to multiple conditionable participants, by, for example, multiple approaches. Specifically, combinations of direct resonance conditioning targeting, harmonic conditioning targeting and non-harmonic heterodyne conditioning targeting, which can be made to interact with one or more frequencies occurring in atoins and/or molecules of a conditionable participant, could be used sequentially or substantially continuously to create desirable conditioned participants. Further, in certain cases, the spectral energy conditioning provider targeting may result in various interactions at predominantly the upper energy levels of one or more of the various forms of matter present as a conditionable participant.

Still further, numerous combinations of the aforementioned applied spectral energy patterns and applied spectral energy conditioning patterns could be used in a cell reaction system to target participants and/or conditionable participants. For example, applied spectral energy patterns could be directed to one or more participants; and/or applied spectral energy conditioning patterns could be directed to one or more conditionable participants. In some cell reaction systems, a spectral energy pattern and a spectral energy conditioning pattern may be substantially similar to each other (e.g., exactly the same or at least comprising similar portions of the electromagnetic spectrum) or very different from each other (e.g., comprising similar or very different portions of the electromagnetic spectrum). The combination of one or more spectral energy patterns with one or more spectral energy conditioning patterns could have significant implications for control of various reaction pathways and/or reaction rates in a cell reaction system.

The invention further recognizes and explains that various environmental reaction conditions are capable of influencing reaction pathways in a cell reaction system when using a spectral energy catalyst such as a spectral catalyst. The invention teaches specific methods for controlling various environmental reaction conditions in order to achieve desirable results in a reaction (e.g., desirable reaction product(s) in one or more desirable reaction pathway(s)) and/or interactions. The invention further discloses an applied spectral energy approach which permits the simulation, at least partially, of desirable environmental reaction conditions by the application of at least one, for example, spectral environmental reaction conditions. Thus, environmental reaction conditions can be controlled and used in combination with at least one spectral energy pattern to achieve a desired reaction pathway. Alternatively, traditionally utilized environmental reaction conditions can be modified in a desirable manner (e.g., application of a reduced temperature and/or reduced pressure) by supplementing and/or replacing the traditional environmental reaction condition(s) with at least one spectral environmental reaction condition.

Similarly, the invention further recognizes and explains that various conditioning environmental reaction conditions are capable of influencing the resultant energy pattern of a conditionable participant, which, when such conditioned participant becomes involved with, and/or activated in, a cell reaction system, can influence reaction pathways in a cell reaction system. The invention teaches specific methods for controlling various conditioning environmental reaction conditions in order to achieve desirable conditioning of at least one conditionable participant which in turn can achieve desirable results (e.g., desirable reaction product(s) and/or one or more desirable reaction pathway(s) and/or desirable interactions and/or desirable reaction raters) in a cell reaction system. The invention further discloses an applied spectral energy conditioning approach which permits the simulation, at least partially, of desirable environmental reaction conditions by the application of at least one, for example, spectral conditioning environmental reaction condition. Thus, conditioning environmental reaction conditions can be controlled and used in combination with at least one spectral energy conditioning pattern to achieve a desired conditioned energy pattern in a conditioned participant. Alternatively, traditionally utilized environmental reaction conditions can be modified in a desirable manner (e.g., application of a reduced temperature and/or reduced pressure) by supplementing and/or replacing the traditional environmental reaction condition(s) with at least one spectral conditioning environmental reaction condition.

The invention also provides a method for determining desirable physical catalysts (i.e., comprising previously known materials or materials not previously known to function as a physical catalyst which can be utilized in a cell reaction system to achieve a desired reaction pathway and/or desired reaction rate. In this regard, the invention may be able to provide a recipe for a physical and/or spectral catalyst for a particular reaction in a cell reaction system where no physical catalyst previously existed. In this embodiment of the invention, spectral energy patterns are determined or calculated by the techniques of the invention and corresponding physical catalysts can be supplied or manufactured and thereafter included in the cell reaction system to generate the calculated required spectral energy patterns. In certain cases, one or more existing physical species could be used or combined in a suitable manner, if a single physical species was deemed to be insufficient, to obtain the appropriate calculated spectral energy pattern to achieve a desired reaction pathway and/or desired reaction rate. Such catalysts can be used alone, in combination with other physical catalysts, spectral energy catalysts, controlled environmental reaction conditions and/or spectral environmental reaction conditions to achieve a desired resultant energy pattern and consequent reaction pathway and/or desired reaction rate.

Similarly, the invention also provides a method for determining desirable physical catalysts (e.g., comprising previously known materials or materials not previously known to function as a physical catalyst) which can be utilized in a cell reaction system by appropriately conditioning at least one conditionable participant to achieve a desired reaction pathway and/or desired reaction rate and/or desired reaction product when the conditioned participant becomes involved with (e.g., is added to or activated in) the cell reaction system. In this regard, the invention may be able to provide a recipe for a physical and/or spectral catalyst for a particular cell reaction system where no physical catalyst previously existed. In this embodiment of the invention, spectral energy conditioning patterns are determined or calculated by the techniques of the invention and corresponding conditionable participants can be supplied or manufactured and thereafter included in the conditioning reaction system to generate the calculated required spectral energy patterns in a conditioned participant. In certain cases, one or more existing physical species of a conditionable participant could be used or combined in a suitable manner, if a single physical species was deemed to be insufficient, to obtain the appropriate calculated spectral energy conditioned pattern to achieve a desired reaction pathway and/or desired reaction rate. Such conditioned participants, can be used alone, in combination with other physical catalysts, spectral energy catalysts, spectral energy catalysts, controlled environmental reaction conditions, spectral environmental reaction conditions and/or spectral environmental reaction conditions to achieve a desired reaction pathway and/or desired reaction rate. Thus, once a desired conditioned energy pattern is achieved in a conditioned participant, the conditioned participant becomes involved with, and/or activated in, the cell reaction system.

The invention discloses many different permutations of one important theme of the invention, namely, that when frequencies of participants in a cell reaction system match, or can be made to match, such as, by conditioning at least one conditionable participant, energy transfers between the components, participants or conditioned participants in the cell reaction system. It should be understood that these many different permutations can be used alone to achieve desirable results (e.g., desired reaction pathways and/or a desired reaction rates and/or desired reaction products) or can be used in a limitless combination of permutations, to achieve desired results (e.g., desired reaction pathways, desired reaction products and/or desired reaction rates). However, in a first preferred embodiment of the invention, so long as a participant, or conditioned participant, has one or more of its frequencies that match with at least one frequency of at least one other participant in a cell reaction system (e.g., spectral patterns overlap), energy can be transferred. If energy is transferred in this targeted manner, desirable interactions, reactions, and/or energy dynamics can result in the cell reaction system, such as increased energy amplitude in key components of one or more reactions in the holoreaction system. Further, the conditioned participant may itself comprise both a reactant and a reaction product, whereby, for example, the chemical composition of the conditioned participant does not substantially change (if at all) but one or more physical properties or structures or phases is changed once the conditioned participant is involved with, and/or activated by, the cell reaction system.

Further, the same targeted frequency or energy can be used with different power amplitudes, in the same holoreaction system, to achieve dramatically different results. For example, the vibrational frequency of a liquid solvent may be input at low power amplitudes to improve the solvent properties of the liquid without causing any substantial change in the chemical composition of the liquid. At higher power levels, the same vibrational frequency can be used to dissociate the liquid solvent, thereby changing its chemical composition. Thus, there is a continuum of effects that can be obtained with a single targeted frequency, ranging from changes in the energy dynamics of a participant, to changes in the actual chemical or physical structure of a participant.

Moreover, the concept of frequencies matching can also be used in the reverse. Specifically, if a reaction in a cell reaction system is occurring because frequencies match, the reaction can be slowed or stopped by causing the frequencies to no longer match or at least match to a lesser degree. In this regard, one or more cell reaction system components (e.g., environmental reaction condition, spectral environmental reaction condition and/or an applied spectral energy pattern) can be modified and/or applied so as to minimize, reduce or eliminate frequencies from matching. This also permits reactions to be started and stopped with ease providing for novel control in a myriad of reactions in a cell reaction system including preventing the formation of certain species, controlling the amount of product formed in a cell reaction system, etc. Further, if a source of, for example, electromagnetic radiation includes a somewhat larger spectrum of wavelengths or frequencies (i.e., energies) than those which are needed to optimize (or prevent) a particular reaction in a cell reaction system, then some of the unnecessary (or undesirable) wavelengths can be prevented from coming into contact with the cell reaction system (e.g., can be blocked, reflected, absorbed, etc.) by an appropriate filtering, absorbing and/or reflecting technique as discussed in greater detail later herein.

Moreover, the concept of frequencies matching can also be used in the reverse for conditionable participants. Specifically, if a reaction is occurring because frequencies match, the reaction can be slowed or stopped by causing the frequencies to no longer match or at least match to a lesser degree. In this regard, one or more cell reaction system components (e.g., environmental reaction condition, spectral environmental reaction condition and/or an applied spectral energy pattern) can be modified by introducing a conditionable participant, once conditioned, so as to minimize, reduce or eliminate frequencies from matching in the cell reaction system. This also permits reactions to be started and stopped with ease providing for novel control in a myriad of reactions in a cell reaction system including preventing the formation of certain species, controlling the amount of product formed in a cell reaction system, etc. Further, if a source of, for example electromagnetic radiation includes a somewhat larger spectrum of wavelengths or frequencies (i.e., energies) than those which are needed to optimize (or prevent) a particular reaction in a cell reaction system, then some of the unnecessary (or undesirable) wavelengths can be prevented from coming into contact with the cell reaction system (e.g., can be blocked, reflected, absorbed, etc.) by an appropriate filtering, absorbing and/or reflecting technique as discussed in greater detail later herein.

It should also be apparent that various conditionable participants, once conditioned, can be used in combination with various participants and/or spectral energy providers in a cell reaction system to control numerous reaction pathways.

Further, a conditionable participant may be conditioned by removing at least a portion of its spectral pattern prior to the conditionable participant being introduced into a cell reaction system.

To simplify the disclosure and understanding of the invention, specific categories or sections have been created in the "Summary of the Invention" and in the "Detailed Description of the Preferred Embodiments". However, it should be understood that these categories are not mutually exclusive and that some overlap exists. Accordingly, these artificially created sections should not be used in an effort to limit the scope of the invention defined in the appended claims.

Further, in the following Sections, attempts have been made to simplify discussions and reduce the overall length of this disclosure. For example, in many instances, "participants" in a cell reaction system or holoreaction system are exclusively referred to. However, it should be understood that "conditionable participants" could also be separately addressed in the disclosure, even though not always expressly referred to herein. Thus, when the various general mechanisms of the invention are referred to herein, even if reference is made directly or indirectly to "participants" only, it should be understood that the discussion also applies to "conditionable participants" with similar relevancy. Efforts have been made throughout the disclosure to refer expressly to all of the novel phenomenon associated with conditionable participants only when required for clarification purposes.

I. Wave Energies

In general, thermal energy has traditionally been used to drive chemical reactions by applying heat and increasing the temperature of a reaction system. The addition of heat increases the kinetic (motion) energy of the chemical reactants. It has been believed that a reactant with more kinetic energy moves faster and farther, and is more likely to take part in a chemical reaction. Mechanical energy likewise, by stirring and moving the chemicals, increases their kinetic energy and thus their reactivity. The addition of mechanical energy often increases temperature, by increasing kinetic energy.

Acoustic energy is applied to chemical reactions as orderly mechanical waves. Because of its mechanical nature, acoustic energy can increase the kinetic energy of chemical reactants, and can also elevate their temperature(s). Electromagnetic (EM) energy consists of waves of electric and magnetic fields. EM energy may also increase the kinetic energy and heat in reaction systems. It also may energize electronic orbitals or vibrational motion in some reactions.

Both acoustic and electromagnetic energy consist of waves. Energy waves and frequency have some interesting properties, and may be combined in some interesting ways. The manner in which wave energy transfers and combines, depends largely on the frequency. For example, when two waves of energy, each having the same amplitude, but one at a frequency of 400 Hz and the other at 100 Hz are caused to interact, the waves will combine and their frequencies will add, to produce a new frequency of 500 Hz (i.e., the "sum" frequency). The frequency of the waves will also subtract when they combine to produce a frequency of 300 Hz (i.e., the "difference" frequency). All wave energies typically add and subtract in this manner, and such adding and subtracting is referred to as heterodyning. Common results of heterodyning are familiar to most as harmonics in music. The importance of heterodyning will be discussed in greater detail later herein.

Another concept important to the invention is wave interactions or interference. In particular, wave energies are known to interact constructively and destructively. These phenomena are important in determining the applied spectral energy pattern. FIGS. 1a-1c show two different incident sine waves 1 (FIG. 1a) and 2 (FIG. 1b) which correspond to two different spectral energy patterns having two different wavelengths $\lambda_1$ and $\lambda_2$ (and thus different frequencies) which could be applied to a cell reaction system. Assume arguendo that the energy pattern of FIG. 1a corresponds to an electromagnetic spectral pattern (or an electromagnetic spectral conditioning pattern) and that FIG. 1b corresponds to one spectral environmental reaction condition (or a spectral conditioning environmental reaction condition). Each of the sine waves 1 and 2 has a different differential equation which describes its individual motion. However, when the sine waves are combined into the resultant additive wave 1+2 (FIG. 1c), the resulting complex differential equation, which describes the totality of the combined energies (i.e., the applied spectral energy pattern; or the applied spectral energy conditioning pattern) actually results in certain of the input energies being high (i.e., constructive interference shown by a higher amplitude) at certain points in time, as well as being low (i.e., destructive interference shown by a lower amplitude) at certain points in time.

Specifically, the portions "X" represent areas where the electromagnetic spectral pattern of wave 1 has constructively interfered with the spectral environmental reaction condition wave 2, whereas the portions "Y" represent areas where the two waves 1 and 2 have destructively interfered. Depending upon whether the portions "X" corresponds to desirable or undesirable wavelengths, frequencies or energies (e.g., causing the applied spectral energy pattern (or the applied spectral energy conditioning pattern) to have positive or negative interactions with, for example, one or more participants and/or components in the cell reaction system), then the portions "X" could enhance a positive effect in the cell reaction system or could enhance a negative effect in the cell reaction system. Similarly, depending on whether the portions "Y" correspond to desirable or undesirable wavelengths, frequencies, or energies, then the portions "Y" may correspond to the effective loss of either a positive or negative effect.

Further, if a source of, for example, electromagnetic radiation includes a somewhat larger spectrum of wavelengths or frequencies (i.e., energies) than those which are needed to optimize a particular reaction, then some of the unnecessary (or undesirable) wavelengths can be prevented from coming into contact with the cell reaction system (e.g., blocked, reflected, absorbed, etc.). Accordingly in the simplified example discussed immediately above, by permitting only desirable wavelengths $\lambda_1$ to interact in a cell reaction system (e.g., filtering out certain wavelengths or frequencies of a broader spectrum electromagnetic emitter) the possibilities of negative effects resulting from the combination of waves 1 (FIG. 1a) and 2 (FIG. 1b) would be minimized or eliminated. In this regard, it is noted that in practice many desirable incident wavelengths can be made to be incident on at least a portion of a cell reaction system. Moreover, it should also be clear that positive or desirable effects include, but are not limited to, those effects resulting from an interaction (e.g., heterodyne, resonance, additive wave, subtractive wave, constructive or destructive interference) between a wavelength or frequency of incident light and a wavelength (e.g., atomic and/or molecular, etc.), frequency or property (e.g., Stark effects, Zeeman effects, etc.) inherent to the cell reaction system itself. Thus, by maximizing the desirable wavelengths (or minimizing undesirable wavelengths), cell reaction system efficiencies never before known can be achieved. Alternatively stated, certain destructive interference effects resulting from the combinations of different energies, frequencies and/or wavelengths can reduce certain desirable results in a cell reaction system. The present invention attempts to mask or screen (e.g., filter) as many of such undesirable energies (or wavelengths) as possible (e.g., when a somewhat larger spectrum of wavelengths is available to be incident on a cell reaction system) from becoming incident on a cell reaction system and thus strive for, for example, the synergistic results that can occur due to, for example, desirable constructive interference effects between the incident wavelengths of, for example, electromagnetic energy.

It should be clear from this particular analysis that constructive interferences (i.e., the points "X") could, for example, maximize both positive and negative effects in a cell reaction system. Accordingly, this simplified example shows that by combining, for example, certain frequencies from a spectral pattern (or a spectral conditioning pattern) with one or more other frequencies from, for example, at least one spectral environmental reaction condition (or at least one spectral environmental conditioning reaction condition), that the applied spectral energy pattern (or applied spectral energy conditioning pattern) that is actually applied to the cell reaction system can be a combination of constructive and destructive interference(s). The degree of interference can also depend on the relative phases of the waves. Accordingly, these factors should also be taken into account when choosing appropriate spectral energy patterns (or applied spectral energy conditioning patterns) that are to be applied to a cell reaction system. In this regard, it is noted that in practice many desirable incident wavelengths can be applied to a cell reaction system or undesirable incident wavelengths removed from a source which is incident upon at least a portion of a cell reaction). Moreover, it should also be clear that wave interaction effects include, but are not limited to, heterodyning, direct resonance, indirect resonance, additive waves, subtractive waves, constructive or destructive interference, etc. Further, as discussed in detail later herein, additional effects such as electric effects and/or magnetic field effects can also influence spectral energy patterns or spectral energy conditioning patterns (e.g., spectral patterns or spectral conditioning patterns).

II. Spectral Catalysts, Spectral Conditioning Catalysts and Spectroscopy

A wide variety of reactions can be advantageously affected and directed with the assistance of a spectral energy catalyst (or spectral energy conditioning catalyst) having a specific spectral energy pattern (e.g., spectral pattern or electromagnetic pattern) which transfers targeted energy to initiate, control and/or promote desirable reaction pathways (e.g., desirable reaction pathways in a single or multiple component cell reaction system) and/or desirable reaction rates within a cell reaction system. This section discusses spectral catalysts (and spectral conditioning catalysts) in more detail and explains various techniques for using spectral catalysts (and/or spectral conditioning catalysts) in various cell reaction systems (and holoreaction systems). For example, a spectral catalyst can be used in a cell reaction system to replace and provide the additional energy normally supplied by a physical catalyst. The spectral catalyst can actually mimic or copy the mechanisms of action of a physical catalyst. The spectral catalyst can act as both a positive catalyst to increase the rate of a reaction or as a negative catalyst or poison to decrease the rate of reaction. Furthermore, the spectral catalyst can augment a physical catalyst by utilizing both a physical catalyst and a spectral catalyst to achieve, for example a desired reaction pathway in a cell reaction system. The spectral catalyst can improve the activity of a physical chemical catalyst. Also, the spectral catalyst can partially replace a specific quantity or amount of the physical catalyst, thereby reducing and/or eliminating many of the difficulties associated with, various processing difficulties in numerous reactions.

Moreover, a conditionable participant can be conditioned by a spectral conditioning catalyst to form a conditioned participant which can thereafter be used in a cell reaction system, alone or in combination with a spectral catalyst. The spectral conditioning catalyst can energize a conditionable participant to result in a conditioned participant which can likewise, for example, replace, augment or otherwise provide additional energy normally provided by a physical catalyst in a cell reaction system, as discussed immediately above with regard to a spectral catalyst.

Further, in the present invention, the spectral energy catalyst provides targeted energy (e.g., electromagnetic radiation comprising a specific frequency or combination of frequencies), in a sufficient amount for a sufficient duration to initiate and/or promote and/or direct a chemical reaction (e.g., follow a particular reaction pathway). The total combination of targeted energy applied at any point in time to the cell reaction system is referred to as the applied spectral energy pattern. The applied spectral energy pattern may be comprised of a single spectral catalyst, multiple spectral catalysts and/or other spectral energy catalysts as well. With the absorption of targeted energy into a cell reaction system (e.g., electromagnetic energy from a spectral catalyst), a reactant may be caused to proceed through one or several reaction pathways including: energy transfer which can, for example, excite electrons to higher energy states for initiation of chemical reaction, by causing frequencies to match; ionize or dissociate reactants which may participate in a chemical reaction; stabilize reaction products; energize and/or stabilize intermediates and/or transients and/or activated complexes that participate in a cell reaction pathway; cause one or more components in a cell reaction system to have spectral patterns which at least partially overlap; altered energy dynamics of one or more components causing them to have altered properties and/or altered resonant exchange of energy, within the holoreaction system.

Moreover, in the present invention, the spectral energy conditioning catalyst provides targeted conditioning energy (e.g., electromagnetic radiation comprising a specific frequency or combination of frequencies), in a sufficient amount for a sufficient duration to condition a conditionable participant to form a conditioned participant and to permit the conditioned participant to initiate and/or promote and/or direct a chemical reaction (e.g., follow a particular reaction pathway) once the conditioned participant is initiated or activated in the cell reaction system. The total combination of targeted conditioning energy applied at any point in time to the conditioning reaction system is referred to as the applied spectral energy conditioning pattern. The applied spectral energy conditioning pattern may be comprised of a single spectral conditioning catalyst, multiple spectral conditioning catalysts and/or other spectral energy conditioning catalysts. With the absorption of targeted conditioning energy into a conditioning reaction system (e.g., electromagnetic energy from a spectral conditioning catalyst), a conditioned participant may cause one or more reactants in a cell reaction system to proceed through one or several reaction pathways including:

energy transfer which can for example, excite electrons to higher energy states for initiation of chemical reaction, by causing frequencies to match; ionize or dissociate reactants which may participate in a chemical reaction; stabilize reaction products; energize and/or stabilize intermediates and/or transients and/or activated complexes that participate in a reaction pathway; cause one or more components in a cell reaction system to have spectral patterns which at least partially overlap; alter the energy dynamics of a component to affect its properties; and/or alter the resonant exchange of energy within a holoreaction system.

For example, in a simple cell reaction system, if a chemical reaction provides for at least one reactant "A" to be converted into at least one reaction product "B", a physical catalyst "C" (or a conditioned participant "C") may be utilized. In contrast, a portion of the catalytic spectral energy pattern (e.g., in this section the catalytic spectral pattern) of the physical catalyst "C" may be applied in the form of, for example, an electromagnetic beam (as discussed elsewhere herein) to catalyze the cell reaction.

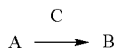

Substances A and B=unknown frequencies, and C=30 Hz;

Therefore, Substance A+30 HZ→Substance B.

In the present invention, for example, the spectral pattern (e.g., electromagnetic spectral pattern) of the physical catalyst "C" can be determined by known methods of spectroscopy. Utilizing spectroscopic instrumentation, the spectral pattern of the physical catalyst is preferably determined under conditions approximating those occurring in the cell reaction system using the physical catalyst (e.g., spectral energy patterns as well as spectral patterns can be influenced by environmental reaction conditions, as discussed later herein).

Spectroscopy in general deals with the interaction of wave energies with matter. Spectroscopy is a process in which, typically, the energy differences between allowed states of any system are measured by determining the frequencies of the corresponding electromagnetic energy which is either being absorbed or emitted. When photons interact with, for example, atoms or molecules, changes in the properties of atoms and molecules are observed.

Atoms and molecules are associated with several different types of motion. The entire molecule rotates, the bonds vibrate, and even the electrons move, albeit so rapidly that electron density distributions have historically been the primary focus of the prior art. Each of these kinds of motion is quantified. That is, the atom, molecule or ion can exist only in distinct states that correspond to discrete energy amounts. The energy difference between the different quantum states depends on the type of motion involved. Thus, the frequency of energy required to bring about a transition is different for the different types of motion. That is, each type of motion corresponds to the absorption of energy in different regions of the electromagnetic spectrum and different spectroscopic instrumentation may be required for each spectral region. The total motion energy of an atom or molecule may be considered to be at least the sum of its electronic, vibrational and rotational energies.

In both emission and absorption spectra, the relation between the energy change in the atom or molecule and the frequency of the electromagnetic energy emitted or absorbed is given by the so-called Bohr frequency condition:

$$\Delta E = h\nu$$

where h is Planck's constant; ν is the frequency; and ΔE, is the difference of energies in the final and initial states.

Electronic spectra are the result of electrons moving from one electronic energy level to another in an atom, molecule or ion. A molecular physical catalyst's spectral pattern includes not only electronic energy transitions but also may involve transitions between rotational and vibrational energy levels. As a result, the spectra of molecules are much more complicated than those of atoms. The main changes observed in the atoms or molecules after interaction with photons include excitation, ionization and/or rupture of chemical bonds, all of which may be measured and quantified by spectroscopic methods including emission or absorption spectroscopy which give the same information about energy level separation.

In emission spectroscopy, when an atom or molecule is subjected to a flame or an electric discharge, such atoms or molecules may absorb energy and become "excited." On their return to their "normal" state they may emit radiation. Such an emission is the result of a transition of the atom or molecule from a high energy or "excited" state to one of lower state. The energy lost in the transition is emitted in the form of electromagnetic energy. "Excited" atoms usually produce line spectra while "excited" molecules tend to produce band spectra.

In absorption spectroscopy, the absorption of nearly monochromatic incident radiation is monitored as it is swept over a range of frequencies. During the absorption process the atoms or molecules pass from a state of low energy to one of high energy. Energy changes produced by electromagnetic energy absorption occur only in integral multiples of a unit amount of energy called a quantum, which is characteristic of each absorbing species. Absorption spectra may be classified into four types: rotational; rotation-vibration; vibrational; and electronic.

The rotational spectrum of a molecule is associated with changes which occur in the rotational states of the molecule. The energies of the rotational states differ only by a relatively small amount, and hence, the frequency which is necessary to effect a change in the rotational levels is very low and the wavelength of electromagnetic energy is very large. The energy spacing of molecular rotational states depends on bond distances and angles. Pure rotational spectra are observed in the far infrared and microwave and radio regions (See Table 1).

Rotation-vibrational spectra are associated with transitions in which the vibrational states of the molecule are altered and may be accompanied by changes in rotational states. Absorption occurs at higher frequencies or shorter wavelength and usually occurs in the middle of the infrared region (See Table 1).

Vibrational spectra from different vibrational energy levels occur because of motion of bonds. A stretching vibration involves a change in the interatomic distance along the axis of the bond between two atoms. Bending vibrations are characterized by a change in the angle between two bonds. The vibrational spectra of a molecule are typically in the near-infrared range. It should be understood that the term vibrational spectra means all manner of bond motion spectra including, but not limited to, stretching, bending, librational, translational, torsional, etc.

Electronic spectra are from transitions between electronic states for atoms and molecules and are accompanied by simultaneous changes in the rotational and vibrational states in molecules. Relatively large energy differences are involved, and hence absorption occurs at rather large frequencies or relatively short wavelengths. Different electronic states of atoms or molecules correspond to energies in the infrared, ultraviolet-visible or x-ray region of the electromagnetic spectrum (see Table 1).

It should be understood that not all molecules absorb and emit electromagnetic energy at the same frequencies. For example, materials with color centers may absorb electromagnetic waves at one frequency, and emit them at a different frequency.

TABLE 1

Approximate Boundaries

| Region Name | Energy, J | Wavelength | Frequency, Hz |
|---|---|---|---|
| X-ray | $2 \times 10^{-14}$-$2 \times 10^{-17}$ | 10-2-10 nm | $3 \times 10^{19}$-$3 \times 10^{16}$ |
| Vacuum Ultraviolet | $2 \times 10^{-17}$-$9.9 \times 10^{-19}$ | 10-200 nm | $3 \times 10^{16}$-$1.5 \times 10^{15}$ |
| Near ultraviolet | $9.9 \times 10^{-19}$-$5 \times 10^{-19}$ | 200-400 nm | $1.5 \times 10^{15}$-$7.5 \times 10^{14}$ |
| Visible | $5 \times 10^{-19}$-$2.5 \times 10^{-19}$ | 400-800 nm | $7.5 \times 10^{14}$-$3.8 \times 10^{14}$ |
| Near Infrared | $2.5 \times 10^{-19}$-$6.6 \times 10^{-20}$ | 0.8-2.5 um | $3.8 \times 10^{14}$-$1 \times 10^{14}$ |
| Fundamental Infrared | $6.6 \times 10^{-20}$-$4 \times 10^{-21}$ | 2.5-50 um | $1 \times 10^{14}$-$6 \times 10^{12}$ |
| Far infrared | $4 \times 10^{-21}$-$6.6 \times 10^{-22}$ | 50-300 um | $6 \times 10^{12}$-$1 \times 10^{12}$ |
| Microwave | $6.6 \times 10^{-22}$-$4 \times 10^{-25}$ | 0.3 mm-0.5 m | $1 \times 10^{12}$-$6 \times 10^{8}$ |
| Radiowave | $4 \times 10^{-25}$-$6.6 \times 10^{-34}$ | 0.5-300 $\times 10^{6}$ m | $6 \times 10^{8}$-1 |

Electromagnetic radiation as a form of energy can be absorbed or emitted, and therefore many different types of electromagnetic spectroscopy may be used in the present invention to determine a desired spectral pattern of a spectral catalyst (e.g., a spectral pattern of a physical catalyst) including, but not limited to, x-ray, ultraviolet, infrared, microwave, atomic absorption, flame emissions, atomic emissions, inductively coupled plasma, DC argon plasma, arc-source emission, spark-source emission, high-resolution laser, radio, Raman and the like.

In order to study the electronic transitions, the material to be studied may need to be heated to a high temperature, such as in a flame, where the molecules are atomized and excited. Another very effective way of atomizing gases is the use of gaseous discharges. When a gas is placed between charged electrodes, causing an electrical field, electrons are liberated from the electrodes and from the gas atoms themselves and may form a plasma or plasma-like conditions. These electrons will collide with the gas atoms which will be atomized, excited or ionized. By using high frequency fields, it is possible to induce gaseous discharges without using electrodes. By varying the field strength, the excitation energy can be varied. In the case of a solid material, excitation by electrical spark or arc can be used. In the spark or arc, the material to be analyzed is evaporated and the atoms are excited.

The basic scheme of an emission spectrophotometer includes a purified silica cell containing the sample which is to be excited. The radiation of the sample passes through a slit and is separated into a spectrum by means of a dispersion element. The spectral pattern can be detected on a screen, photographic film or by a detector.

Typically, an atom will most strongly absorb electromagnetic energy at the same frequencies it emits. Measurements of absorption are often made so that electromagnetic radiation that is emitted from a source passes through a wavelength-limiting device, and impinges upon the physical catalyst sample that is held in a cell. When a beam of white light passes through a material, selected frequencies from the beam are absorbed. The electromagnetic radiation that is not absorbed by the physical catalyst passes through the cell and strikes a detector. When the remaining beam is spread out in a spectrum, the frequencies that were absorbed show up as dark lines in the otherwise continuous spectrum. The position of these dark lines correspond exactly to the positions of lines in an emission spectrum of the same molecule or atom. Both emission and absorption spectrophotometers are available through regular commercial channels.

In 1885, Balmer discovered that hydrogen vibrates and produces energy at frequencies in the visible light region of the electromagnetic spectrum which can be expressed by a simple formula:

$$1/\lambda = R(½^2 - 1/m^2)$$

when $\lambda$ is the wavelength of the light, R is Rydberg's constant and m is an integer greater than or equal to 3 (e.g., 3, 4, or 5, etc.). Subsequently, Rydberg discovered that this equation could be adapted to result in all the wavelengths in the hydrogen spectrum by changing the $½^2$ to $1/n^2$, as in, $$1/\lambda = R(1/n^2 - 1/m^2)$$

where n is an integer $\geq 1$, and m is an integer $\geq n+1$. Thus, for every different number n, the result is a series of numbers for wavelength, and the names of various scientists were assigned to each such series which resulted. For instance, when n=2 and m$\geq$3, the energy is in the visible light spectrum and the series is referred to as the Balmer series. The Lyman series is in the ultraviolet spectrum with n=1, and the Paschen series is in the infrared spectrum with n=3.

In the prior art, energy level diagrams were the primary means used to describe energy levels in the hydrogen atom (see FIGS. 7a and 7b).

After determining the electromagnetic spectral pattern of a desired catalyst (e.g., a physical catalyst), the catalytic spectral pattern may be duplicated, at least partially, and applied to the cell reaction system. Any generator of one or more frequencies within an acceptable approximate range of, for example, frequencies of electromagnetic radiation may be used in the present invention. When duplicating one or more frequencies of, for example, a spectral pattern (or a spectral conditioning pattern), it is not necessary to duplicate the frequency exactly. For instance, the effect achieved by a frequency of 1,000 THz, can also be achieved by a frequency very close to it, such as 1,001 or 999 THz. Thus, there will be a range above and below each exact frequency which will also catalyze a reaction. Specifically, FIG. 12 shows a typical bell-curve "B" distribution of frequencies around the desired frequency $f_0$, wherein desirable frequencies can be applied which do not correspond exactly to $f_0$, but are close enough to the frequency $f_0$ to achieve a desired effect, such as those frequencies between and including the frequencies within the range of $f_1$ and $f_2$. Note that $f_1$ and $f_2$ correspond to about one half the maximum amplitude, $a_{max}$, of the curve "B". Thus, whenever the term "exact" or specific reference to "frequency" or the like is used, it should be understood to have this meaning. In addition, harmonics of spectral catalyst (or spectral conditioning catalyst) frequencies, both above and below the exact spectral catalyst frequency (or spectral conditioning catalyst frequency), will cause sympathetic resonance with the exact frequency and will catalyze the reaction. Finally, it is possible to catalyze reactions by duplicating one or more of the mechanisms of action of the exact frequency, rather than using the exact frequency itself. For example, platinum catalyzes the formation of water from hydrogen and oxygen, in part, by energizing the hydroxyl radical at its frequency of roughly 1,060 THz. The desired reaction can also be catalyzed by energizing the hydroxy radical with its microwave frequency, thereby duplicating platinum's mechanism of action.

An electromagnetic radiation-emitting source should have the following characteristics: high intensity of the desired wavelengths; long life; stability; and the ability to emit the electromagnetic energy in a pulsed and/or continuous mode. Moreover, in certain cell reaction systems, it may be desirable for the electromagnetic energy emitted to be capable of being directed to an appropriate point (or area) within at least a portion of the cell reaction system. Suitable techniques include optical waveguides, optical fibers, etc.

Irradiating sources can include, but are not limited to, arc lamps, such as xenon-arc, hydrogen and deuterium, krypton-arc, high-pressure mercury, platinum, silver; plasma arcs, discharge lamps, such as As, Bi, Cd, Cs, Ge, Hg, K, Na, P, Pb, Rb, Sb, Se, Sn, Ti, Tl and Zn; hollow-cathode lamps, either single or multiple elements such as Cu, Pt, and Ag; and sunlight and coherent electromagnetic energy emissions, such as masers and lasers. A more complete list of irradiating sources are listed in Table D.

Masers are devices which amplify or generate electromagnetic energy waves with great stability and accuracy. Masers operate on the same principal as lasers, but produce electromagnetic energy in the radio and microwave, rather than visible range of the spectrum. In masers, the electromagnetic energy is produced by the transition of molecules between rotational energy levels.

Lasers are powerful coherent photon sources that produce a beam of photons having the same frequency, phase and direction, that is, a beam of photons that travel exactly alike. Accordingly, for example, the predetermined spectral pattern of a desired catalyst can be generated by a series or grouping of lasers producing one or more required frequencies.

Any laser capable of emitting the necessary electromagnetic radiation with a frequency or frequencies of the spectral energy provider may be used in the present invention. Lasers are available for use throughout much of the spectral range. They can be operated in either a continuous or a pulsed mode. Lasers that emit lines and lasers that emit a continuum may be used in the present invention. Line sources may include argon ion laser, ruby laser, the nitrogen laser, the Nd:YAG laser, the carbon dioxide laser, the carbon monoxide laser and the nitrous oxide-carbon dioxide laser. In addition to the spectral lines that are emitted by lasers, several other lines are available, by addition or subtraction in a crystal of the frequency emitted by one laser to or from that emitted by another laser. Devices that combine frequencies and may be used in the present invention include difference frequency generators and sum frequency mixers. Other lasers that may be used in this invention include, but are not limited to: crystal, such as $Al_2O_3$ doped with $Cr^{3+}$, $Y_3Al_5O_{12}$ doped with $Nd^{3+}$; gas, such as He—Ne, Kr-ion; glass, chemical, such as vibrationally excited HCL and HF; dye, such as Rhodamine 6G in methanol; and semiconductor lasers, such as $Ga_{1-x}Al_xAs$. Many models can be tuned to various frequency ranges, thereby providing several different frequencies from one instrument and applying them to the crystallization reaction system (See Examples in Table 2).

TABLE 2

SEVERAL POPULAR LASERS

| Medium | Type | Emitted wavelength, nm |
|---|---|---|
| Ar | Gas | 334, 351.1, 363.8, 454.5, 457.9, 465.8, 472.7, 476.5, 488.0, 496.5, 501.7, 514.5, 528.7 |
| Kr | Gas | 350.7, 356.4, 406.7, 413.1, 415.4, 468.0, 476.2, 482.5, 520.8, 530.9, 568.2, 647.1, 676.4, 752.5, 799.3 |
| He—Ne | Gas | 632.8 |
| He—Cd | Gas | 325.0, 441.6 |
| $N_2$ | Gas | 337.1 |
| XeF | Gas | 351 |
| KrF | Gas | 248 |
| ArF | Gas | 193 |
| Ruby | Solid | 693.4 |
| Nd:YAG | Solid | 266, 355, 532 |
| $Pb_{1-x}Cd_xS$ | Solid | $2.9 \times 10^3$-$2.6 \times 10^4$ |
| $Pb_{1-x}Se_x$ | Solid | $2.9 \times 10^3$-$2.6 \times 10^4$ |
| $Pb_{1-x}Sn_xSe$ | Solid | $2.9 \times 10^3$-$2.6 \times 10^4$ |
| Dyes | Liquid | 217-1000 |

The coherent light from a single laser or a series of lasers is simply brought to focus or introduced to the region of the cell reaction system where a desired reaction is to take place. The light source should be close enough to avoid a "dead space" in which the light does not reach the desired area in the cell reaction system, but far enough apart to assure complete incident-light absorption. Since ultraviolet sources generate heat, such sources may need to be cooled to maintain efficient operation. Irradiation time, causing excitation of one or more components in the cell reaction system, may be individually tailored for each reaction: some short-term for a continuous reaction with large surface exposure to the light source; or long light-contact time for other systems. In addition, exposure times and energy amplitudes or intensities may be controlled depending on the desired effect (e.g., altered energy dynamics, ionizations, bond rupture, etc.).

An object of this invention is to provide a spectral energy pattern (e.g., a spectral pattern of electromagnetic energy) to one or more reactants in a cell reaction system by applying at least a portion of (or substantially all of) a required spectral energy catalyst (e.g., a spectral catalyst) determined and calculated by, for example, waveform analysis of the spectral patterns of, for example, the reactant(s) and the reaction product(s). Accordingly, in the case of a spectral catalyst, a calculated electromagnetic pattern will be a spectral pattern or will act as a spectral catalyst to generate a preferred reaction pathway and/or preferred reaction rate. In basic terms, spectroscopic data for identified substances can be used to perform a simple waveform calculation to arrive at, for example, the correct electromagnetic energy frequency, or combination of frequencies, needed to catalyze a reaction. In simple terms,

A→B

Substance A=50 Hz, and Substance B=80 Hz

80 Hz–50 Hz=30 Hz:

Therefore, Substance A+30 Hz→Substance B.

The spectral energy pattern (e.g., spectral patterns) of both the reactant(s) and reaction product(s) can be determined. In the case of a spectral catalyst, this can be accomplished by the spectroscopic means mentioned earlier. Once the spectral patterns are determined (e.g., having a specific frequency or combination of frequencies) within an appropriate set of environmental reaction conditions, the spectral energy pattern(s) (e.g., electromagnetic conditioning spectral pattern(s)) of the spectral energy catalyst (e.g., spectral conditioning catalyst) can be determined. Using the spectral energy pattern (s) (e.g., spectral patterns) of the reactant(s) and reaction product(s), a waveform analysis calculation can determine the energy difference between the reactant(s) and reaction product(s) and at least a portion of the calculated spectral energy pattern (e.g., electromagnetic spectral pattern) in the form of a spectral energy pattern (e.g., a spectral pattern) of a spectral energy catalyst (e.g., a spectral catalyst) can be applied to the desired reaction in a cell reaction system to cause the desired reaction to follow along the desired cell reaction pathway. The specific frequency or frequencies of the calculated spectral energy pattern (e.g., spectral pattern) corresponding to the spectral energy catalyst (e.g., spectral catalyst) will provide the necessary energy input into the desired reaction in the cell reaction system to affect and initiate a desired reaction pathway.

Performing the waveform analysis calculation to arrive at, for example, the correct electromagnetic energy frequency or frequencies can be accomplished by using complex algebra, Fourier transformation or Wavelet Transforms, which is available through commercial channels under the trademark Mathematica® and supplied by Wolfram, Co. It should be noted that only a portion of a calculated spectral energy catalyst (e.g., spectral catalyst) may be sufficient to catalyze a reaction or a substantially complete spectral energy catalyst (e.g., spectral catalyst) may be applied depending on the particular circumstances.

In addition, at least a portion of the spectral energy pattern (e.g., electromagnetic pattern of the required spectral catalyst) may be generated and applied to the cell reaction system by, for example, the electromagnetic radiation emitting sources defined and explained earlier.

Another object of this invention is to provide a spectral energy conditioning pattern (e.g., a spectral conditioning pattern of electromagnetic energy) to one or more conditionable participants in a conditioning reaction system by applying at least a portion of (or substantially all of) a required spectral energy conditioning catalyst (e.g., a spectral conditioning catalyst) determined and calculated by, for example, waveform analysis of the spectral patterns of, for example, the conditionable participant, and the conditioned participant. Accordingly, in the case of a spectral conditioning catalyst, a calculated electromagnetic conditioning pattern will be a spectral conditioning pattern which, when applied to a conditionable participant, will permit the conditioned participant to act as a spectral catalyst to generate a preferred reaction pathway and/or preferred reaction rate in a cell reaction system. In basic terms, spectroscopic data for identified substances can be used to perform a simple waveform calculation to arrive at, for example, the correct electromagnetic energy frequency, or combination of frequencies, needed to catalyze a reaction. In simple terms,

A→B

Conditionable substance A=50 Hz, and Conditioned Substance B=80 Hz

80 Hz–50 Hz=30 Hz:

Therefore, Substance A+30 Hz→Substance B.

The spectral energy conditioning pattern (e.g., spectral conditioning pattern) of both the conditionable participant and the conditioned product can be determined. In the case of a spectral conditioning catalyst, this can be accomplished by the spectroscopic means mentioned earlier. Once the spectral patterns are determined (e.g., having a specific frequency or combination of frequencies) within an appropriate set of environmental reaction conditioning conditions, the spectral energy conditioning pattern(s) (e.g., electromagnetic spectral conditioning pattern(s)) of the spectral energy conditioning catalyst (e.g., spectral conditioning catalyst) can be determined. Using the spectral energy conditioning pattern(s) (e.g., spectral conditioning patterns) of the conditionable participant and the conditioned participant, a waveform analysis calculation can determine the energy difference between the reactant(s) and reaction product(s) and at least a portion of the calculated spectral energy conditioning pattern (e.g., electromagnetic spectral conditioning pattern) in the form of a spectral energy conditioning (e.g., a spectral conditioning pattern) of a spectral energy conditioning catalyst (e.g., a spectral conditioning catalyst) can be applied to the desired conditionable participant in a conditioning reaction system to subsequently result in the desired reaction in the cell reaction system, once the conditioned participant is introduced in the cell reaction system. The specific frequency or frequencies of the calculated spectral energy conditioning pattern (e.g., a spectral conditioning pattern) corresponding to the spectral energy conditioning catalyst (e.g., spectral conditioning catalyst) required to form a conditioned participant, will provide the necessary energy input into the desired reaction I the cell reaction system to affect and initiate a desired reaction pathway.

Performing the waveform analysis calculation to arrive at, for example, the correct electromagnetic energy frequency or frequencies can be accomplished by using complex algebra, Fourier transformation or Wavelet Transforms, which is available through commercial channels under the trademark Mathematica® and supplied by Wolfram, Co. It should be noted that only a portion of a calculated spectral energy conditioning catalyst (e.g., spectral conditioning catalyst) used to form a conditioned participant may be sufficient to catalyze a reaction or a substantially complete spectral energy conditioning catalyst (e.g., spectral conditioning catalyst) used to form a conditioned participant may be applied depending on the particular circumstances in a holoreaction system.

In addition, at least a portion of the spectral energy conditioning pattern (e.g., electromagnetic pattern of the required spectral catalyst) may be generated and applied to the conditioning reaction system by, for example, the electromagnetic radiation emitting sources defined and explained earlier.

The specific physical catalysts that may be replaced or augmented by a conditioned participant in the present invention may include any solid, liquid, gas or plasma catalyst, having either homogeneous or heterogeneous catalytic activity. A homogeneous physical catalyst is defined as a catalyst whose molecules are dispersed in the same phase as the reacting chemicals. A heterogeneous physical catalyst is defined as one whose molecules are not in the same phase as the reacting chemicals. In addition, enzymes which are considered biological catalysts are to be included in the present invention. Some examples of physical catalysts that may be replaced or augmented comprise both elemental and molecular catalysts, including, not limited to, metals, such as silver, platinum, nickel, palladium, rhodium, ruthenium and iron; semiconducting metal oxides and sulfides, such as $NiO_2$, Zn), MgO, $Bi_2O_3/MoO_3$, $TiO_2$, $SrTiO_3$, CdS, CdSe, SiC, GaP, $Wo_2$ and $Mgo_3$; copper sulfate; insulating oxides such as $Al_2O_3$, $SiO_2$ and MgO; and Ziegler-Natta catalysts, such as titanium tetrachloride, and trialkyaluminum.

III. Targeting

The frequency and wave nature of energy has been discussed herein. Additionally, Section I entitled "Wave Energies" disclosed the concepts of various potential interactions between different waves. The general concepts of "targeting", "direct resonance targeting", "harmonic targeting" and "non-harmonic heterodyne targeting" (all defined terms herein) build on these and other understandings.

Targeting has been defined generally as the application of a spectral energy provider (e.g., spectral energy catalyst, spectral catalyst, spectral energy pattern, spectral pattern, catalytic spectral energy pattern, catalytic spectral pattern, spectral environmental reaction conditions and applied spectral energy pattern) to a desired reaction in a cell reaction system. The application of these types of energies to a desired reaction can result in interaction(s) between the applied spectral energy provider(s) and matter (including all components thereof) in the cell reaction system. This targeting can result in at least one of direct resonance, harmonic resonance, and/or non-harmonic heterodyne resonance with at least a portion, for example, at least one form of matter in a cell reaction system. In this invention, targeting should be generally understood as meaning applying a particular spectral energy provider (e.g., a spectral energy pattern) to another entity comprising matter (or any component thereof) to achieve a particular desired result (e.g., desired reaction product and/or desired reaction product at a desired reaction rate). Further, the invention provides techniques for achieving such desirable results without the production of, for example, undesirable transients, intermediates, activated complexes and/or reaction products. In this regard, some limited prior art techniques exist which have applied certain forms of energies (as previously discussed) to various reactions. These certain forms of energies have been limited to direct resonance and harmonic resonance with some electronic frequencies and/or vibrational frequencies of some reactants. These limited forms of energies used by the prior art were due to the fact that the prior art lacked an adequate understanding of the spectral energy mechanisms and techniques disclosed herein. Moreover, it has often been the case in the prior art that at least some undesirable intermediate, transient, activated complex and/or reaction product was formed, and/or a less than optimum reaction rate for a desired reaction pathway occurred. The present invention overcomes the limitations of the prior art by specifically targeting, for example, various forms of matter in a cell reaction system (and/or components thereof), with, for example, an applied spectral energy pattern. Heretofore, such selective targeting of the invention was never disclosed or suggested. Specifically, at best, the prior art has been reduced to using random, trial and error or feedback-type analyses which, although may result in the identification of a single spectral catalyst frequency, such approach may be very costly and very time-consuming, not to mention potentially unreproducible under a slightly different set of reaction conditions. Such trial and error techniques for determining appropriate catalysts also have the added drawback, that having once identified a particular catalyst that works, one is left with no idea of what it means. If one wishes to modify the reaction, including simple reactions using size and shape, another trial and error analysis becomes necessary rather than a simple, quick calculation offered by the techniques of the present invention.

Accordingly, whenever use of the word "targeting" is made herein, it should be understood that targeting does not correspond to undisciplined energy bands being applied to a cell reaction system; but rather to well defined, targeted, applied spectral energy patterns, each of which has a particular desirable purpose in, for example, a reaction pathway to achieve a desired result and/or a desired result at a desired reaction rate.

IV. Conditioning Targeting

Conditioning targeting has been defined generally as the application of a spectral energy conditioning provider (e.g., spectral energy conditioning catalyst, spectral conditioning catalyst, spectral energy conditioning pattern, spectral conditioning pattern, catalytic spectral energy conditioning pattern, catalytic spectral conditioning pattern, spectral conditioning environmental reaction conditions and applied spectral energy conditioning pattern) to a conditionable participant to form at least one conditioned participant, prior to the conditioned participant becoming involved in (e.g., introduced into and/or activated in) a cell reaction system. The application of these types of conditioning energies to conditionable participants to form conditioned participants, prior to the conditioned participants being introduced to a cell reaction system, can result in interaction(s) between the conditioned participant matter, and the components(s) in the reaction system (including all components thereof) so that the conditioned matter can then initiate and/or direct desirable reaction pathways and/or desirable reaction rates within a cell reaction system. This conditioning targeting can result in at least one of direct conditioning resonance, harmonic conditioning resonance, and/or non-harmonic conditioning heterodyne resonance with at least a portion of, for example, at least one form of conditionable participant matter (of any form) to form conditioned participant matter, which is later introduced into, or activated in, a cell reaction system. In this invention, conditioning targeting should be generally understood as meaning applying a particular spectral energy conditioning provider (e.g., a spectral energy conditioning pattern) to another conditionable entity comprising conditionable matter (or any component thereof) to achieve a particular desired result (e.g., ultimately achieve a desired reaction product and/or desired reaction product at a desired reaction rate in the cell reaction system due to the conditioned matter being introduced into the cell reaction system.). It should be noted that introduction into the cell reaction system should not be construed as meaning only a physical introduction of a conditioned participant that has been conditioned in a conditioning reaction vessel, but should also be understood as meaning that a conditionable participant can be conditioned in situ in a reaction vessel (or the reaction vessel per se can be conditioned) and the cell reaction system is thereafter initiated, activated, or turned on (e.g., initiated by the application of, for example, temperature, pressure, etc.) once the conditioned participant is present in the reaction vessel. Thus, the invention provides techniques for achieving such desirable results without the production of, for example, undesirable transients, intermediates, activated complexes and/or reaction products by using a conditioned participant. In this regard, some limited prior art techniques exist which have applied certain forms of energies directly to cell reaction systems. These certain forms of energies directly applied to cell reaction systems have been limited to direct resonance and harmonic resonance with some electronic frequencies and/or vibrational frequencies of some reactants in the cell reaction system. These limited forms of energies used by the prior art were due to the fact that the prior art lacked an adequate understanding of the spectral energy mechanisms and techniques disclosed herein.

Moreover, it has often been the case in the prior art that at least some undesirable intermediate, transient, activated complex and/or reaction product was formed, and/or a less than optimum reaction rate for a desired reaction pathway occurred. The present invention overcomes the limitations of the prior art by specifically targeting, for example, various forms of conditionable matter (and/or components thereof) to form conditioned matter prior to the conditioned matter being involved with reactions in a cell reaction system. Heretofore, such selective conditioning targeting of the invention was never disclosed or suggested. Specifically, at best, the prior art has been reduced to using random, trial and error or feedback-type analyses in various reactions which, although may result in the identification of a single spectral energy conditioning provider, such approach may be very costly and very time-consuming, not to mention potentially unreproducible under a slightly different set of reaction conditions and further, not to mention the simplicity of the application of a conditioning energy to a conditionable participant that eventually becomes involved in a cell reaction system. Such trial and error techniques for determining appropriate conditioning providers also have the added drawback, that having once identified a particular conditioning provider that works, one is left with no idea of what it means. If one wishes to modify the reaction, including simple reactions using size and shape, another trial and error analysis becomes necessary rather than a simple, quick calculation offered by the techniques of the present invention.

Accordingly, whenever use of the word "conditioning targeting" is made herein, it should be understood that conditioning targeting does not correspond to undisciplined energy bands being applied to a conditionable participant to form a conditioned participant which then becomes involved in a cell reaction system; but rather to well defined, targeted, applied spectral energy conditioning patterns, each of which has a particular desirable purpose to form a conditioned participant so that the conditioned participant can, for example, permit a desired reaction pathway to be followed, and/or achieve a desired result and/or a desired result at a desired reaction rate in a cell reaction system. These results include conditioning targeting a single form of conditionable participant matter to form conditioned matter which, when such conditioned matter is activated or initiated in a cell reaction system, causes the conditioned matter to behave favorably, or conditioning targeting multiple forms of conditionable participant matter to achieve desirable results.

V. Environmental Reaction Conditions

Environmental reaction conditions are important to understand because they can influence, positively or negatively, reaction pathways in a cell reaction system. Traditional environmental reaction conditions include temperature, pressure, surface area of catalysts, catalyst size and shape, solvents, support materials, poisons, promoters, concentrations, electromagnetic radiation, electric fields, magnetic fields, mechanical forces, acoustic fields, reaction vessel size, shape and composition and combinations thereof, etc.

The following reaction can be used to discuss the effects of environmental reaction conditions which may need to be taken into account in order to cause the reaction to proceed along the simple reaction pathway shown below.

Specifically, in some instances, reactant A will not form into reaction product B in the presence of any catalyst C unless the environmental reaction conditions in the cell reaction system include certain maximum or minimum conditions of environmental reaction conditions such as pressure and/or temperature. In this regard, many reactions will not occur in the presence of a physical catalyst unless the environmental reaction conditions include, for example, an elevated temperature and/or an elevated pressure. In the present invention, such environmental reaction conditions should be taken into consideration when applying a particular spectral energy catalyst (e.g., a spectral catalyst). Many specifics of the various environmental reaction conditions are discussed in greater detail in the Section herein entitled "Description of the Preferred Embodiments".

VI. Conditioning Environmental Reaction Conditions

Conditioning environmental reaction conditions are also important to understand because they can also influence, positively or negatively, the energy dynamics and conditioning of a conditionable participant and can ultimately lead to different reaction pathways in a cell reaction system when a conditioned participant is introduced into, or activated, in the cell reaction system. The same traditional environmental reaction conditions listed above also apply here, namely temperature, pressure, surface area of catalysts, catalyst size and shape, solvents, support materials, poisons, promoters, concentrations, electromagnetic radiation, electric fields, magnetic fields, mechanical forces, acoustic fields, reaction vessel size, shape and composition and combinations thereof, etc.

In the present invention, such conditioning environmental reaction conditions should be taken into consideration when applying a particular spectral energy conditioning catalyst (e.g., a spectral conditioning catalyst) to a conditionable participant. Similar environmental considerations to those discussed above need to be taken into account when the conditioned participant is introduced into a cell reaction system. Many specifics of the various environmental and/or conditioning environmental reaction conditions are discussed in greater detail in the Section herein entitled "Description of the Preferred Embodiments".

VII. Spectral Environmental Reaction Conditions

If it is known that certain reaction pathways will not occur within a cell reaction system (or not occur at a desirable rate) even when a catalyst is present unless, for example, certain minimum or maximum environmental reaction conditions are present (e.g., the temperature and/or pressure is/are elevated), then an additional frequency or combination of frequencies (i.e., an applied spectral energy pattern) can be applied to the cell reaction system. In this regard, spectral environmental reaction condition(s) can be applied instead of, or to supplement, those environmental reaction conditions that are naturally present, or need to be present, in order for a desired reaction pathway and/or desired reaction rate to be followed. The environmental reaction conditions that can be supplemented or replaced with spectral environmental reaction conditions include, for example, temperature, pressure, surface area of catalysts, catalyst size and shape, solvents, support materials, poisons, promoters, concentrations, electric fields, magnetic fields, etc.

Still further, a particular frequency or combination of frequencies and/or fields that can produce one or more spectral environmental reaction conditions can be combined with one or more spectral energy catalysts and/or spectral catalysts to generate an applied spectral energy pattern which can be focussed on a particular area in a cell reaction system. Accordingly, various considerations can be taken into account for what particular frequency or combination of frequencies and/or fields may be desirable to combine with (or replace) various environmental reaction conditions, for example.

As an example, in a simple reaction, assume that a first reactant "A" has a frequency or simple spectral pattern of 3 THz and a second reactant "B" has a frequency or simple spectral pattern of 7 THz. At room temperature, no reaction occurs. However, when reactants A and B are exposed to high temperatures, their frequencies, or simple spectral patterns, both shift to 5 THz. Since their frequencies match, they transfer energy and a reaction occurs. By applying a frequency of 2 THz, at room temperature, the applied 2 THz frequency will heterodyne with the 3 THz pattern to result in, both 1 Thz and 5 THz heterodyned frequencies; while the applied frequency of 2 THz will heterodyne with the spectral pattern of 7 THz of reactant "B" and result in heterodyned frequencies of 5 THz and 9 THz in reactant "B". Thus, the heterodyned frequencies of 5 THz are generated at room temperature in each of the reactants "A" and "B". Accordingly, frequencies in each of the reactants match and thus energy can transfer between the reactants "A" and "B". When the energy can transfer between such reactants, all desirable reactions along a reaction pathway may be capable of being achieved. However, in certain reactions, only some desirable reactions along a reaction pathway are capable of being achieved by the application of a singular frequency. In these instances, additional frequencies and/or fields may need to be applied to result in all desirable steps along a reaction pathway being met, including but not limited to, the formation of all required reaction intermediates and/or transients.

Thus, by applying a frequency, or combination of frequencies and/or fields (i.e., creating an applied spectral energy pattern) which corresponds to at least one spectral environmental reaction condition, the spectral energy patterns (e.g., spectral patterns of, for example, reactant(s), intermediates, transients, catalysts, etc.) can be effectively modified which may result in broader spectral energy patterns (e.g., broader spectral patterns), in some cases, or narrower spectral energy patterns (e.g., spectral patterns) in other cases. Such broader or narrower spectral energy patterns (e.g., spectral patterns) may correspond to a broadening or narrowing of line widths in a spectral energy pattern (e.g., a spectral pattern). As stated throughout herein, when frequencies match, energy transfers. In this particular embodiment, frequencies can be caused to match by, for example, broadening the spectral pattern of one or more participants in a cell reaction system. For example, as discussed in much greater detail later herein, the application of temperature to a cell reaction system typically causes the broadening of one or more spectral patterns (e.g., line width broadening) of, for example, one or more reactants in the cell reaction system. It is this broadening of spectral patterns that can cause spectral patterns of one or more reactants to, for example, overlap. The overlapping of the spectral patterns can cause frequencies to match, and thus energy to transfer. When energy is transferred, reactions can occur. The scope of reactions which occur, include all of those reactions along any particular reaction pathway. Thus, the broadening of spectral pattern(s) can result in, for example, formation of reaction product, formation of and/or stimulation and/or stabilization of reaction intermediates and/or transients, catalyst frequencies, poisons, promoters, etc. All of the environmental reaction conditions that are discussed in detail in the section entitled "Detailed Description of the Preferred Embodiments" can be at least partially simulated in a cell reaction system by the application of a spectral environmental reaction condition.

Similarly, spectral patterns can be caused to become non-overlapping by changing, for example, at least one spectral environmental reaction condition, and thus changing the applied spectral energy pattern. In this instance, energy will not transfer (or the rate at which energy transfers can be reduced) and reactions will not occur (or the rates of reactions can be slowed).

Finally, by controlling spectral environmental reaction conditions, the energy dynamics within a holoreaction system may be controlled. For example, with a first spectral environmental reaction condition, a first set of frequencies may match and hence energy may transfer at a first set of energy levels and types. When the spectral environmental reacation condition is changed, a second set of frequencies may match, resulting in transfer of energy at different levels or types.

Spectral environmental reaction conditions can be utilized to start and/or stop reactions in a reaction pathway. Thus, certain reactions can be started, stopped, slowed and/or speeded up by, for example, applying different spectral environmental reaction conditions at different times during a reaction and/or at different intensities. Thus, spectral environmental reaction conditions are capable of influencing, positively or negatively, reaction pathways and/or reaction rates in a cell reaction system.

VIII. Spectral Conditioning Environmental Reaction Conditions

Similarly, spectral conditioning environmental reaction conditions considerations apply in a parallel manner in this section as well. Specifically, if it is known that certain conditioning of a conditioned participant will not occur (or not occur at a desirable rate), unless for example, certain minimum or maximum conditioning environmental reaction conditions are present (e.g., the temperature and/or pressure is/are elevated), then an additional frequency or combination of frequencies (i.e., an applied spectral energy conditioning pattern) can be applied to the conditionable participant. In this regard, spectral conditioning environmental reaction condition(s) can be applied instead of, or to supplement, those conditioning environmental reaction conditions that are naturally present, or need to be present, in order for a desired conditioning of a conditionable participant to occur (i.e., to form a desired conditioned participant). The conditioning environmental reaction conditions that can be supplemented or replaced with spectral conditioning environmental reaction conditions include, for example, temperature, pressure, surface area of catalysts, catalyst size and shape, solvents, support materials, poisons, promoters, concentrations, electric fields, magnetic fields, etc.

Still further, a particular frequency or combination of frequencies and/or fields that can produce one or more spectral conditioning environmental reaction conditions can be combined with one or more spectral energy conditioning catalysts and/or spectral conditioning catalysts to generate an applied spectral energy conditioning pattern. Accordingly, various considerations can be taken into account for what particular frequency or combination of frequencies and/or fields may be desirable to combine with (or replace) various conditioning environmental reaction conditions, for example.

Thus, by applying a frequency, or combination of frequencies and/or fields (i.e., creating an applied spectral energy conditioning pattern) which corresponds to at least one spectral environmental conditioning reaction condition, the spectral energy conditioning patterns of a conditionable participant can be effectively modified which may result in broader spectral energy conditioning patterns (e.g., broader spectral conditioning patterns), in some cases, or narrower spectral energy conditioning patterns (e.g., spectral conditioning patterns) in other cases. Such broader or narrower spectral energy patterns (e.g., spectral conditioning patterns) may correspond to a broadening or narrowing of line widths in a spectral conditioning energy pattern (e.g., a spectral conditioning pattern). As stated throughout herein, when frequencies match, energy transfers. In this particular embodiment, frequencies can be caused to match by, for example, broadening the spectral conditioning pattern of one or more participants in a cell reaction system. For example, as discussed in much greater detail later herein, the application of temperature to a conditioning reaction system typically causes the broadening of one or more spectral conditioning patterns (e.g., line width broadening) of, for example, one or more conditionable participants in a conditioning reaction system. It is this broadening of spectral conditioning patterns that can cause spectral conditioning patterns of one or more constituents in a conditioning reaction system to, for example, overlap. The overlapping of the spectral conditioning patterns can cause frequencies to match, and thus energy to transfer to result in a conditioned participant. The same conditionable participant may be conditioned with different spectral energy patterns or amounts to result in conditioned participants with different energy dynamics (e.g., energized electronic level versus energized rotation). The scope of reactions which occur once a conditioned participant is introduced into a cell reaction system, include all of those reactions along any particular reaction pathway. Thus, the broadening of spectral conditioned pattern(s) in a conditioned participant can result in, for example, formation of reaction product, formation of and/or stimulation and/or stabilization of reaction intermediates and/or transients, catalyst frequencies, poisons, promoters, etc., in a cell reaction system. All of the conditioning environmental reaction conditions that are discussed in detail in the section entitled "Detailed Description of the Preferred Embodiments" can be at least partially simulated in a conditioning reaction system by the application of a spectral conditioning environmental reaction condition.

Spectral conditioning environmental reaction conditions can be utilized to start direct, contain and/or appropriately condition a conditionable participant so that the conditioned participant can stop reactions or reaction pathways in a cell reaction system. Thus, certain reactions can be started, stopped, slowed and/or speeded up in a cell reaction system by, for example, applying different spectral conditioning environmental reaction conditions to a conditionable participant and introducing the conditioned participant into a cell reaction system at different times during a reaction and/or at different intensities. Thus, spectral conditioning environmental reaction conditions are capable of influencing, positively or negatively, reaction pathways and/or reaction rates in a cell reaction system by providing different spectral energy patterns in one or more conditioned participants.

IX. Designing Physical and Spectral Catalysts

Moreover, by utilizing the above techniques to design (e.g., calculate or determine) a desirable spectral energy pattern, such as a desirable spectral pattern for a spectral energy catalyst rather than applying the spectral energy catalyst (e.g., spectral catalyst) per se, for example, the designed spectral pattern can be used to design and/or determine an optimum physical and/or spectral catalyst that could be used in the cell reaction system to obtain a particular result. Further, the invention may be able to provide a recipe for a physical and/or spectral catalyst for a particular cell reaction where no catalyst previously existed. For example in a reaction where:

where A=reactant, B=product and I=known intermediate, and there is no known catalyst, either a physical or spectral catalyst could be designed which, for example, resonates with the intermediate "I", thereby catalyzing the formation of one or more desirable reaction product(s).

As a first step, the designed spectral pattern could be compared to known spectral patterns for existing materials to determine if similarities exist between the designed spectral pattern and spectral patterns of known materials. If the designed spectral pattern at least partially matches against a spectral pattern of a known material, then it is possible to utilize the known material as a physical catalyst to obtain a desired reaction and/or desired reaction pathway or rate in a cell reaction system. In this regard, it may be desirable to utilize the known material alone or in combination with a spectral energy catalyst and/or a spectral catalyst. Still further, it may be possible to utilize environmental reaction conditions and/or spectral environmental reaction conditions to cause the known material to behave in a manner which is even closer to the designed energy pattern or spectral pattern. Further, the application of different spectral energy patterns may cause the designed catalyst to behave in different manners, such as, for example, encouraging a first reaction pathway with the application of a first spectral energy pattern and encouraging a second reaction pathway with the application of a second spectral energy pattern. Likewise, the changing of one or more environmental reaction conditions could have a similar effect.

Further, this designed catalyst has applications in all types of reactions including, but not limited to, chemical (organic and inorganic), biological, physical, energy, etc.

Still further, in certain cases, one or more physical species could be used or combined in a suitable manner, for example, physical mixing or by a chemical reaction, to obtain a physical catalyst material exhibiting the appropriate designed spectral energy pattern (e.g., spectral pattern) to achieve a desired reaction pathway. Accordingly, a combination of designed catalyst(s) (e.g., a physical catalyst which is known or manufactured expressly to function as a physical catalyst), spectral energy catalyst(s) and/or spectral catalyst(s) can result in a resultant energy pattern (e.g., which in this case can be a combination of physical catalyst(s) and/or spectral catalyst(s)) which is conducive to forming desired reaction product(s) and/or following a desired reaction pathway at a desired reaction rate. In this regard, various line width broadening and/or narrowing of spectral energy pattern(s) and/or spectral pattern(s) may occur when the designed catalyst is combined with various spectral energy patterns and/or spectral patterns.

It is important to consider the energy interactions between all components involved in the desired reaction in a cell reaction system when calculating or determining an appropriate designed catalyst. There will be a particular combination of specific energy pattern(s) (e.g., electromagnetic energy) that will interact with the designed catalyst to form an applied spectral energy pattern. The particular frequencies, for example, of electromagnetic radiation that should be caused to be applied to a cell reaction system should be as many of those frequencies as possible, when interacting with the frequencies of the designed catalyst, that can result in desirable effects to one or more participants in the cell reaction system, while eliminating as many of those frequencies as possible which result in undesirable effects within the cell reaction system.

X. Designing Conditionable Participants

Moreover, by utilizing the above techniques to design (e.g., calculate or determine) a desirable spectral energy pattern, such as a desirable spectral pattern for a spectral energy catalyst (e.g., spectral catalyst) rather than applying the spectral energy catalyst (e.g., spectral catalyst) per se, for example, the designed spectral pattern can be achieved in a conditioned participant (e.g., appropriately conditioning a conditionable participant) which may function as an optimum physical and/or spectral catalyst that could be used in the cell reaction system when the conditioned participant is introduced into or activated in the cell reaction system. Further, the invention may be able to provide a recipe for a conditioned physical participant for a particular reaction system where no catalyst previously existed. For example in a reaction where:

where A=reactant, B=product and I=known intermediate, and there is no known catalyst, a conditionable physical participant could be conditioned which, for example, resonates with the intermediate "I", when the conditioned participant is, for example, introduced into the cell reaction system. Thus, the conditioned physical participant could catalyze the reaction when the conditioned physical participant is introduced to the cell reaction system.

As a first step, the desired spectral pattern for resonating with known intermediate "I" could be compared to known spectral patterns for existing conditionable materials to determine if similarities exist between the desired spectral pattern and spectral patterns of known conditionable materials. If the desired spectral pattern at least partially matches against a spectral pattern of a known conditionable material, then it may be possible to condition the known conditionable material to form a conditioned material which then could function as, for example, a physical catalyst, in a cell reaction system. In this regard, it may be desirable to utilize the conditioned material(s) alone or in combination with a spectral energy catalyst and/or a spectral catalyst in a cell reaction system. Still further, it may be possible to utilize environmental reaction conditions and/or spectral environmental reaction conditions to cause the conditioned material to behave in a manner which is even closer to the desired energy pattern or spectral pattern required in a cell reaction system. Further, the application of different spectral energy patterns may cause the conditioned material to behave in different manners, such as, for example, encouraging a first reaction pathway with the application of a first spectral energy pattern and encouraging a second reaction pathway with the application of a second spectral energy pattern once the conditioned material is introduced to the cell reaction system. Thus, various phases, compositions, products, etc., could be achieved from the same or similar reaction system(s) merely by altering the spectral energy conditioning pattern which is exposed to the conditionable participant prior to the conditionable participant being introduced into the cell reaction system as a conditioned participant. In addition, various desirable results may occur when the conditioned participant is introduced into the cell reaction system and thereafter various spectral energy patterns and/or spectral patterns are introduced into the cell reaction system along with the conditioned participant.

Further, this designed conditioned participant has applications in all types of reactions including, but not limited to, chemical (organic and inorganic), biological, physical, energy, etc.

Still further, in certain cases, one or more physical species could be used or combined in a suitable manner, for example, physical mixing or by a chemical reaction, to obtain a physical conditionable material exhibiting the appropriate designed spectral energy conditioned pattern (e.g., once suitably conditioned) to achieve a desired reaction pathway once the conditioned matter is introduced into a cell reaction system. Accordingly, a combination of designed conditionable participant(s) (e.g., a physical conditionable material which is known or manufactured expressly to function as a physical catalyst once it is suitably targeted with a conditioning energy), spectral energy conditioning catalyst(s) and/or spectral conditioning catalyst(s) can result in a resultant conditioned energy pattern (e.g., which in this case can be a combination of physical material(s) and/or spectral conditioned catalyst(s)) which is conducive to forming desired reaction product(s) and/or following a desired reaction pathway at a desired reaction rate once the conditioned material is introduced into the cell reaction system. In this regard, various line width broadening and/or narrowing of spectral energy pattern(s) and/or spectral pattern(s) may occur when the designed conditionable participant is combined with various spectral energy conditioning patterns and/or spectral conditioning patterns to form a conditioned participant.

It is important to consider the energy interactions between all components of the holoreaction system when calculating or determining an appropriate designed conditionable participant. There will be a particular combination of specific energy pattern(s) (e.g., electromagnetic energy) that will interact with the conditioned participant to result in an applied spectral energy pattern once the conditioned participant is introduced into the cell reaction system. The particular frequencies, for example, of electromagnetic radiation that should be caused to be applied to a conditioning reaction system should be as many of those frequencies as possible, when interacting with the frequencies of the conditionable participant, that can result in desirable effects in the cell reaction system when the conditioned participant is introduced therein, while eliminating as many of those frequencies as possible which result in undesirable effects within the cell reaction system.

XI. Objects of the Invention

All of the above information disclosing the invention should provide a comprehensive understanding of the main aspects of the invention. However, in order to understand the invention further, the invention shall now be discussed in terms of some of the representative objects or goals to be achieved.

1. One object of this invention is to control or direct a reaction pathway in a cell reaction system by applying a spectral energy pattern in the form of a spectral catalyst having at least one electromagnetic energy frequency which may initiate, activate, and/or affect at least one of the participants involved in the cell reaction system.

2. Another object of the invention is to provide an efficient, selective and economical process for replacing a known physical catalyst (e.g., present in or near at least a portion of an electrode and/or electrolyte) in a cell reaction system comprising the steps of:

duplicating at least a portion of a spectral pattern of a physical catalyst (e.g., at least one frequency of a spectral pattern of a physical catalyst) to form a catalytic spectral pattern; and applying to at least a portion of the cell reaction system at least a portion of the catalytic spectral pattern.

3. Another object of the invention is to provide a method to augment a physical catalyst in a cell reaction system with its own catalytic spectral pattern comprising the steps of:

determining an electromagnetic spectral pattern of the physical catalyst; and duplicating at least one frequency of the spectral pattern of the physical catalyst with at least one electromagnetic energy emitter source to form a catalytic spectral pattern; and applying to at least a portion of the cell reaction system at least one frequency of the catalytic spectral pattern at a sufficient intensity and for a sufficient duration to catalyze the formation of reaction product(s) in a desired portion of the cell reaction system. Said at least one frequency can be applied by at least one of: (1) a wave guide: (2) an optical fiber array; (3) at least one element added adjacent to, on and/or in at least one of the electrode and/or electrolyte to the cell reaction system which permits energy to be radiated therefrom; (4) an electric field; (5) a magnetic field; (6) an acoustic field and/or (7) a transducer, etc.

4. Another object of the invention is to provide an efficient, selective and economical process for replacing a known physical catalyst in a cell reaction system comprising the steps of:

duplicating at least a portion of a spectral pattern of a physical catalyst (e.g., at least one frequency of a spectral pattern of a physical catalyst) to form a catalytic spectral pattern; and applying to the cell reaction system at least a portion of the catalytic spectral pattern; and, applying at least one additional spectral energy pattern which forms an applied spectral energy pattern when combined with said catalytic spectral pattern.

5. Another object of the invention is to provide a method to replace a physical catalyst in a cell reaction system comprising the steps of:

determining an electromagnetic spectral pattern of the physical catalyst;

duplicating at least one frequency of the electromagnetic spectral pattern of the physical catalyst with at least one electromagnetic energy emitter source to form a catalytic spectral pattern;

applying to the cell reaction system at least one frequency of the catalytic spectral pattern; and applying at least one additional spectral energy pattern to form an applied spectral energy pattern, said applied spectral energy pattern being applied at a sufficient intensity and for a sufficient duration to catalyze the formation of at least one reaction product in the cell reaction system.

6. Another object of this invention is to provide a method to affect and/or direct a particular reaction pathway in a cell reaction system with a spectral catalyst by augmenting a physical catalyst comprising the steps of:

duplicating at least a portion of a spectral pattern of a physical catalyst (e.g., at least one frequency of a spectral pattern of the physical catalyst) with at least one energy emitter source to form a catalytic spectral pattern;

applying to the cell reaction system, (e.g., irradiating) at least a portion of the catalytic spectral pattern (e.g., an electromagnetic spectral pattern having a frequency range of from about radio frequency to about ultraviolet frequency) at a sufficient intensity and for a sufficient duration to catalyze one or more particular reactions in the cell reaction system; and introducing the physical catalyst into the cell reaction system.

The above method may be practiced by introducing the physical catalyst into the cell reaction system before, and/or during, and/or after applying said catalytic spectral pattern to the cell reaction system.

7. Another object of this invention is to provide a method to affect and/or direct a particular reaction in a cell reaction system with a spectral energy catalyst by augmenting a physical catalyst comprising the steps of:

applying at least one spectral energy catalyst at a sufficient intensity and for a sufficient duration to catalyze the particular cell reaction in the cell reaction system;

introducing the physical catalyst into the cell reaction system.

The above method may be practiced by introducing the physical catalyst into the cell reaction system before, and/or during, and/or after applying the spectral energy catalyst to the cell reaction system.

8. Another object of this invention is to provide a method to affect and/or direct a desired reaction pathway in a cell reaction system with a spectral catalyst and a spectral energy catalyst by augmenting a physical catalyst comprising the steps of:

applying at least one spectral catalyst at a sufficient intensity and for a sufficient duration to at least partially catalyze the desired cell reaction system;

applying at least one spectral energy catalyst at a sufficient intensity and for a sufficient duration to at least partially catalyze the desired cell reaction system; and introducing the physical catalyst into the cell reaction system.

The above method may be practiced by introducing the physical catalyst into the cell reaction system before, and/or during, and/or after applying the spectral catalyst and/or the spectral energy catalyst to the cell reaction system. Moreover, the spectral catalyst and spectral energy catalyst may be applied simultaneously to form an applied spectral energy pattern or they may be applied sequentially either at the same time or at different times from when the physical catalyst is introduced into the cell reaction system.

9. Another object of this invention is to provide a method to affect and/or direct a desired reaction into a cell reaction system with a spectral catalyst and a spectral energy catalyst and a spectral environmental reaction condition, with or without a physical catalyst, comprising the steps of:

applying at least one spectral catalyst at a sufficient intensity and for a sufficient duration to catalyze a reaction pathway;

applying at least one spectral energy catalyst at a sufficient intensity and for a sufficient duration to catalyze a reaction pathway;

applying at last one spectral environmental reaction condition at a sufficient intensity and for a sufficient duration to catalyze a reaction pathway, whereby when any of said at least one spectral catalyst, said at least one spectral energy catalyst and/or at least one spectral environmental reaction condition are applied at the same time, they form an applied spectral energy pattern; and introducing the physical catalyst into the cell reaction system (e.g., into and/or onto at least a portion of the anode and/or cathode and/or electrolyte).

The above method may be practiced by introducing the physical catalyst into the cell reaction system before, and/or during, and/or after applying any one of, or any combination of, the spectral catalyst and/or the spectral energy catalyst and/or the spectral environmental reaction condition to the cell reaction system. Likewise, the spectral catalyst and/or the spectral energy catalyst and/or the spectral environmental reaction condition can be provided sequentially or continuously.

10. Another object of this invention is to provide a method to affect and direct a cell reaction system with an applied spectral energy pattern and a spectral energy catalyst comprising the steps of:

applying at least one applied spectral energy pattern at a sufficient intensity and for a sufficient duration to catalyze a particular reaction in a cell reaction system, whereby said at least one applied spectral energy pattern comprises at least two members selected from the group consisting of catalytic spectral energy pattern, catalytic spectral pattern, spectral catalyst, spectral energy catalyst, spectral energy pattern, spectral environmental reaction condition and spectral pattern; and applying at least one spectral energy catalyst to the cell reaction system.

The above method may be practiced by introducing the applied spectral energy pattern into the cell reaction system before, and/or during, and/or after applying the spectral energy catalyst to the cell reaction system. Moreover, the spectral energy catalyst and the applied spectral energy pattern can be provided sequentially or continuously. If applied continuously, a new applied spectral energy pattern is formed.

11. Another object of this invention is to provide a method to affect and/or direct a cell reaction system with a spectral energy catalyst comprising the steps of:

determining at least a portion of a spectral energy pattern for starting reactant(s) in a particular reaction in said cell reaction system;

determining at least a portion of a spectral energy pattern for reaction product(s) in said particular reaction in said cell reaction system;

calculating an additive and/or subtractive spectral energy pattern (e.g., at least one electromagnetic frequency) from said reactant(s) and reaction product(s) spectral energy patterns to determine a required spectral energy catalyst (e.g., a spectral catalyst);

generating at least a portion of the required spectral energy catalyst (e.g., at least one electromagnetic frequency of the required spectral catalyst); and applying to the particular reaction in said cell reaction system (e.g., irradiating with electromagnetic energy) said at least a portion of the required spectral energy catalyst (e.g., spectral catalyst) to form at least one desired reaction product(s).

12. Another object of the invention is to provide a method to affect and/or direct a cell reaction system with a spectral energy catalyst comprising the steps of:

targeting at least one participant in said cell reaction system with at least one spectral energy catalyst to cause the formation and/or stimulation and/or stabilization of at least one transient and/or at least one intermediate to result in desired reaction product(s).

13. Another object of the invention is to provide a method for catalyzing a cell reaction system with a spectral energy pattern to result in at least one reaction product comprising:

applying at least one spectral energy pattern for a sufficient time and at a sufficient intensity to cause the formation and/or stimulation and/or stabilization of at least one transient and/or at least one intermediate to result in desired reaction product(s) at a desired reaction rate.

14. Another object of the invention is to provide a method to affect and direct a cell reaction system with a spectral energy catalyst and at least one of the spectral environmental reaction conditions comprising the steps of:

applying at least one applied spectral energy catalyst to at least one participant in said cell reaction system; and applying at least one spectral environmental reaction condition to said cell reaction system to cause the formation and/or stimulation and/or stabilization of at least one transient and/or at least one intermediate to permit desired reaction product(s) to form.

15. Another object of the invention is to provide a method for catalyzing a cell reaction system with a spectral energy catalyst to result in at least one reaction product comprising:

applying at least one frequency (e.g., electromagnetic) which heterodynes with at least one reactant frequency to cause the formation of and/or stimulation and/or stabilization of at least one transient and/or at least one intermediate to result in desired reaction product(s).

16. Another object of the invention is to provide a method for catalyzing a cell reaction system with at least one spectral energy pattern resulting in at least one reaction product comprising:

applying a sufficient number of frequencies (e.g., electromagnetic) and/or fields (e.g., electric, magnetic and/or acoustic) to result in an applied spectral energy pattern which stimulates all transients and/or intermediates required in a reaction pathway to result in desired reaction product(s).

17. Another object of the invention is to provide a method for catalyzing a cell reaction system with a spectral energy catalyst resulting in at least one reaction product comprising:

targeting at least one participant in said cell reaction system with at least one frequency and/or field to form, indirectly, at least one transient and/or at least one intermediate, whereby formation of said at least one transient and/or at least one intermediate results in the formation of an additional at least one transient and/or at least one additional intermediate.

18. It is another object of the invention to provide a method for catalyzing a cell reaction system with a spectral energy catalyst resulting in at least one reaction product comprising:

targeting at least one spectral energy catalyst to at least one participant in said cell reaction system to form indirectly at least one transient and/or at least one intermediate, whereby formation of said at least one transient and/or at least one intermediate results in the formation of an additional at least one transient and/or at least one additional intermediate.

19. It is a further object of the invention to provide a method for directing a cell reaction system along a desired reaction pathway comprising:

applying at least one targeting approach selected from the group of approaches consisting of direct resonance targeting, harmonic targeting and non-harmonic heterodyne targeting.

In this regard, these targeting approaches can cause the formation and/or stimulation and/or stabilization of at least one transient and/or at least one intermediate in at least a portion of said cell reaction system to result in desired reaction product(s).

20. It is another object of the invention to provide a method for catalyzing a cell reaction system comprising:

applying at least one frequency to at least one participant and/or at least one component in said cell reaction system to cause the formation and/or stimulation and/or stabilization of at least one transient and/or at least one intermediate to result in desired reaction product(s), whereby said at least one frequency comprises at least one frequency selected from the group consisting of direct resonance frequencies, harmonic resonance frequencies, non-harmonic heterodyne resonance frequencies, electronic frequencies, vibrational frequencies, rotational frequencies, rotational-vibrational frequencies, librational frequencies, translational frequencies, gyrational frequencies, fine splitting frequencies, hyperfine splitting frequencies, electric field induced frequencies, magnetic field induced frequencies, cyclotron resonance frequencies, orbital frequencies, acoustic frequencies and/or nuclear frequencies.

In this regard, the applied frequencies can include any desirable frequency or combination of frequencies which resonates directly, harmonically or by a non-harmonic heterodyne technique, with at least one participant and/or at least one component in said cell reaction system.

21. It is another object of the invention to provide a method for directing a cell reaction system along with a desired reaction pathway with a spectral energy pattern comprising:

applying at least one frequency and/or field to cause the spectral energy pattern (e.g., spectral pattern) of at least one participant and/or at least one component in said cell reaction system to at least partially overlap with the spectral energy pattern (e.g., spectral pattern) of at least one other participant and/or at least one other component in said cell reaction system to permit the transfer of energy between said at least two participants and/or components.

22. It is another object of the invention to provide a method for catalyzing a cell reaction system with a spectral energy pattern resulting in at least one reaction product comprising:

applying at least one spectral energy pattern to cause the spectral energy pattern of at least one participant and/or component in said cell reaction system to at least partially overlap with a spectral energy pattern of at least one other participant and/or component in said cell reaction system to permit the resonant transfer of energy between the at least two participants and/or components, thereby causing the formation of said at least one reaction product.

23. It is a further object of the invention to provide a method for catalyzing a cell reaction system with a spectral energy catalyst resulting in at least one reaction product comprising:

applying at least one frequency and/or field to cause spectral energy pattern (e.g., spectral pattern) broadening of at least one participant (e.g., at least one reactant) and/or component in said cell reaction system to cause a transfer of energy to occur resulting in transformation (e.g., chemically, physically, phase, property or otherwise) of at least one participant and/or at least one component in said cell reaction system.

In this regard, the transformation may result in a reaction product which is of a different chemical composition and/or different physical or crystalline composition and/or phases than any of the chemical and/or physical or crystalline compositions and/or phases of any starting reactant. Thus, only transients may be involved in the conversion of a reactant into a reaction product.

24. It is a further object of the invention to provide a method for catalyzing a cell reaction system with a spectral energy catalyst resulting in at least one reaction product comprising:

applying an applied spectral energy pattern to cause spectral energy pattern (e.g., spectral pattern) broadening of at least one participant (e.g., at least one reactant) and/or component in said cell reaction system to cause a resonant transfer of energy to occur resulting in transformation (e.g., chemically, physically, phase, property or otherwise) of at least one participant and/or at least one component in said cell reaction system.

In this regard, the transformation may result in a reaction product which is of a different chemical composition and/or different physical or crystalline composition and/or phase and/or exhibits different properties than the chemical and/or physical or crystalline compositions and/or phases of any starting reactant. Thus, only transients may be involved in the conversion of a reactant into a reaction product.

25. Another object of the invention is to provide a method for controlling a reaction and/or directing a reaction pathway in a cell reaction system by utilizing at least one spectral environmental reaction condition, comprising:

forming a cell reaction system; and applying at least one spectral environmental reaction condition to direct said cell reaction system along at least one desired reaction pathway.

In this regard, the applied spectral environmental reaction condition can be used alone or in combination with other environmental reaction conditions to achieve desired results. Further, additional spectral energy patterns may also be applied, simultaneously and/or continuously with said spectral environmental reaction condition.

26. Another object of the invention is to provide a method for designing a catalyst where no catalyst previously existed (e.g., a physical catalyst and/or spectral energy catalyst), to be used in a cell reaction system, comprising:

determining a required spectral pattern to obtain a desired reaction and/or desired reaction pathway and/or desired cell reaction rate; and designing a catalyst (e.g., material or combination of materials, and/or spectral energy catalysts) that exhibit(s) a spectral pattern that approximates the required spectral pattern.

In this regard, the designed catalyst material may comprise a physical admixing of one or more materials and/or more materials that have been combined by an appropriate reaction, such as a chemical reaction. The designed material may be enhanced in function by one or more spectral energy patterns that may also be applied to the cell reaction system. Moreover, the application of different spectral energy patterns may cause the designed material to behave in different manners, such as, for example, encouraging a first reaction pathway with the application of a first spectral energy pattern and encouraging a second reaction pathway with the application of a second spectral energy pattern. Likewise, the changing of one or more environmental reaction conditions could have a similar effect.

Further, this designed material has applications in all types of reactions including, but not limited to, chemical (organic and inorganic), biological, physical, etc.

27. Another object of the invention is to provide a method for controlling a reaction and/or directing a reaction pathway in a cell reaction system by preventing at least a portion of certain undesirable spectral energy from interacting with a cell reaction system comprising:

providing at least one control means for absorbing, filtering, trapping, reflecting, etc., spectral energy incident thereon;

permitting desirable spectral energy emitted from said control means and contacting at least a portion of a cell reaction system with said emitted spectral energy; and causing said emitted spectral energy from said control means to desirably interact with said cell reaction system thereby directing said cell reaction system along at least one desired reaction pathway.

28. It should be understood that in each of the aforementioned 27 Objects of the Invention, that cell reaction systems also include preventing certain reaction phenomena from occurring, when desirable.

29. One object of this invention is to control or direct a reaction pathway in a cell reaction system with a conditioned participant, and forming the conditioned participant by applying a spectral energy conditioning pattern (e.g., a spectral conditioning catalyst) to at least one conditionable participant, said conditionable participant thereafter having at least one conditioned energy frequency (e.g., electromagnetic energy frequency) which may initiate, activate, and/or affect at least one of the participants involved in the cell reaction system and/or may itself be affected by a subsequent application of spectral energy in the cell reaction system.

30. Another object of the invention is to provide an efficient, selective and economical process for replacing a known physical catalyst (e.g., present in or near at least a portion of an electrode and/or electrolyte) in a cell reaction system comprising the steps of:

duplicating at least a portion of a spectral pattern of a physical catalyst (e.g., at least one frequency of a spectral pattern of a physical catalyst) by modifying a conditionable participant so that the conditionable participant forms a catalytic spectral pattern; and applying or introducing to the cell reaction system the conditioned participant.

31. Another object of the invention is to provide a method to augment a physical catalyst in a cell reaction system with its own catalytic spectral pattern comprising the steps of:

determining an electromagnetic spectral pattern of the physical catalyst; and duplicating at least one frequency of the spectral pattern of the physical catalyst by conditioning a conditionable participant with at least one electromagnetic energy emitter source to form a catalytic spectral pattern in the conditioned participant; and applying to the cell reaction system the conditioned participant at a sufficient intensity and for a sufficient duration to catalyze the formation of reaction product(s) in a desired portion of the cell reaction system. Said at least one frequency can be applied by at least one of: (1) a wave guide: (2) an optical fiber array; (3) at least one element added adjacent to, on and/or in at least one of the electrode and/or electrolyte to the cell reaction system which permits energy to be radiated therefrom; (4) an electric field; (5) a magnetic field; (6) an acoustic field and/or (7) a transducer, etc.

32. Another object of the invention is to provide an efficient, selective and economical process for replacing a known physical catalyst in a cell reaction system comprising the steps of:

duplicating at least a portion of a spectral pattern of a physical catalyst (e.g., at least one frequency of a spectral pattern of a physical catalyst by conditioning a conditionable participant to form a catalytic spectral pattern in the conditioned participant;

applying to the cell reaction system the conditioned participant; and, applying or introducing at least one additional spectral energy pattern which forms an applied spectral energy pattern when combined with said catalytic spectral pattern of the conditioned participant.

33. Another object of the invention is to provide a method to replace a physical catalyst in a cell reaction system comprising the steps of:

determining an electromagnetic spectral pattern of the physical catalyst;

duplicating at least one frequency of the electromagnetic spectral pattern of the physical catalyst by conditioning a conditionable participant with at least one electromagnetic energy emitter source to form a catalytic spectral pattern in the conditioned participant;

applying or introducing to the cell reaction system the conditioned participant; and applying at least one additional spectral energy pattern to form an applied spectral energy pattern, said applied spectral energy pattern being applied at a sufficient intensity and for a sufficient duration to catalyze the formation of at least one reaction product in the cell reaction system.

34. Another object of this invention is to provide a method to affect and/or direct a cell reaction system with a spectral catalyst by augmenting a physical catalyst comprising the steps of:

duplicating at least a portion of a spectral pattern of a physical catalyst (e.g., at least one frequency of a spectral pattern of the physical catalyst) by conditioning a conditionable participant with at least one electromagnetic energy emitter source to form a catalytic spectral pattern in the conditioned participant;

applying or introducing to the cell reaction system, the conditioned participant; and introducing the physical catalyst into the cell reaction system.

The above method may be practiced by introducing the physical catalyst into the cell reaction system before, and/or during, and/or after applying said conditioned participant to the cell reaction system.

35. Another object of this invention is to provide a method to affect and/or direct a cell reaction system with a conditioned participant by augmenting a physical catalyst comprising the steps of:

applying or introducing at least one conditioned participant to the cell reaction system; and introducing the physical catalyst into the cell reaction system.

The above method may be practiced by introducing the physical catalyst into the cell reaction system before, and/or during, and/or after applying the conditioned participant to the cell reaction system.

36. Another object of this invention is to provide a method to affect and/or direct a cell reaction system with a conditioned participant and a spectral energy catalyst by augmenting a physical catalyst comprising the steps of:

applying or introducing at least one conditioned participant to the cell reaction system;

applying at least one spectral energy catalyst at a sufficient intensity and for a sufficient duration to at least partially catalyze the cell reaction system; and introducing the physical catalyst into the cell reaction system.

The above method may be practiced by introducing the physical catalyst into the cell reaction system before, and/or during, and/or after applying the conditioned participant and/or the spectral energy catalyst to the cell reaction system. Moreover, the conditioned participant and spectral energy catalyst may be applied simultaneously to form an applied spectral energy pattern or they may be applied sequentially either at the same time or at different times from when the physical catalyst is introduced into the cell reaction system.

37. Another object of this invention is to provide a method to affect and/or direct a cell reaction system with a conditioned participant and a spectral energy catalyst and a spectral environmental reaction condition, with or without a physical catalyst, comprising the steps of:

applying or introducing at least one conditioned participant to the cell reaction system;

applying at least one spectral energy catalyst at a sufficient intensity and for a sufficient duration to catalyze a reaction pathway;

applying at last one spectral environmental reaction condition at a sufficient intensity and for a sufficient duration to catalyze a reaction pathway, whereby when any of said at least one conditioned participant, said at least one spectral energy catalyst and/or at least one spectral environmental reaction condition are applied at the same time, they form an applied spectral energy pattern; and introducing the physical catalyst into the cell reaction system (e.g., into and/or onto at least a portion of the anode and/or cathode and/or electrolyte).

The above method may be practiced by introducing the physical catalyst into the cell reaction system before, and/or during, and/or after applying any one of, or any combination of, the conditioned participant and/or the spectral energy catalyst and/or the spectral environmental reaction condition to the cell reaction system. Likewise, the conditioned participant and/or the spectral energy catalyst and/or the spectral environmental reaction condition can be provided sequentially or continuously.

38. Another object of this invention is to provide a method to condition a conditionable participant with an applied spectral energy conditioning pattern and/or a spectral energy conditioning catalyst comprising the steps of:

applying at least one applied spectral energy conditioning pattern at a sufficient intensity and for a sufficient duration to condition the conditionable participant, whereby said at least one applied spectral energy conditioning pattern comprises at least one member selected from the group consisting of catalytic spectral energy conditioning pattern, catalytic spectral conditioning pattern, spectral conditioning catalyst, spectral energy conditioning catalyst, spectral energy conditioning pattern, spectral conditioning environmental reaction condition and spectral conditioning pattern.

The above method may be combined with introducing an applied spectral energy pattern into a cell reaction system before, and/or during, and/or after introducing a conditioned participant into the cell reaction system. Moreover, the conditioned participant and the applied spectral energy pattern can be provided sequentially or continuously. If applied continuously, a new applied spectral energy pattern is formed.

The above method may also comprise conditioning the conditionable participant in a conditioning reaction vessel and/or in a reaction vessel. If the conditionable participant is first conditioned in a reaction vessel, the conditioning occurs prior to some or all other components comprising the cell reaction system being introduced into the cell reaction system.

Further, the reaction vessel and/or conditioning reaction vessel per se may be treated with conditioning energy. In the case of the reaction vessel being treated with conditioning energy, such conditioning treatment occurs prior to some or all other components comprising the cell reaction system being introduced into the reaction vessel.

39. Another object of this invention is to provide a method to affect and direct a cell reaction system with a conditioned participant comprising the steps of:

determining at least a portion of a spectral energy pattern for starting reactant(s) in said cell reaction system;

determining at least a portion of a spectral energy pattern for reaction product(s) in said cell reaction system;

calculating an additive spectral energy pattern (e.g., at least one electromagnetic frequency) from said reactant(s) and reaction product(s) spectral energy patterns to determine a required conditioned participant (e.g., a spectral conditioned catalyst);

generating at least a portion of the required spectral energy conditioning catalyst (e.g., at least one electromagnetic frequency of the required spectral conditioning catalyst); and applying to the conditionable participant (e.g., irradiating with electromagnetic energy) said at least a portion of the required spectral energy conditioning catalyst (e.g., spectral conditioning catalyst) to form desired conditioned participant; and introducing the conditioned participant to the cell reaction system to form a desired reaction product and/or desired reaction product at a desired reaction rate.

40. Another object of the invention is to provide a method to affect and direct a cell reaction system with a conditioned participant comprising the steps of:

targeting at least one conditionable participant in said conditioning reaction system with at least one spectral conditioning pattern to cause the formation and/or stimulation and/or stabilization of at least one conditioned participant to result in at least one desired reaction product in said cell reaction system; and applying or introducing the conditioned participant to the reaction system to result in at least one desired reaction product and/or a desired or controlled reaction rate in said cell reaction system.

41. Another object of the invention is to provide a method for catalyzing a cell reaction system with a conditioned participant to result in at least one reaction product and/or at least one desired reaction rate comprising:

applying at least one spectral energy conditioning pattern for a sufficient time and at a sufficient intensity to cause the formation and/or stimulation and/or stabilization of at least one conditioned participant, so as to result in desired reaction product(s) at a desired reaction rate when said conditioned participant communicates with said cell reaction system.

42. Another object of the invention is to provide a method to affect and direct a cell reaction system with a conditioned participant and at least one spectral environmental reaction condition comprising the steps of:

applying or introducing at least one conditioned participant to the cell reaction system; and applying at least one spectral environmental reaction condition to said cell reaction system to cause the formation and/or stimulation and/or stabilization of at least one transient and/or at least one intermediate to permit desired reaction product(s) to form.

43. Another object of the invention is to provide a method for forming a conditioned participant with a spectral energy conditioning pattern to result in at least one conditioned participant comprising:

applying at least one frequency (e.g., electromagnetic) which heterodynes with at least one conditionable participant frequency to cause the formation of and/or stimulation and/or stabilization of at least one conditioned participant.

44. Another object of the invention is to provide a method for forming a conditioned participant with at least one spectral energy conditioning pattern resulting in at least one conditioned participant comprising:

applying a sufficient number of frequencies (e.g., electromagnetic) and/or fields (e.g., electric and/or magnetic) to result in an applied spectral energy conditioning pattern which results in the formation of at least one conditioned participant.

45. Another object of the invention is to provide a method for forming a conditioned participant with a spectral energy conditioning catalyst resulting in at least one conditioned participant comprising:

conditioning targeting at least one conditionable participant prior to being introduced to said cell reaction system with at least one frequency and/or field to form a conditioned participant, whereby formation of said at least one conditioned participant results in the formation of at least one transient and/or at least one intermediate when said conditioned participant is introduced into said cell reaction system.

46. It is another object of the invention to provide a method for catalyzing a cell reaction system with a conditioned participant resulting in at least one reaction product comprising:

conditioning targeting at least one spectral energy conditioning catalyst to form at least one conditioned participant (e.g., at least one spectral energy catalyst) which is present in said cell reaction system when at least one reaction in said cell reaction system is initiated, such that at least one transient and/or at least one intermediate, and/or at least one reaction product is formed in the cell reaction system.

47. It is a further object of the invention to provide a method for directing a cell reaction system along a desired reaction pathway comprising:

applying at least one conditioning targeting approach to at least one conditionable participant, said at least one conditioning targeting approach being selected from the group of approaches consisting of direct resonance conditioning targeting, harmonic conditioning targeting and non-harmonic heterodyne conditioning targeting.

In this regard, these conditioning targeting approaches can result in the formation of a conditioned participant which can cause the formation and/or stimulation and/or stabilization of at least one transient and/or at least one intermediate to result in desired reaction product(s) at a desired reaction rate.

48. It is another object of the invention to provide a method for conditioning at least one conditionable participant comprising:

applying at least one conditioning frequency to at least one conditionable participant to cause the formation and/or stimulation and/or stabilization of at least one conditioned participant, whereby said at least one frequency comprises at least one frequency selected from the group consisting of direct resonance conditioning frequencies, harmonic resonance conditioning frequencies, non-harmonic heterodyne conditioning resonance frequencies, electronic conditioning frequencies, vibrational conditioning frequencies, rotational conditioning frequencies, rotational-vibrational conditioning frequencies, fine splitting conditioning frequencies, hyperfine splitting conditioning frequencies, electric field splitting conditioning frequencies, magnetic field splitting conditioning frequencies, cyclotron resonance conditioning frequencies, orbital conditioning frequencies and nuclear conditioning frequencies.

In this regard, the applied conditioning frequencies can include any desirable conditioning frequency or combination of conditioning frequencies which resonates directly, harmonically or by a non-harmonic heterodyne technique, with at least one conditionable participant and/or at least one component of said conditionable participant.

49. It is another object of the invention to provide a method for directing a cell reaction system along a desired reaction pathway with a conditioned participant comprising:

applying at least one conditioning frequency and/or conditioning field to cause the conditioned spectral energy pattern (e.g., spectral conditioning pattern) of at least one conditioned participant to at least partially overlap with the spectral energy pattern (e.g., spectral pattern) of at least one participant and/or at least one other component in said cell reaction system to permit the transfer of energy between said conditioned participant and said participant and/or other components.

50. It is another object of the invention to provide a method for catalyzing a cell reaction system with a conditioned participant resulting in at least one reaction product comprising:

applying at least one spectral energy conditioning pattern to at least one conditionable participant to cause the conditioned spectral energy pattern of at least one conditioned participant in said cell reaction system to at least partially overlap with a spectral energy pattern of at least one other participant and/or component in said cell reaction system to permit the transfer of energy between the said conditioned participant and said participant and/or components, thereby causing the formation of said at least one reaction product.

51. It is a further object of the invention to provide a method for catalyzing a cell reaction system with a conditioned participant resulting in at least one reaction product comprising:

applying at least one frequency and/or field to cause a conditioned spectral energy pattern (e.g., conditioned spectral pattern) broadening of said conditioned participant to cause a transfer of energy to occur between the conditioned participant and at least one participant in the cell reaction system, resulting in transformation (e.g., chemically, physically, phase or otherwise) of at least one participant and/or at least one component in said cell reaction system.

In this regard, the transformation may result in a reaction product which is of a different chemical composition and/or different physical composition and/or phases than any of the chemical and/or physical compositions and/or phases of any starting reactant and/or conditioned participant. Thus, only transients may be involved in the conversion of a reactant into a reaction product.

52. Another object of the invention is to provide a method for controlling a reaction and/or directing a reaction pathway by utilizing at least one conditioned participant and at least one spectral environmental reaction condition, comprising:

forming a cell reaction system comprising said conditioned participant; and applying at least one spectral environmental reaction condition to direct said cell reaction system along a desired reaction pathway.

In this regard, the applied spectral environmental reaction condition can be used alone or in combination with other environmental reaction conditions to achieve desired results. Further, additional spectral energy patterns may also be applied, simultaneously and/or continuously with said spectral environmental reaction condition.

53. Another object of the invention is to provide a method for designing a conditionable participant to be used as a catalyst, once conditioned, in a cell reaction system where no catalyst previously existed (e.g., a physical catalyst and/or spectral energy catalyst), to be used in a cell reaction system, comprising:

determining a required spectral pattern to obtain a desired reaction and/or desired reaction pathway and/or desired reaction rate; and designing a conditionable participant (e.g., material or combination of materials), that exhibit(s) a conditioned spectral pattern that approximates the required spectral pattern, when exposed to a suitable spectral energy conditioning pattern.

In this regard, the designed conditionable participant may comprise a physical admixing of one or more materials and/or more materials that have been combined by an appropriate reaction, such as a chemical reaction. The designed conditionable participant material may be enhanced in function by one or more spectral energy conditioning patterns that may also be applied to the conditioning reaction system. Moreover, the application of different spectral energy conditioning patterns may cause the designed conditionable material, once conditioned, to behave in different manners in a cell reaction system, such as, for example, encouraging a first reaction pathway in a cell reaction system with the application of a first spectral energy conditioning pattern in a conditioning reaction system and encouraging a second reaction pathway with the application of a second spectral energy conditioning pattern in a cell reaction system. Likewise, the changing of one or more environmental conditioning reaction conditions could have a similar effect.

Further, this designed conditionable participant or material has applications in all types of cell reaction systems including, but not limited to, chemical (organic and inorganic), biological, physical, etc.

54. It should be understood that in each of 29-53 Objects of the Invention, that cell reaction systems also include preventing certain reaction phenomena from occurring, when desirable.

55. Another object of the invention is to use at least one conditioned participant with each of the techniques set forth in Objects 1-28 above; and to use at least one additional spectral energy pattern with each of the techniques set forth in Objects 29-54 above.

In each of the above-mentioned 55 Objects of the Invention, the particular energy or energies can be applied by at least one of the following techniques: (1) a waveguide; (2) an optical fiber array; (3) at least one element added adjacent to, on and/or in at least one of the electrode and/or electrolyte which permits energy to be radiated therefrom; and/or a transducer, etc.

While not wishing to be bound by any particular theory or explanation of operation, it is believed that when frequencies match, energy transfers. The transfer of energy can be a sharing of energy between two entities and, for example, a transfer of energy from one entity into another entity. The entities may both be, for example, matter, or one entity may be matter and the other energy (e.g. energy may be a spectral energy pattern such as electromagnetic frequencies, and/or an electric field and/or a magnetic field). Reactions and transformations of matter may be controlled and directed, by controlling the resonant exchange of energy within a holoreaction system.

BRIEF DESCRIPTION OF THE FIGURES

FIG. 2a shows a low amplitude wave and FIG. 2b shows a high amplitude wave.

FIG. 3a shows a time vs. amplitude plot and FIG. 3b shows a frequency vs. amplitude plot.

FIG. 6 shows fractal diagrams.

FIGS. 7a and 7b show hydrogen energy level diagrams.

FIG. 13a shows a narrow resonance curve with a high Q and FIG. 13b shows a broad resonance curve with a low Q.

FIG. 15a is at a low temperature, FIG. 15b is at a moderate temperature and FIG. 15c is at a high temperature.

FIG. 17a shows distinct spectral curves at low temperature; and FIG. 17b shows overlapping of spectral curves at a higher temperature.

FIG. 21a corresponds to a spectral pattern representing the absorption of water vapor in air and FIG. 21b is a spectral pattern which corresponds to the absorption of $NH_3$ at one atmosphere pressure.

FIG. 23a is a standard spectral curve not showing any self-absorption; FIG. 23b shows the shifting of resonant frequency due to self absorption; FIG. 23c shows a self-reversal spectral pattern due to self-absorption; and FIG. 23d shows an attenuation example of a self-reversal spectral pattern.

FIG. 39b shows the same spectrum of FIG. 39a at a lower resolution (i.e., not showing any fine frequencies).

FIG. 43a shows rotational and vibrational frequencies (MHz) for LiF. FIG. 43b shows differences between rotational and vibrational frequencies for LiF.

FIG. 46 shows a fine structure spectrum for $SF_6$ from zero to 300 being magnified.

FIGS. 47a and 47b show the magnification of two curves from fine structure of $SF_6$ showing hyperfine structure frequencies. Note the regular spacing of the hyperfine structure curves. FIG. 47a shows magnification of the curve marked with a single asterisk (*) in FIG. 46 and FIG. 47b shows the magnification of the curved marked with a double asterisk (**) in FIG. 46.

FIG. 48 shows an energy level diagram corresponding to the hyperfine splitting for the hyperfine structure in the n=2 to n=3 transition for hydrogen.

FIG. 49 shows the hyperfine structure in the J=1→2 to rotational transition of $CH_3I$.

FIG. 50 shows the hyperfine structure of the J=1→2 transition for ClCN in the ground vibrational state.

FIG. 59a shows the J=4→5 transitions; and FIG. 59b shows the J=4→4 transitions. The electric field is large enough for complete spectral resolution.

FIG. 62a shows the Zeeman effect for sodium "D" lines; and FIG. 62b shows the energy level diagram for transitions in the Zeeman effect for sodium "D" lines.

FIG. 63 is a graph which shows the splitting of the ground term of the oxygen atom as a function of magnetic field.

FIG. 64 is a graphic which shows the dependence of the Zeeman effect on magnetic field strength for the "3P" state of silicon.

FIG. 69 shows the frequencies of hydrogen listed horizontally across the Table; and the frequencies of platinum listed vertically on the Table.

FIG. 70 shows a schematic of the experimental set-up which corresponds to a Bunsen burner heating a solution of sodium chloride and water on a hot plate, which is discussed in Example 12a.

FIG. 74a is a graph of the experimental data which shows pH as a function of time and corresponds to the experimental set-up of Example 12a.

FIG. 75a is a graph of the experimental data which shows conductivity as a function of time for three separate sets of Bunsen burner-only data.

FIG. 75b is a graph of the experimental data which shows conductivity as a function of temperature (two separate data points only) for Bunsen burner-only data.

FIG. 75c is a graph of the experimental data which shows conductivity as a function of time for three separate sets of Bunsen burner-only data, the plot beginning with the data point generated two minutes after sodium chloride was added to the water.

FIG. 77 shows a graph of the change in current as a function of time.

DESCRIPTION OF THE PREFERRED EMBODIMENTS

In general, thermal energy is used to drive chemical reactions by applying heat and increasing the temperature. The addition of heat increases the kinetic (motion) energy of the chemical reactants. A reactant with more kinetic energy moves faster and farther, and is more likely to take part in a chemical reaction. Mechanical energy likewise, by stirring and moving the chemicals, increases their kinetic energy and thus their reactivity. The addition of mechanical energy often increases temperature, by increasing kinetic energy.

Acoustic energy is applied to chemical reactions as orderly mechanical waves. Because of its mechanical nature, acoustic energy can increase the kinetic energy of chemical reactants, and can also elevate their temperature(s). Electromagnetic (EM) energy consists of waves of electric and magnetic fields. Electromagnetic energy may also increase the kinetic energy and heat in cell reaction systems. It may energize electronic orbitals or vibrational motion in some reactions.

Figure 1A:
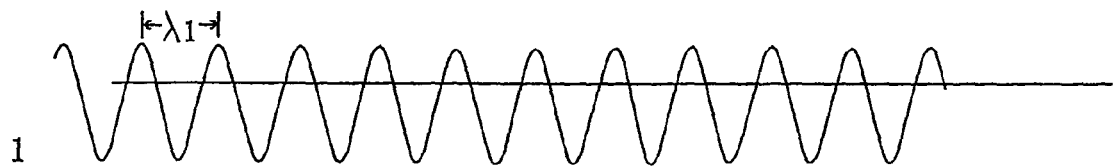
FIGS. 1a and 1b show a graphic representation of an acoustic or electromagnetic wave.
Figure 1B:
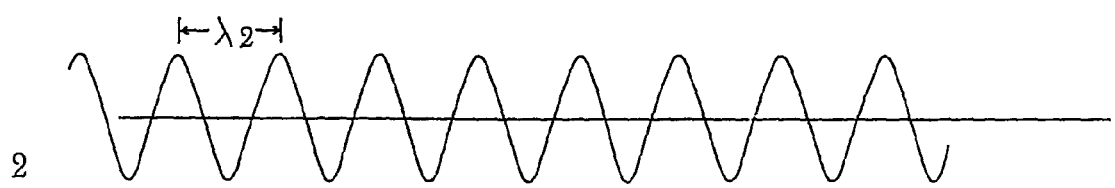
Figure 1C:
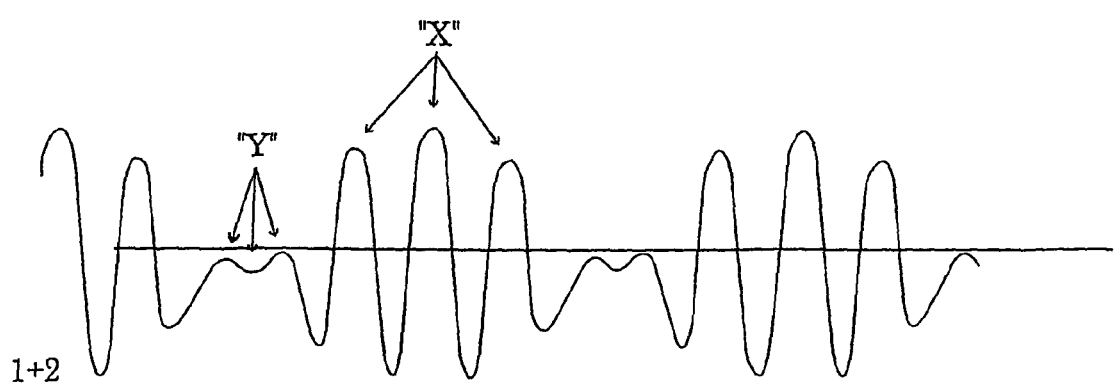
FIG. 1c shows the combination wave which results from the combining of the waves in FIG. 1a and FIG. 1b.
Figure 2A:
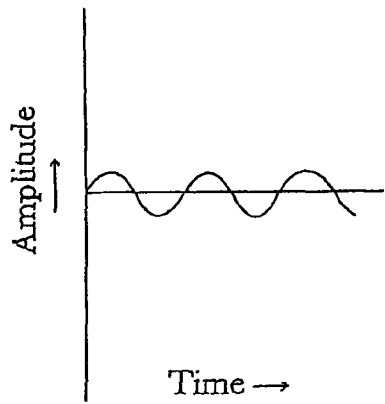
FIGS. 2a and 2b show waves of different amplitudes but the same frequency.
Figure 2B:
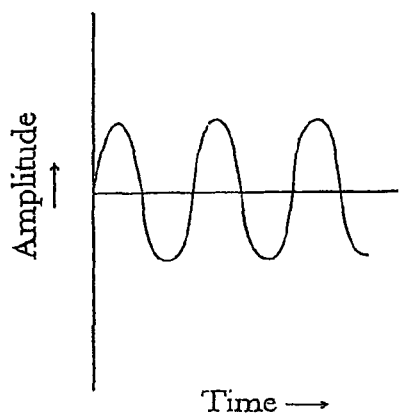

Both acoustic and electromagnetic energy may consist of waves. The number of waves in a period of time can be counted. Waves are often drawn, as in FIG. 1a. Usually, time is placed on the horizontal X-axis. The vertical Y-axis shows the strength or intensity of the wave. This is also called the amplitude. A weak wave will be of weak intensity and will have low amplitude (see FIG. 2a). A strong wave will have high amplitude (see FIG. 2b).

Traditionally, the number of waves per second is counted, to obtain the frequency.

Frequency=Number of waves/time=Waves/second=Hz.

Figure 3A:
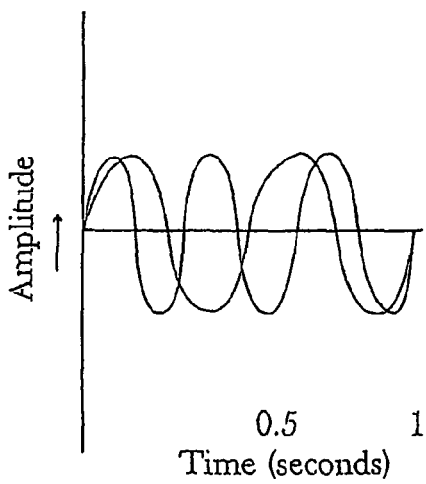
FIGS. 3a and 3b show frequency diagrams.
Figure 3B:
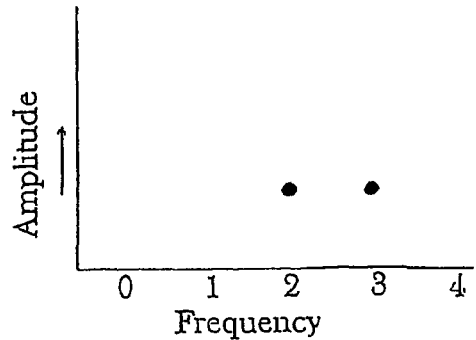

Another name for "waves per second", is "hertz" (abbreviated "Hz"). Frequency is drawn on wave diagrams by showing a different number of waves in a period of time (see FIG. 3a which shows waves having a frequency of 2 Hz and 3 Hz). It is also drawn by placing frequency itself, rather than time, on the X-axis (see FIG. 3b which shows the same 2 Hz and 3 Hz waves plotted differently).

Energy waves and frequency have some interesting properties, and may interact in some interesting ways. The manner in which wave energies interact, depends largely on the frequency. For example, when two waves of energy interact, each having the same amplitude, but one at a frequency of 400 Hz and the other at 100 Hz, the waves will add their frequencies, to produce a new frequency of 500 Hz (i.e., the "sum" frequency). The frequency of the waves will also subtract to produce a frequency of 300 HZ (i.e., the "difference" frequency). All wave energies typically add and subtract in this manner, and such adding and subtracting is referred to as heterodyning. Common results of heterodyning are familiar to most as harmonics in music.

Figures 4, 5:
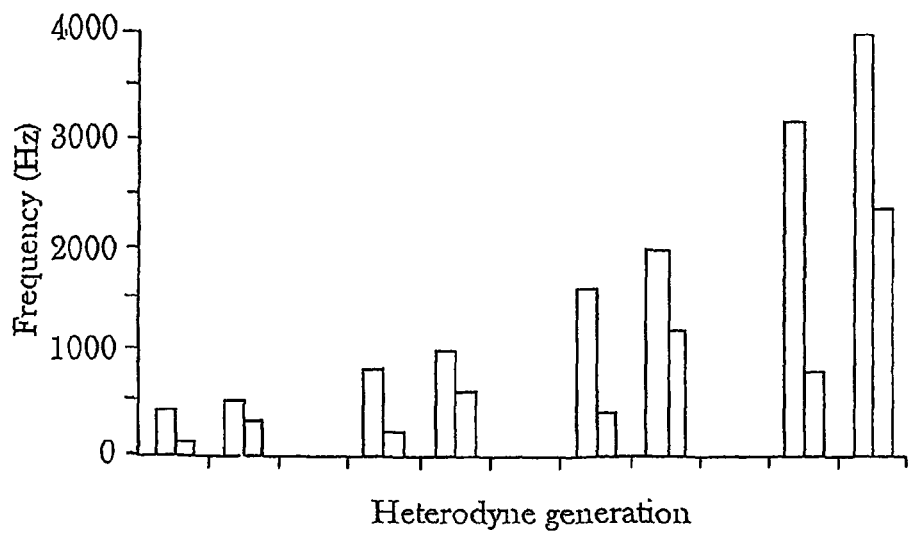
FIG. 4 shows a specific example of a heterodyne progression.
FIG. 5 shows a graphical example of the heterodyned series from FIG. 4.

There is a mathematical, as well as musical basis, to the harmonics produced by heterodyning. Consider, for example, a continuous progression of heterodyned frequencies. As discussed above, beginning with 400 Hz and 100 Hz, the sum frequency is 500 Hz and the difference frequency is 300 Hz. If these frequencies are further heterodyned (added and subtracted) then new frequencies of 800 (i.e., 500+300) and 200 (i.e., 500−300) are obtained. The further heterodyning of 800 and 200 results in 1,000 and 600 Hz as shown in FIG. 4.

A mathematical pattern begins to emerge. Both the sum and the difference columns contain alternating series of numbers that double with each set of heterodynes. In the sum column, 400 Hz, 800 Hz, and 1,600 Hz, alternates with 500 Hz, 1000 Hz, and 2000 Hz. The same sort of doubling phenomenon occurs in the difference column.

Heterodyning of frequencies is the natural process that occurs whenever waveform energies interact. Heterodyning results in patterns of increasing numbers that are mathematically derived. The number patterns are integer multiples of the original frequencies. These multiples are called harmonics. For example, 800 Hz and 1600 Hz are harmonics of 400 Hz. In musical terms, 800 Hz is one octave above 400 Hz, and 1600 Hz is two octaves higher. It is important to understand the mathematical heterodyne basis for harmonics, which occurs in all waveform energies, and thus in all of nature.

The mathematics of frequencies is very important. Frequency heterodynes increase mathematically in visual patterns (see FIG. 5). Mathematics has a name for these visual patterns of FIG. 5. These patterns are called fractals. A fractal is defined as a mathematical function which produces a series of self-similar patterns or numbers. Fractal patterns have spurred a great deal of interest historically because fractal patterns are found everywhere in nature. Fractals can be found in the patterning of large expanses of coastline, all the way down to microorganisms. Fractals are found in the behavior of organized insects and in the behavior of fluids. The visual patterns produced by fractals are very distinct and recognizable. A typical fractal pattern is shown in FIG. 6.

A heterodyne is a mathematical function, governed by mathematical equations, just like a fractal. A heterodyne also produces self-similar patterns of numbers, like a fractal. If graphed, a heterodyne series produces the same familiar visual shape and form which is so characteristic of fractals. It is interesting to compare the heterodyne series in FIG. 5, with the fractal series in FIG. 6.

Heterodynes are fractals; the conclusion is inescapable. Heterodynes and fractals are both mathematical functions which produce a series of self-similar patterns or numbers. Wave energies interact in heterodyne patterns. Thus, all wave energies interact as fractal patterns. Once it is understood that the fundamental process of interacting energies is itself a fractal process, it becomes easier to understand why so many creatures and systems in nature also exhibit fractal patterns. The fractal processes and patterns of nature are established at a fundamental or basic level.

Accordingly, since energy interacts by heterodyning, matter should also be capable of interacting by a heterodyning process. All matter whether in large or small forms, has what is called a natural oscillatory frequency. The natural oscillatory frequency ("NOF") of an object, is the frequency at which the object prefers to vibrate, once set in motion. The NOF of an object is related to many factors including size, shape, dimension, and composition. The smaller an object is, the smaller the distance it has to cover when it oscillates back and forth. The smaller the distance, the faster it can oscillate, and the higher its NOF.

For example, consider a wire composed of metal atoms. The wire has a natural oscillatory frequency. The individual metal atoms also have unique natural oscillatory frequencies.

The NOF of the atoms and the NOF of the wire heterodyne by adding and subtracting, just the way energy heterodynes.

$$NOF_{atom} + NOF_{wire} = \text{Sum Frequency}_{atom+wire}$$

and $$NOF_{atom} - NOF_{wire} = \text{Difference Frequency}_{atom-wire}$$

If the wire is stimulated with the Difference Frequency$_{atom-wire}$, the difference frequency will heterodyne (add) with the NOF$_{wire}$ to produce NOF$_{atom}$, (natural oscillatory frequency of the atom) and the atom will absorb with the energy, thereby becoming stimulated to a higher energy level. Cirac and Zoeller reported this phenomenon in 1995, and they used a laser to generate the Difference Frequency.

$$\text{Difference Frequency}_{atom-wire} + NOF_{wire} = NOF_{atom}$$

Matter heterodynes with matter in a manner similar to the way in which wave energies heterodyne with other wave energies. This means that matter in its various states may also interact in fractal processes. This interaction of matter by fractal processes assists in explaining why so many creatures and systems in nature exhibit fractal processes and patterns. Matter, as well as energy, interacts by the mathematical equations of heterodynes, to produce harmonics and fractal patterns. That is why there are fractals everywhere around us.

Thus, energy heterodynes with energy, and matter heterodynes with matter. However, perhaps even more important is that matter can heterodyne with energy (and visa versa). In the metal wire discussion above, the Difference Frequency$_{atom-wire}$ in the experiment by Cirac and Zoeller was provided by a laser which used electromagnetic wave energy at a frequency equal to the Difference Frequency$_{atom-wire}$. The matter in the wire, via its natural oscillatory frequency, heterodyned with the electromagnetic wave energy frequency of the laser to produce the frequency of an individual atom of matter. This shows that energy and matter do heterodyne with each other.

In general, when energy encounters matter, one of three possibilities occur. The energy either bounces off the matter (i.e., is reflected energy), passes through the matter (i.e., is transmitted energy), or interacts and/or combines with the matter (e.g., is absorbed or heterodynes with the matter). If the energy heterodynes with the matter, new frequencies of energy and/or matter will be produced by mathematical processes of sums and differences. If the frequency thus produced matches an NOF of the matter, the energy will be, at least partially, absorbed, and the matter will be stimulated to, for example, a higher energy level, (i.e., it possesses more energy). A crucial factor which determines which of these three possibilities will happen is the frequency of the energy compared to the frequency of the matter. If the frequencies do not match, the energy will either be reflected, or will pass on through as transmitted energy. If the frequencies of the energy and the matter match either directly (e.g., are close to each other, as discussed in greater detail later herein), or match indirectly (e.g., heterodynes), then the energy is capable of interacting and/or combining with the matter.

Another term often used for describing the matching of frequencies is resonance. In this invention, use of the term resonance will typically mean that frequencies of matter and/or energy match. For example, if the frequency of energy and the frequency of matter match, the energy and matter are in resonance and the energy is capable of combining with the matter. Resonance, or frequency matching, is merely an aspect of heterodyning that permits the coherent transfer and combination of energy with matter.

In the example above with the wire and atoms, resonance could have been created with the atom, by stimulating the atom with a laser frequency exactly matching the NOF of the atom. In this case, the atom would be energized with its own resonant frequency and the energy would be transferred to the atom directly. Alternatively, as was performed in the actual wire/laser experiment, resonance could also have been created with the atom by using the heterodyning that naturally occurs between differing frequencies. Thus, the resonant frequency of the atom (NOF$_{atom}$) can be produced indirectly, as an additive (or subtractive) heterodyned frequency, between the resonant frequency of the wire (NOF$_{wire}$) and the applied frequency of the laser. Either direct resonance, or indirect resonance through heterodyned frequency matching, produces resonance and thus permits the combining of matter and energy. When frequencies match, energy transfers and amplitudes may increase.

Heterodyning produces indirect resonance. Heterodyning also produces harmonics, (i.e., frequencies that are integer multiples of the resonant (NOF) frequency. For example, the music note "A" is approximately 440 Hz. If that frequency is doubled to about 880 Hz, the note "A" is heard an octave higher. This first octave is called the first harmonic. Doubling the note or frequency again, from 880 Hz to 1,760 Hz (i.e., four times the frequency of the original note) results in another "A", two octaves above the original note. This is called the third harmonic. Every time the frequency is doubled another octave is achieved, so these are the even integer multiples of the resonant frequency.

In between the first and third harmonic is the second harmonic, which is three times the original note. Musically, this is not an octave like the first and third harmonics. It is an octave and a fifth, equal to the second "E" above the original "A". All of the odd integer multiples are fifths, rather than octaves. Because harmonics are simply multiples of the fundamental natural oscillatory frequency, harmonics stimulate the NOF or resonant frequency indirectly. Thus by playing the high "A" at 880 Hz on a piano, the string for middle "A" at 440 Hz should also begin to vibrate due to the phenomenon of harmonics.

Matter and energy in chemical reactions respond to harmonics of resonant frequencies much the way musical instruments do. Thus, the resonant frequency of the atom (NOF$_{atom}$) can be stimulated indirectly, using one or more of its' harmonic frequencies. This is because the harmonic frequency heterodynes with the resonant frequency of the atom itself (NOF$_{atom}$). For example, in the wire/atom example above, if the laser is tuned to 800 THz and the atom resonates at 400 THz, heterodyning the two frequencies results in:

$$800\ THz - 400\ THz = 400\ THz$$

The 800 THz (the atom's first harmonic), heterodynes with the resonant frequency of the atom, to produce the atom's own resonant frequency. Thus the first harmonic indirectly resonates with the atom's NOF, and stimulates the atom's resonant frequency as a first generation heterodyne.

Of course, the two frequencies will also heterodyne in the other direction, producing:

$$800\ THz + 400\ THz = 1{,}200\ THz$$

The 1,200 THz frequency is not the resonant frequency of the atom. Thus, part of the energy of the laser will heterodyne to produce the resonant frequency of the atom. The other part of the energy of the laser heterodynes to a different frequency, that does not itself stimulate the resonant frequency of the atom. That is why the stimulation of an object by a harmonic frequency of particular strength of amplitude, is typically less than the stimulation by its' own resonant (NOF) frequency at the same particular strength.

Although it appears that half the energy of a harmonic is wasted, that is not necessarily the case. Referring again to the exemplary atom vibrating at 400 THz, exposing the atom to electromagnetic energy vibrating at 800 THz will result in frequencies subtracting and adding as follows:

$$800\ THz - 400\ THz = 400\ THz$$

and $$800\ THz + 400\ THz = 1{,}200\ THz$$

The 1,200 THz heterodyne, for which about 50% of the energy appears to be wasted, will heterodyne with other frequencies also, such as 800 THz. Thus, $$1{,}200\ THz - 800\ THz = 400\ THz$$

Figure 14:
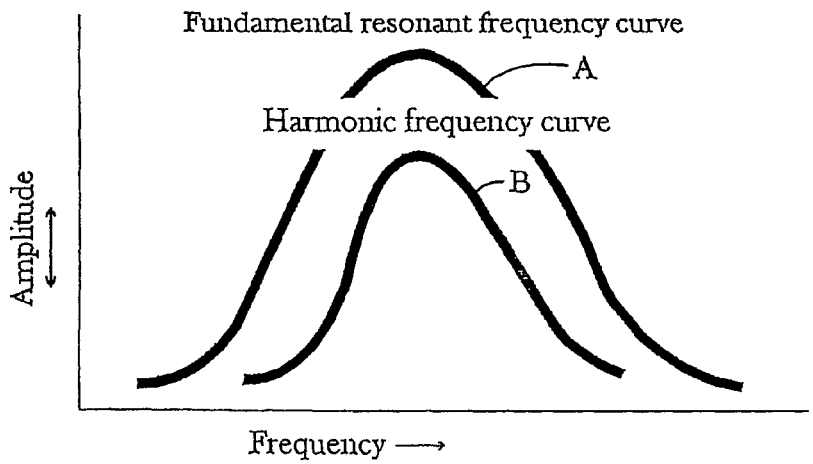
FIG. 14 shows two different energy transfer curves at fundamental resonance frequencies (curve A) and a harmonic frequency (curve B).

Also, the 1,200 THz will heterodyne with 400 THz:

$$1{,}200\ THz - 400\ THz = 800\ THz,$$

thus producing 800 THz, and the 800 THz will heterodyne with 400 THz:

$$800\ THz - 400\ THz = 400\ THz,$$

thus producing 400 THz frequency again. When other generations of heterodynes of the seemingly wasted energy are taken into consideration, the amount of energy transferred by a first harmonic frequency is much greater than the previously suggested 50% transfer of energy. There is not as much energy transferred by this approach when compared to direct resonance, but this energy transfer is sufficient to produce a desired effect (see FIG. 14).

As stated previously, Ostwald's theories on catalysts and bond formation were based on the kinetic theories of chemistry from the turn of the century. However, it should now be understood that chemical reactions are interactions of matter, and that matter interacts with other matter through resonance and heterodyning of frequencies; and energy can just as easily interact with matter through a similar processes of resonance and heterodyning. With the advent of spectroscopy (discussed in more detail elsewhere herein), it is evident that matter produces, for example, electromagnetic energy at the same or substantially the same frequencies at which it vibrates. Energy and matter can move about and recombine with other energy or matter, as long as their frequencies match, because when frequencies match, energy transfers. In many respects, both philosophically and mathematically, both matter and energy can be fundamentally construed as corresponding to frequency. Accordingly, since chemical reactions are recombinations of matter driven by energy, chemical reactions are in effect, driven just as much by frequency.

Analysis of a typical chemical reaction should be helpful in understanding the normal processes disclosed herein. A representative reaction to examine is the formation of water from hydrogen and oxygen gases, catalyzed by platinum. Platinum has been known for some time to be a good hydrogen catalyst, although the reason for this has not been well understood.

$$H_2 + 1/2 O_2 \xrightarrow{Pt} \longrightarrow H_2O$$

This reaction is proposed to be a chain reaction, depending on the generation and stabilization of the hydrogen and hydroxy intermediates. The proposed reaction chain is:

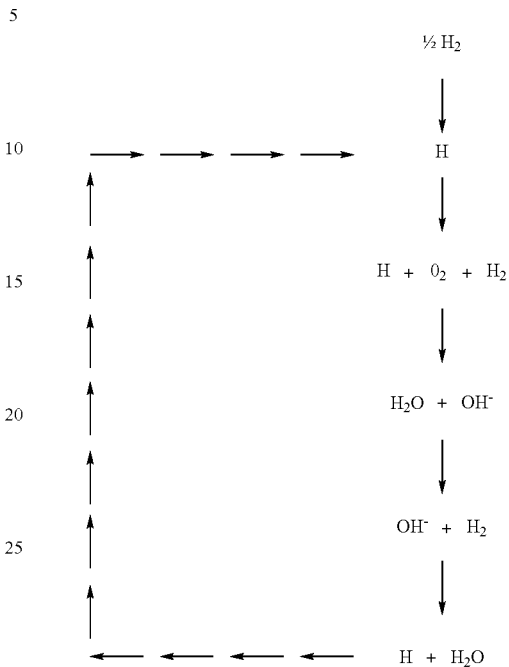

Generation of the hydrogen and hydroxy intermediates are thought to be crucial to this reaction chain. Under normal circumstances, hydrogen and oxygen gas can be mixed together for an indefinite amount of time, and they will not form water. Whenever the occasional hydrogen molecule splits apart, the hydrogen atoms do not have adequate energy to bond with an oxygen molecule to form water. The hydrogen atoms are very short-lived as they simply re-bond again to form a hydrogen molecule. Exactly how platinum catalyzes this reaction chain is a mystery to the prior art.

The present invention teaches that an important step to catalyzing this reaction is the understanding now provided that it is crucial not only to generate the intermediates, but also to energize and/or stabilize (i.e., maintain the intermediates for a longer time), so that the intermediates have sufficient energy to, for example, react with other components in the reaction system. In the case of platinum, the intermediates react with the reactants to form product and more intermediates (i.e., by generating, energizing and stabilizing the hydrogen intermediate, it has sufficient energy to react with the molecular oxygen reactant, forming water and the hydroxy intermediate, instead of falling back into a hydrogen molecule). Moreover, by energizing and stabilizing the hydroxy intermediates, the hydroxy intermediates can react with more reactant hydrogen molecules, and again water and more intermediates result from this chain reaction. Thus, generating energizing and/or stabilizing the intermediates, influences this reaction pathway. Paralleling nature in this regard would be desirable (e.g., nature can be paralleled by increasing the energy levels of the intermediates). Specifically, desirable, intermediates can be energized and/or stabilized by applying at least one appropriate electromagnetic frequency resonant with the intermediate, thereby stimulating the intermediate to a higher energy level. Interestingly, that is what platinum does (e.g., various platinum frequencies resonate with the intermediates on the reaction pathway for water formation). Moreover, in the process of energizing and stabilizing the reaction intermediates, platinum fosters the generation of more intermediates, which allows the reaction chain to continue, and thus catalyzes the reaction.

As a catalyst, platinum takes advantage of many of the ways that frequencies interact with each other. Specifically, frequencies interact and resonate with each other: 1) directly, by matching a frequency; or 2) indirectly, by matching a frequency through harmonics or heterodynes. In other words, platinum vibrates at frequencies which both directly match the natural oscillatory frequencies of the intermediates, and which indirectly match their frequencies, for example, by heterodyning harmonics with the intermediates.

Further, in addition to the specific intermediates of the reaction discussed above herein, it should be understood that in this reaction, like in all reactions, various transients or transient states also exist. In some cases, transients or transient states may only involve different bond angles between similar chemical species or in other cases transients may involve completely different chemistries altogether. In any event, it should be understood that numerous transient states exist between any particular combination of reactant and reaction product.

Figure 8A:
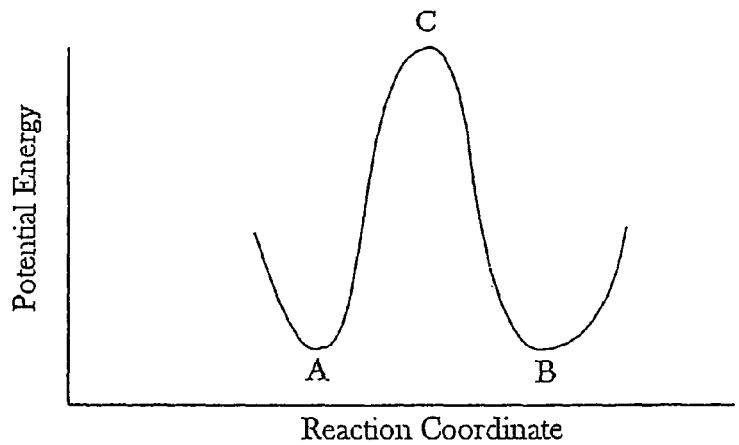
FIGS. 8a-8c show three different simple reaction profiles.

It should now be understood that physical catalysts produce effects by generating, energizing and/or stabilizing all manner of transients, as well as intermediates. In this regard, FIG. 8a shows a single reactant and a single product. The point "A" corresponds to the reactant and the point "B" corresponds to the reaction product. The point "C" corresponds to an activated complex. Transients correspond to all those points on the curve between reactant "A" and product "B", and can also include the activated complex "C".

Figure 8B:
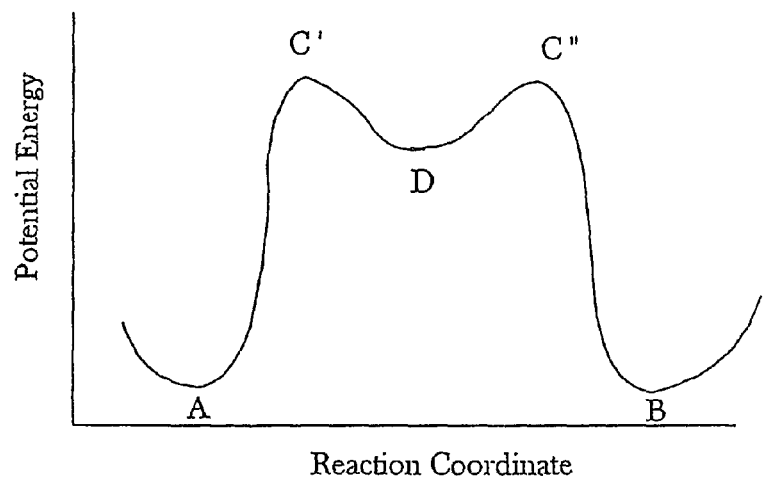
Figure 8C:
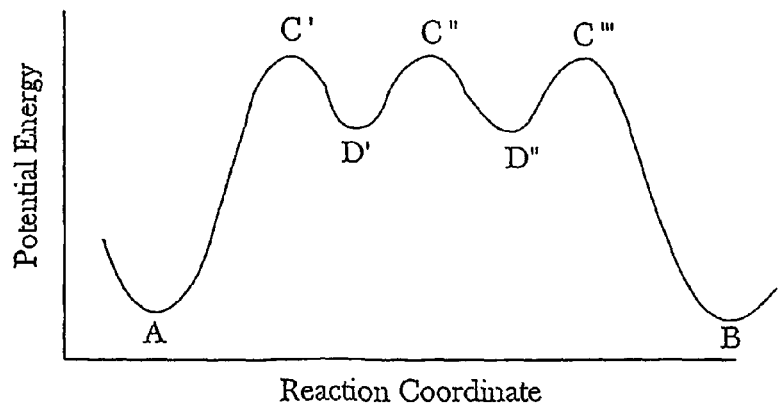

In a more complex reaction which involves formation of at least one intermediate, the reaction profile looks somewhat different. In this regard, reference is made to FIG. 8b, which shows reactant "A", product "B", activated complex "C'" and C", and intermediate "D". In this particular example, the intermediate "D" exists as a minimum in the energy reaction profile of the reaction, while it is surrounded by the activated complexes C' and C". However, again, in this particular reaction, transients correspond to anything between the reactant "A" and the reaction product "B", which in this particular example, includes the two activated complexes "C'''" and "C''''", as well as the intermediate "D". In the particular example of hydrogen and oxygen combining to form water, the reaction profile is closer to that shown in FIG. 8c. In this particular reaction profile, "D'" and "D''" could correspond generally to the intermediates of the hydrogen atom and hydroxy molecule.

Figure 69D:
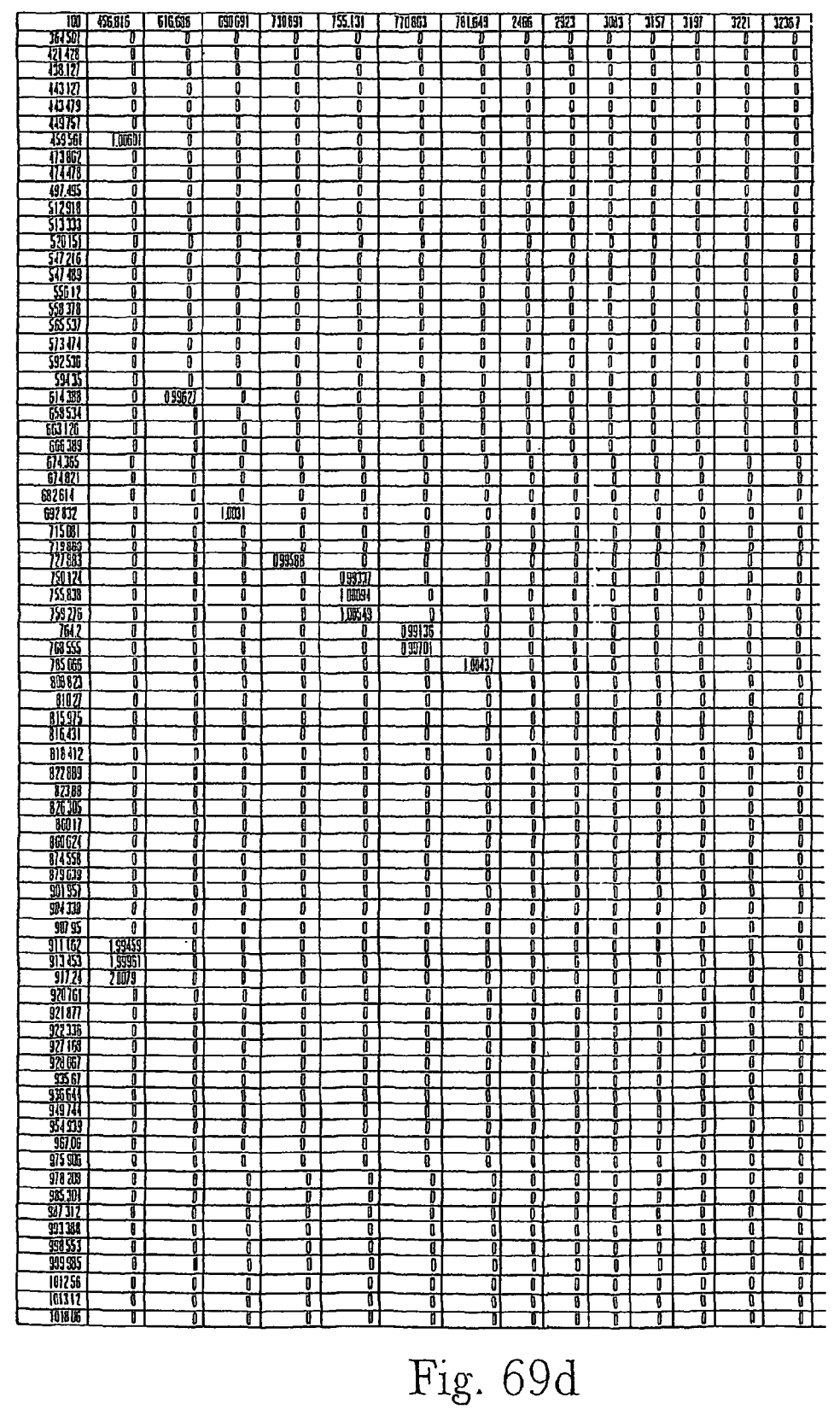

Now, with specific reference to the reaction to form water, both intermediates are good examples of how platinum produces resonance in an intermediate by directly matching a frequency. Hydroxy intermediates vibrate strongly at frequencies of 975 THz and 1,060 THz. Platinum also vibrates at 975 THz and 1,060 THz. By directly matching the frequencies of the hydroxy intermediates, platinum can cause resonance in hydroxy intermediates, enabling them to be energized, stimulated and/or stabilized long enough to take part in chemical reactions. Similarly, platinum also directly matches frequencies of the hydrogen intermediates. Platinum resonates with about 10 out of about 24 hydrogen frequencies in its electronic spectrum (see FIG. 69). Specifically, FIG. 69 shows the frequencies of hydrogen listed horizontally across the Table and the frequencies of platinum listed vertically on the Table. Thus, by directly resonating with the intermediates in the above-described reaction, platinum facilitates the generation, energizing, stimulating, and/or stabilizing of the intermediates, thereby catalyzing the desired reaction.

Platinum's interactions with hydrogen are also a good example of matching frequencies through heterodyning. It is disclosed herein, and shown clearly in FIG. 69, that many of the platinum frequencies resonate indirectly as harmonics with the hydrogen atom intermediate (e.g., harmonic heterodynes). Specifically, fifty-six (56) frequencies of platinum (i.e., 33% of all its frequencies) are harmonics of nineteen (19) hydrogen frequencies (i.e., 80% of its 24 frequencies). Fourteen (14) platinum frequencies are first harmonics (2×) of seven (7) hydrogen frequencies. And, twelve (12) platinum frequencies are third harmonics (4×) of four (4) hydrogen frequencies. Thus, the presence of platinum causes massive indirect harmonic resonance in the hydrogen atom, as well as significant direct resonance.

Figure 9A:
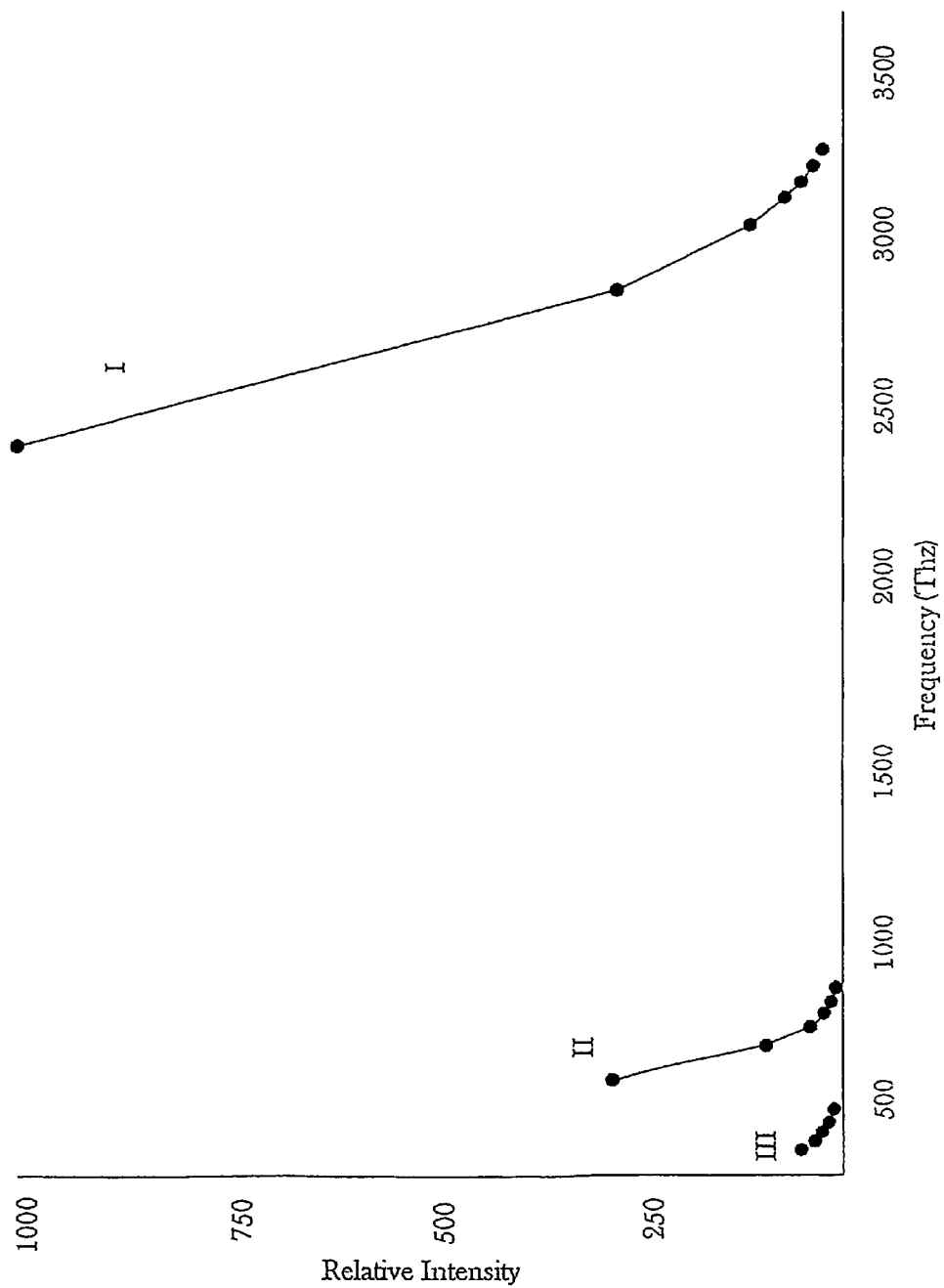
FIGS. 9a and 9b show fine frequency diagram curves for hydrogen.
Figures 9B, 10:
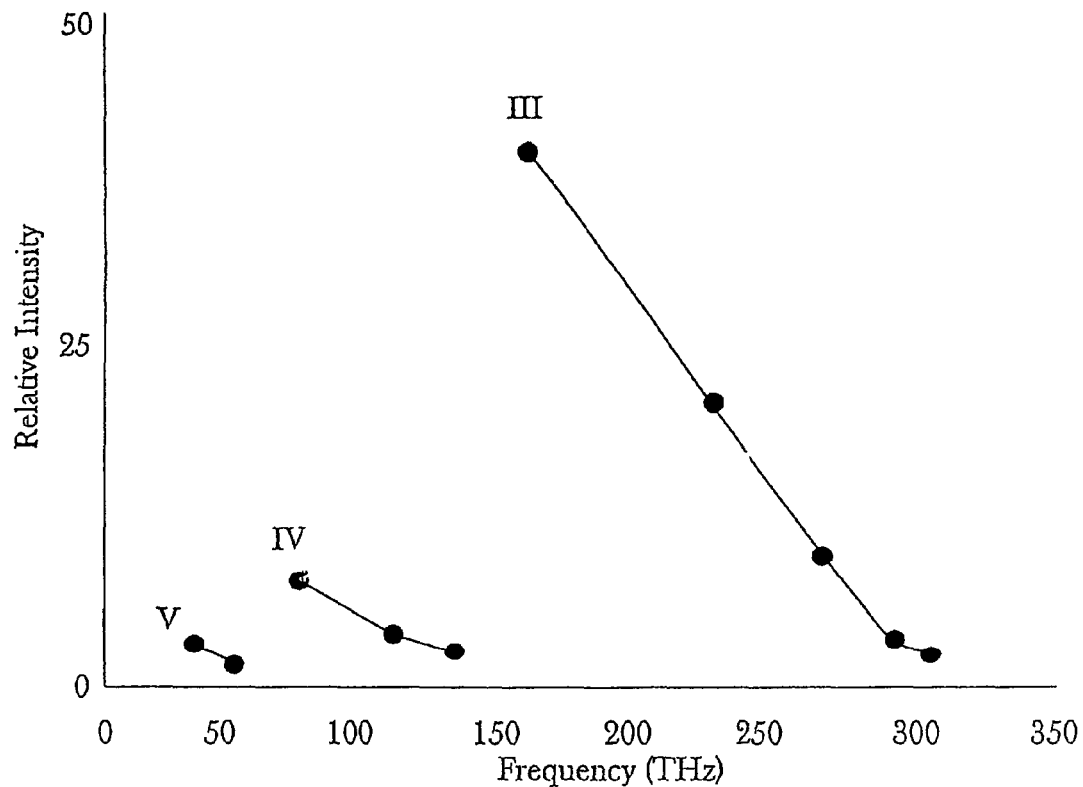
FIG. 10 shows various frequencies and intensities for hydrogen.

Further focus on the individual hydrogen frequencies is even more informative. FIGS. 9-10 show a different picture of what hydrogen looks like when the same information used to make energy level diagrams is plotted as actual frequencies and intensities instead. Specifically, the X-axis shows the frequencies emitted and absorbed by hydrogen, while the Y-axis shows the relative intensity for each frequency. The frequencies are plotted in terahertz (THz, $10^{12}$ Hz) and are rounded to the nearest THz. The intensities are plotted on a relative scale of 1 to 1,000. The highest intensity frequency that hydrogen atoms produce is 2,466 THz. This is the peak of curve I to the far right in FIG. 9a. This curve I shall be referred to as the first curve. Curve I sweeps down and to the right, from 2,466 THz at a relative intensity of 1,000 to 3,237 THz at a relative intensity of only about 15.

The second curve in FIG. 9a, curve II, starts at 456 THz with a relative intensity of about 300 and sweeps down and to the right. It ends at a frequency of 781 THz with a relative intensity of five (5). Every curve in hydrogen has this same downward sweep to the right. Progressing from right to left in FIG. 9, the curves are numbered I through V; going from high to low frequency and from high to low intensity.

The hydrogen frequency chart shown in FIG. 10 appears to be much simpler than the energy level diagrams. It is thus easier to visualize how the frequencies are organized into the different curves shown in FIG. 9. In fact, there is one curve for each of the series described by Rydberg. Curve 'I' contains the frequencies in the Lyman series, originating from what quantum mechanics refers to as the first energy level. The second curve from the right, curve "II", equates to the second energy level, and so on.

The curves in the hydrogen frequency chart of FIG. 9 are composed of sums and differences (i.e., they are heterodyned). For example, the smallest curve at the far left, labeled curve "V", has two frequencies shown, namely 40 THz and 64 THz, with relative intensities of six (6) and four (4), respectively (see also FIG. 10). The next curve, IV, begins at 74 THz, proceeds to 114 THz and ends with 138 THz. The summed heterodyne calculations are thus:

40+74=114

64+74+138.

The frequencies in curve IV are the sum of the frequencies in curve V plus the peak intensity frequency in curve IV.

Alternatively, the frequencies in curve IV, minus the frequencies in curve V, yield the peak of curve IV:

114−40=74

138−64=74.

This is not just a coincidental set of sums or differences in curves IV and V. Every curve in hydrogen is the result of adding each frequency in any one curve, with the highest intensity frequency in the next curve.

These hydrogen frequencies are found in both the atom itself, and in the electromagnetic energy it radiates. The frequencies of the atom and its energy, add and subtract in regular fashion. This is heterodyning. Thus, not only matter and energy heterodyne interchangeably, but matter heterodynes its' own energy within itself.

Moreover, the highest intensity frequencies in each curve are heterodynes of heterodynes. For example, the peak frequency in Curve I of FIG. 9 is 2,466 THz, which is the third harmonic of 616 THz;

4×616 *THz*=2,466 *THz*.

Thus, 2,466 THz is the third harmonic of 616 THz (Recall that for heterodyned harmonics, the result is even multiples of the starting frequency, i.e., for the first harmonic 2× the original frequency and the third harmonic is 4× the original frequency. Multiplying a frequency by four (4) is a natural result of the heterodyning process.) Thus, 2,466 THz is a fourth generation heterodyne, namely the third harmonic of 616 THz.

The peak of curve II of FIG. 9, a frequency corresponding to 456 THz, is the third harmonic of 114 THz in curve IV. The peak of curve III, corresponding to a frequency of 160 THz, is the third harmonic of 40 THz in curve V. The peaks of the curves shown in FIG. 9 are not only heterodynes between the curves but are also harmonics of individual frequencies which are themselves heterodynes. The whole hydrogen spectrum turns out to be an incestuously heterodyned set of frequencies and harmonics.

Theoretically, this heterodyne process could go on forever. For example, if 40 is the peak of a curve, that means the peak is four (4) times a lower number, and it also means that the peak of the previous curve is 24 (64−40=24). It is possible to mathematically extrapolate backwards and downwards this way to derive lower and lower frequencies. Peaks of successive curves to the left are 24.2382, 15.732, and 10.786 THz, all generated from the heterodyne process. These frequencies are in complete agreement with the Rydberg formula for energy levels 6, 7 and 8, respectively. Not much attention has historically been given by the prior art to these lower frequencies and their heterodyning.

This invention teaches that the heterodyned frequency curves amplify the vibrations and energy of hydrogen. A low intensity frequency on curve IV or V has a very high intensity by the time it is heterodyned out to curve I. In many respects, the hydrogen atom is just one big energy amplification system. Moving from low frequencies to high frequencies, (i.e., from curve V to curve I in FIG. 9), the intensities increase dramatically. By stimulating hydrogen with 2,466 THz at an intensity of 1,000, the result will be 2,466 THz at 1,000 intensity. However, if hydrogen is stimulated with 40 THz at an intensity of 1,000, by the time it is amplified back out to curve I of FIG. 9, the result will be 2,466 THz at an intensity of 167,000. This heterodyning turns out to have a direct bearing on platinum, and on how platinum interacts with hydrogen. It all has to do with hydrogen being an energy amplification system. That is why the lower frequency curves are perceived as being higher energy levels. By understanding this process, the low frequencies of low intensity suddenly become potentially very significant.

Platinum resonates with most, if not all, of the hydrogen frequencies with one notable exception, the highest intensity curve at the far right in the frequency chart of FIG. 9 (i.e., curve I) representing energy level 1, and beginning with 2,466 THz. Platinum does not appear to resonate significantly with the ground state transition of the hydrogen atom. However, it does resonate with multiple upper energy levels of lower frequencies.

With this information, one ongoing mystery can be solved. Ever since lasers were developed, the prior art chemists believed that there had to be some way to catalyze a reaction using lasers. Standard approaches involved using the single highest intensity frequency of an atom (such as 2,466 THz of hydrogen) because it was apparently believed that the highest intensity frequency would result in the highest reactivity. This approach was taken due to considering only the energy level diagrams. Accordingly, prior art lasers are typically tuned to a ground state transition frequency. This use of lasers in the prior art has been minimally successful for catalyzing chemical reactions. It is now understood why this approach was not successful. Platinum, the quintessential hydrogen catalyst, does not resonate with the ground state transition of hydrogen. It resonates with the upper energy level frequencies, in fact, many of the upper level frequencies. Without wishing to be bound by any particular theory or explanation, this is probably why platinum is such a good hydrogen catalyst.

Platinum resonates with multiple frequencies from the upper energy levels (i.e., the lower frequencies). There is a name given to the process of stimulating many upper energy levels, it is called a laser.

Einstein essentially worked out the statistics on lasers at the turn of the century when atoms at the ground energy level ($E_1$) are resonated to an excited energy level ($E_2$). Refer to the number of atoms in the ground state as "$N_1$," and the number of excited atoms as "$N_2$", with the total "$N_{total}$". Since there are only two possible states that atoms can occupy:

$$N_{total} = N_1 + N_2.$$

After all the mathematics are performed, the relationship which evolves is:

$$\frac{N_2}{N_{total}} = \frac{N_2}{N_1 + N_2} < \frac{1}{2}$$

In a two level system, it is predicted that there will never by more than 50% of the atoms in the higher energy level, $E_2$, at the same time.

If, however, the same group of atoms is energized at three (3) or more energy levels (i.e., a multi-level system), it is possible to obtain more than 50% of the atoms energized above the first level. By referring to the ground and energized levels as $E_1$, $E_2$, and $E_3$, respectively, and the numbers of atoms as $N_{total}$, $N_1$, $N_2$, and $N_3$, under certain circumstances, the number of atoms at an elevated energy level ($N_3$) can be more than the number at a lower energy level ($N_2$). When this happens, it is referred to as a "population inversion". Population inversion means that more of the atoms are at higher energy levels that at the lower energy levels.

Figure 11A:
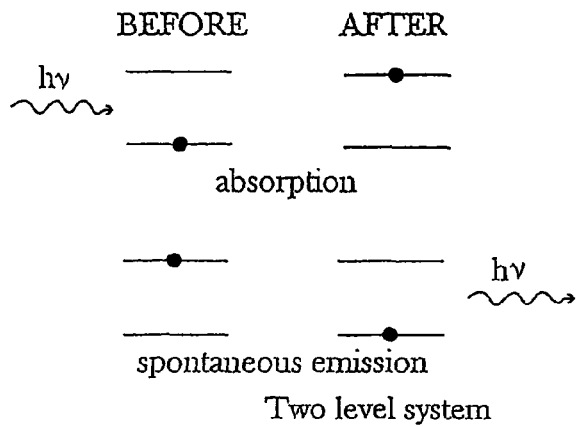
FIGS. 11a and 11b show two light amplification diagrams with stimulated emission/population inversions.
Figure 11B:
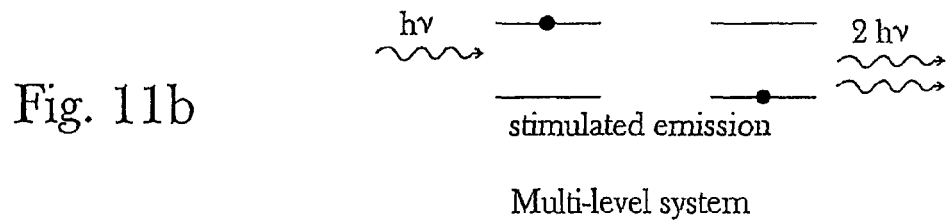

Population inversion in lasers is important. Population inversion causes amplification of light energy. For example, in a two-level system, one photon in results in one photon out. In a system with three (3) or more energy levels and population inversion, one photon in may result in 5, 10, or 15 photons out (see FIG. 11). The amount of photons out depends on the number of levels and just how energized each level becomes. All lasers are based on this simple concept of producing a population inversion in a group of atoms, by creating a multi-level energized system among the atoms. Lasers are simply devices to amplify electromagnetic wave energy (i.e., light). Laser is actually an abbreviation for Light Amplification System for Emitting Radiation.

By referring back to the interactions discussed herein between platinum and hydrogen, platinum energizes 19 upper level frequencies in hydrogen (i.e., 80% of the total hydrogen frequencies). But only three frequencies are needed for a population inversion. Hydrogen is stimulated at 19. This is a clearly multi-level system. Moreover, consider that seventy platinum frequencies do the stimulating. On average, every hydrogen frequency involved is stimulated by three or four (i.e., 70/19) different platinum frequencies; both directly resonant frequencies and/or indirectly resonant harmonic frequencies. Platinum provides ample stimulus, atom per atom, to produce a population inversion in hydrogen. Finally, consider the fact that every time a stimulated hydrogen atom emits some electromagnetic energy, that energy is of a frequency that matches and stimulates platinum in return.

Platinum and hydrogen both resonate with each other in their respective multi-level systems. Together, platinum and hydrogen form an atomic scale laser (i.e., an energy amplification system on the atomic level). In so doing, platinum and hydrogen amplify the energies that are needed to stabilize both the hydrogen and hydroxy intermediates, thus catalyzing the reaction pathway for the formation of water. Platinum is such a good hydrogen catalyst because it forms a lasing system with hydrogen on the atomic level, thereby amplifying their respective energies.

Further, this reaction hints that in order to catalyze a cell reaction system and/or control the reaction pathway in a cell reaction system it is possible for only a single transient and/or intermediate to be formed and/or energized by an applied frequency (e.g., a spectral catalyst) and that by forming and/or stimulating at least one transient and/or at least one intermediate that is required to follow for a desired reaction pathway (e.g., either a complex reaction or a simple reaction), then a frequency, or combination of frequencies, which result in such formation or stimulation of only one of such required transients and/or intermediates may be all that is required. Accordingly, the present invention recognizes that in some cell reaction systems, by determining at least one required transient and/or intermediate, and by applying at least one frequency which generates, energizes and/or stabilizes said at least one transient and/or intermediate, then all other transients and/or intermediates required for a reaction to proceed down a desired reaction pathway may be self-generated. However, in some cases, the reaction could be increased in rate by applying the appropriate frequency or spectral energy pattern, which directly stimulates all transients and/or intermediates that are required in order for a reaction to proceed down a desired reaction pathway. Accordingly, depending upon the particulars of any cell reaction system, it may be desirable for a variety of reasons, including equipment, environmental reaction conditions, etc., to provide or apply a frequency or spectral energy pattern which results in the formation and/or stimulation and/or stabilization of any required transients and/or intermediates. Thus, in order to determine an appropriate frequency or spectral energy pattern, it is first desirable to determine which transients and/or intermediates are present in any reaction pathway. Similarly, a conditioned participant could be formulated to accomplish a similar task.

Specifically, once all known required transients and/or intermediates are determined, then, one can determine experimentally or empirically which transients and/or intermediates are essential to a reaction pathway and then determine, which transients and or intermediates can be self-generated by the stimulation and/or formation of a different transient or intermediate. Once such determinations are made, appropriate spectral energies (e.g., electromagnetic frequencies) can then be applied to the cell reaction system to obtain the desirable reaction product and/or desirable reaction pathway.

It is known that an atom of platinum interacts with an atom of hydrogen and/or a hydroxy intermediate. And, that is exactly what modern chemistry has taught for the last one hundred years, based on Ostwald's theory of catalysis. However, the prior art teaches that catalysts must participate in the reaction by binding to the reactants, in other words, the prior art teaches a matter:matter bonding interaction is required for physical catalysts. As previously stated, these reactions follow these steps:

1. Reactant diffusion to the catalyst site;
2. Bonding of reactant to the catalyst site;
3. Reaction of the catalyst-reactant complex;
4. Bond rupture at the catalytic site (product); and
5. Diffusion of the product away from the catalyst site.

However, according to the present invention, for example, energy:energy frequencies can interact as well as energy:matter frequencies. Moreover, matter radiates energy, with the energy frequencies being substantially the same as the matter frequencies. So platinum vibrates at the frequency of 1,060 THz, and it also radiates electromagnetic energy at 1,060 THz. Thus, according to the present invention, the distinction between energy frequencies and matter frequencies starts to look less important.

Resonance can be produced in, for example, the reaction intermediates by permitting them to come into contact with additional matter vibrating at substantially the same frequencies, such as those frequencies of a platinum atom (e.g., platinum stimulating the reaction between hydrogen and oxygen to form water). Alternatively, according to the present invention, resonance can be produced in the intermediates by introducing electromagnetic energy corresponding to one or more platinum energies, which also vibrate at the same frequencies, thus at least partially mimicking (an additional mechanism of platinum is resonance with the $H_2$ molecule, a pathway reactant) the mechanism of action of a platinum catalyst. Matter, or energy, it makes no difference as far as the frequencies are concerned, because when the frequencies match, energy transfers. Thus, physical catalysts are not required. Rather, the application of at least a portion of the spectral pattern of a physical catalyst may be sufficient (i.e. at least a portion of the catalytic spectral pattern). However, in another preferred embodiment, substantially all of a spectral pattern can be applied.

Still further, by understanding the catalyst mechanism of action, particular frequencies can be applied to, for example, one or more reactants in a reaction system and, for example, cause the applied frequencies to heterodyne with existing frequencies in the matter itself to result in frequencies which correspond to one or more platinum catalyst or other relevant spectral frequencies. For example, both the hydrogen atom and the hydrogen molecule have unique frequencies. By heterodyning the frequencies a subtractive frequency can be determined:

$$NOF_{H\ atom} - NOF_{H\ molecule} = Difference_{H\ atom-molecule}$$

The $Difference_{H\ atom-molecule}$ frequency applied to the $H_2$ molecule reactant will heterodyne with the molecule and energize the individual hydrogen atoms as intermediates.

Similarly, any reaction participant can serve as the heterodyning backboard for stimulation of another participant. For example,

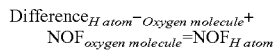

or

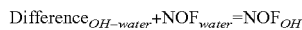

This approach enables greater flexibility for choice of appropriate equipment to apply appropriate frequencies. However, the key to this approach is understanding catalyst mechanisms of action and the reaction pathway so that appropriate choices for application of frequencies can be made.

Specifically, whenever reference is made to, for example, a spectral catalyst duplicating at least a portion of a physical catalyst's spectral pattern, this reference is to all the different frequencies produced by a physical catalyst; including, but not necessarily limited to, electronic, vibrational, rotational, and NOF frequencies. To catalyze, control, and/or direct a chemical reaction then, all that is needed is to duplicate one or more frequencies from a physical catalyst, with, for example, an appropriate electromagnetic energy. The actual physical presence of the catalyst is not necessary. A spectral catalyst can substantially completely replace a physical catalyst, if desired.

A spectral catalyst can also augment or promote the activity of a physical catalyst. The exchange of energy at particular frequencies, between hydrogen, hydroxy, and platinum is primarily what drives the conversion to water. These participants interact and create a miniature atomic scale lasing system that amplify their respective energies. The addition of these same energies to a cell reaction system, using a spectral catalyst, does the same thing. The spectral catalyst amplifies the participant energies by resonating with them and when frequencies match, energy transfers and the chemicals (matter) can absorb the energy. Thus, a spectral catalyst can augment a physical catalyst, as well as replace it. In so doing, the spectral catalyst may increase the reaction rate, enhance specificity, and/or allow for the use of less physical catalyst.

Figure 12:
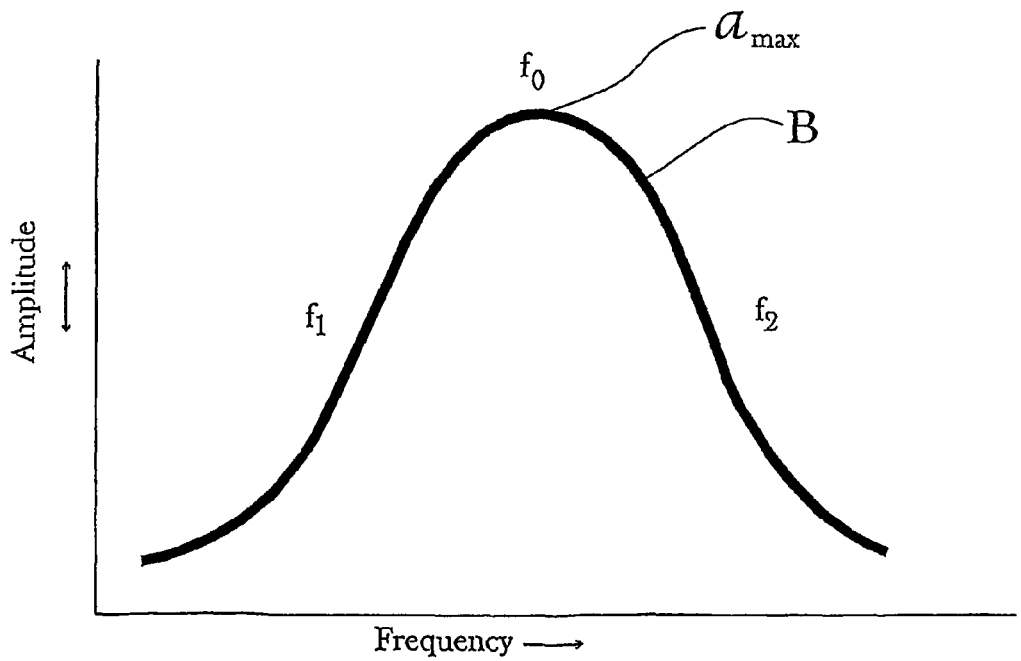
FIG. 12 shows a resonance curve where the resonance frequency is $f_0$, an upper frequency=$f_2$ and a lower frequency=$f_1$, wherein $f_1$ and $f_2$ are at about 50% of the amplitude of $f_0$.

FIG. 12 shows a basic bell-shaped curve produced by comparing how much energy an object absorbs, as compared to the frequency of the energy. This curve is called a resonance curve. As elsewhere herein stated, the energy transfer between, for example, atoms or molecules, reaches a maximum at the resonant frequency ($f_0$). The farther away an applied frequency is from the resonant frequency, $f_0$, the lower the energy transfer (e.g., matter to matter, energy to matter, etc.). At some point the energy transfer will fall to a value representing only about 50% of that at the resonant frequency $f_0$. The frequency higher than the resonant frequency, at which energy transfer is only about 50% is called "$f_2$." The frequency lower than the resonant frequency, at which about 50% energy transfer occurs, is labeled "$f_1$."

The resonant characteristics of different objects can be compared using the information from the simple exemplary resonance curve shown in FIG. 12. One such useful characteristic is called the "resonance quality" or "Q" factor. To determine the resonance quality for an object the following equation is utilized:

$$Q = \frac{f_0}{(f_2 - f_1)}$$

Figure 13A:
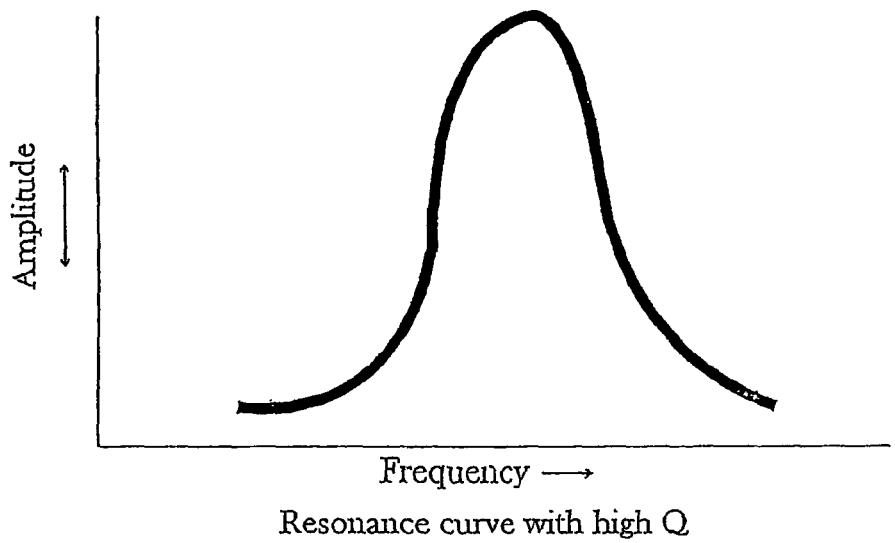
FIGS. 13a and 13b show two different resonance curves having different quality factors.
Figure 13B:
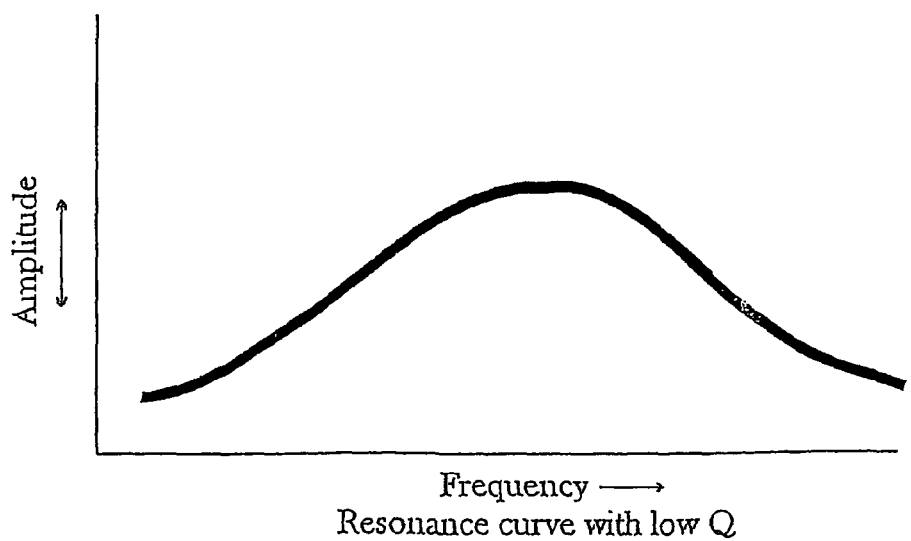

Accordingly, as shown from the equation, if the bell-shaped resonance curve is tall and narrow, then ($f_2-f_1$) will be a very small number and Q, the resonance quality, will be high (see FIG. 13a). An example of a material with a high "Q" is a high quality quartz crystal resonator. If the resonance curve is low and broad, then the spread or difference between $f_2$ and $f_1$ will be relatively large. An example of a material with a low "Q" is a marshmallow. The dividing of the resonant frequency by this large number will produce a much lower Q value (see FIG. 13b).

Atoms and molecules, for example, have resonance curves which exhibit properties similar to larger objects such as quartz crystals and marshmallows. If the goal is to stimulate atoms in a reaction (e.g., hydrogen in the reaction to produce water as mentioned previously) a precise resonant frequency produced by a cell reaction system component or environmental reaction condition (e.g., hydrogen) can be used. It is not necessary to use the precise frequency, however. Use of a frequency that is near a resonant frequency of, for example, one or more cell reaction system components or environmental reaction conditions is adequate. There will not be quite as much of an effect as using the exact resonant frequency, because less energy will be transferred, but there will still be an effect. The closer the applied frequency is to the resonant frequency, the more the effect. The farther away the applied frequency is from the resonant frequency, the less effect that is present (i.e., the less energy transfer that occurs).

Harmonics present a similar situation. As previously stated, harmonics are created by the heterodyning (i.e., adding and subtracting) of frequencies, allowing the transfer of significant amounts of energy. Accordingly, for example, desirable results can be achieved in chemical reactions if applied frequencies (e.g., at least a portion of a spectral catalyst) are harmonics (i.e., matching heterodynes) with one or more resonant frequency(ies) of one or more cell reaction system components or environmental reaction conditions.

Further, similar to applied frequencies being close to resonant frequencies, applied frequencies which are close to the harmonic frequency can also produce desirable results. The amplitude of the energy transfer will be less relative to a harmonic frequency, but an effect will still occur. For example, if the harmonic produces 70% of the amplitude of the fundamental resonant frequency and by using a frequency which is merely close to the harmonic, for example, about 90% on the harmonic's resonance curve, then the total effect will be 90% of 70%, or about 63% total energy transfer in comparison to a direct resonant frequency. Accordingly, according to the present invention, when at least a portion of the frequencies of one or more cell reaction system components or environmental reaction conditions at least partially match, then at least some energy will transfer and at least some reaction will occur (i.e., when frequencies match, energy transfers).

Duplicating the Catalyst Mechanisms of Action

As stated previously, to catalyze, control, and/or direct a chemical reaction, a spectral catalyst can be applied. The spectral catalyst may correspond to at least a portion of a spectral pattern of a physical catalyst or the spectral catalyst may correspond to frequencies which form or stimulate required participants (e.g., heterodyned frequencies) or the spectral catalyst may substantially duplicate environmental reaction conditions such as temperature or pressure. Thus, as now taught by the present invention, the actual physical presence of a catalyst is not required to achieve the desirable chemical reactions. The removal of a physical catalyst is accomplished by understanding the underlying mechanism inherent in catalysis, namely that desirable energy can be exchanged (i.e., transferred) between, for example, (1) at least one participant (e.g., reactant, transient, intermediate, activated complex, reaction product, promoter and/or poison) and/or at least one component in a cell reaction system and (2) an applied electromagnetic energy (e.g., spectral catalyst) when such energy is present at one or more specific frequencies. In other words, the targeted mechanism that nature has built into the catalytic process can be copied according to the teachings of the present invention. Nature can be further mimicked because the catalyst process reveals several opportunities for duplicating catalyst mechanisms of action, and hence improving the use of spectral catalysts, as well as the control of countless chemical reactions.

For example, the previously discussed reaction of hydrogen and oxygen to produce water, which used platinum as a catalyst, is a good starting point for understanding catalyst mechanisms of action. For example, this invention discloses that platinum catalyzes the reaction in several ways not contemplated by the prior art:

Platinum directly resonates with and energizes reaction intermediates and/or transients (e.g., atomic hydrogen and hydroxy radicals);

Platinum harmonically resonates with and energizes at least one reaction intermediate and or transient (e.g., atomic hydrogen); and Platinum energizes multiple upper energy levels of at least one reaction intermediate and or transient (e.g., atomic hydrogen).

This knowledge can be utilized to improve the functioning of the spectral catalyst and/or spectral energy catalyst to design spectral catalysts and spectral energy catalysts which differ from actual catalytic spectral patterns, and to design physical catalysts (or conditionable participants that can be conditioned to function as physical catalysts) and to optimize environmental reaction conditions. For example, the frequencies of atomic platinum are in the ultraviolet, visible light, and infrared regions of the electromagnetic spectrum. The electronic spectra of virtually all atoms are in these same regions. However, these very high electromagnetic frequencies can be a problem for large-scale and industrial applications because wave energies having high frequencies typically do not penetrate matter very well (i.e., do not penetrate far into matter). The tendency of wave energy to be absorbed rather than transmitted, can be referred to as attenuation. High frequency wave energies have a high attenuation, and thus do not penetrate far into a typical industrial scale reaction vessel containing typical reactants for a chemical reaction. Thus, the duplication and application of at least a portion of the spectral pattern of platinum into a commercial scale reaction vessel will typically be a slow process because a large portion of the applied spectral pattern of the spectral catalysts may be rapidly absorbed near the edges of the reaction vessel.

Thus, in order to input energy into a large industrial-sized commercial reaction vessel, a lower frequency energy could be used that would penetrate farther into the reactants housed within the reaction vessel. The present invention teaches that this can be accomplished in a unique manner by copying nature. As discussed herein, the spectra of atoms and molecules are broadly classified into three (3) different groups: electronic, vibrational, and rotational. The electronic spectra of atoms and small molecules are said to result from transitions of electrons from one energy level to another, and have the corresponding highest frequencies, typically occurring in the ultraviolet (UV), visible, and infrared (IR) regions of the EM spectrum. The vibrational spectra are said to result primarily from this movement of bonds between individual atoms within molecules, and typically occur in the infrared and microwave regions. Rotational spectra occur primarily in the microwave and radiowave regions of the EM spectrum due, primarily, to the rotation of the molecules.

Microwave or radiowave radiation could be an acceptable frequency to be used as a spectral catalyst because it would penetrate well into a large reaction vessel. Unfortunately, platinum atoms do not produce frequencies in the microwave or radiowave portions of the electromagnetic spectrum because they do not have vibrational or rotational spectra. However, by copying the mechanism of action platinum, selected platinum frequencies can be used as a model for a spectral catalyst in the microwave portion of the spectrum. Specifically, as previously discussed, one mechanism of action of platinum in the cell reaction system to produce water involves energizing at least one reaction intermediate and/or transient. Reaction intermediates in this reaction are atomic hydrogen and the hydroxy radical. Atomic hydrogen has a high frequency electronic spectrum without vibrational or rotational spectra. The hydroxy radical, on the other hand, is a molecule, and has vibrational and rotational spectra as well as an electronic spectrum. Thus, the hydroxy radical emits, absorbs and heterodynes frequencies in the microwave portion of the electromagnetic spectrum.

Thus, to copy the mechanism of action of platinum in the reaction to form water, namely resonating with at least one reaction intermediate and/or transient, the hydroxy intermediate can be specifically targeted via resonance. However, instead of resonating with the hydroxy radical in its electronic spectrum, as physical platinum catalyst does, at least one hydroxy frequency in the microwave portion of the EM spectrum can be used to resonate with the hydroxy radical. Hydroxy radicals heterodyne at a microwave frequency of about 21.4 GHz. Energizing a reaction system of hydrogen and oxygen gas with a spectral catalyst at about 21.4 GHz will catalyze the formation of water. In this instance, the mechanism of action of the physical catalyst platinum has been partially copied and the mechanism has been shifted to a different region of the electromagnetic spectrum.

The second method discussed above for platinum catalyzing a reaction, involves harmonically energizing at least one reaction intermediate in the reaction system. For example, assume that one or more lasers was available to catalyze the hydrogen-oxygen reaction to form water, however, the frequency range of such lasers was only from, for example, 1,500 to 2,000 THz. Platinum does not produce frequencies in that portion of the EM spectrum. Moreover, the two hydroxy frequencies that platinum resonates with, 975 and 1,060 THz, are outside the frequency range that the lasers, in this example, can generate. Likewise, the hydrogen spectrum does not have any frequencies between 1,500 and 2,000 THz (see FIGS. 9-10).

However, according to the present invention, by again copying the mechanism of action of platinum, frequencies can be adapted or selected to be convenient and/or efficient for the equipment available. Specifically, harmonic frequencies corresponding to the reaction intermediates and/or transients, and also corresponding to frequencies capable of being generated by the lasers of this example, can be utilized. For the hydroxy radical, having a resonant frequency of 975 Thz, the first harmonic is 1,950 THz. Thus, a laser of this example could be tuned to 1,950 THz to resonate harmonically with the hydroxy intermediate. The first harmonics of three different hydrogen frequencies also fall within the operational range of the lasers of this example. The fundamental frequencies are 755, 770 and 781 THz and the first harmonics are 1,510, 1,540, and 1,562 THz, respectively. Thus, a laser of this example could be tuned to the first harmonics 1,510, 1,540, and 1,562 THz in order to achieve a heterodyned matching of frequencies between electromagnetic energy and matter and thus achieve a transfer and absorption of said energy.

Thus, depending on how many lasers are available and the frequencies to which the lasers can be tuned, third or fourth harmonics could also be utilized. The third harmonic of the hydrogen frequency, 456 THz, occurs at 1,824 THz, which is also within the operating range of the lasers of this example. Similarly, the fourth harmonic of the hydrogen frequency, 314 THz, occurs at 1,570 THz, which again falls within the operating range of the lasers of this example. In summary, a mechanism of action of a physical catalyst can be copied, duplicated or mimicked while moving the relevant spectral catalyst frequencies, to a portion of the electromagnetic spectrum that matches equipment available for the reaction system and the application of electromagnetic energy.

The third method discussed above for platinum catalyzing this reaction involves energizing at least one reaction intermediate and/or transient at multiple upper energy levels and setting up, for example, an atomic scale laser system. Again, assume that the same lasers discussed above are the only electromagnetic energy sources available and assume that there are a total of ten (10) lasers available. There are four (4) first harmonics available for targeting within the operating frequency range of 1,500 to 2,000 THz. Some portion of the lasers should be adjusted to four (4) first harmonics and some should be adjusted to the third, fourth, and higher harmonics. Specifically, the present invention has discovered that a mechanism of action that physical platinum uses is to resonate with multiple upper energy levels of at least one reaction participant. It is now understood that the more upper energy levels that are involved, the better. This creates an atomic scale laser system with amplification of the electromagnetic energies being exchanged between the atoms of platinum and hydrogen. This amplification of energy catalyzes the reaction at a much faster rate than the reaction would ordinarily proceed. This mechanism of action can also be exploited to catalyze, for example, the reaction with the available lasers discussed above.

For example, rather than setting all ten (10) lasers to the four (4) first harmonics and energizing only four (4) levels, it should now be understood that it would be desirable to energize as many different energy levels as possible. This task can be accomplished by setting each of the ten (10) lasers to a different frequency. Even though the physical catalyst platinum is not present, the energizing of multiple upper energy levels in the hydrogen will amplify the energies being exchanged between the atoms, and the hydrogen system will form its' own laser system between the hydrogen atoms. This will permit the reaction to proceed at a much faster rate than it ordinarily would. Once again, nature can be mimicked by duplicating one of her mechanisms of action by specifically targeting multiple energy levels with a spectral catalyst to achieve energy transfer in a novel manner.

The preceding discussion on duplicating catalyst mechanisms of action is just the beginning of an understanding of many variables associated with the use of spectral catalysts. These additional variables should be viewed as potentially very useful tools for enhancing the performance of spectral energy, and/or physical catalysts. There are many factors and variables that affect both catalyst performance, and chemical reactions in general. For example, when the same catalyst (or conditioned participant) is mixed with the same reactant, but exposed to different environmental reaction conditions such as temperature or pressure, different products can be produced. Consider the following example:

The same catalyst with the same reactant, produces quite different products in these two reactions, namely molecular hydrogen or cyclohexane, depending on the reaction temperature.

Many factors are known in the art which affect the direction and intensity with which a physical catalyst guides a reaction or with which a reaction proceeds in general. Temperature is but one of these factors. Other factors include pressure, volume, surface area of physical catalysts, solvents, support materials, contaminants, catalyst size and shape and composition, reactor vessel size, shape and composition, electric fields, magnetic fields, acoustic fields, and whether a conditioning energy was introduced to a conditionable participant prior to the conditioned participant being involved or activated in a cell reaction system, etc. The present invention teaches that these factors all have one thing in common. These factors are capable of changing the spectral patterns (i.e., frequency pattern) of, for example, participants and/or cell reaction system components. Some changes in spectra are very well studied and thus much information is available for consideration and application thereof. The prior art does not contemplate, however, the spectral chemistry basis for each of these factors, and how they relate to catalyst mechanisms of action, and chemical reactions in general. Further, alternatively, effects of the aforementioned factors can be enhanced or diminished by the application of additional spectral, spectral energy, and/or physical catalyst frequencies. Moreover, these environmental reaction conditions can be at least partially simulated in a cell reaction system by the application of one or more corresponding spectral environmental reaction conditions (e.g., a spectral energy pattern which duplicates at least a portion of one or more environmental reaction conditions). Alternatively, one spectral environmental reaction condition (e.g., a spectral energy pattern corresponding to temperature) could be substituted for another (e.g., spectral energy pattern corresponding to pressure) so long as the goal of matching of frequencies was met.

Temperature

Figure 15A:
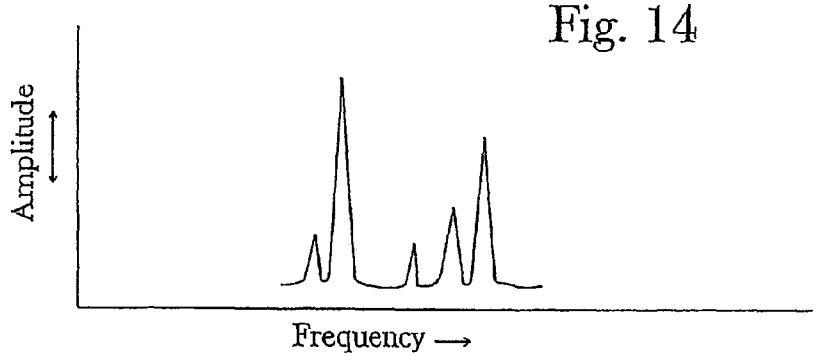
FIGS. 15a-c show how a spectral pattern varies at three different temperatures.
Figure 15B:
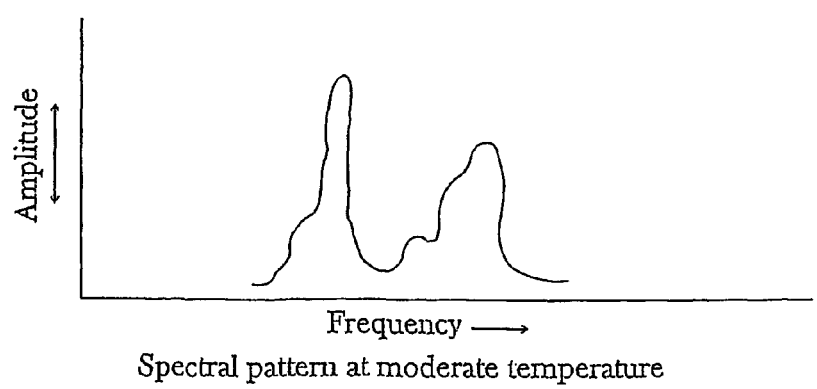
Figure 15C:
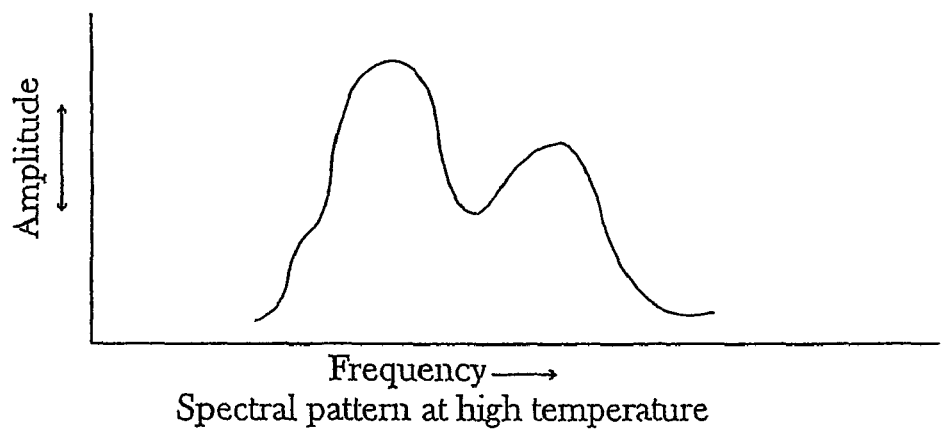

At very low temperatures, the spectral pattern of an atom or molecule has clean, crisp peaks (see FIG. 15a). As the temperature increases, the peaks begin to broaden, producing a bell-shaped curve of a spectral pattern (see FIG. 15b). At even higher temperatures, the bell-shaped curve broadens even more, to include more and more frequencies on either side of the primary frequency (see FIG. 15c). This phenomenon is called "broadening".

These spectral curves are very much like the resonance curves discussed in the previous section. Spectroscopists use resonance curve terminology to describe spectral frequency curves for atoms and molecules (see FIG. 16). The frequency at the top of the curve, $f_0$, is called the resonance frequency. There is a frequency ($f_2$) above the resonance frequency and another ($f_1$) below it (i.e., in frequency), at which the energy or intensity (i.e., amplitude) is 50% of that for the resonance frequency $f_0$. The quantity $f_2-f_1$ is a measure of how wide or narrow the spectral frequency curve is. This quantity ($f_2-f_1$) is the "line width". A spectrum with narrow curves has a small line width, while a spectrum with wide curves has a large line width.

Figure 17A:
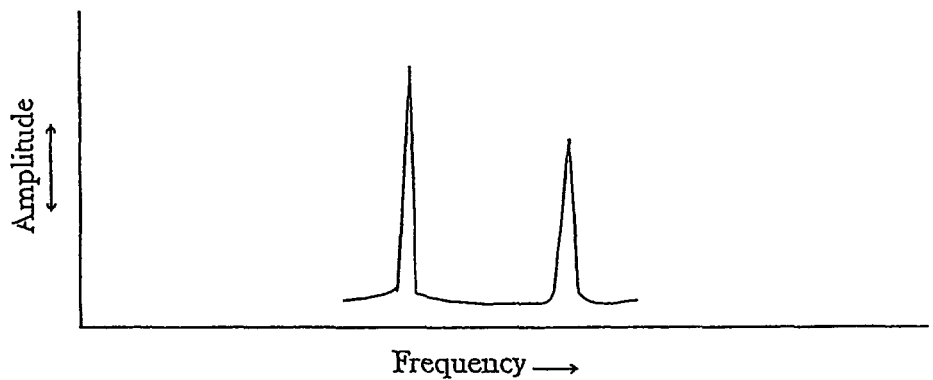
FIGS. 17a and 17b show two amplitude vs. frequency curves.
Figure 17B:
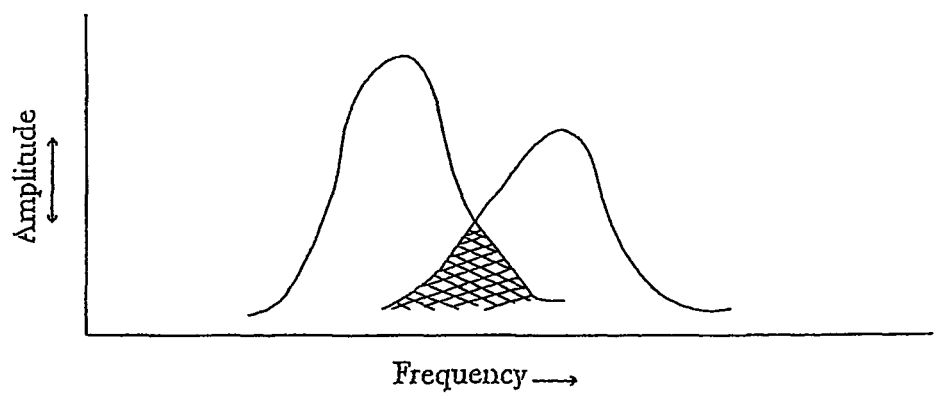

Temperature affects the line width of spectral curves. Line width can affect catalyst performance, chemical reactions and/or reaction pathways. At low temperatures, the spectral curves of chemical species will be separate and distinct, with a lesser possibility for the transfer of resonant energy between potential cell reaction system components (see FIG. 17a). However, as the line widths of potentially reactive chemical species broaden, their spectral curves may start to overlap with spectral curves of other chemical species (see FIG. 17b). When frequencies match, or spectral energy patterns overlap, energy transfers. Thus, when temperatures are low, frequencies do not match and reactions are slow. At higher temperatures, resonant transfer of energy can take place and reactions can proceed very quickly or proceed along a different reaction pathway than they otherwise would have at a lower temperature.

Figure 18A:
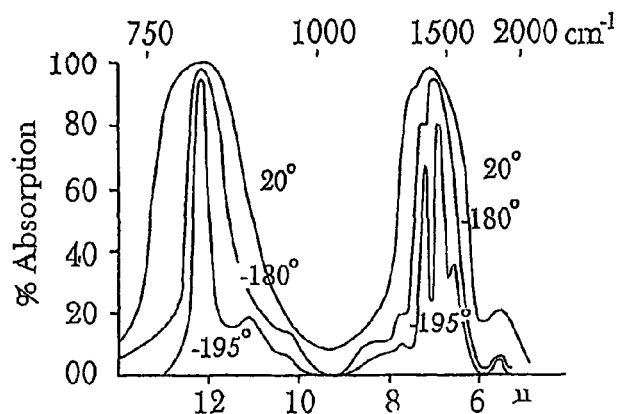
FIG. 18a shows the influence of temperature on the resolution of infrared absorption spectra.
Figure 18B:
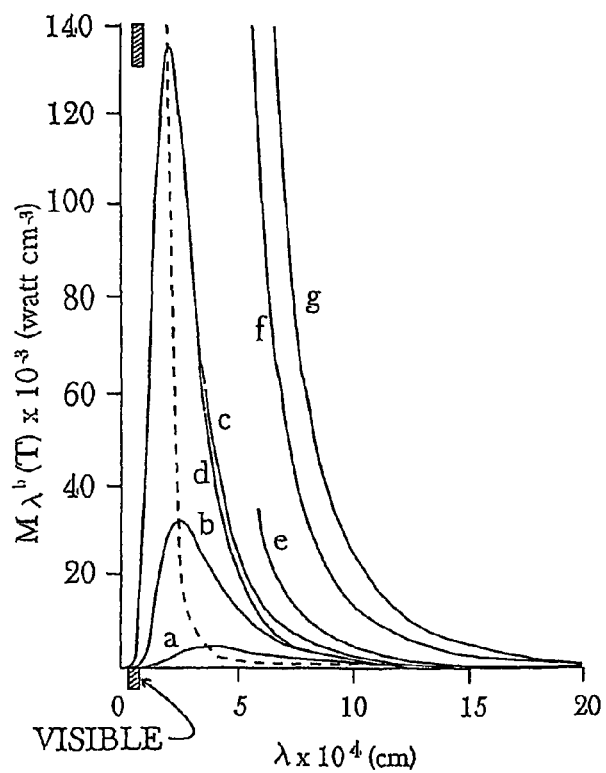
FIG. 18b shows blackbody radiation.
Figure 18C:
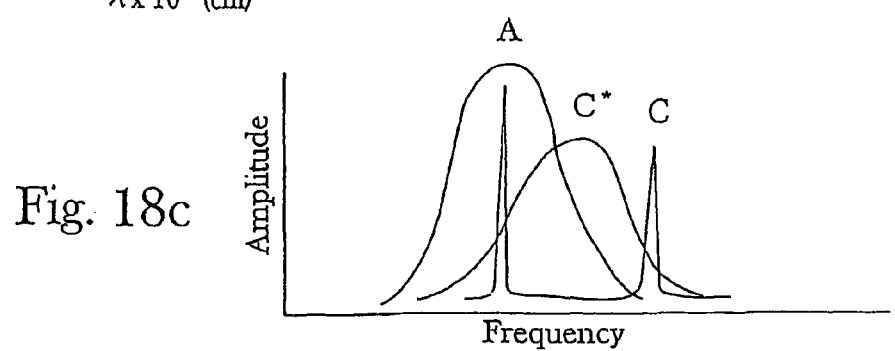
FIG. 18c shows curves A and C at low temperature, and broadened curves A and C* at higher temperature, with C* also shifted.

Besides affecting the line width of the spectral curves, temperature also can change, for example, the resonant frequency of holoreaction system components. For some chemical species, the resonant frequency will shift as temperature changes. This can be seen in the infrared absorption spectra in FIG. 18a and blackbody radiation graphs shown in FIG. 18b. Further, atoms and molecules do not all shift their resonant frequencies by the same amount or in the same direction, when they are at the same temperature. This can also affect catalyst performance. For example, if a catalyst resonant frequency shifts more with increased temperature than the resonant frequency of its targeted chemical species, then the catalyst could end up matching the frequency of a chemical species, and resonance may be created where none previously existed (see FIG. 18c). Specifically, FIG. 18c shows catalyst "C" at low temperature and "C*" at high temperature. The catalyst "C*" resonates with reactant "A" at high temperatures, but not at low temperatures.

The amplitude or intensity of a spectral line may be affected by temperature also. For example, linear and symmetric rotor molecules will have an increase in intensity as the temperature is lowered while other molecules will increase intensity as the temperature is raised. These changes of spectral intensity can also affect catalyst performance. Consider the example where a low intensity spectral curve of a catalyst is resonant with one or more frequencies of a specific chemical target. Only small amounts of energy can be transferred from the catalyst to the target chemical (e.g., a hydroxy intermediate). As temperature increases, the amplitude of the catalyst's curve increases also. In this example, the catalyst can transfer much larger amounts of energy to the chemical target when the temperature is raised.

If the chemical target is the intermediate chemical species for an alternative reaction route, the type and ratio of end products may be affected. By examining the above cyclohexene/palladium reaction again, at temperatures below 300° C., the products are benzene and hydrogen gas. However, when the temperature is above 300° C., the products are benzene and cyclohexane. Temperature is affecting the palladium and/or other constituents in the cell reaction system (including, for example, reactants, intermediates, and/or products) in such a way that an alternative reaction pathway leading to the formation of cyclohexane is favored above 300° C. This could be a result of, for example, increased line width, altered resonance frequencies, or changes in spectral curve intensities for any of the components in the cell reaction system.

It is important to consider not only the spectral catalyst frequencies one may wish to use to catalyze a reaction, but also the reaction conditions under which those frequencies are supposed to work. For example, in the palladium/cyclohexene reaction at low temperatures, the palladium may match frequencies with an intermediate for the formation of hydrogen molecules ($H_2$). At temperatures above 300° C. the reactants and transients may be unaffected, but the palladium may have an increased line width, altered resonant frequency and/or increased intensity. The changes in the line width, resonant frequency and/or intensity may cause the palladium to match frequencies and transfer energy to an intermediate in the formation of cyclohexane instead. If a spectral catalyst was to be used to assist in the formation of cyclohexane at room temperature, the frequency for the cyclohexane intermediate would be more effective if used, rather than the spectral catalyst frequency used at room temperature.

Thus, it may be important to understand the cell reaction system dynamics in designing and selecting an appropriate spectral catalyst. The transfer of energy between different cell reaction system components will vary, depending on temperature. Once understood, this allows one to knowingly adjust temperature to optimize a reaction, reaction product, interaction and/or formation of reaction product at a desirable reaction rate, without the trial and error approaches of prior art. Further, it allows one to choose catalysts such as physical catalysts, spectral catalysts, and/or spectral energy patterns to optimize a desired reaction pathway. This understanding of the spectral impact of temperature allows one to perform customarily high temperature (and, sometimes high danger) chemical processes at safer, room temperatures. It also allows one to design physical catalysts which work at much broader temperature ranges (e.g., frigid arctic temperatures or hot furnace temperatures), as desired.

Pressure

Figure 19:
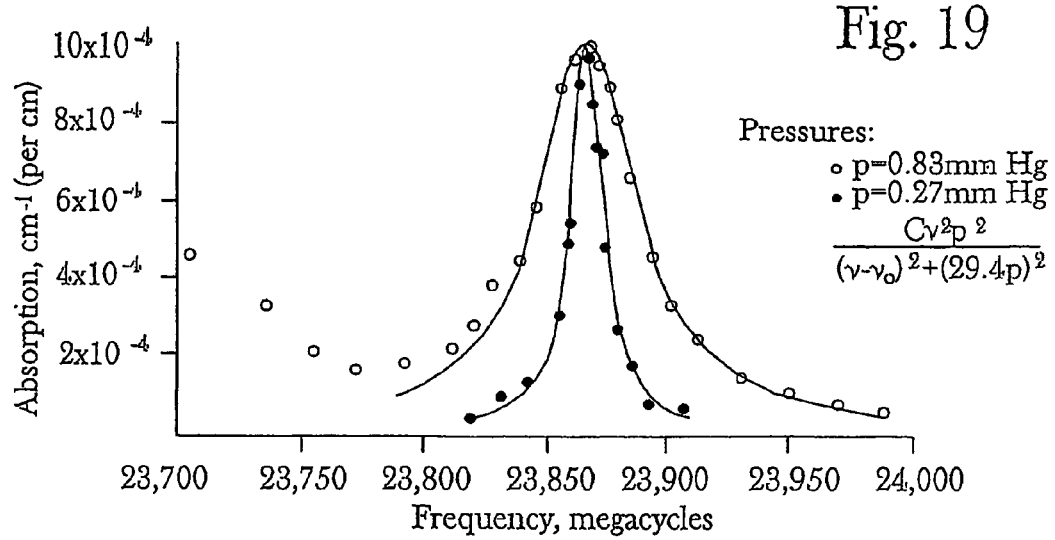
FIG. 19 shows spectral patterns which exhibit the effect of pressure broadening on the compound $NH_3$.

Pressure and temperature are directly related to each other. Specifically, from the ideal gas law, we know that $$PV=nRT$$

where P is pressure, V is volume, n is the number of moles of gas, R is the gas constant, and T is the absolute temperature. Thus, at equilibrium, an increase in temperature will result in a corresponding increase in pressure. Pressure also has an effect on spectral patterns. Specifically, increases in pressure can cause broadening and changes in spectral curves, just as increases in temperature do (see FIG. 19 which shows the pressure broadening effects on the $NH_3$ 3.3 absorption line).

Mathematical treatments of pressure broadening are generally grouped into either collision or statistical theories. In collision theories, the assumption is made that most of the time an atom or molecule is so far from other atoms or molecules that their energy fields do not interact. Occasionally, however, the atoms or molecules come so close together that they collide. In this case, the atom or molecule may undergo a change in wave phase (spectral) function, or may change to a different energy level. Collision theories treat the matter's emitted energy as occurring only when the atom or molecule is far from others, and is not involved in a collision. Because collision theories ignore spectral frequencies during collisions, collision theories fail to predict accurately chemical behavior at more than a few atmospheres of pressure, when collisions are frequent.

Statistical theories, however, consider spectral frequencies before, during and after collisions. They are based on calculating the probabilities that various atoms and/or molecules are interacting with, or perturbed by other atoms or molecules. The drawback with statistical treatments of pressure effects is that the statistical treatments do not do a good job of accounting for the effects of molecular motion. In any event, neither collision nor statistical theories adequately predict the rich interplay of frequencies and heterodynes that take place as pressure is increased. Experimental work has demonstrated that increased pressure can have effects similar to those produced by increased temperature, by:

1) broadening of the spectral curve, producing increased line width; and 2) shifting of the resonant frequency ($f_o$).

Figure 20:
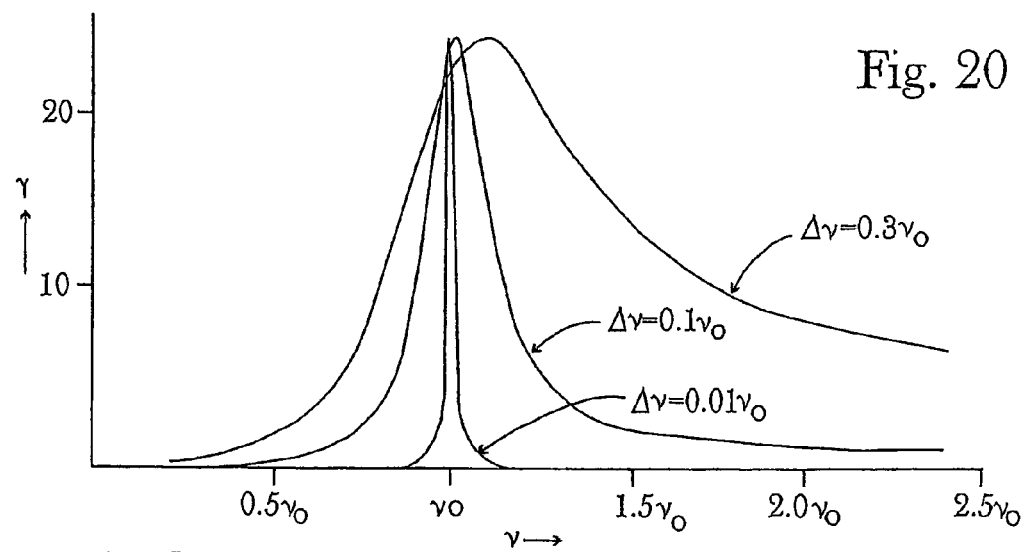
FIG. 20 shows the theoretical shape of pressure-broadened lines at three different pressures for a single compound.
Figure 21A:
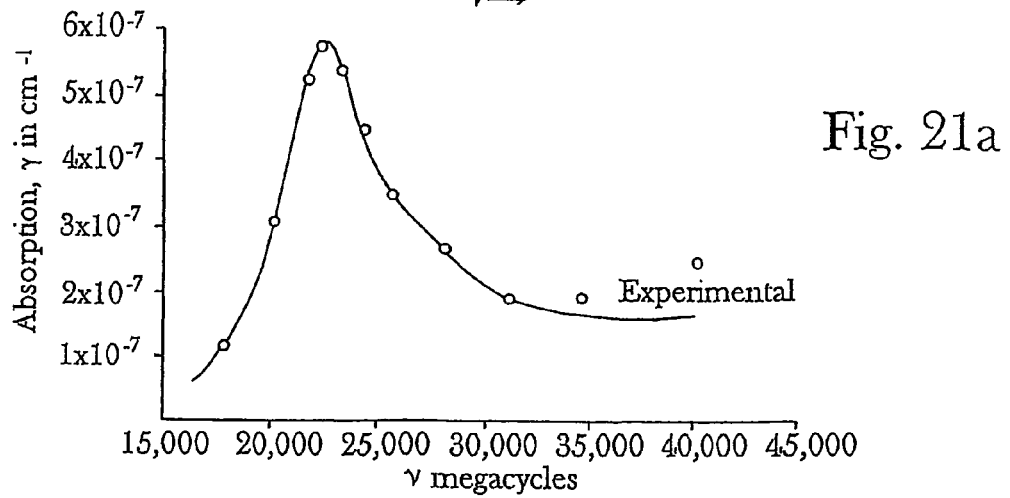
FIGS. 21a and 21b are two graphs which show experimental confirmation of changes in spectral patterns at increased pressures.
Figure 21B:
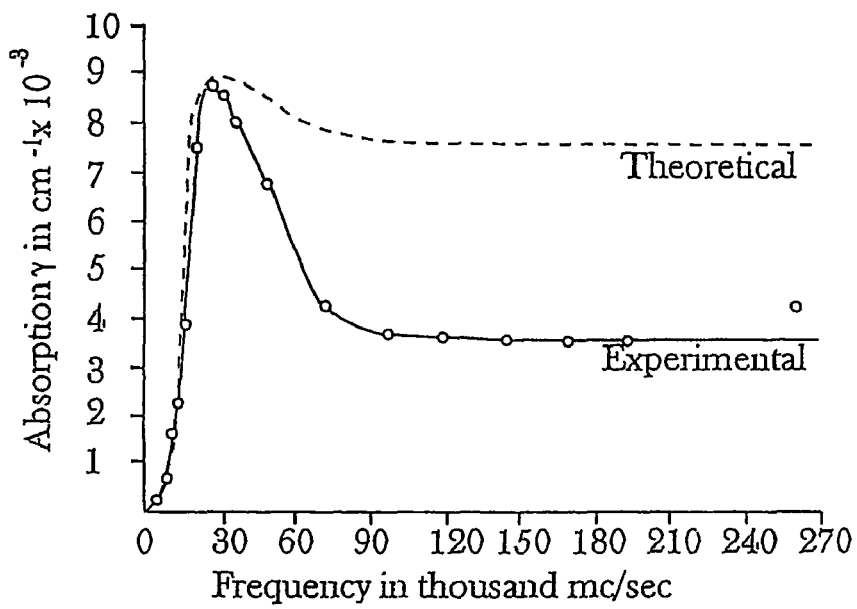

Pressure effects different from those produced by temperatures are: (1) pressure changes typically do not affect intensity, (see FIG. 20 which shows a theoretical set of curves exhibiting an unchanged intensity for three applied different pressures) as with temperature changes; and (2) the curves produced by pressure broadening are often less symmetric than the temperature-affected curves. Consider the shape of the three theoretical curves shown in FIG. 20. As the pressure increases, the curves become less symmetrical. A tail extending into the higher frequencies develops. This upper frequency extension is confirmed by the experimental work shown in FIG. 21. Specifically, FIG. 21a shows a pattern for the absorption by water vapor in air (log of $H_2O$ per cubic meter); and FIG. 21b shows the absorption in $NH_3$ at 1 atmosphere pressure.

Pressure broadening effects on spectral curves are broadly grouped into two types: resonance or "Holtsmark" broadening, and "Lorentz" broadening. Holtsmark broadening is secondary to collisions between atoms of the same element, and thus the collisions are considered to be symmetrical. Lorentz broadening results from collisions between atoms or molecules which are different. The collisions are asymmetric, and the resonant frequency, $f_o$, is often shifted to a lower frequency. This shift in resonant frequency is shown in FIG. 20. The changes in spectral curves and frequencies that accompany changes in pressure can affect catalysts, both physical and spectral, and chemical reactions and/or reaction pathways. At low pressures, the spectral curves tend to be fairly narrow and crisp, and nearly symmetrical about the resonant frequency. However, as pressures increase, the curves may broaden, shift, and develop high frequency tails.

At low pressures the spectral frequencies in the cell reaction system might be so different for the various atoms and molecules that there may be little or no resonant effect, and thus little or no energy transfer. At higher pressures, however, the combination of broadening, shifting and extension into higher frequencies can produce overlapping between the spectral curves, resulting in the creation of resonance, where none previously existed, and thus, the transfer of energy. The cell reaction system may proceed down one reaction pathway or another, depending on the changes in spectral curves produced by various pressure changes. One reaction pathway may be resonant and proceed at moderate pressure, while another reaction pathway may be resonant and predominate at higher pressures. As with temperature, it is important to consider the cell reaction system frequencies and mechanisms of action of various catalysts under the environmental reaction conditions one wishes to duplicate. Specifically, in order for an efficient transfer of energy to occur between, for example, a spectral catalyst and at least one reactant in a cell reaction system, there must be at least some overlap in frequencies.

For example, a reaction with a physical catalyst at 400 THz and a key transient at 500 THz may proceed slowly at atmospheric pressure. Where the frequency pressure is raised to about five (5) atmospheres, the catalyst broadens out through the 500 THz, for example, of the transient. This allows the transfer of energy between the catalyst and transient by, for example, energizing and stimulating the transient. The reaction then proceeds very quickly. Without wishing to be bound by any particular theory or explanation, it appears that, the speed of the reaction has much less to do with the number of collisions (as taught by the prior art) than it has to do with the spectral patterns of the cell reaction system components. In the above example, the reaction could be energized at low pressures by applying the 500 THz frequency to directly stimulate the key transient. This could also be accompanied indirectly using various heterodynes, (e.g., @ 1,000 THz harmonic, or a 100 THz non-harmonic heterodyne between the catalyst and transient (500 THz–400 THz=100 THz.).

As shown herein, the transfer of energy between different cell reaction system components will vary, depending on pressure. Once understood, this allows one to knowingly adjust pressure to optimize a reaction, without the trial and error approaches of prior art. Further, it allows one to choose catalysts such as physical catalysts, spectral catalysts, and/or spectral energy patterns to optimize one or more desired reaction pathways. This understanding of the spectral impact of pressure allows one to perform customarily high pressure (and thus, typically, high danger) chemical processes at safer, room pressures. It also allows one to design physical catalysts which work over a large range of acceptable pressures (e.g., low pressures approaching a vacuum to several atmospheres of pressure).

Surface Area

Traditionally, the surface are of a catalyst has been considered to be important because the available surface area controls the number of available binding sites. Supposedly, the more exposed binding sites, the more catalysis. In light of the spectral mechanisms disclosed in the present invention, surface area may be important for another reason.

Many of the spectral catalyst frequencies that correspond to physical catalysts are electronic frequencies in the visible light and ultraviolet regions of the spectrum. These high frequencies have relatively poor penetrance into, for example, large reaction vessels that contain one or more reactants. The high frequency spectral emissions from a catalyst such as platinum or palladium (or the equivalent spectral catalyst) will thus not travel very far into such a cell reaction system before such spectral emissions (or spectral catalysts) are absorbed. Thus, for example, an atom or molecule must be fairly close to a physical catalyst so that their respective electronic frequencies can interact.

Thus, surface area primarily affects the probability that a particular chemical species, will be close enough to the physical catalyst to interact with its electromagnetic spectra emission(s). With small surface area, few atoms or molecules will be close enough to interact. However, as surface area increases, so too does the probability that more atoms or molecules will be within range for reaction. Thus, rather than increasing the available number of binding sites, larger surface area probably increases the volume of the cell reaction system exposed to the spectral catalyst frequencies or patterns. This is similar to the concept of assuring adequate penetration of a spectral catalyst into a cell reaction system (e.g., assuming that there are adequate opportunities for species to interact with each other).

An understanding of the effects of surface area on catalysts and cell reaction system components allows one to knowingly adjust surface area and other cell reaction system components to optimize a reaction, reaction pathway and/or formation of reaction product(s), at a desirable reaction rate, without the drawbacks of the prior art. For instance, surface area is currently optimized by making catalyst particles as small as possible, thereby maximizing the overall surface area. The small particles have a tendency to, for example, sinter (merge or bond together) which decreases the overall surface area and catalytic activity. Rejuvenation of a large surface area catalyst can be a costly and time-consuming process. This process can be avoided with an understanding of the herein presented invention in the field of spectral chemistry. For example, assume a reaction is quickly catalyzed by a 3 $m^2$ catalyst bed (in a transfer of energy from catalyst to a key reactant and product). After sintering takes place, however, the surface area is reduced to 1 $m^2$. Thus, the transfer of energy from the catalyst is dramatically reduced, and the reaction slows down. The costly and time-consuming process of rejuvenating the surface area can be avoided (or at least delayed) by augmenting the cell reaction system with one or more desirable spectral energy patterns. In addition, because spectral energy patterns can affect the final physical form or phase of a material, as well as its chemical formula, the sintering process itself may be reduced or eliminated.

Catalyst Size and Shape

In a related line of reasoning, catalyst size and shape are classically thought to affect physical catalyst activity. Selectivity of reactions controlled by particle size has historically been used to steer catalytic pathways. As with surface area, certain particle sizes are thought to provide a maximum number of active binding sites and thus maximize the reaction rate. The relationship between size and surface area has been previously discussed.

Figure 22A:
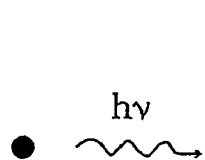
FIG. 22a shows a representation of radiation from a single atom and FIG. 22b shows a representation of radiation from a group of atoms.
Figure 22B:
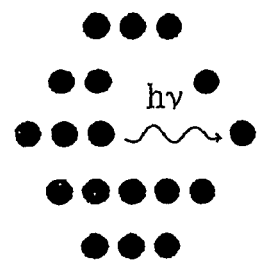
Figure 23A:
FIGS. 23a-d show four different spectral curves, three of which exhibit self-absorption patterns.
Figure 23B:
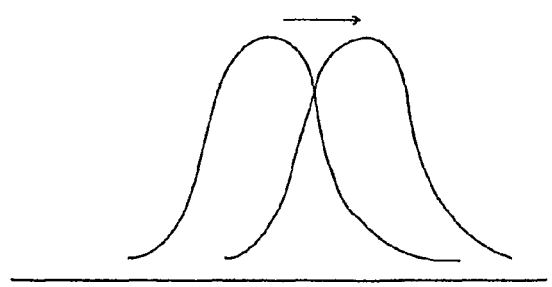
Figure 23C:
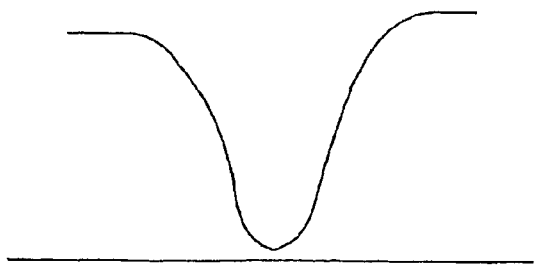
Figure 23D:
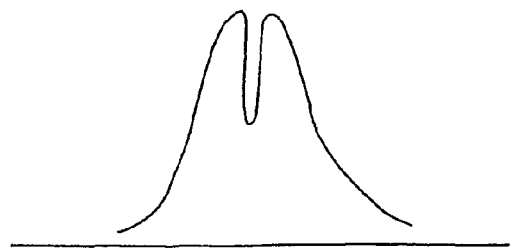

In light of the current understanding of the spectral mechanisms underlying the activity of physical catalysts and reactions in general, catalyst size and shape may be important for other reasons. One of those reasons is a phenomenon called "self absorption". When a single atom or molecule produces its' classical spectral pattern it radiates electromagnetic energy which travels outward from the atom or molecule into neighboring space. FIG. 22a shows radiation from a single atom versus radiation from a group of atoms as shown in FIG. 22b. As more and more atoms or molecules group together, radiation from the center of the group is absorbed by its' neighbors and may never make it out into space. Depending on the size and shape of the group of atoms, self absorption can cause a number of changes in the spectral emission pattern (see FIG. 23). Specifically, FIG. 23a shows a normal spectral curve produced by a single atom; FIG. 23b shows a resonant frequency shift due to self absorption; FIG. 23c shows a self-reversal spectral pattern produced by self absorption in a group of atoms and FIG. 23d shows a self-reversal spectral pattern produced by self absorption in a group of atoms. These changes include a shift in resonant frequency and self-reversal patterns.

The changes in spectral curves and frequencies that accompany changes in catalyst size and shape can affect catalysts, chemical reactions and/or reaction pathways. For example, atoms or molecules of a physical catalyst may produce spectral frequencies in the cell reaction system which resonate with a key transient and/or reaction product. With larger groups of atoms, such as in a sintered catalyst, the combination of resonant frequency shifting and self-reversal may eliminate overlapping between the spectral curves of chemical species, thereby minimizing or destroying conditions of resonance.

A cell reaction system may proceed down one reaction pathway or another, depending on the changes in spectral curves produced by the particle sizes. For example, a catalyst) or conditioned participant) having a moderate particle size may proceed down a first reaction pathway while a larger size catalyst may direct the reaction down another reaction pathway.

The changes in spectral curves and frequencies that accompany changes in catalyst size and shape are relevant for practical applications. Industrial catalysts are manufactured in a range of sizes and shapes, depending on the design requirements of the process and the type of reactor used. Catalyst activity is typically proportional to the surface area of the catalyst bed in the reactor. Surface area increases as the size of the catalyst particles decreases. Seemingly, the smaller the catalyst particles, the better for industrial applications. This is not always the case, however. When a very fine bed of catalyst particles is used, high pressures may be required to force the reacting chemicals across or through the catalyst bed. The chemicals enter the catalyst bed under high pressure, and exit the bed (e.g., the other side) at a lower pressure. This large difference between entry and exit pressures is called a "pressure drop". A compromise is often required between catalyst size, catalyst activity, and pressure drop across the catalyst bed.

The use of spectral catalysts according to the present invention allows for much finer tuning of this compromise. For example, a large catalyst size can be used so that pressure drops across the catalyst bed are minimized. At the same time, the high level of catalyst activity obtained with a smaller catalyst size can still be obtained by, for example, augmenting the physical catalyst with at least a portion of one or more spectral catalyst(s).

For example, assume that a 10 mm average particle size catalyst has 50% of the activity of a 5 mm average particle size catalyst. With a 5 mm-diameter catalyst, however, the pressure drop across the reactor may be so large that the reaction cannot be economically performed. The compromise in historical processes has typically been to use twice as much of the 10 mm catalyst, to obtain the same, or approximately the same, amount of activity as with the original amount of 5 mm catalyst. However, an alternative desirable approach is to use the original amount of 10 mm physical catalyst and augment the physical catalyst with at least a portion of at least one spectral catalyst. Catalyst activity can be effectively doubled (or increased even more) by the spectral catalyst, resulting in approximately the same degree of activity (or perhaps even greater activity) as with the 5 mm catalyst. Thus, the present invention permits the size of the catalyst to be larger, while retaining favorable reactor vessel pressure conditions so that the reaction can be performed economically, using half as much (or less) physical catalyst as compared to traditional prior art approaches.

Another manner to approach the problem of pressure drops in physical catalyst beds, is to eliminate the physical catalyst completely. For example, in another embodiment of the invention, a fiberoptic sieve, (e.g., one with very large pores) can be used in a flow-through reactor vessel. If the pore size is designed to be large enough there can be virtually no pressure drop across the sieve, compared to a pressure drop accompanying the use of a 5 mm diameter or even a 10 mm diameter physical catalyst discussed above. According to the present invention, the spectral catalyst can be emitted through the fiberoptic sieve, thus catalyzing the reacting species as they flow by. This improvement over the prior art approaches has significant processing implications including lower costs, higher rates and improved safety, to mention only a few.

Industrial catalysts are also manufactured in a range of shapes, as well as sizes. Shapes include spheres, irregular granules, pellets, extrudate, and rings. Some shapes are more expensive to manufacture than others, while some shapes have superior properties (e.g., catalyst activity, strength, and less pressure drop) than others. While spheres are inexpensive to manufacture, a packed bed of spheres produces high-pressure drops and the spheres are typically not very strong. Physical catalyst rings on the other hand, have superior strength and activity and produce very little pressure drop, but they are also relatively expensive to produce.

Spectral energy catalysts permit a greater flexibility in choosing catalyst shape. For example, instead of using a packed bed of inexpensive spheres, with the inevitable high pressure drop and resulting mechanical damage to the catalyst particles, a single layer of spheres augmented, for example, with a spectral energy catalyst can be used. This catalyst is inexpensive, activity is maintained, and large pressure drops are not produced, thus preventing mechanical damage and extending the useful life of physical catalyst spheres. Similarly, far smaller numbers of catalyst rings can be used while obtaining the same or greater catalyst activity by, for example, supplementing with at least a portion of a spectral catalyst. The process can proceed at a faster flow-through rate because the catalyst bed will be smaller relative to a bed that is not augmented with a spectral catalyst.

The use of spectral energy catalysts and/or spectral environmental reaction conditions to augment existing physical catalysts has the following advantages:
  permit the use of less expensive shaped catalyst particles;
  permit the use of fewer catalyst particles overall;
  permit the use of stronger shapes of catalyst particles; and
  permit the use of catalyst particle shapes with better pressure drop characteristics.

Their use to replace existing physical catalysts has similar advantages:
  eliminate the use and expense of catalyst particles altogether;
  allow use of spectral catalyst delivery systems that are stronger; and
  delivery systems can be designed to incorporate superior pressure drop characteristics.

Catalyst size and shape are also important to spectral emission patterns because all objects have an NOF depending on their size and shape. The smaller an object is in dimension, the higher its NOF will be in frequency (because speed=length× frequency). Also, two (2) objects of the same size, but different shape will have different NOF's (e.g., the resonant NOF frequency of a 1.0 m diameter sphere, is different from the NOF for a 1.0 m edged cube). Wave energies (both acoustic and EM) will have unique resonant frequencies for particular objects. The objects, such as physical catalyst particles or powder granules of reactants in a slurry, will act like antennas, absorbing and emitting energies at their structurally resonant frequencies. With this understanding, one is further able to manipulate and control the size and shape of cell reaction system components (e.g., physical catalysts, reactants, etc.) to achieve desired effects. For example, a transient for a desired reaction pathway may produce a spectral rotational frequency of 30 GHz. Catalyst spheres 1 cm in diameter with structural EM resonant frequency of 30 GHz ($3\times10^8$ m/s $1\times10^{-2}$ m=$30\times10^9$ Hz), can be used to catalyze the reaction. The catalyst particles will structurally resonate with the rotational frequency of the transient, providing energy to the transient and catalyzing the reaction. Likewise, the structurally resonant catalyst particles may be further energized by a spectral energy catalyst, such as, for example, 30 GHz microwave radiation. Thus understood, the spectral dynamics of chemical reactions can be much more precisely controlled than in prior art trial and error approaches.

Solvents

Typically, the term solvent is applied to mixtures for which the solvent is a liquid, however, it should be understood that solvents may also comprise solids, liquids, gases or plasmas and/or mixtures and/or components thereof. The prior art typically groups liquid solvents into three broad classes: aqueous, organic, and non-aqueous. If an aqueous solvent is used, it means that the solvent is water. Organic solvents include hydrocarbons such as alcohols and ethers. Non-aqueous solvents include inorganic non-water substances. Many catalyzed reactions take place in solvents.

Because solvents are themselves composed of atoms, molecules and/or ions they can have pronounced effects on chemical reactions. Solvents are comprised of matter and they emit their own spectral frequencies. The present invention teaches that these solvent frequencies undergo the same basic processes discussed earlier, including heterodyning, resonance, and harmonics. Spectroscopists have known for years that a solvent can dramatically affect the spectral frequencies produced by its' solutes. Likewise, chemists have known for years that solvents can affect catalyst activity. However, the spectroscopists and chemists in the prior art have apparently not associated these long studied changes in solute frequencies with changes in catalyst activity. The present invention recognizes that these changes in solute spectral frequencies can affect catalyst activity and chemical reactions and/or reaction pathways in general, changes include spectral curve broadening. Changes of curve intensity, gradual or abrupt shifting of the resonant frequency $f_o$, and even abrupt rearrangement of resonant frequencies.

Further, the present invention recognizes that one or more spectral frequencies in a solvent may be targeted by a spectral energy pattern or spectral energy conditioning pattern to change one or more properties of the solvent, and hence may change the reaction and energy dynamics in a holoreaction system. Similarly, a spectral energy pattern or a spectral energy conditioning pattern may be applied to a solute, causing a change in one or more properties of the solute, solvent, or solute/solvent system, and hence may change the reaction and energy dynamics in a holoreaction sysetsm.

Figure 24A:
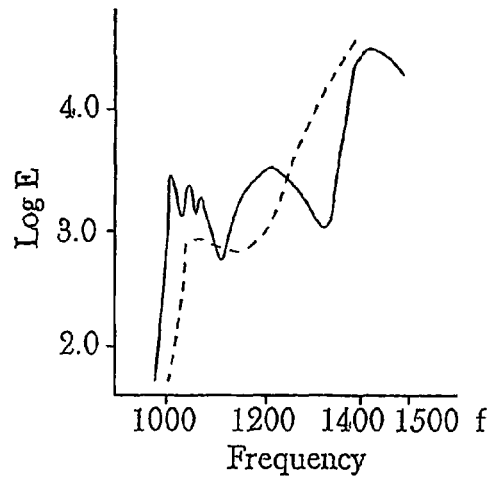
FIG. 24a shows an absorption spectra of alcohol and phthalic acid in hexane.

When reviewing FIG. 24a, the solid line represents a portion of the spectral pattern of phthalic acid in alcohol while the dotted line represents phthalic acid in the solvent hexane. Consider a reaction taking place in alcohol, in which the catalyst resonates with phthalic acid at a frequency of 1,250, the large solid curve in the middle. If the solvent is changed to hexane, the phthalic acid no longer resonates at a frequency of 1,250 and the catalyst can not stimulate and energize it. The change in solvent will render the catalyst ineffective.

Figure 24B:
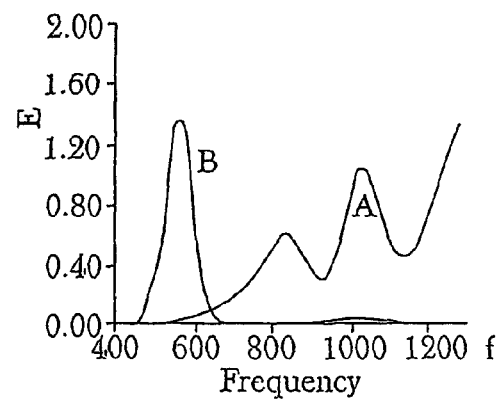
FIG. 24b shows an absorption spectra for the absorption of iodine in alcohol and carbon tetrachloride.

Similarly, in reference to FIG. 24b, iodine produces a high intensity curve at 580 when dissolved in carbon tetrachloride, as shown in curve B. In alcohol, as shown by curve A the iodine produces instead, a moderate intensity curve at 1,050 and a low intensity curve at 850. Accordingly, assume that a reaction uses a spectral catalyst that resonates directly with the iodine in carbon tetrachloride at 580. If the spectral catalyst does not change and the solvent is changed to alcohol, the spectral catalyst will no longer function because frequencies no longer match and energy will not transfer. Specifically, the spectral catalyst's frequency of 580 will no longer match and resonate with the new iodine frequencies of 850 and 1,050.

However, there is the possibility that the catalyst will change its spectral pattern with a change in the solvent. The catalyst could change in a similar manner to the iodine, in which case the catalyst may continue to catalyze the reaction regardless of the change in solvent. Conversely, the spectral catalyst pattern could change in a direction opposite to the spectral pattern of the iodine. In this instance, the catalyst will again fail to catalyze the original reaction. There is also the possibility that the change in the catalyst could bring the catalyst into resonance with a different chemical species and help the reaction proceed down an alternative reaction pathway.

Figure 24C:
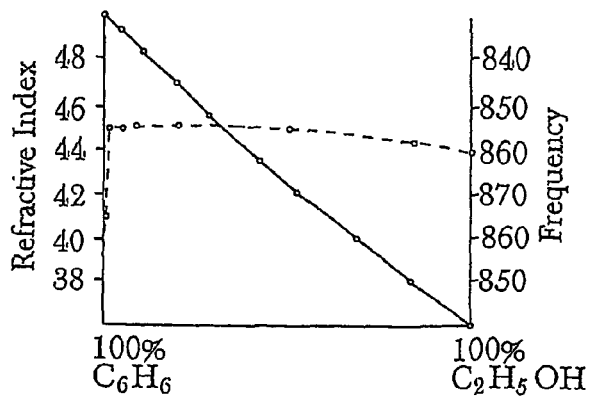
FIG. 24c shows the effect of mixtures of alcohol and benzene on the solute phenylazophenol.

Finally, consider the graph in FIG. 24c, which shows a variety of solvent mixtures ranging from 100% benzene at the far left, to a 50:50 mixture of benzene and alcohol in the center, to 100% alcohol at the far right. The solute is phenylazophenol. The phenylazophenol has a frequency of 855-860 for most of the solvent mixtures. For a 50:50 benzene:alcohol mixture the frequency is 855; or for a 98:2 benzene:alcohol mixture the frequency is still 855. However, at 99.5:0.5 benzene:alcohol mixture, the frequency abruptly changes to about 865. A catalyst active in 100% benzene by resonating with the phenylazophenol at 865, will lose its activity if there is even a slight amount of alcohol (e.g., 0.5%) in the solvent.

Thus understood, the principles of spectral chemistry presented herein can be applied to catalysis, and reactions and/or reaction pathways in general. Instead of using the prior art trial and error approach to the choice of solvents and/or other cell reaction system components, solvents can be tailored and/or modified to optimize the spectral environmental reaction conditions. For example, a reaction may have a key reaction participant which resonates at 400 THz, while the catalyst resonates at 800 THz transferring energy harmonically. Changing the solvent may cause the resonant frequencies of both the participant and the catalyst to abruptly shift to 600 THz. There the catalyst would resonate directly with the participant, transferring even more energy, and catalyzing the cell reaction system more efficiently.

Further, the properties of solvents, solutes, and solvent/solute systems may be affected by spectral energy providers. Water is the universal solvent. It is commonly known and understood that if water is heated, its kinetic energy increases, and hence, the rate at which solutes dissolve also increases. After a solute has been added to a solvent, such as water, physical properties such as pH and conductivity change at a rate related to their kinetic energy and the temperature of the solute/solvent system.

A novel aspect of the present invention is the understanding that the properties of solvents, solutes and solvent/solute systems may be affected and controlled by spectral energy providers outside the realm of simple thermal or kinetic mechanisms. For example, water at about 28° C. will dissolve salt (sodium chloride) at a particular rate. Water at about 28° C. which has been conditioned with its own vibrational overtones will dissolve salt faster, even though there is no apparent difference in temperature. Similarly, if salt is added to water, there is a predictable rate of change in the pH and conductivity of the solution. If the water is conditioned or spectrally activated with its own vibrational overtones, either before or after, respectively, the addition of the salt, the rate of change of pH and conductivity is enhanced even though there is no difference in temperature. These effects are shown in greater detail in the Examples section herein.

Further, if the salt is conditioned with some of its own electronic frequencies prior to adding it to water, the rate of change of conductivity is again enhanced, even though there is again no apparent difference in temperature. These effects are shown in greater detail in the Examples section herein.

In general, delivery of spectral energy patterns and/or spectral energy conditioning patterns to solvents, solutes: and solvent/solute systems may change the energy dynamics of the solvent and/or solute and hence their properties in a holoreaction system. These spectral techniques disclosed herein can be used to control many aspects of matter transformations such as chemical reactions, phase changes, and material properties (all of which are described in the Examples section herein).

Support Materials

Catalysts can be either unsupported or supported. An unsupported catalyst is a formulation of the pure catalyst, with substantially no other molecules present. Unsupported catalysts are rarely used industrially because these catalysts generally have low surface area and hence low activity. The low surface area can result from, for example, sintering, or coalescence of small molecules of the catalyst into larger particles in a process which reduces surface tension of the particles. An example of an unsupported catalyst is platinum alloy gauze, which is sometimes used for the selective oxidation of ammonia to nitric oxide. Another example is small silver granules, sometimes used to catalyze the reaction of methanol with air, to form formaldehyde. When the use of unsupported catalysts is possible, their advantages include straightforward fabrication and relatively simple installation in various industrial processes.

A supported catalyst is a formulation of the catalyst with other particles, the other particles acting as a supporting skeleton for the catalyst. Traditionally, the support particles are thought to be inert, thus providing a simple physical scaffolding for the catalyst molecules. Thus, one of the traditional functions of the support material is to give the catalyst shape and mechanical strength. The support material is also said to reduce sintering rates. If the catalyst support is finely divided similar to the catalyst, the support will act as a "spacer" between the catalyst particles, and hence prevent sintering. An alternative theory holds that an interaction takes place between the catalyst and support, thereby preventing sintering. This theory is supported by the many observations that catalyst activity is altered by changes in support material structure and composition.

Supported catalysts are generally made by one or more of the following three methods: impregnation, precipitation, and/or crystallization. Impregnation techniques use preformed support materials, which are then exposed to a solution containing the catalyst or its precursors. The catalyst or precursors diffuse into the pores of the support. Heating, or another conversion process, drives off the solvent and transforms the catalyst or precursors into the final catalyst. The most common support materials for impregnation are refractory oxides such as aluminas and aluminum hydrous oxides. These support materials have found their greatest use for catalysts that must operate under extreme conditions such as steam reforming, because they have reasonable mechanical strengths.

Precipitation techniques use concentrated solutions of catalyst salts (e.g., usually metal salts). The salt solutions are rapidly mixed and then allowed to precipitate in a finely divided form. The precipitate is then prepared using a variety of processes including washing, filtering, drying, heating, and pelleting. Often a graphitic lubricant is added. Precipitated catalysts have high catalytic activity secondary to high surface area, but they are generally not as strong as impregnated catalysts.

Figure 25A:
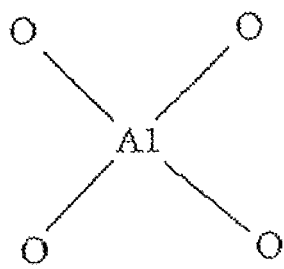
FIG. 25a shows a tetrahedral unit representation of aluminum oxide and FIG. 25b shows a representation of a tetrahedral unit for silicon dioxide.
Figure 25B:
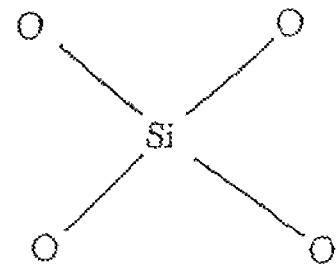
Figure 26A:
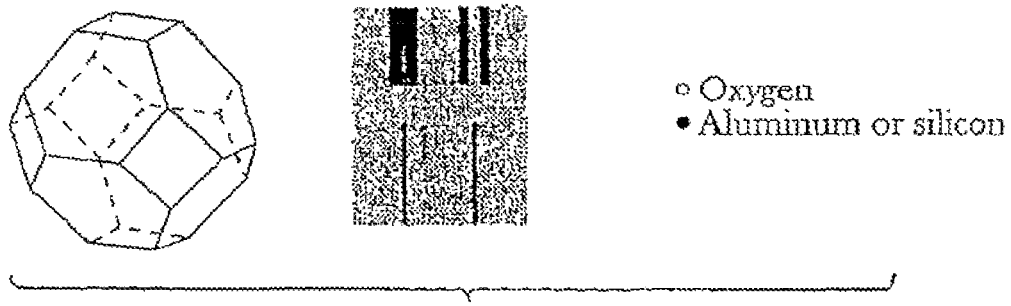
FIG. 26a shows a truncated octahedron crystal structure for aluminum or silicon combined with oxygen and FIG. 26b shows a plurality of truncated octahedrons joined together to represent zeolite.
Figure 26B:
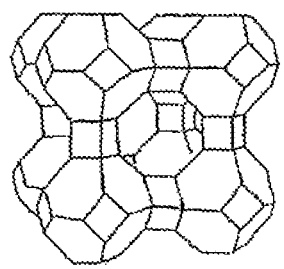
Figure 26C:
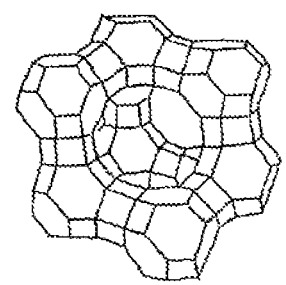
FIG. 26c shows truncated octahedrons for zeolites "X" and "Y" which are joined together by oxygen bridges.

Crystallization techniques produce support materials called zeolites. The structure of these crystallized catalyst zeolites is based on $SiO_4$ and $AlO_4$ (see FIG. 25a which shows the tetrahedral units of silicon; and FIG. 25b which shows the tetrahedral units of aluminum). These units link in different combinations to form structural families, which include rings, chains, and complex polyhedra. For example, the $SiO_4$ and $AlO_4$ tetrahderal units can form truncated octahedron structures, which form the building blocks for A, X, and Y zeolites (see FIG. 26a which shows a truncated octahedron structure with lines representing oxygen atoms and corners are Al or Si atoms; FIG. 26b which shows zeolite with joined truncated octahedrons joined by oxygen bridges between square faces; and FIG. 26c which shows zeolites X and Y with joined truncated octahedrons joined by oxygen bridges between hexagonal faces).

The crystalline structure of zeolites gives them a well defined pore size and structure. This differs from the varying pore sizes found in impregnated or precipitated support materials. Zeolite crystals are made by mixing solutions of silicates and aluminates and the catalyst. Crystallization is generally induced by heating (see spectral effects of temperature in the Section entitled "Temperature"). The structure of the resulting zeolite depends on the silicon/aluminum ratio, their concentration, the presence of added catalyst, the temperature, and even the size of the reaction vessels used, all of which are environmental reaction conditions. Zeolites generally have greater specificity than other catalyst support materials (e.g., they do not just speed up the reaction). They also may steer the reaction towards a particular reaction pathway.

Support materials can affect the activity of a catalyst. Traditionally, the prior art has attributed these effects to geometric factors. However, according to the present invention, there are spectral factors to consider as well. It has been well established that solvents affect the spectral patterns produced by their solutes. Solvents can be liquids, solids, gases and/or plasmas Support materials can, in many cases, be viewed as nothing more than solid solvents for catalysts. As such, support materials can affect the spectral patterns produced by their solute catalysts.

Just as dissolved sugar can be placed into a solid phase solvent (ice), catalysts can be placed into support materials that are solid phase solvents. These support material solid solvents can have similar spectral effects on catalysts that liquid solvents have. Support materials can change spectral frequencies of their catalyst solutes by, for example, causing spectral curve broadening, changing of curve intensity, gradual or abrupt shifting of the resonant frequency $f_0$, and even abrupt rearrangement of resonant frequencies.

Further, uses of spectral techniques to affect matter transformations are not limited to solvent/solute or support/catalysts systems, but rather apply broadly to all material systems and phases of matter, and their respective properties (e.g., chemical, physical, electrical, magnetic, thermal, etc.).

The use of targeted spectral techniques in numerous materials systems (including solid, liquid and gas to control chemical reactions, phase changes and material properties (e.g., chemical physical, electrical, thermal, etc.) is described more fully in the Examples section later herein.

Support materials can be simply viewed as solid solvents for their catalyst solutes. The present invention teaches that spectral techniques can be used to control many aspects of matter transformation in solvent/solute systems such as chemical reactions, phase changes, and material properties. Similarly, spectral techniques can be used to control many aspects such as chemical reactions, phase changes, and material properties of support/catalyst systems. These spectral techniques can be used to affect the synthesis of support/catalyst systems, or to affect the subsequent properties of the support/catalyst system in a holoreaction system.

Thus, due to the disclosure herein, it should become clear to an artisan of ordinary skill that changes in support materials can have dramatic effects on catalyst activity. The support materials affect the spectral frequencies produced by the catalysts. The changes in catalyst spectral frequencies produce varying effects on chemical reactions and catalyst activity, including accelerating the rate of reaction and also guiding the reaction on a particular reaction path. Thus support materials can potentially influence the matching of frequencies and can thus favor the possibility of transferring energy between cell reaction system components and/or spectral energy patterns, thus permitting certain reactions to occur.

Poisoning

Poisoning of catalysts occurs when the catalyst activity is reduced by adding a small amount of another constituent, such as a chemical species. The prior art has attributed poisoning to chemical species that contain excess electrons (e.g., electron donor materials) and to adsorption of poisons onto the physical catalyst surface where the poison physically blocks reaction sites. However, neither of these theories satisfactorily explains poisoning.

Consider the case of nickel hydrogenation catalysts. These physical catalysts are substantially deactivated if only 0.1% sulphur compounds by weight are adsorbed onto them. It is difficult to believe that 0.1% sulphur by weight could contribute so many electrons as to inactivate the nickel catalyst. Likewise, it is difficult to believe that the presence of 0.1% sulphur by weight occupies so many reaction sites that it completely deactivates the catalyst. Accordingly, neither prior art explanation is satisfying.

Poisoning phenomena can be more logically understood in terms of spectral chemistry. In reference to the example in the Solvent Section using a benzene solvent and phenylazophenol as the solute, in pure benzene the phenylazophenol had a spectral frequency of 865 Hz. The addition of just a few drops of alcohol (0.5%) abruptly changed the phenylazophenol frequency to 855. If the expectation was for the phenylazophenol to resonate at 865, then the alcohol would have poisoned that particular reaction. The addition bf small quantities of other chemical species can change the resonant frequencies ($f_0$) of catalysts and reacting chemicals. The addition of another chemical species can act as a poison to take the catalyst and reacting species out of resonance (i.e., the presence of the additional species can remove any substantial overlapping of frequencies and thus prevent any significant transfer of energy).

Figure 27:
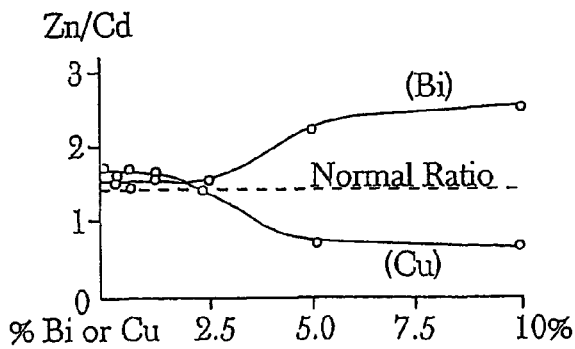
FIG. 27 is a graph which shows the influence of copper and bismuth on zinc/cadmium line ratios.

Besides changing resonant frequencies of chemical species, adding small amounts of other chemicals can also affect the spectral intensities of the catalyst and, for example, other atoms and molecules in the cell reaction system by either increasing or decreasing the spectral intensities. Consider cadmium and zinc mixed in an alumina-silica precipitate (see FIG. 27 which shows the influences of copper and bismuth on the zinc/cadmium line ratio). A normal ratio between the cadmium 3252.5 spectral line and the zinc 3345.0 spectral line was determined. The addition of sodium, potassium, lead, and magnesium had little or no effect on the Cd/Zn intensity ratio. However, the addition of copper reduced the relative intensity of the zinc line and increased the cadmium intensity. Conversely, addition of bismuth increased the relative intensity of the zinc line while decreasing cadmium.

Figure 28:
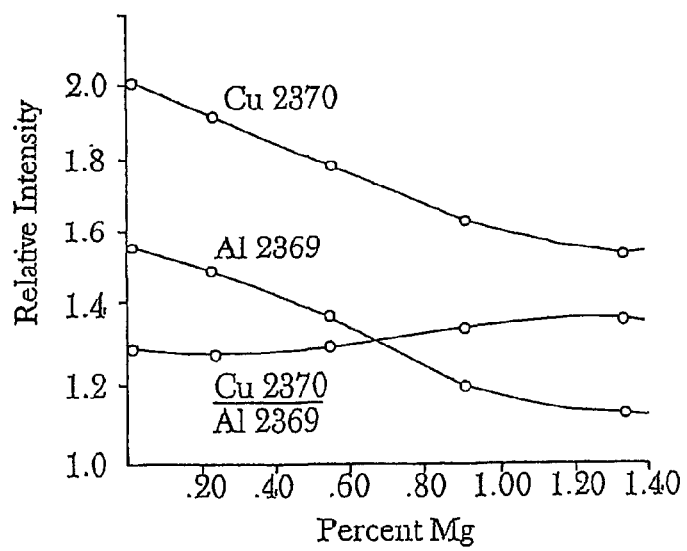
FIG. 28 is a graph which shows the influence of magnesium on copper/aluminum intensity ratio.

Also, consider the effect of small amounts of magnesium on a copper-aluminum mixture (see FIG. 28 which shows the influence of magnesium on the copper aluminum intensity ratio). Magnesium present at 0.6%, caused significant reductions in line intensity for copper and for aluminum. At 1.4% magnesium, the spectral intensities for both copper and aluminum were reduced by about a third. If the copper frequency is important for catalyzing a reaction, adding this small amount of magnesium would dramatically reduce the catalyst activity. Thus, it could be concluded that the copper catalyst had been poisoned by the magnesium.

In summary, poisoning effects on catalysts are due to spectral changes. Adding a small amount of another chemical species to a physical catalyst and/or cell reaction system can change the resonance frequencies or the spectral intensities of one or more chemical species (e.g., reactant). The catalyst might remain the same, while a crucial intermediate is changed. Likewise, the catalyst might change, while the intermediate stays the same. They might both change, or they might both stay the same and be oblivious to the added poison species. This understanding is important to achieving the goals of the present invention which include targeting species to cause an overlap in frequencies, or in this instance, specifically targeting one or more species so as to prevent any substantial overlap in frequencies and thus prevent reactions from occurring by blocking the transfer of energy.

Promoters

Just as adding a small amount of another chemical species to a catalyst and cell reaction system can poison the activity of the catalyst, the opposite can also happen. When an added species enhances the activity of a catalyst, it is called a promoter. For instance, adding a few percent calcium and potassium oxide to iron-alumina compounds promotes activity of the iron catalyst for ammonia synthesis. Promoters act by all the mechanisms discussed previously in the Sections entitled Solvents, Support Materials, and Poisoning. Not surprisingly, some support materials actually are promoters. Promoters enhance catalysts and specific reactions and/or reaction pathways by changing spectral frequencies and intensities. While a catalyst poison takes the reacting species out of resonance (i.e., the frequencies do not overlap), the promoter brings them into resonance (i.e., the frequencies do overlap). Likewise, instead of reducing the spectral intensity of crucial frequencies, the promoter may increase the crucial intensities.

Thus, if it was desired for phenylazophenol to react at 855 in a benzene solvent, alcohol could be added and the alcohol would be termed a promoter. If it was desired for the phenylazophenol too react at 865, alcohol could be added and the alcohol could be considered a poison. Thus understood, the differences between poisons and promoters are a matter of perspective, and depend on which reaction pathways and/or reaction products are desired. They both act by the same underlying spectral chemistry mechanisms of the present invention.

Concentrations

Figure 29:
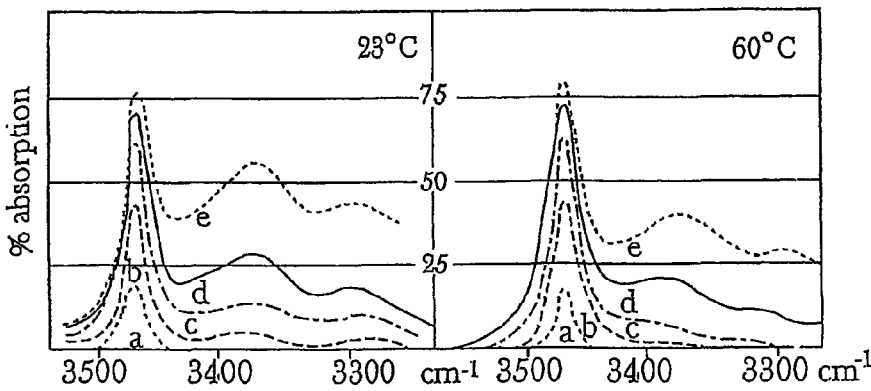
FIG. 29 shows the concentration effects on the atomic spectra frequencies of N-methyl urethane in carbon tetrachloride solutions at the following concentrations: a) 0.01M; b) 0.03M; c) 0.06M; d) 0.10M; 3) 0.15M.

Concentrations of chemical species are known to affect reaction rates and dynamics. Concentration also affects catalyst activity. The prior art explains these effects by the probabilities that various chemical species will collide with each other. At high concentrations of a particular species, there are many individual atoms or molecules present. The more atoms or molecules present, the more likely they are to collide with something else. However, this statistical treatment by the prior art does not explain the entire situation. FIG. 29 shows various concentrations of N-methyl urethane in a carbon tetrachloride solution. At low concentrations, the spectral lines have a relatively low intensity. However, as the concentration is increased, the intensities of the spectral curves increase also. At 0.01 molarity, the spectral curve at 3,460 $cm^{-1}$ is the only prominent frequency. However, at 0.15 molarity, the curves at 3,370 and 3,300 $cm^{-1}$ are also prominent.

As the concentration of a chemical species is changed, the spectral character of that species in the reaction mixture changes also. Suppose that 3,300 and 3,370 $cm^{-1}$ are important frequencies for a desired reaction pathway. At low concentrations the desired reaction pathway will not occur. However, if the concentrations are increased (and hence the intensities of the relevant frequencies) the reaction will proceed down the desired pathway. Concentration is also related to solvents, support structures, poisons and promoters, as previously discussed.

Fine Structure Frequencies

The field of science concerned generally with measuring the frequencies of energy and matter, known as spectroscopy, has already been discussed herein. Specifically, the three broad classes of atomic and molecular spectra were reviewed. Electronic spectra, which are due to electron transitions, have frequencies primarily in the ultraviolet (UV), visible, and infrared (IR) regions, and occur in atoms and molecules. Vibrational spectra, which are due to, for example, bond motion between individual atoms within molecules, are primarily in the IR, and occur in molecules. Rotational spectra are due primarily to rotation of molecules in space and have microwave or radiowave frequencies, and also occur in molecules.

The previous discussion of various spectra and spectroscopy has been oversimplified. There are actually at least three additional sets of spectra, which comprise the spectrum discussed above herein, namely, the fine structure spectra and the hyperfine structure spectra and the superfine structure spectra. These spectra occur in atoms and molecules, and extend, for example, from the ultraviolet down to the low radio regions. These spectra are often mentioned in prior art chemistry and spectroscopy books typically as an aside, because prior art chemists typically focus more on the traditional types of spectroscopy, namely, electronic, vibrational, and rotational.

The fine and hyperfine spectra are quite prevalent in the areas of physics and radio astronomy. For example, cosmologists map the locations of interstellar clouds of hydrogen, and collect data regarding the origins of the universe by detecting signals from outerspace, for example, at 1.420 GHz, a microwave frequency which is one of the hyperfine splitting frequencies for hydrogen. Most of the large databases concerning the microwave and radio frequencies of molecules and atoms have been developed by astronomers and physicists, rather than by chemists. This apparent gap between the use by chemists and physicists, of the fine and hyperfine spectra in chemistry, has apparently resulted in prior art chemists not giving much, if any, attention to these potentially useful spectra.

Figure 30A:
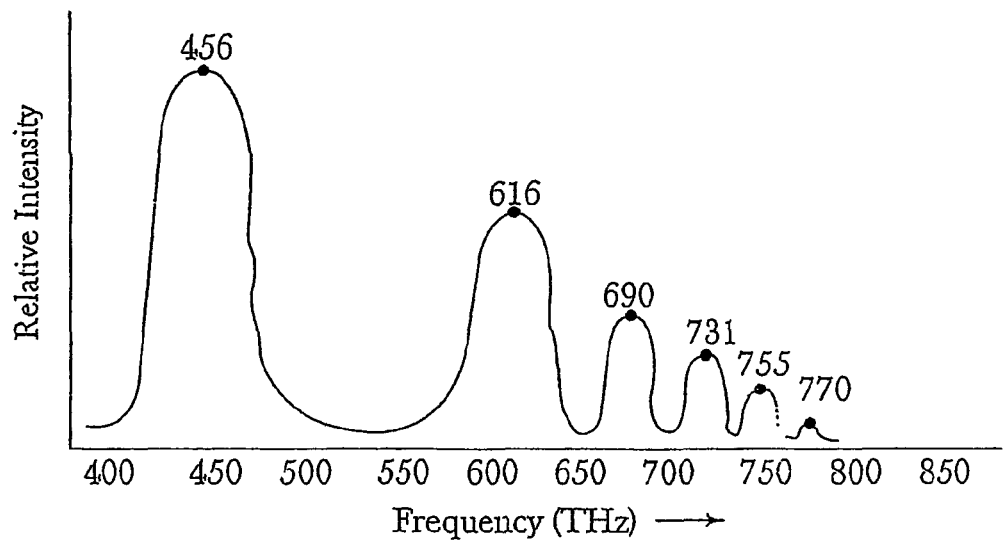
FIG. 30 shows plots corresponding to the emission spectrum of hydrogen. Specifically, FIG. 30a corresponds to Balmer Series 2 for hydrogen.
FIG. 30b corresponds to emission spectrum for the 456 THz frequency of hydrogen.
Figure 30B:
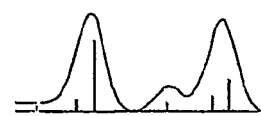
Figure 31:
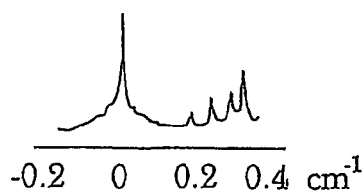
FIG. 31 corresponds to a high resolution laser saturation spectrum for the 456 THz frequency of hydrogen.

Referring again to FIGS. 9a and 9b, the Balmer series (i.e., frequency curve II), begins with a frequency of 456 THz (see FIG. 30a). Closer examination of this individual frequency shows that instead of there being just one crisp narrow curve at 456 THz, there are really seven different curves very close together that comprise the curve at 456 THz. The seven (7) different curves are fine structure frequencies. FIG. 30b shows the emission spectrum for the 456 THz curve in hydrogen. A high-resolution laser saturation spectrum, shown in FIG. 31, gives even more detail. These seven different curves, which are positioned very close together, are generally referred to as a multiplet.

Although there are seven different fine structure frequencies shown, these seven frequencies are grouped around two major frequencies. These are the two, tall, relatively high intensity curves shown in FIG. 30b. These two high intensity curves are also shown in FIG. 31 at zero $cm^{-1}$ (456.676 THz), and at relative wavenumber 0.34 $cm^{-1}$ (456.686 THz). What appears to be a single frequency of (456 THz), is actually composed predominantly of two slightly different frequencies (456.676 and 456.686 THz), and the two frequencies are typically referred to as doublet and the frequencies are said to be split. The difference or split between the two predominant frequencies in the hydrogen 456 THz doublet is 0.010 THz (100 THz) or 0.34 $cm^{-1}$ wavnumbers. This difference frequency, 10 GHz, is called the fine splitting frequency for the 456 THz frequency of hydrogen.

Figure 32:
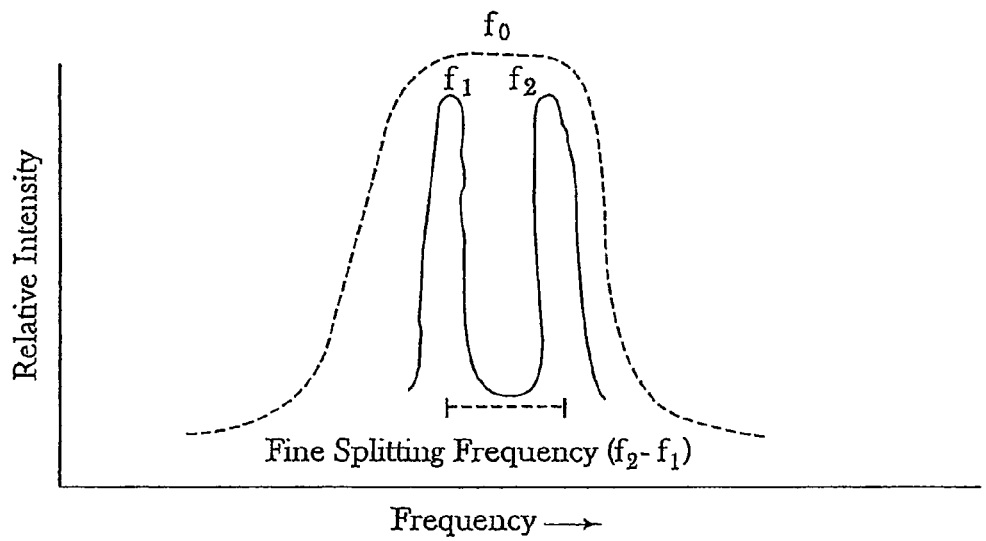
FIG. 32 shows fine splitting frequencies which exist under a typical spectral curve.

Thus, the individual frequencies that are typically shown in ordinary electronic spectra are composed of two or more distinct frequencies spaced very close together. The distinct frequencies spaced very close together are called fine structure frequencies. The difference, between two fine structure frequencies that are split apart by a very slight amount, is a fine splitting frequency (see FIG. 32 which shows $f_1$ and $f_2$ which comprise $f_0$ and which are shown as underneath $f_0$. The difference between $f_1$ and $f_2$ is known as the fine splitting frequency). This "difference" between two fine structure frequencies is important because such a difference between any two frequencies is a heterodyne.

Almost all the hydrogen frequencies shown in FIGS. 9a and 9b are doublets or multiplets. This means that almost all the hydrogen electronic spectrum frequencies have fine structure frequencies and fine splitting frequencies (which means that these heterodynes are available to be used as spectral catalysts, if desired). The present invention discloses that these "differences" or heterodynes can be quite useful for certain reactions. However, prior to discussing the use of these heterodynes, in the present invention, more must be understood about these heterodynes. Some of the fine splitting frequencies (i.e., heterodynes) for hydrogen are listed in Table 3. These fine splitting heterodynes range from the microwave down into the upper reaches of the radio frequency region.

TABLE 3

Fine Splitting Frequencies for Hydrogen

| Frequency (THz) | Orbital | Wavenumber ($cm^{-1}$) | Fine Splitting Frequency |
|---|---|---|---|
| 2,466 | 2p | 0.365 | 10.87 GHz |
| 456 | n2→3 | 0.340 | 10.02 GHz |
| 2,923 | 3p | 0.108 | 3.23 GHz |
| 2,923 | 3d | 0.036 | 1.06 GHz |
| 3,082 | 4p | 0.046 | 1.38 GHz |
| 3,082 | 4d | 0.015 | 448.00 MHz |
| 3,082 | 4f | 0.008 | 239.00 MHz |

There are more than 23 fine splitting frequencies (i.e., heterodynes) for just the first series or curve I in hydrogen. Lists of the fine splitting heterodynes can be found, for example, in the classic 1949 reference "Atomic Energy Levels" by Charlotte Moore. This reference also lists 133 fine splitting heterodyned intervals for carbon, whose frequencies range from 14.1 THz (473.3 $cm^{-1}$) down to 12.2. GHz (0.41 $cm^{-1}$). Oxygen has 287 fine splitting heterodynes listed from 15.9 THz (532.5 $cm^{-1}$) down to 3.88 GHz (0.13 $cm^{-1}$). The 23 platinum fine splitting intervals detailed are from 23.3 THz (775.9 $cm^{-1}$) to 8.62 THz in frequency (287.9 $cm^{-1}$).

Figure 33:
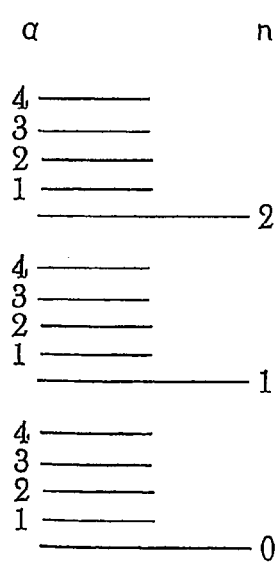
FIG. 33 corresponds to a diagram of atomic electron levels (n) in fine structure frequencies ($\alpha$).
Figure 34:
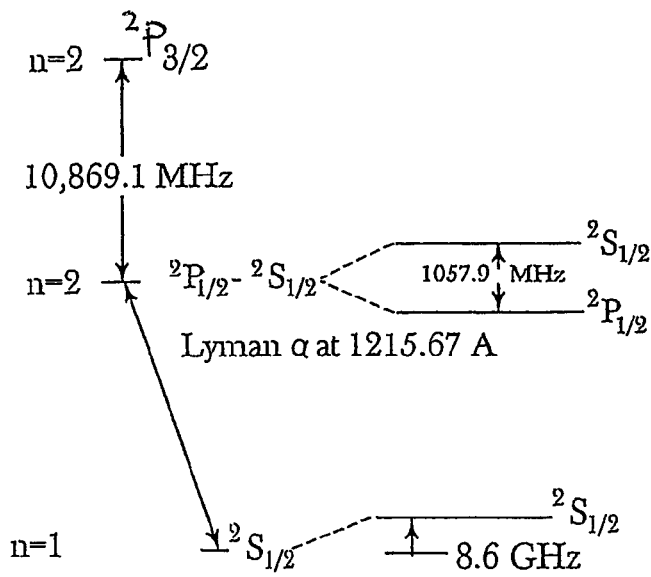
FIG. 34 shows fine structures of the n=1 and n=2 levels of a hydrogen atom.
Figure 35:
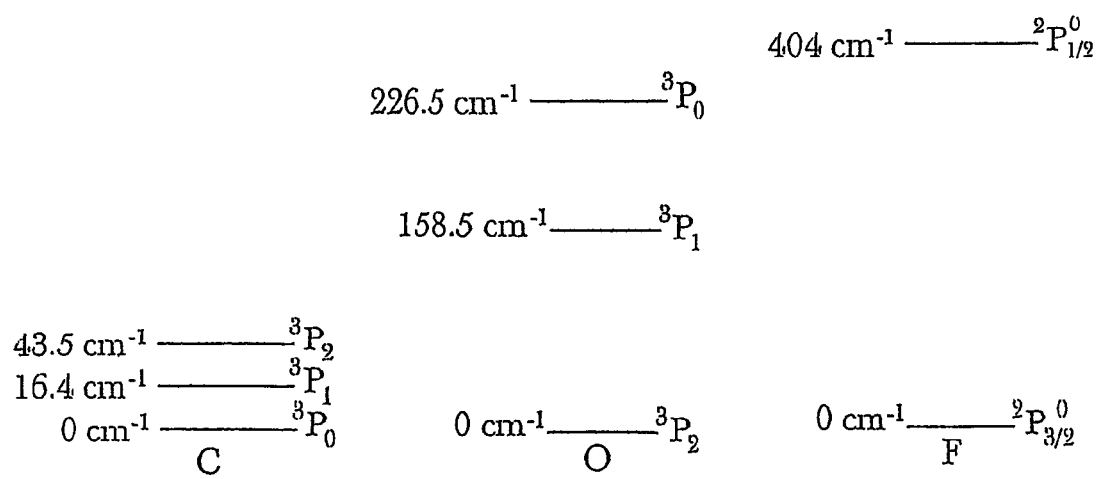
FIG. 35 shows multiplet splittings for the lowest energy levels of carbon, oxygen and fluorine: 43.5 $cm^{-1}$=1.3 THz; 16.4 $cm^{-1}$=490 GHz; 226.5 $cm^{-1}$=6.77 THz; 158.5 $cm^{-1}$=4.74 THz; 404 $cm^{-1}$=12.1 THz.

Diagrammatically, the magnification and resolution of an electronic frequency into several closely spaced fine frequencies is depicted in FIG. 33. The electronic orbit is designated by the orbital number n=0, 1, 2, etc. The fine structure is designated as a. A quantum diagram for the hydrogen fine structure is shown in FIG. 34. Specifically, shown is the fine structure of the n=1 and n=2 levels of the hydrogen atom. FIG. 35 shows the multiplet splittings for the lowest energy levels of carbon, oxygen, and fluorine, as represented by "C", "O" and "F", respectively.

In addition to the fine splitting frequencies for atoms (i.e., heterodynes), molecules also have similar fine structure frequencies. The origin and derivation for molecular fine structure and splitting is different from that for atoms, however, the graphical and practical results are quite similar. In atoms, the fine structure frequencies are said to result from the interaction of the spinning electron with its' own magnetic field. Basically, this means the electron cloud of a single atomic sphere, rotating and interacting with its' own magnetic field, produces the atomic fine structure frequencies. The prior art refers to this phenomena as "spin-orbit coupling". For molecules, the fine structure frequencies correspond to the actual rotational frequencies of the electronic or vibrational frequencies. So the fine structure frequencies for atoms and molecules both result from rotation. In the case of atoms, it is the atom spinning and rotating around itself, much the way the earth rotates around its axis. In the case of molecules, it is the molecule spinning and rotating through space.

Figure 36:
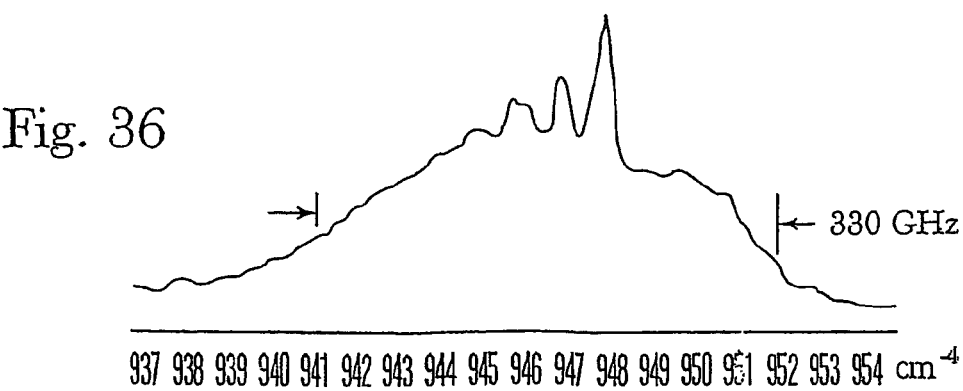
FIG. 36 shows a vibration band of $SF_6$ at a wavelength of 10 $\mu m^2$.

FIG. 36 shows the infrared absorption spectrum of the $SP_6$ vibration band near 28.3 THz (10.6 μm wavelength, wavenumber 948 $cm^{-1}$) of the $SF_6$ molecule. The molecule is highly symmetrical and rotates somewhat like a top. The spectral tracing was obtained with a high resolution grating spectrometer. There is a broad band between 941 and 952 $cm^{-1}$ (28.1 and 28.5 THz) with three sharp spectral curves at 946, 947, and 948 $cm^{-1}$ (28.3, 28.32, and 23.834 THz).

Figure 37A:
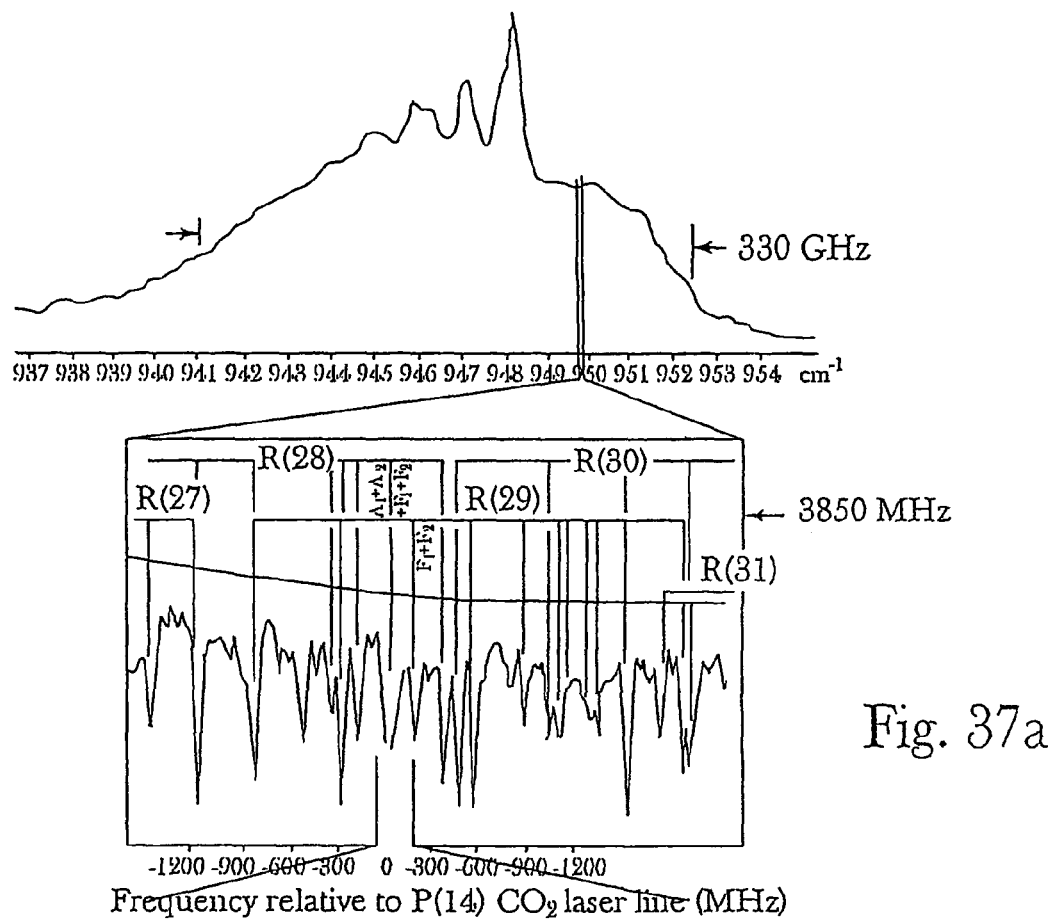
FIG. 37a shows a spectral pattern similar to that shown in FIG. 36, with a particular frequency magnified.
Figure 37B:
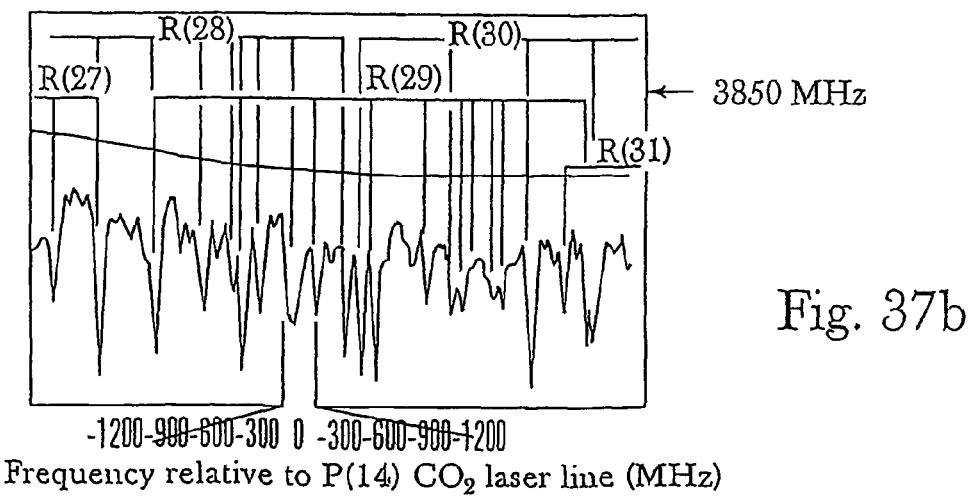
FIG. 37b shows fine structure frequencies in greater detail for the compound $SF_6$.
Figure 38:
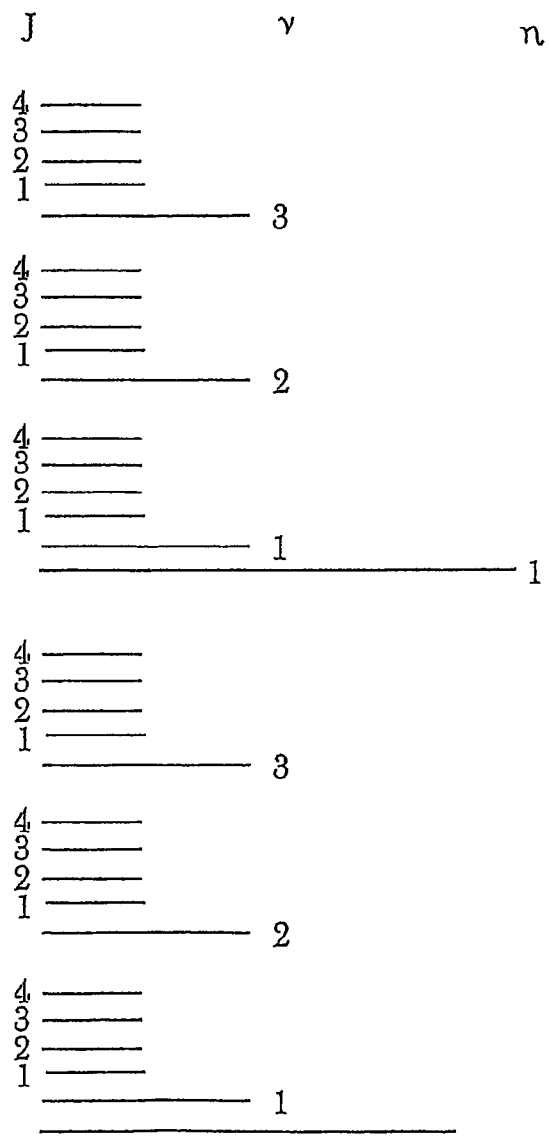
FIG. 38 shows an energy level diagram which corresponds to different energy levels for a molecule where rotational corresponds to "J", vibrational corresponds to "v" and electronic levels correspond to "n".

FIG. 37a shows a narrow slice being taken from between 949 and 950 $cm^{-1}$, which is blown up to show more detail in FIG. 37b. A tunable semiconductor diode laser was used to obtain the detail. There are many more spectral curves which appear when the spectrum is reviewed in finer detail. These curves are called the fine structure frequencies for this molecule. The total energy of an atom or molecule is the sum of its' electronic, vibrational, and rotational energies. Thus, the simple Planck equation discussed previously herein:

E=hv can be rewritten as follows:

$E=E_e+E_v+E_r$ where E is the total energy, $E_e$ is the electronic energy, $E_v$ is the vibrational energy, and $E_r$ is the rotational energy. Diagrammatically, this equation is shown in FIG. 38 for molecules. The electronic energy, $E_e$, involves a change in the orbit of one of the electrons in the molecule. It is designated by the orbital number n=0, 1, 2, 3, etc. The vibrational energy, $E_v$, is produced by a change in the vibration rate between two atoms within the molecule, and is designated by a vibrational number v=1, 2, 3, etc. Lastly, the rotational energy, $E_r$, is the energy of rotation caused by the molecule rotating around its' center of mass. The rotational energy is designated by the quantum number J=1, 2, and 3, etc., as determined from angular momentum equations.

Thus, by examining the vibrational frequencies of $SF_6$ in more detail, the fine structure molecular frequencies become apparent. These fine structure frequencies are actually produced by the molecular rotations, "r", as a subset of each vibrational frequency. Just as the rotational levels "J" are substantially evenly separated in FIG. 38, they are also substantially evenly separated when plotted as frequencies.

Figure 39A:
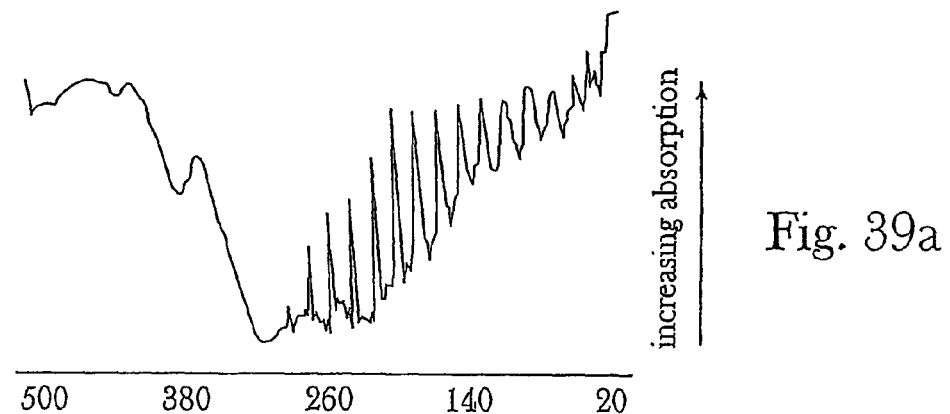
FIGS. 39a and 39b correspond to pure rotational absorption spectrum of gaseous hydrogen chloride as recorded with an interferometer.
Figure 39B:
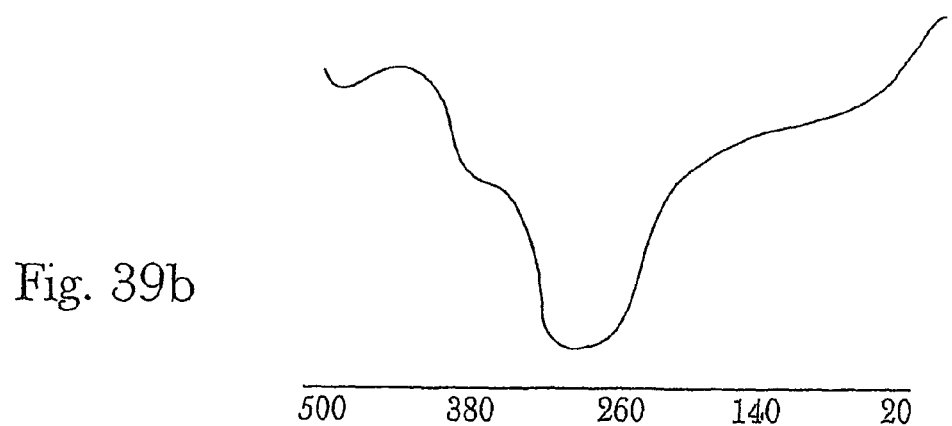

This concept may be easier to understand by viewing some additional frequency diagrams. For example, FIG. 39a shows the pure rotational absorption spectrum for gaseous hydrogen-chloride and FIG. 39b shows the same spectrum at low resolution. In FIG. 39a, the separate waves, that look something like teeth on a "comb", correspond to the individual rotational frequencies. The complete wave (i.e., that wave comprising the whole comb) that extends in frequency from 20 to 500 $cm^{-1}$ corresponds to the entire vibrational frequency. At low resolution or magnification, this set of rotational frequencies appear to be a single frequency peaking at about 20 $cm^{-1}$ (598 GHz) (see FIG. 39b). This is very similar to the way atomic frequencies such as the 456 THz hydrogen frequency appear (i.e., just one frequency at low resolution, that turn out to be several different frequencies at higher magnification).

Figure 40:
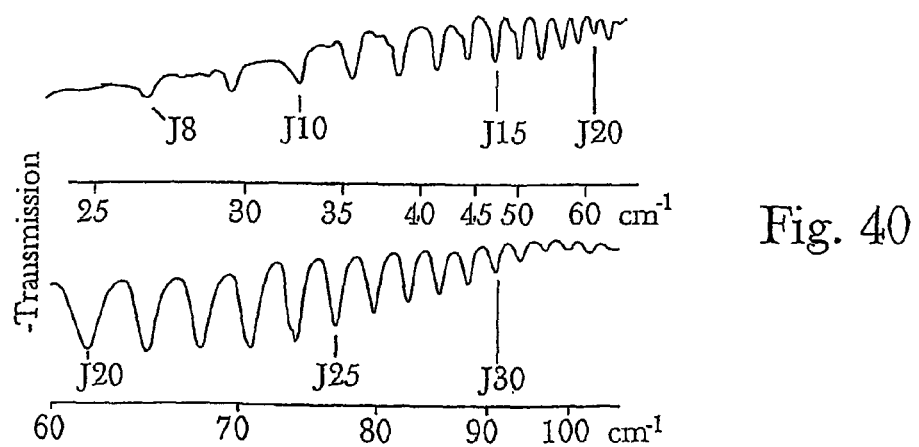
FIG. 40 corresponds to the rotational spectrum for hydrogen cyanide. "J" corresponds to the rotational level.

In FIG. 40, the rotational spectrum (i.e., fine structure) of hydrogen cyanide is shown, where "J" is the rotational level. Note again, the regular spacing of the rotational levels. (Note that this spectrum is oriented opposite of what is typical). This spectrum uses transmission rather than emission on the horizontal Y-axis, thus, intensity increases downward on the Y-axis, rather than upwards.

Figure 41:
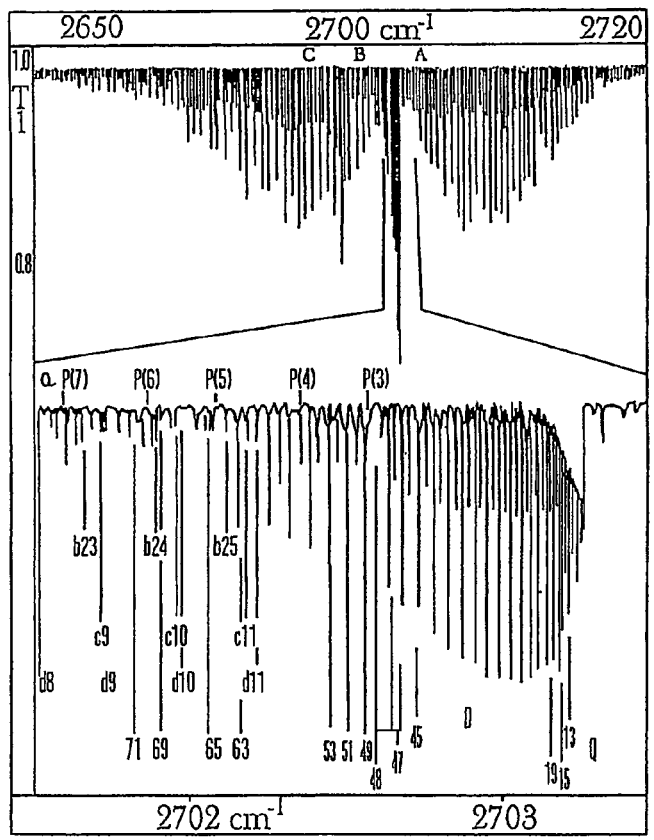
FIG. 41 shows a spectrum corresponding to the additive heterodyne of $v_1$ and $v_5$ in the spectral band showing the frequency band at A ($v_1-v_5$), B=$v_1-2v_5$.

Additionally, FIG. 41 shows the $v_1$–$v_5$ vibrational bands for FCCF (where $v_1$ is vibrational level 1 and $v_5$ vibrational level 5) which includes a plurality of rotational frequencies. All of the fine sawtooth spikes are the fine structure frequencies which correspond to the rotational frequencies. Note the substantially regular spacing of the rotational frequencies. Also note, the undulating pattern of the rotational frequency intensity, as well as the alternating pattern of the rotational frequency intensities.

Consider the actual rotational frequencies (i.e., fine structure frequencies) for the ground state of carbon monoxide listed in Table 4.

TABLE 4

Rotational Frequencies and Derived Rotational Constant for CO in the Ground State

| J Transition | Frequency (MHz) | Frequency (GHz) |
|---|---|---|
| 0 → 1 | 115,271.204 | 115 |
| 1 → 2 | 230,537.974 | 230 |
| 2 → 3 | 345,795.989 | 346 |
| 3 → 4 | 461,040.811 | 461 |
| 4 → 5 | 576,267.934 | 576 |
| 5 → 6 | 691,472.978 | 691 |
| 6 → 7 | 806,651.719 | 807 |

Where; $B_o$ = 57,635.970 MHz

Each of the rotational frequencies is regularly spaced at approximately 115 GHz apart. Prior art quantum theorists would explain this regular spacing as being due to the fact that the rotational frequencies are related to Planck's constant and the moment of inertia (i.e., center of mass for the molecule) by the equation:

$$B = \frac{h}{8\pi^2 I}$$

where B is the rotational constant, h is Planck's constant, and I is the moment of inertia for the molecule. From there the prior art established a frequency equation for the rotational levels that corresponds to:

$f=2B(J+1)$ where f is the frequency, B is the rotational constant, and J is the rotational level. Thus, the rotational spectrum (i.e., fine structure spectrum) for a molecule turns out to be a harmonic series of lines with the frequencies all spaced or split (i.e., heterodyned) by the same amount. This amount has been referred to in the prior art as "2B", and "B" has been referred to as the "rotational constant". In existing charts and databases of molecular frequencies, "B" is usually listed as a frequency such as MHz. This is graphically represented for the first four rotational frequencies for CO in FIG. 42.

This fact is interesting for several reasons. The rotational constant "B", listed in many databases, is equal to one half of the difference between rotational frequencies for a molecule. That means that B is the first subharmonic frequency, to the fundamental frequency "2B", which is the heterodyned difference between all the rotational frequencies. The rotational constant B listed for carbon monoxide is 57.6 GHz (57,635.970 MHz). This is basically half of the 115 GHz difference between the rotational frequencies. Thus, according to the present invention, if it is desired to stimulate a molecule's rotational levels, the amount "2B" can be used, because it is the fundamental first generation heterodyne. Alternatively, the same "B" can be used because "B" corresponds to the first subharmonic of that heterodyne.

Further, the prior art teaches that if it is desired to use microwaves for stimulation, the microwave frequencies used will be restricted to stimulating levels at or near the ground state of the molecule (i.e., n=0 in FIG. 38). The prior art teaches that as you progress upward in FIG. 38 to the higher electronic and vibrational levels, the required frequencies will correspond to the infrared, visible, and ultraviolet regions. However, the prior art is wrong about this point.

By referring to FIG. 38 again, it is clear that the rotational frequencies are evenly spaced out no matter what electronic or vibrational level is under scrutiny. The even spacing shown in FIG. 38 is due to the rotational frequencies being evenly spaced as progression is made upwards through all the higher vibrational and electronic levels. Table 5 lists the rotational frequencies for lithium fluoride (LiF) at several different rotational and vibrational levels.

TABLE 5

Rotational Frequencies for Lithium Fluoride (LiF)

| Vibrational Level | Rotational Transition | Frequency (MHz) |
|---|---|---|
| 0 | 0 → 1 | 89,740.46 |
| 0 | 1 → 2 | 179,470.35 |
| 0 | 2 → 3 | 269,179.18 |
| 0 | 3 → 4 | 358,856.19 |
| 0 | 4 → 5 | 448,491.07 |
| 0 | 5 → 6 | 538,072.65 |
| 1 | 0 → 1 | 88,319.18 |
| 1 | 1 → 2 | 176,627.91 |
| 1 | 2 → 3 | 264,915.79 |
| 1 | 3 → 4 | 353,172.23 |
| 1 | 4 → 5 | 441,386.83 |
| 2 | 0 → 1 | 86,921.20 |
| 2 | 1 → 2 | 173,832.04 |
| 2 | 2 → 3 | 260,722.24 |
| 2 | 3 → 4 | 347,581.39 |
| 3 | 1 → 2 | 171,082.27 |
| 3 | 2 → 3 | 256,597.84 |
| 3 | 3 → 4 | 342,082.66 |

It is clear from Table 5 that the differences between rotational frequencies, no matter what the vibrational level, is about 86,000 to about 89,000 MHz (i.e., 86-89 GHz). Thus, according to the present invention, by using a microwave frequency between about 86,000 MHz and 89,000 MHz, the molecule can be stimulated from the ground state level all the way up to its' highest energy levels. This effect has not been even remotely suggested by the prior art. Specifically, the rotational frequencies of molecules can be manipulated in a unique manner. The first rotational level has a natural oscillatory frequency (NOF) of 89,740 MHz. The second rotational level has an NOF of 179,470 MHz. Thus, $NOF_{rotational\ 1\to 2} - NOF_{rotational\ 0\to 1} = $ Subtracted Frequency$_{rotational\ 2-1}$;

or 179,470 MHz−89,740 MHz=89,730 MHz.

Thus, the present invention has discovered that the NOF's of the rotational frequencies heterodyne by adding and subtracting in a manner similar to the manner that all frequencies heterodyne. Specifically, the two rotational frequencies heterodyne to produce a subtracted frequency. This subtracted frequency happens to be exactly twice as big as the derived rotational constant "B" listed in nuclear physics and spectroscopy manuals. Thus, when the first rotational frequency in the molecule is stimulated with the Subtracted Frequency$_{rotational\ 2-1}$, the first rotational frequency will heterodyne (i.e., in this case add) with the NOF$_{rotational\ 0\to 1}$ (i.e., first rotational frequency) to produce NOF$_{rotational\ 1\to 2}$, which is the natural oscillatory frequency of the molecule's second rotational level. In other words:

Subtracted Frequency$_{rotational\ 2-1}$ + NOF$_{rotational\ 0\to 1}$ = NOF$_{rotational\ 1\to 2}$;

or 89,730 MHz+89,740 MHz=179,470 MHz

Since the present invention has disclosed that the rotational frequencies are actually evenly spaced harmonics, the subtracted frequency will also add with the second level NOF to produce the third level NOF. The subtracted frequency will add with the third level NOF to produce the fourth level NOF. This procedure can be repeated over and over. Thus, according to the present invention, by using one single microwave frequency, it is possible to stimulate all the rotational levels in a vibratory band.

Moreover, if all the rotational levels for a vibrational frequency are excited, then the vibrational frequency will also be correspondingly excited. Further, if all the vibrational levels for an electronic level are excited, then the electronic level will be excited as well. Thus, according to the teachings of the present invention, it is possible to excite the highest levels of the electronic and vibrational structure of a molecule by using a single microwave frequency. This is contrary to the prior art teachings that the use of microwaves is restricted to the ground state of the molecule. Specifically, if the goal is to resonate directly with an upper vibrational or electronic level, the prior art teaches that microwave frequencies can not be used. If, however, according to the present invention, a catalytic mechanism of action is initiated by, for example, resonating with target species indirectly through heterodynes, then one or more microwave frequencies can be used to energize at least one upper level vibrational or electronic state. Accordingly, by using the teachings of the present invention in conjunction with the simple processes of heterodyning it becomes readily apparent that microwave frequencies are not limited to the ground state levels of molecules.

Figure 42:
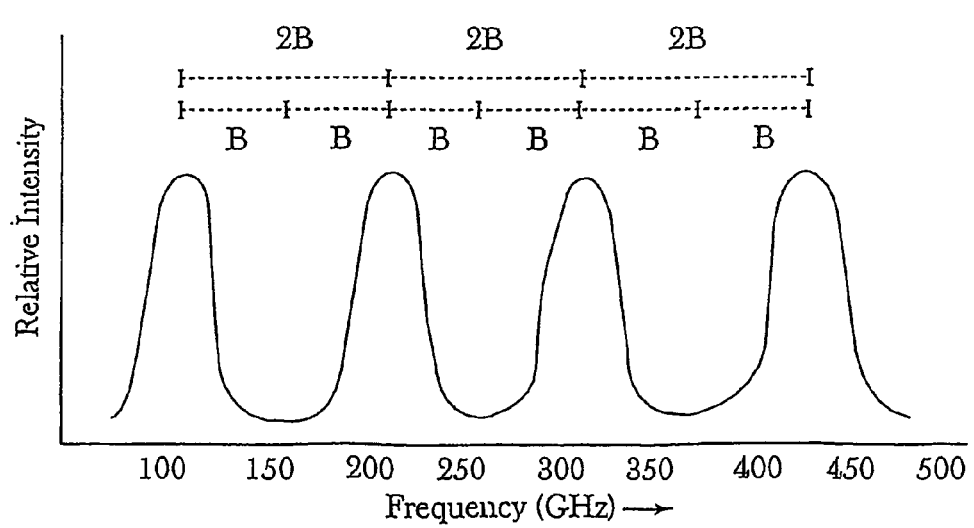
FIG. 42 shows a graphical representation of fine structure spectrum showing the first four rotational frequencies for CO in the ground state. The difference (heterodyne) between the molecular fine structure rotational frequencies is 2× the rotational constant B (i.e., $f_2-f_1$=2B). In this case, B=57.6 GHz (57,635.970 MHz).

The present invention has determined that catalysts can actually stimulate target species indirectly by utilizing at least one heterodyne frequency (e.g., harmonic). However, catalysts can also stimulate the target species by direct resonance with at least one fundamental frequency of interest. However, the rotational frequencies can result in use of both mechanisms. For example, FIG. 42 shows a graphical representation of fine structure spectrum showing the first four rotational frequencies for CO in the ground state. The first rotational frequency for CO is 115 GHz. The heterodyned difference between rotational frequencies is also 115 GHz. The first rotational frequency and the heterodyned difference between frequencies are identical. All of the upper level rotational frequencies are harmonics of the first frequency. This relationship is not as apparent when one deals only with the rotational constant "B" of the prior art. However, frequency-based spectral chemistry analyses, like those, of the present invention, makes such concepts easier to understand.

Examination of the first level rotational frequencies for LiF shows that it is nearly identical to the heterodyned difference between it and the second level rotational frequency. The rotational frequencies are sequential harmonics of the first rotational frequency. Accordingly, if a molecule is stimulated with a frequency equal to 2B (i.e., a heterodyned harmonic difference between rotational frequencies) the present invention teaches that energy will resonate with all the upper rotational frequencies indirectly through heterodynes, and resonate directly with the first rotational frequency. This is an important discovery.

The prior art discloses a number of constants used in spectroscopy that relate in some way or another to the frequencies of atoms and molecule, just as the rotational constant "B" relates to the harmonic spacing of rotational fine structure molecular frequencies. The alpha (α) rotation-vibration constant is a good example of this. The alpha rotation-vibration frequency constant is related to slight changes in the frequencies for the same rotational level, when the vibrational level changes. For example, FIG. 43a shows the frequencies for the same rotational levels, but different vibrational levels for LiF.

The frequencies are almost the same, but vary by a few percent between the different vibrational levels.

Referring to FIG. 43b, the differences between all the frequencies for the various rotational transitions at different vibrational levels of FIG. 43a are shown. The rotational transition 0→1 in the top line of FIG. 43b has a frequency of 89,740.46 MHz at vibrational level 0. At vibrational level 1, the 0→1 transition is 88,319.18 MHz. The difference between these two rotational frequencies is 1,421.28 MHz. At vibrational level 2, the 0→1 transition is 86,921.20 MHz. The difference between it and the vibrational level 1 frequency (88,319.18 MHz) is 1,397.98 MHz. These slight differences for the same J rotational level between different vibrational levels are nearly identical. For the J=0→1 rotational level they center around a frequency of 1,400 MHz.

For the J=1→2 transition, the differences center around 2,800 Hz, and for the J=2→3 transition, the differences center around 4,200 Hz. These different frequencies of 1,400, 2,800 and 4,200,Hz etc., are all harmonics of each other. Further, they are all harmonics of the alpha rotation-vibration constant. Just as the actual molecular rotational frequencies are harmonics of the rotational constant B, the differences between the rotational frequencies are harmonics of the alpha rotation-vibration constant. Accordingly, if a molecule is stimulated with a frequency equal to the alpha vibration-rotation frequencies, the present invention teaches that energy will resonate with all the rotational frequencies indirectly through heterodynes. This is an important discovery.

Figure 44:
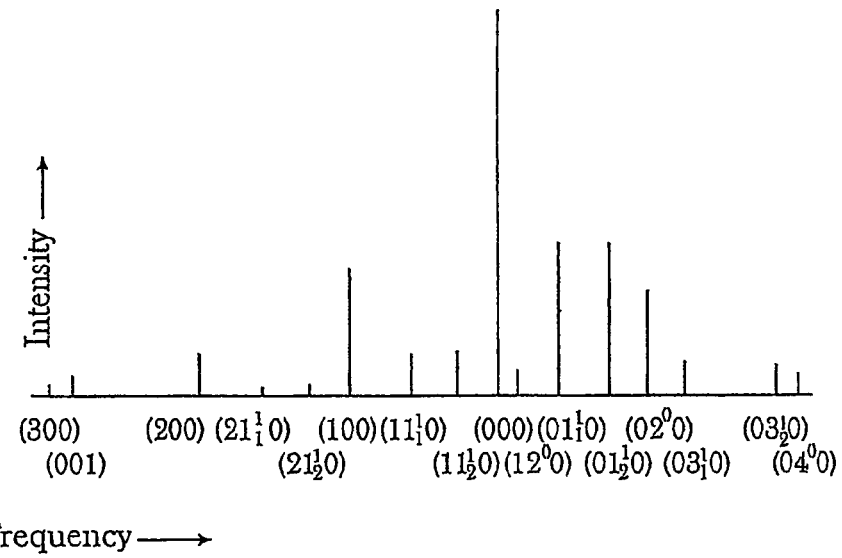
FIG. 44 shows the rotational transition J=1→2 for the triatomic molecule OCS. The vibrational state is given by vibrational quantum numbers in brackets ($v_1, v_2, v_3$), $v_2$ have a superscript [l]. In this case, l=1. A subscript 1 is applied to the lower-frequency component of the l-type doublet, and 2 to the higher-frequency components. The two lines at ($01^10$) and ($01^10$) are an l-type doublet, separated by $q_1$.

Consider the rotational and vibrational states for the triatomic molecule OCS shown in FIG. 44. FIG. 44 shows the same rotational level (J=1→2) for different vibrational states in the OCS molecule. For the ground vibrational (000) level, J=1→2 transition; and the excited vibrational state (100) J=1→2 transition, the difference between the two frequencies is equal to 4× $alpha_1$ ($4\alpha_1$). In another excited state, the frequency difference between the ground vibrational (000) level, J=1→2 transition, and the center of the two l-type doublets is 4× $alpha_2$ ($4\alpha_2$). In a higher excited vibrational state, the frequency difference between (000) and (02°0) is 8× $alpha_2$ ($8\alpha_2$). Thus, it can be seen that the rotation-vibration constants "α" are actually harmonics of molecular frequencies. Thus, according to the present invention, stimulating a molecule with an "α" frequency, or a harmonic of "α", will either directly resonate with or indirectly heterodyne harmonically with various rotational-vibrational frequencies of the molecule.

Another interesting constant is the l-type doubling constant. This constant is also shown in FIG. 44. Specifically, FIG. 44 shows the rotational transition J=1→2 for the triatomic molecule OCS. Just as the atomic frequencies are sometimes split into doublets or multiplets, the rotational frequencies are also sometimes split into doublets. The difference between them is called the l-type doubling constant. These constants are usually smaller (i.e., of a lower frequency) than the a constants. For the OCS molecule, the a constants are 20.56 and 10.56 MHz while the l-type doubling constant is 6.3 MHz. These frequencies are all in the radiowave portion of the electromagnetic spectrum.

As discussed previously herein, energy is transferred by two fundamental frequency mechanisms. If frequencies are substantially the same or match, then energy transfers by direct resonance. Energy can also transfer indirectly by heterodyning, (i.e., the frequencies substantially match after having been added or subtracted with another frequency). Further, as previously stated, the direct or indirect resonant frequencies do not have to match exactly. If they are merely close, significant amounts of energy will still transfer. Any of these constants or frequencies that are related to molecules or other matter via heterodynes, can be used to transfer, for example, energy to the matter and hence can directly interact with the matter.

In the reaction in which hydrogen and oxygen are combined to form water, the present invention teaches that the energizing of the reaction intermediates of atomic hydrogen and the hydroxy radical are crucial to sustaining the reaction. In this regard, the physical catalyst platinum energizes both reaction intermediates by directly and indirectly resonating with them. Platinum also energizes the intermediates at multiple energy levels, creating the conditions for energy amplification. The present invention also teaches how to copy platinum's mechanism of action by making use of atomic fine structure frequencies.

The invention has previously discussed resonating with the fine structure frequencies with only slight variations between the frequencies (e.g., 456.676 and 456.686 THz). However, indirectly resonating with the fine structure frequencies, is a significant difference. Specifically, by using the fine splitting frequencies, which are simply the differences or heterodynes between the fine structure frequencies, the present invention teaches that indirect resonance can be achieved. By examining the hydrogen 456 THz fine structure and fine splitting frequencies (see, for example, FIGS. 30 and 31 and Table 3 many heterodynes are shown). In other words, the difference between the fine structure frequencies can be calculated as follows:

$$456.686 \text{ THz} - 456.676 \text{ THz} = 0.0102 \text{ THz} = 10.2 \text{ GHz}$$

Thus, if hydrogen atoms are subjected to 10.2 GHz electromagnetic energy (i.e., energy corresponding to microwaves), then the 456 THz electronic spectrum frequency is energized by resonating with it indirectly. In other words, the 10.2 GHz will add to 456.676 THz to produce the resonant frequency of 456.686 THz. The 10.2 GHz will also subtract from the 456.686 THz to produce the resonant frequency of 456.676 THz. Thus, by introducing 10.2 GHz to a hydrogen atom, the hydrogen atom is excited at the 456 THz frequency. A microwave frequency can be used to stimulate an electronic level.

According to the present invention, it is also possible to use a combination of mimicked catalyst mechanisms. For example, it is possible to: 1) resonate with the hydrogen atom frequencies indirectly through heterodynes (i.e., fine splitting frequencies); and/or 2) resonate with the hydrogen atom at multiple frequencies. Such multiple resonating could occur using a combination of microwave frequencies either simultaneously, in sequence, and/or in chirps or bursts. For example, the individual microwave fine splitting frequencies for hydrogen of 10.87 GHz, 10.2 GHz, 3.23 GHz, 1.38 GHz, and 1.06 GHz could be used in a sequence. Further, there are many fine splitting frequencies for hydrogen that have not been expressly included herein, thus, depending on the frequency range of equipment available, the present invention provides a means for tailoring the chosen frequencies to the capabilities of the available equipment. Thus, the flexibility according to the teachings of the present invention is enormous.

Another method to deliver multiple electromagnetic energy frequencies according to the present invention, is to use a lower frequency as a carrier wave for a higher frequency. This can be done, for example, by producing 10.2 GHz EM energy in short bursts, with the bursts coming at a rate of about 239 MHz. Both of these frequencies are fine splitting frequencies for hydrogen. This can also be achieved by continuously delivering EM energy and by varying the amplitude at a rate of about 239 MHz. These techniques can be used alone or in combination with the various other techniques disclosed herein.

Thus, by mimicking one or more mechanisms of action of catalysts and by making use of the atomic fine structure and splitting frequencies, it is possible to energize upper levels of atoms using microwave and radiowave frequencies. Accordingly, by selectively energizing or targeting particular atoms, it is possible to catalyze and guide desirable reactions to desired end products. Depending on the circumstances, the option to use lower frequencies may have many advantages. Lower frequencies typically have much better penetration into large reaction spaces and volumes, and may be better suited to large-scale industrial applications. Lower frequencies may be easier to deliver with portable, compact equipment, as opposed to large, bulky equipment which delivers higher frequencies (e.g., lasers). The choice of frequencies of a spectral catalyst may be for as simple a reason as to avoid interference from other sources of EM energy. Thus, according to the present invention, an understanding of the basic processes of heterodyning and fine structure splitting frequencies confers greater flexibility in designing and applying spectral energy catalysts in a targeted manner. Specifically, rather than simply reproducing the spectral pattern of a physical catalyst, the present invention teaches that is possible to make full use of the entire range of frequencies in the electromagnetic spectrum, so long as the teachings of the present invention are followed. Thus, certain desirable frequencies can be applied while other not so desirable frequencies could be left out of an applied spectral energy catalyst targeted to a particular participant and/or component in the cell reaction system.

As a further example, reference is again made to the hydrogen and oxygen reaction for the formation of water. If it is desired to catalyze the water reaction by duplicating the catalyst's mechanism of action in the microwave region, the present invention teaches that several options are available. Another such option is use of the knowledge that platinum energizes the reaction intermediates of the hydroxy radical. In addition to the hydrogen atom, the B frequency for the hydroxy radical is 565.8 GHz. That means that the actual heterodyned difference between the rotational frequencies is 2B, or 1,131.6 GHz. Accordingly, such a frequency could be utilized to achieve excitement of the hydroxy radical intermediate.

Further, the $\alpha$ constant for the hydroxy radical is 21.4 GHz. Accordingly, this frequency could also be applied to energizing the hydroxy radical. Thus, by introducing hydrogen and oxygen gases into a chamber and irradiating the gases with 21.4 GHz, water will be formed. This particular gigahertz energy is a harmonic heterodyne of the rotational frequencies for the same rotational level but different vibrational levels. The heterodyned frequency energizes all the rotational frequencies, which energize the vibrational levels, which energize the electronic frequencies, which catalyze the reaction. Accordingly, the aforementioned reaction could be catalyzed or targeted with a spectral catalyst applied at several applicable frequencies, all of which match with one or more frequencies in one or more participants and thus permit energy to transfer.

Still further, delivery of frequencies of 565.8 GHz, or even 1,131.6 GHz, would result in substantially all of the rotational levels in the molecule becoming energized, from the ground state all the way up. This approach copies a catalyst mechanism of action in two ways. The first way is by energizing the hydroxy radical and sustaining a crucial reaction intermediate to catalyze the formation of water. The second mechanism copied from the catalyst is to energize multiple levels in the molecule. Because the rotational constant "B" relates to the rotational frequencies, heterodynes occur at all levels in the molecule. Thus, using the frequency "B" energizes all levels in the molecule. This potentiates the establishment of an energy amplification system such as that which occurs with the physical catalyst platinum.

Still further, if a molecule was energized with a frequency corresponding to an l-type doubling constant, such frequency could be used in a substantially similar manner in which a fine splitting frequency from an atomic spectrum is used. The difference between the two frequencies in a doublet is a heterodyne, and energizing the doublet with its' heterodyne frequency (i.e., the splitting frequency) would energize the basic frequency and catalyze the reaction.

A still further example utilizes a combination of frequencies for atomic fine structure. For instance, by utilizing a constant central frequency of 1,131.6 GHz (i.e., the heterodyned difference between rotational frequencies for a hydroxy radical) with a vibrato varying around the central frequency by ±21.4 GHz (i.e., the a constant harmonic for variations between rotational frequencies), use could be made of 1.131.6 GHz EM energy in short bursts, with the bursts coming at a rate of 21.4 GHz.

Since there is slight variation between rotational frequencies for the same level, that frequency range can be used to construct bursts. For example, if the largest "B" is 565.8 GHz, then a rotational frequency heterodyne corresponds to 1,131.6 GHz. If the smallest "B" is 551.2 GHz, this corresponds to a rotational frequency heterodyne of 1,102 GHz. Thus, "chirps" or bursts of energy starting at 1,100 GHz and increasing in frequency to 1,140 GHz, could be used. In fact, the transmitter could be set to "chirp" or burst at a rate of 21.4 GHz.

In any event, there are many ways to make use of the atomic and molecular fine structure frequencies, with their attendant heterodynes and harmonics. An understanding of catalyst mechanisms of action enables one of ordinary skill armed with the teachings of the present invention to utilize a spectral catalyst from the high frequency ultraviolet and visible light regions, down into the sometimes more manageable microwave and radiowave regions. Moreover, the invention enables an artisan of ordinary skill to calculate and/or determine the effects of microwave and radiowave energies on chemical reactions and/or reaction pathways.

Hyperfine Frequencies

Hyperfine structure frequencies are similar to the fine structure frequencies. Fine structure frequencies can be seen by magnifying a portion of a standard frequency spectrum. Hyperfine frequencies can be seen by magnifying a portion of a fine structure spectrum. Fine structure splitting frequencies occur at lower frequencies than the electronic spectra, primarily in the infrared and microwave regions of the electromagnetic spectrum. Hyperfine splitting frequencies occur at even lower frequencies than the fine structure spectra, primarily in the microwave and radio wave regions of the electromagnetic spectrum. Fine structure frequencies are generally caused by at least the electron interacting with its' own magnetic field. Hyperfine frequencies are generally caused by at least the electron interacting with the magnetic field of the nucleus.

Figure 45:
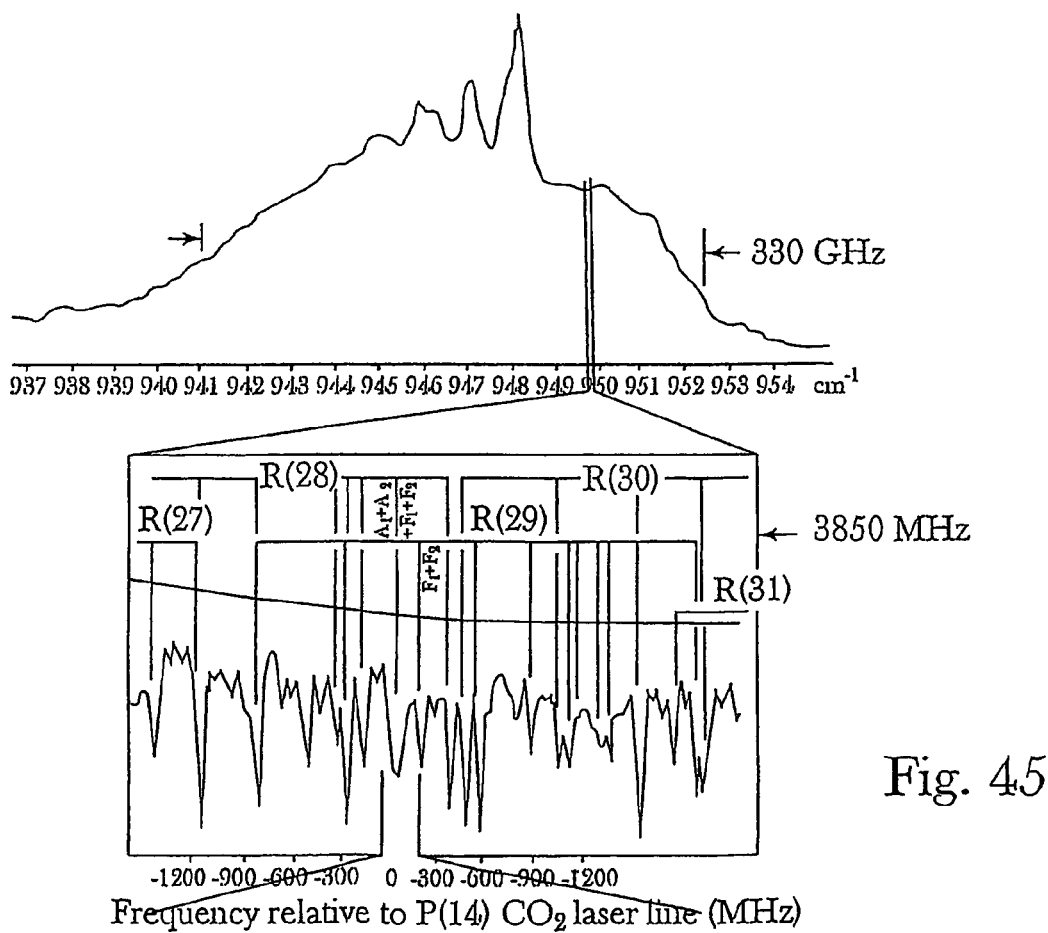
FIG. 45 shows the rotation-vibration band and fine structure frequencies for $SF_6$.

FIG. 36 shows the rotation-vibration band frequency spectra for an $SF_6$ molecule. The rotation-vibration band and fine structure are shown again in FIG. 45. However, the fine structure frequencies are seen by magnifying a small section of the standard vibrational band spectrum (i.e., the lower portion of FIG. 45 shows some of the fine structure frequencies). In many respects, looking at fine structure frequencies is like using a magnifying glass to look at a standard spectrum. Magnification of what looks like a flat and uninteresting portion of a standard vibrational frequency band shows many more curves with lower frequency splitting. These many other curves are the fine structure curves. Similarly, by magnifying a small and seemingly uninteresting portion of the fine structure spectrum of the result is yet another spectrum of many more curves known as the hyperfine spectrum.

A small portion (i.e., from zero to 300) of the $SF_6$ fine structure spectrum is magnified in FIG. 46. The hyperfine spectrum includes many curves split part by even lower frequencies. This time the fine structure spectrum was magnified instead of the regular vibrational spectrum. What is found is even more curves, even closer together. FIGS. 47a and 47b show a further magnification of the two curves marked with asterisks (i.e., "*" and "") in FIG. 46**.

What appears to be a single crisp curve in FIG. 46, turns out to be a series of several curves spaced very close together. These are the hyperfine frequency curves. Accordingly, the fine structure spectra is comprised of several more curves spaced very close together. These other curves spaced even closer together correspond to the hyperfine frequencies.

FIGS. 47a and 47b show that the spacing of the hyperfine frequency curves are very close together and at somewhat regular intervals. The small amount that the hyperfine curves are split apart is called the hyperfine splitting frequency. The hyperfine splitting frequency is also a heterodyne. This concept is substantially similar to the concept of the fine splitting frequency. The difference between two curves that are split apart is called a splitting frequency. As before, the difference between two curves is referred to as a heterodyne frequency. So, hyperfine splitting frequencies are all heterodynes of hyperfine frequencies.

Because the hyperfine frequency curves result from a magnification of the fine structure curves, the hyperfine splitting frequencies occur at only a fraction of the fine structure splitting frequencies. The fine structure splitting frequencies are really just several curves, spaced very close together around the regular spectrum frequency. Magnification of fine structure splitting frequencies results in hyperfine splitting frequencies. The hyperfine splitting frequencies are really just several more curves, spaced very close together. The closer together the curves are, the smaller the distance or frequency separating them. Now the distance separating any two curves is a heterodyne frequency. So, the closer together any two curves are, the smaller (lower) is the heterodyne frequency between them. The distance between hyperfine splitting frequencies (i.e., the amount that hyperfine frequencies are split apart) is the hyperfine splitting frequency. It can also be called a constant or interval.

The electronic spectrum frequency of hydrogen is 2,466 THz. The 2,466 THz frequency is made up of fine structure curves spaced 10.87 GHz (0.01087 THz) apart. Thus, the fine splitting frequency is 10.87 GHz. Now the fine structure curves are made up of hyperfine curves. These hyperfine curves are spaced just 23.68 and 59.21 MHz apart. Thus, 23 and 59 MHz are both hyperfine splitting frequencies for hydrogen. Other hyperfine splitting frequencies for hydrogen include 2.71, 4.21, 7.02, 17.55, 52.63, 177.64, and 1,420.0 MHz. The hyperfine splitting frequencies are spaced even closer together than the fine structure splitting frequencies, so the hyperfine splitting frequencies are smaller and lower than the fine splitting frequencies.

Thus, the hyperfine splitting frequencies are lower than the fine splitting frequencies. This means that rather than being in the infrared and microwave regions, as the fine splitting frequencies can be, the hyperfine splitting frequencies are in the microwave and radiowave regions. These lower frequencies are in the MHz ($10^6$ hertz) and Khz ($10^3$ hertz) regions of the electromagnetic spectrum. Several of the hyperfine splitting frequencies for hydrogen are shown in FIG. 48. (FIG. 48 shows hyperfine structure in the n=2 to n=3 transition of hydrogen).

FIG. 49 shows the hyperfine frequencies for $CH_3I$. These frequencies are a magnification of the fine structure frequencies for that molecule. Since fine structure frequencies for molecules are actually rotational frequencies, what is shown is actually the hyperfine splitting of rotational frequencies. FIG. 49 shows the hyperfine splitting of just the J=1→2 rotational transition. The splitting between the two tallest curves is less than 100 MHz.

FIG. 50 shows another example of the molecule ClCN. This set of hyperfine frequencies is from the J=1→2 transition of the ground vibrational state for ClCN. Notice that the hyperfine frequencies are separated by just a few megahertz, (MHz) and in a few places by less than even one megahertz.

Figure 51:
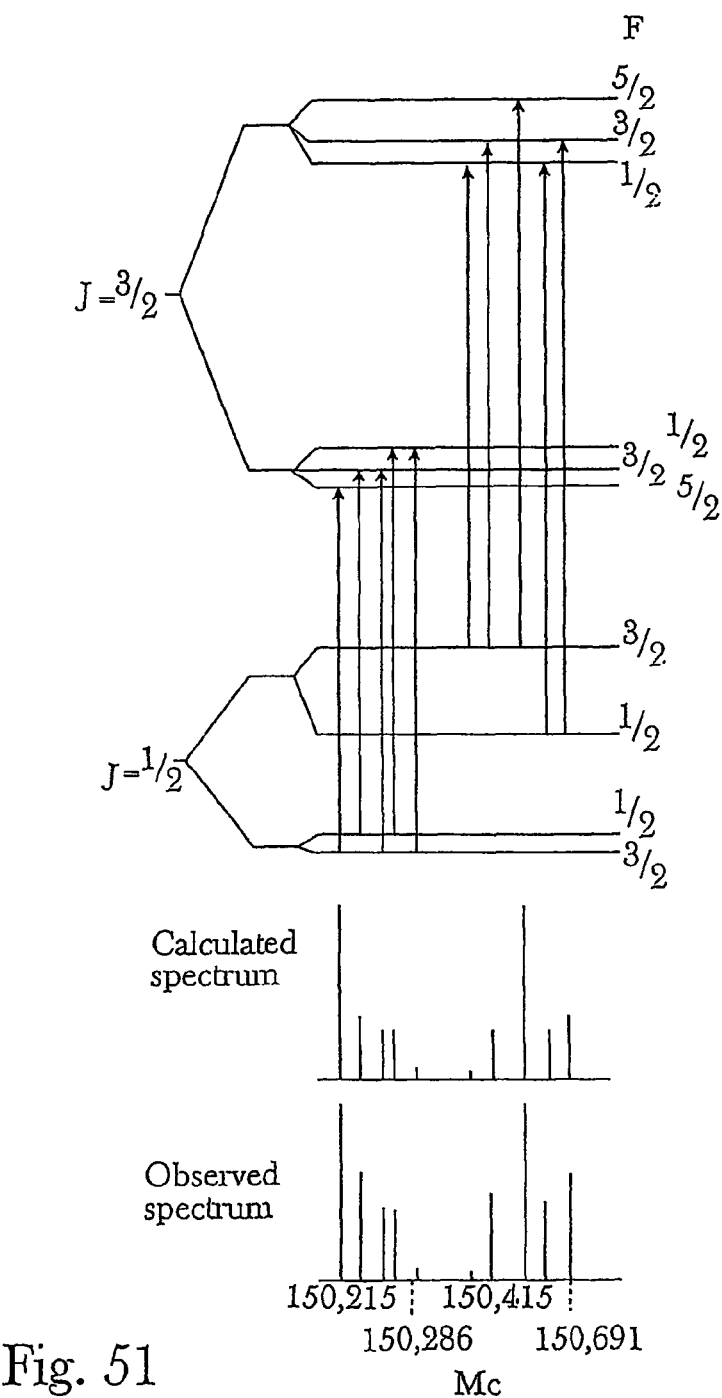
FIG. 51 shows energy level diagrams and hyperfine frequencies for the NO molecule.

The energy-level diagram and spectrum of the J=½→3/2 rotational transition for NO is shown if FIG. 51.

Figure 52:
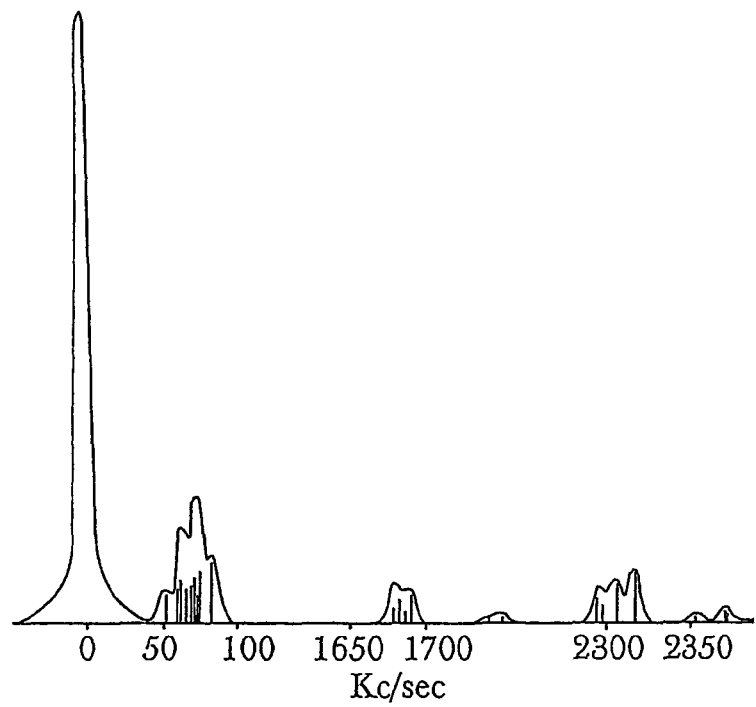
FIG. 52 shows a spectrum corresponding to the hyperfine frequencies for $NH_3$.

In FIG. 52, the hyperfine splitting frequencies for $NH_3$ are shown. Notice that the frequencies are spaced so close together that the scale at the bottom is in kilohertz (Kc/sec). The hyperfine features of the lines were obtained using a beam spectrometer.

Just as with fine splitting frequencies, the hyperfine splitting frequencies are heterodynes of atomic and molecular frequencies. Accordingly, if an atom or molecule is stimulated with a frequency equal to a hyperfine splitting frequency (a heterodyned difference between hyperfine frequencies), the present invention teaches that the energy will equal to a hyperfine splitting frequency will resonate with the hyperfine frequencies indirectly through heterodynes. The related rotational, vibrational, and/or electronic energy levels will, in turn, be stimulated. This is an important discovery. It allows one to use more radio and microwave frequencies to selectively stimulate and target specific cell reaction system components (e.g., atomic hydrogen intermediates can be stimulated with, for example, (2.55, 23.68 59.2 and/or 1,420 MHz).

Figure 53:
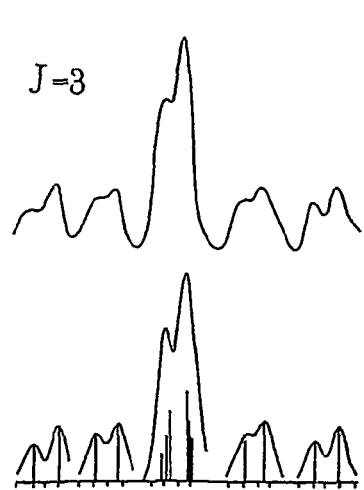
FIG. 53 shows hyperfine structure and doubling of the $NH_3$ spectrum for rotational level J=3. The upper curves in FIG. 53 show experimental data, while the lower curves are derived from theoretical calculations. Frequency increases from left to right in 60 KHz intervals.
Figure 54:
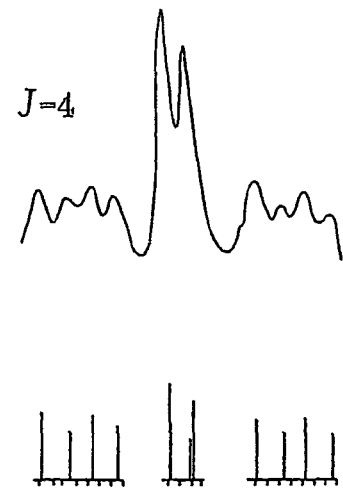
FIG. 54 shows a hyperfine structure and doubling of $NH_3$ spectrum for rotational level J=4. The upper curves in each of FIG. 54 show experimental data, while the lower curves are derived from theoretical calculations. Frequency increases from left to right in 60 KHz intervals.

Hyperfine frequencies, like fine frequencies, also contain features such as doublets. Specifically, in a region where one would expect to find only a single hyperfine frequency curve, there are two curves instead, typically, one on either side of the location where a single hyperfine frequency was expected. Hyperfine doubling is shown in FIGS. 53 and 54. This hyperfine spectrum is also from $NH_3$. FIG. 53 corresponds to the J=3 rotational level and FIG. 54 corresponds to the J=4 rotational level. The doubling can be seen most easily in the J=3 curves (i.e., FIG. 53). There are two sets of short curves, a tall one, and then two more short sets. Each of the short sets of curves is generally located where one would expect to find just one curve. There are two curves instead, one on either side of the main curve location. Each set of curves is a hyperfine doublet.

There are different notations to indicate the source of the doubling such as 1-type doubling, K doubling, and Λ doubling, etc., and they all have their own constants or intervals. Without going into the detailed theory behind the formation of various types of doublets, the interval between any two hyperfine multiplet curves is also a heterodyne, and thus all of these doubling constants represent frequency heterodynes. Accordingly, those frequency heterodynes (i.e., hyperfine constants) can also be used as spectral energy catalysts according to the present invention.

Specifically, a frequency in an atom or molecule can be stimulated directly or indirectly. If the goal was to stimulate the 2,466 THz frequency of hydrogen for some reason, then, for example, an ultraviolet laser could irradiate the hydrogen with 2,466 THz electromagnetic radiation. This would stimulate the atom directly. However, if such a laser was unavailable, then hydrogen's fine structure splitting frequency of 10.87 GHz could be achieved with microwave equipment. The gigahertz frequency would heterodyne (i.e., add or subtract) with the two closely spaced fine structure curves at 2,466, and stimulate the 2,466 THz frequency band. This would stimulate the atom indirectly.

Still further, the atom could be stimulated by using the hyperfine splitting frequency for hydrogen at 23.68 MHz as produced by radiowave equipment. The 23.68 MHz frequency would heterodyne (i.e., add or subtract) with the two closely spaced hyperfine frequency curves at 2,466, and stimulate the fine structure curves at the 2,466 THz. Stimulation of the fine structure curves would in turn lead to stimulation of the 2,466 THz electronic frequency for the hydrogen atom.

Still further, additional hyperfine splitting frequencies for hydrogen in the radiowave and microwave portions of the electromagnetic spectrum could also be used to stimulate the atom. For example, a radio wave pattern with 2.7 MHz, 4.2 MHz, 7 MHz, 18 MHz, 23 MHz, 52 MHz, and 59 MHz could be used. This would stimulate several different hyperfine frequencies of hydrogen, and it would stimulate them essentially all at the same time. This would cause stimulation of the fine structure frequencies, which in turn would stimulate the electronic frequencies in the hydrogen atom.

Still further, depending on available equipment and/or design, and/or processing constraints, some delivery mode variations can also be used. For example, one of the lower frequencies could be a carrier frequency for the upper frequencies. A continuous frequency of 52 MHz could be varied in amplitude at a rate of 2.7 MHz. Or, a 59 MHz frequency could be pulsed at a rate of 4.2 MHz. There are various ways in which these frequencies can be combined and/or delivered, including different wave shapes durations, intensity shapes, duty cycles, etc. Depending on which of the hyperfine splitting frequencies are stimulated, the evolution of, for example, various and specific transients may be precisely tailored and controlled, allowing precise control over cell reaction systems using the fine and/or hyperfine splitting frequencies.

Accordingly, a major point of the present invention is once it is understood the energy transfers when frequencies match, then determining which frequencies are available for matching is the next step. This invention discloses precisely how to achieve that goal. Interactions between equipment limitations, processing constraints, etc., can decide which frequencies are best suited for a particular purpose. Thus, both direct resonance and indirect resonance are suitable approaches for the use of spectral energy catalysts.

Electric Fields

Another means for modifying the spectral pattern of substances, is to expose a substance to an electric field. Specifically, in the presence of an electric field, spectral frequency lines of atoms and molecules can be split, shifted, broadened, or changed in intensity. The effect of an electric field on spectral lines is known as the "Stark Effect", in honor of its' discoverer, J. Stark. In 1913, Stark discovered that the Balmer series of hydrogen (i.e., curve II of FIGS. 9a and 9b) was split into several different components, while Stark was using a high electric field in the presence of a hydrogen flame. In the intervening years, Stark's original observation has evolved into a separate branch of spectroscopy, namely the study of the structure of atoms and molecules by measuring the changes in their respective spectral lines caused by an electric field.

The electric field effects have some similarities to fine and hyperfine splitting frequencies. Specifically, as previously discussed herein, fine structure and hyperfine structure frequencies, along with their low frequency splitting or coupling constants, were caused by interactions inside the atom or molecule, between the electric field of the electron and the magnetic field of the electron or nucleus. Electric field effects are similar, except that instead of the electric field coming from inside the atom, the electric field is applied from outside the atom. The Stark effect is primarily the interaction of an external electric field, from outside the atom or molecule, with the electric and magnetic fields already established within the atom or molecule.

When examining electric field effects on atoms, molecules, ions and/or components thereof, the nature of the electric field should also be considered (e.g., such as whether the electric field is static or dynamic). A static electric field may be produced by a direct current. A dynamic electric field is time varying, and may be produced by an alternating current. If the electric field is from an alternating current, then the frequency of the alternating current compared to the frequencies of the, for instance atom or molecule, should also be considered.

In atoms, an external electric field disturbs the charge distribution of the atom's electrons. This disturbance of the electron's own electric field induces a dipole moment in it (i.e., slightly lopsided charge distribution). This lopsided electron dipole moment then interacts with the external electric field. In other words, the external electric field first induces a dipole moment in the electron field, and then interacts with the dipole. The end result is that the atomic frequencies become split into several different frequencies. The amount the frequencies are split apart depends on the strength of the electric field. In other words, the stronger the electric field, the farther apart the splitting.

Figure 55:
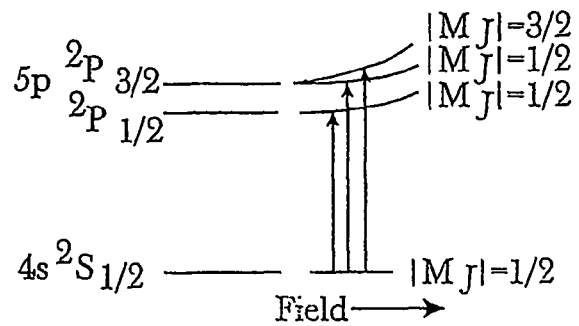
FIG. 55 shows a Stark effect for potassium. In particular, the schematic dependence of the $4_s$ and $5_p$ energy levels on the electric field.
Figure 56:
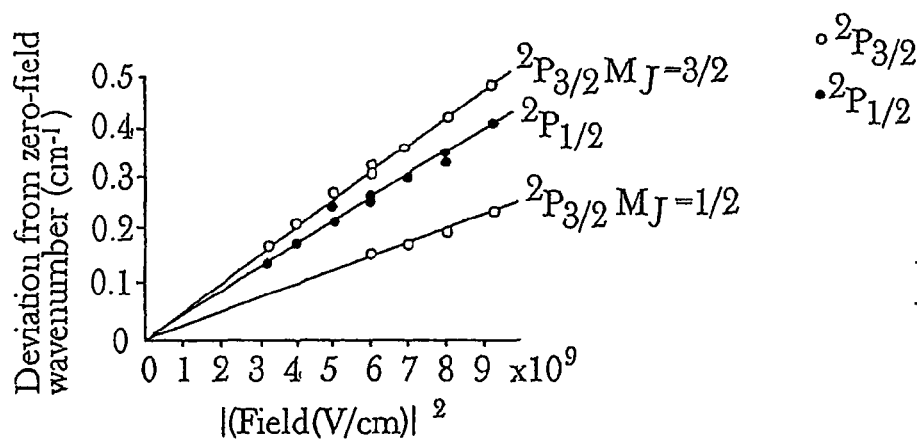
FIG. 56 shows a graph plotting the deviation from zero-field positions of the $5p^2P_{1/2}$←$4s^2S_{1/2,3/2}$ transition wavenumbers against the square of the electric field.

If the splitting varies directly with the electric field strength, then it is called first order splitting (i.e., $\Delta v = AF$ where $\Delta v$ is the splitting frequency, A is a constant and F is the electric field strength. When the splitting varies with the square of the field strength, it is called a second order or quadriatic effect (i.e., $\Delta v = BF^2$). One or both effects may be seen in various forms of matter. For example, the hydrogen atom exhibits first order Stark effects at low electric field strengths, and second order effects at high field strengths. Other electric field effects which vary with the cube or the fourth power, etc., of the electric field strength are less studied, but produce splitting frequencies nonetheless. A second order electric field effect for potassium is shown in FIGS. 55 and 56. FIG. 55 shows the schematic dependence of the 4s and 5p energy levels on the electric field. FIG. 56 shows a plot of the deviation from zero-field positions of the 5 P1/2.3/2←4s²S1/2 transition wavenumbers against the square of the electric field. Note that the frequency splitting or separation of the frequencies (i.e., deviation from zero-field wavenumber) varies with the square of the electric field strength $(v/cm)^2$.

The mechanism for the Stark effect in molecules is simpler than the effect is in atoms. Most molecules already have an electric dipole moment (i.e., a slightly uneven charge distribution). The external electric field simply interacts with the electric dipole moment already inside the molecule. The type of interaction, a first or a second order Stark effect, is different for differently shaped molecules. For example, most symmetric top molecules have first-order Stark effects. Asymmetric rotors typically have second-order Stark effects. Thus, in molecules, as in atoms, the splitting or separation of the frequencies due to the external electric field, is proportional either to the electric field strength itself, or to the square of the electric field strength.

Figure 57:
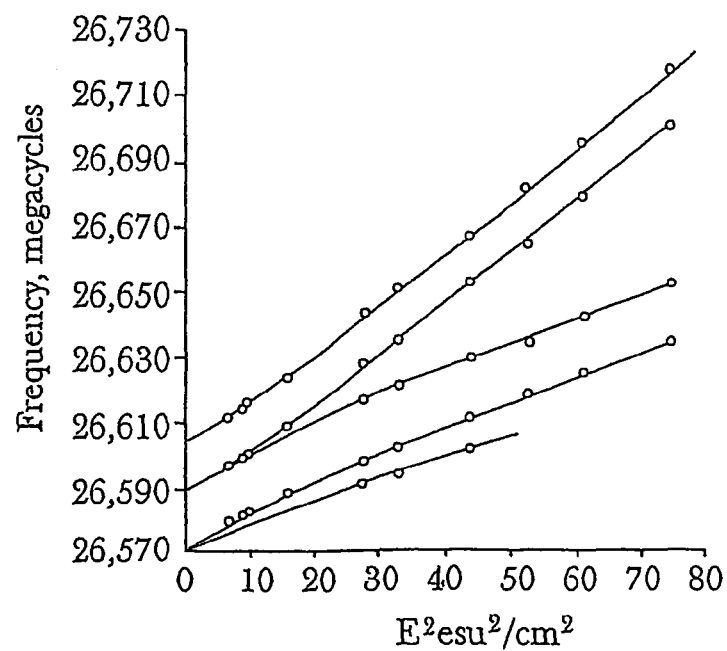
FIG. 57 shows the frequency components of the J=0→1 rotational transition for $CH_3Cl$, as a function of field strength. Frequency is given in megacycles (MHz) and electric field strength (esu cm) is given as the square of the field $E^2$, in $esu^2/cm^2$.

An example of this is shown in FIG. 57, which diagrams how frequency components of the J=0→1 rotational transition for the molecule $CH_3Cl$ respond to an external electric field. When the electric field is very small (e.g., less than 10 $E^2$ $esu^2/cm^2$), the primary effect is shifting of the three rotational frequencies to higher frequencies. As the field strength is increased (e.g., between 10 and 20 $E^2$ $esu^2/cm^2$), the three rotational frequencies split into five different frequencies. With continued increases in the electric field strength, the now five frequencies continue to shift to even higher frequencies. Some of the intervals or differences between the five frequencies remain the same regardless of the electric field strength, while other intervals become progressively larger and higher. Thus, a heterodyned frequency might stimulate splitting frequencies at one electric field strength, but not at another.

Figure 58:
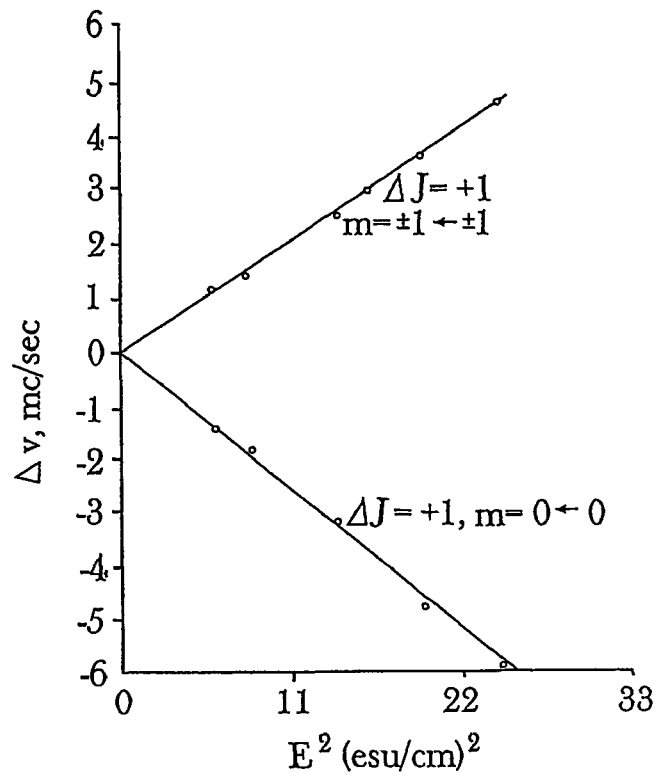
FIG. 58 shows the theoretical and experimental measurements of Stark effect in the J=1→2 transition of the molecule OCS. The unaltered absolute rotational frequency is plotted at zero, and the frequency splitting and shifting is denoted as MHz higher or lower than the original frequency.

Another molecular example is shown in FIG. 58. (This is a diagram of the Stark Effect in the same OCS molecule shown in FIG. 44 for the J=1→2). The J=1→2 rotational transition frequency is shown centered at zero on the horizontal frequency axis in FIG. 58. That frequency centered at zero is a single frequency when there is no external electric field. When an electric field is added, however, the single rotational frequency splits into two. The stronger the electric field is, the wider the splitting is between the two frequencies. One of the new frequencies shifts up higher and higher, while the other frequency shifts lower and lower. Because the difference between the two frequencies changes when the electric field strength changes, a heterodyned splitting frequency might stimulate the rotational level at one electric field strength, but not at another. An electric field can effect the spectral frequencies of reaction participants, and thus impact the spectral chemistry of a reaction.

Broadening and shifting of spectral lines also occurs with the intermolecular Stark effect. The intermolecular Stark effect is produced when the electric field from surrounding atoms, ions, or molecules, affects the spectral emissions of the species under study. In other words, the external electric field comes from other atoms and molecules rather than from a DC or AC current. The other atoms and molecules are in constant motion, and thus their electric fields are inhomogeneous in space and time. Instead of a frequency being split into several easily seen narrow frequencies, the original frequency simply becomes much wider, encompassing most, if not all, of what would have been the split frequencies, (i.e., it is broadened). Solvents, support materials, poisons, promoters, etc., are composed of atoms and molecules and components thereof. It is now understood that many of their effects are the result of the intermolecular Stark effect.

Figure 59:
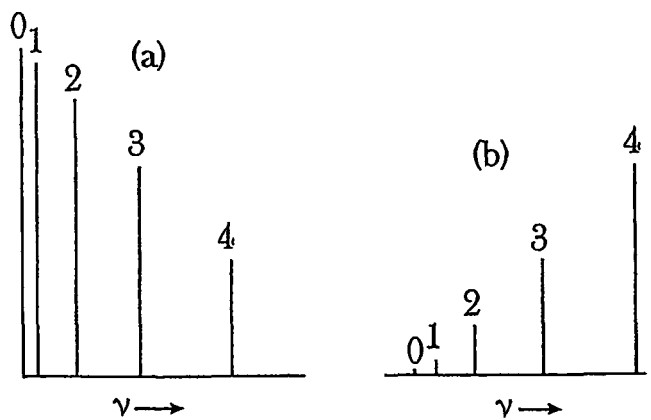
FIG. 59 shows patterns of Stark components for transitions in the rotation of an asymmetric top molecule. Specifically.

The above examples demonstrate how an electric field splits, shifts, and broadens spectral frequencies for matter. However, intensities of the lines can also be affected. Some of these variations in intensity are shown in FIGS. 59a and 59b. FIG. 59a shows patterns of Stark components for transitions in the rotation of an asymmetric top molecule for the J=4→5 transition; whereas FIG. 59b corresponds to J=4→4. The intensity variations depend on rotational transitions, molecular structure, etc., and the electric field strength.

An interesting Stark effect is shown in a structure such as a molecule, which has hyperfine (rotational) frequencies. The general rule for the creation of hyperfine frequencies is that the hyperfine frequencies result from an interaction between electrons and the nucleus. This interaction can be affected by an external electric field. If the applied external electric field is weak, then the Stark energy is much less than the energy of the hyperfine energy (i.e., rotational energy). The hyperfine lines are split into various new lines, and the separation (i.e., splitting) between the lines is very small (i.e., at radio frequencies and extra low frequencies).

If the external electric field is very strong, then the Stark energy is much larger than the hyperfine energy, and the molecule is tossed, sometimes violently, back and forth by the electric field. In this case, the hyperfine structure is radically changed. It is almost as though there no longer is any hyperfine structure. The Stark splitting is substantially the same as that which would have been observed if there were no hyperfine frequencies, and the hyperfine frequencies simply act as a small perturbation to the Stark splitting frequencies.

If the external electric field is intermediate in strength, then the Stark and hyperfine energies are substantially equivalent. In this case, the calculations become very complex. Generally, the Stark splitting is close to the same frequencies as the hyperfine splitting, but the relative intensities of the various components can vary rapidly with slight changes in the strength of the external electric field. Thus, at one electric field strength one splitting frequency may predominate, while at an electric field strength just 1% higher, a totally different Stark frequency could predominate in intensity.

All of the preceding discussion on the Stark effect has concentrated on the effects due to a static electric field, such as one would find with a direct current. The Stark effects of a dynamic, or time-varying electric field produced by an alternating current, are quite interesting and can be quite different. Just which of those affects appear, depends on the frequency of the electric field (i.e., alternating current) compared to the frequency of the matter in question. If the electric field is varying very slowly, such as with 60 Hz wall outlet electricity, then the normal or static type of electric field effect occurs. As the electric field varies from zero to maximum field strength, the matter frequencies vary from their unsplit frequencies to their maximally split frequencies at the rate of the changing electric field. Thus, the electric field frequency modulates the frequency of the splitting phenomena.

Figure 16:
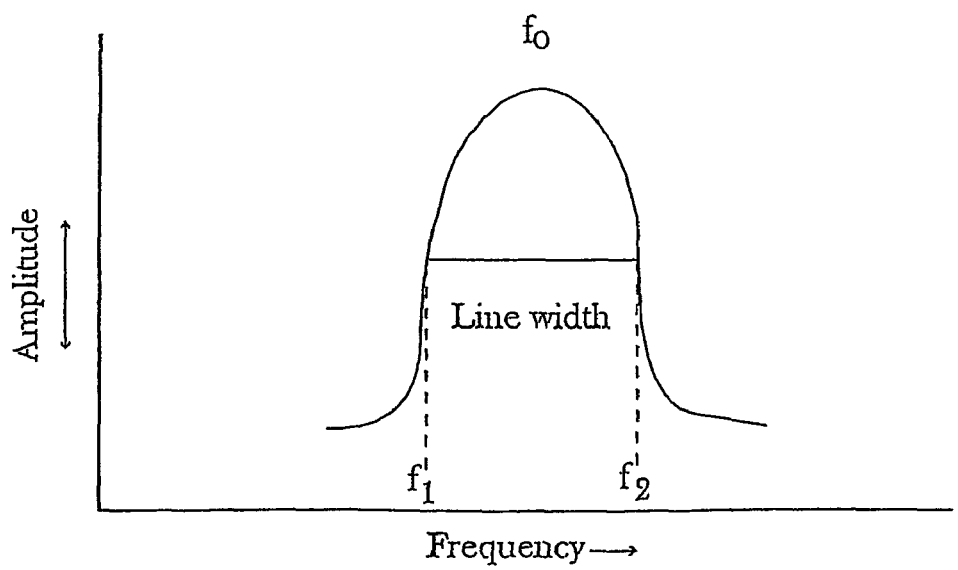
FIG. 16 is spectral curve showing a line width which corresponds to $f_2-f_1$.

However, as the electrical frequency increases, the first frequency measurement it will begin to overtake is the line width (see FIG. 16 for a diagram of line width). The line width of a curve is its' distance across, and the measurement is actually a very tiny heterodyne frequency measurement from one side of the curve to the other side. Line width frequencies are typically around 100 KHz at room temperature. In practical terms, line width represents a relaxation time for molecules, where the relaxation time is the time required for any transient phenomena to disappear. So, if the electrical frequency is significantly smaller than the line width frequency, the molecule has plenty of time to adjust to the slowly changing electric field, and the normal or static-type Stark effects occur.

Figure 60:
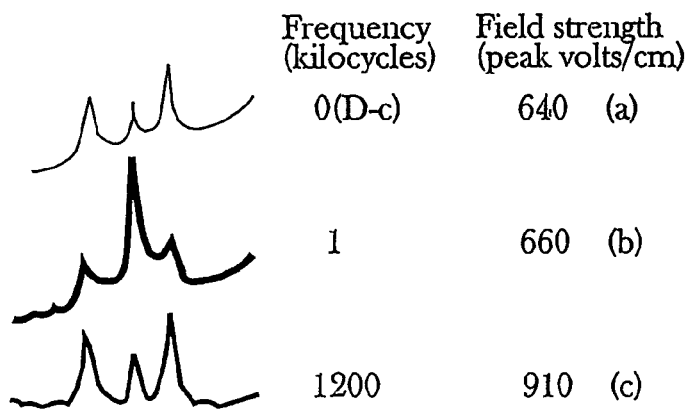
FIG. 60 shows the Stark effect for the OCS molecule on the J=1→2 transition with applied electric fields at various frequencies. The "a" curve represents the Stark effect with a static DC electric field; the "b" curve represents broadening and blurring of the Stark frequencies with a 1 KHz electric field; and the "c" curve represents normal Stark type effect with electric field of 1,200 KHz.

If the electrical frequency is slightly less than the line width frequency, the molecule changes its' frequencies substantially in rhythm with the frequency of the electric field (i.e., it entrains to the frequency of the electric field). This is shown in FIG. 60 which shows the Stark effect for OCS on the J=1→2 transition with applied electric fields at various frequencies. The letter "a" corresponds to the Stark effect with a static DC electric field; "b" corresponds to a broadening and blurring of the Stark frequencies with a 1 KHz electric field; and "c" corresponds to a normal Stark effect with an electric field of 1,200 KHz. As the electric field frequency approaches the KHz line width range, the Stark curves vary their frequencies with the electric field frequency and become broadened and somewhat blurred. When the electric field frequency moves up and beyond the line width range to about 1,200 KHz, the normal Stark type curves again become crisp and distinguishable. In many respects, the molecule cannot keep up with the rapid electrical field variation and simply averages the Stark effect. In all three cases, the cyclic splitting of the Stark frequencies is modulated with the electrical field frequency, or its' first harmonic (i.e., 2× the electrical field frequency).

The next frequency measurement that an ever-increasing electrical frequency will overtake in a molecule is the transitional frequency between two rotational levels (i.e., hyperfine frequencies). As the electric field frequency approaches a transitional frequency between two levels, the radiation of the transitional frequency in the molecule will induce transitions back and forth between the levels. The molecule oscillates back and forth between both levels, at the frequency of the electric field. When the electric field and transition level frequencies are substantially the same (i.e., in resonance), the molecule will be oscillating back and forth in both levels, and the spectral lines for both levels will appear simultaneously and at approximately the same intensity. Normally, only one frequency level is seen at a time, but a resonant electric field causes the molecule to be at both levels at essentially the same time, and so both transitional frequencies appear in its' spectrum.

Moreover, for sufficiently large electric fields (e.g., those used to generate plasmas) additional transition level frequencies can occur at regular spacings substantially equal to the electric field frequency. Also, splitting of the transition level frequencies can occur, at frequencies of the electric field frequency divided by odd numbers (e.g., electric field frequency "$f_E$" divided by 3, or 5, or 7, i.e., $f_E/3$ or $f_E/5$, etc.).

All the varied effects of electric fields cause new frequencies, new splitting frequencies and new energy level states.

Further, when the electric field frequency equals a transition level frequency of for instance, an atom or molecule, a second component with an opposite frequency charge and equal intensity can develop. This is negative Stark effect, with the two components of equal and opposite frequency charges destructively canceling each other. In spectral chemistry terms this amounts to a negative catalyst or poison in the cell reaction system, if the transition thus targeted was important to the reaction pathway. Thus, electric fields cause the Stark effect, which is the splitting, shifting, broadening, or changing intensity and changing transitional states of spectral frequencies for matter, (e.g., atoms and molecules). As with many of the other mechanisms that have been discussed herein, changes in the spectral frequencies of cell reaction systems can affect the reaction rate and/or reaction pathway. For example, consider a cell reaction system like the following:

where A&B are reactants, C is a physical catalyst, I stands for the intermediates, and D&F are the products.

Assume arguendo that the reaction normally progresses at only a moderate rate, by virtue of the fact that the physical catalyst produces several frequencies that are merely close to harmonics of the intermediates. Further assume that when an electric field is added, the catalyst frequencies are shifted so that several of the catalyst frequencies are now exact or substantially exact harmonics of the intermediates. This will result in, for example, the reaction being catalyzed at a faster rate. Thus, the Stark effect can be used to obtain a more efficient energy transfer through the matching of frequencies (i.e., when frequencies match, energies transfer).

If a reaction normally progresses at only a moderate rate, many "solutions" have included subjecting the cell reaction system to extremely high pressures. The high pressures result in a broadening of the spectral patterns, which improves the transfer of energy through a matching of resonant frequencies. By understanding the underlying catalyst mechanisms of action, high-pressure systems could be replaced with, for example, a simple electric field which produces broadening. Not only would this be less costly to an industrial manufacturer, it could be much safer for manufacturing due to the removal of, for example, high-pressure equipment.

Some reactants when mixed together do not react very quickly at all, but when an electric field is added they react rather rapidly. The prior art may refer to such a reaction as being catalyzed by an electric field and the equations would look like this:

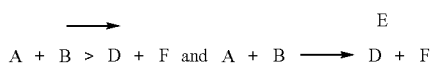

where E is the electric field. In this case, rather than applying a catalyst "C" (as discussed previously) to obtain the products "D+F", an electric field "E" can be applied. In this instance, the electric field works by changing the spectral frequencies (or spectral pattern) of one or more components in the cell reaction system so that the frequencies come into resonance, and the reaction can proceed along a desired reaction pathway (i.e., when frequencies match, energy is transferred). Understood in this way, the electric field becomes just another tool to change spectral frequencies of atoms and molecules, and thereby affect reaction rates in spectral chemistry.

Reaction pathways are also important. In the absence of an electrical field, a reaction pathway will progress to one set of products:

However, if an electrical field is added, at some particular strength of the field, the spectral frequencies may change so much, that a different intermediate is energized and the reaction proceeds down a different reaction pathway:

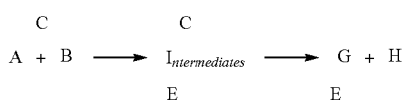

This is similar to the concept discussed earlier herein, regarding the formation of different products depending on temperature. The changes in temperature caused changes in spectral frequencies, and hence different reaction pathways were favored at different temperatures. Likewise, electric fields cause changes in spectral frequencies, and hence different reactions pathways are favored by different electric fields. By tailoring an electric field to a particular cell reaction system, one can control not only the rate of the reaction but also the reaction products produced.

The ability to tailor reactions, with or without a physical catalyst, by varying the strength of an electric field should be useful in many manufacturing situations. For example, it might be more cost effective to build only one physical set-up for a cell reaction system and to use one or more electric fields to change the reaction dynamics and products, depending on which product is desired. This would save the expense of having a separate physical set-up for production of each group of products.

Besides varying the strength of an electric field, the frequency of an electric field can also be varied. Assuming that a reaction will proceed at a much faster rate if a particular strength static electric field (i.e., direct current) is added as in the following:

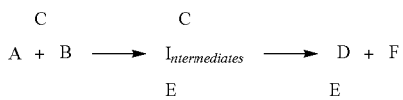

But further assume, that because of reactor design and location, it is much easier to deliver a time-varying electric field with alternating current. A very low frequency field, such as with a 60 Hz wall outlet, can produce the normal or static-type Stark effect. Thus, the reactor could be adapted to the 60 Hz electric field and enjoy the same increase in reaction rate that would occur with the static electric field.

If a certain physical catalyst produces spectral frequencies that are close to intermediate frequencies, but are not exact, it is possible that the activity of the physical catalyst in the past may have been improved by using higher temperatures. As disclosed earlier herein, the higher temperatures actually broadened the physical catalyst's spectral pattern to cause the frequency of the physical catalyst to be at least a partial match for at least one of the intermediates. What is significant here is that high temperature boilers can be minimized, or eliminated altogether, and in their stead a moderate frequency electric field which, for example, broadened the spectral frequencies, could be used. For example, a frequency of around 100 Khz, equivalent to the typical line width frequencies at room temperature, could broaden substantially all of the spectral curves and cause the physical catalyst's spectral curves to match those of, for example, required intermediates. Thus, the electric field could cause the matter to behave as though the temperature had been raised, even though it had not been. (Similarly, any spectral manipulation, (e.g., electric fields acoustics, heterodynes, etc., that cause changes in the spectral line width, may cause a material to behave as though its temperature had been changed).

The cyclic splitting of the Stark frequencies can be modulated with the electrical field frequency or its' first harmonic (i.e., first-order Stark effects are modulated with the electrical field frequency, while second-order Stark effects are modulated by two times the electrical field, frequency). Assume that a metallic platinum catalyst is used in a hydrogen reaction and it is desired to stimulate the 2.7 MHz hyperfine frequency of the hydrogen atoms. Earlier herein it was disclosed that electromagnetic radiation could be used to deliver the 2.7 MHz frequency. However, use of an alternating electric field at 2.7 MHz could be used instead. Since platinum is a metal and conducts electricity well, the platinum can be considered to be a part of the alternating current circuit. The platinum will exhibit a Stark effect, with all the frequencies splitting at a rate of 2.7 MHz. At sufficiently strong electric fields, additional transition frequencies or "sidebands" will occur at regular spacings equal to the electric field frequency. There will be dozens of split frequencies in the platinum atoms that are heterodynes of 2.7 MHz. This massive heterodyned output may stimulate the hydrogen hyperfine frequency of 2.7 MHz and direct the reaction.

Figure 61A:
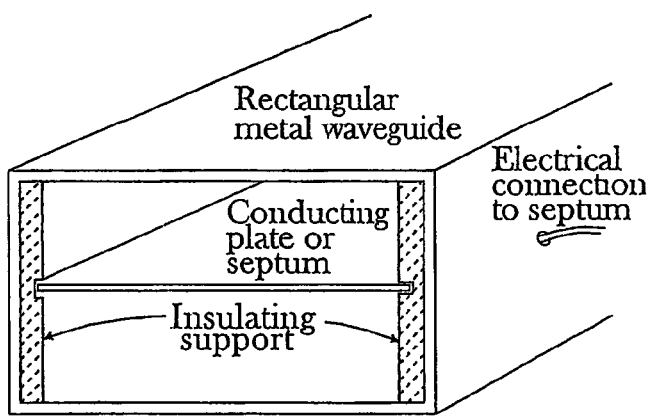
FIG. 61a shows a construction of a Stark waveguide and FIG. 61b shows a distribution of fields in the Starck waveguide.
Figure 61B:
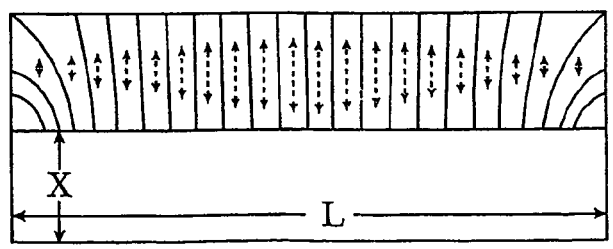

Another way to achieve this reaction, of course, would be to leave the platinum out of the reaction altogether. The 2.7 MHz field will have a resonant Stark effect on the hydrogen, separate and independent of the platinum catalyst. Copper is not normally catalytic for hydrogen, but copper could be used to construct a reaction vessel like a Stark waveguide to energize the hydrogen. A Stark waveguide is used to perform Stark spectroscopy. It is shown as FIGS. 61*a* and 61*b*. Specifically, FIG. 61*a* shows the construction of the Stark waveguide, whereas FIG. 61*b* shows the distribution of fields in the Stark waveguide. The electrical field is delivered through the conducting plate. A reaction vessel could be made for the flow-through of gases and use an economical metal such as copper for the conducting plate. When the 2.7 MHz alternating current is delivered through the electrical connection to the copper conductor plate, the copper spectral frequencies, none of which are particularly resonant with hydrogen, will exhibit a Stark effect with normal-type splitting. The Stark frequencies will be split at a rate of 2.7 MHz. At a sufficiently strong electric field strength, additional sidebands will appear in the copper, with regular spacings (i.e., heterodynes) of 2.7 MHz even though none of the actual copper frequencies matches the hydrogen frequencies, the Stark splitting or heterodynes will match the hydrogen frequency. Dozens of the copper split frequencies may resonate indirectly with the hydrogen hyperfine frequency and direct the reaction (i.e., when frequencies match, energies transfer).

With sophisticated equipment and a good understanding of a particular system, Stark resonance can be used with a transition level frequency. For example, assume that to achieve a particular reaction pathway, a molecule needs to be stimulated with a transition level frequency of 500 MHz. By delivering the 500 MHz electrical field to the molecule, this resonant electrical field may cause the molecule to oscillate back and forth between the two levels at the rate of 500 MHz. This electrically creates the conditions for light amplification (i.e., laser via stimulation of multiple upper energy levels) and any added electromagnetic radiation at this frequency will be amplified by the molecule. In this manner, an electrical field may substitute for the laser effects of physical catalysts.

In summary, by understanding the underlying spectral mechanisms of chemical reactions, electric fields can be used as yet another tool to catalyze and modify those chemical reactions and/or reaction pathways by modifying the spectral characteristics, for example, at least one participant and/or one or more components in the cell reaction system. Thus, another tool for mimicking catalyst mechanisms of reactions can be utilized.

Magnetic Fields

In spectral terms, magnetic fields behave similar to electric fields in their effect. Specifically, the spectral frequency lines, for instance of atoms and molecules, can be split and shifted by a magnetic field. In this case, the external magnetic field from outside the atom or molecule, interacts with the electric and magnetic fields already inside the atom or molecule.

This action of an external magnetic field on spectral lines is called the "Zeeman Effect", in honor of its' discoverer, Dutch physicist Pieter Zeeman. In 1896, Zeeman discovered that the yellow flame spectroscopy "D" lines of sodium were broadened when the flame was held between strong magnetic poles. It was later discovered that the apparent broadening of the sodium spectral lines was actually due to their splitting and shifting. Zeeman's original observation has evolved into a separate branch of spectroscopy, relating to the study of atoms and molecules by measuring the changes in their spectral lines caused by a magnetic field. This in turn has evolved into the nuclear magnetic resonance spectroscopy and magnetic resonance imaging used in medicine, as well as the laser magnetic resonance and electron spin resonance spectroscopy used in physics and chemistry.

The Zeeman effect for the famous "D" lines of sodium is shown in FIGS. 62a and 62b. FIG. 62a shows the Zeeman effect for sodium "D" lines; whereas FIG. 62b shows the energy level diagram for the transitions in the Zeeman effect for the sodium "D" lines. The "D" lines are traditionally said to result from transition between the $3p^2p$ and $3s^2S$ electron orbitals. As is shown, each of the single spectral frequencies is split into two or more slightly different frequencies, which center around the original unsplit frequency.

In the Zeeman effect, the amount that the spectral frequencies are split apart depends on the strength of the applied magnetic field. FIG. 63 shows Zeeman splitting effects for the oxygen atom as a function of magnetic field. When there is no magnetic field, there are two single frequencies at zero and 4.8. When the magnetic field is at low strength (e.g., 0.2 Tesla) there is just slight splitting and shifting of the original two frequencies. However, as the magnetic field is increased, the frequencies are split and shifted farther and farther apart.

The degree of splitting and shifting in the Zeeman effect, depending on magnetic field strength, is shown in FIG. 64 for the $^3P$ state of silicon.

As with the Stark effect generated from an external electric field, the Zeeman effect, generated from an external magnetic field, is slightly different depending on whether an atom or molecule is subjected to the magnetic field. The Zeeman effect on atoms can be divided into three different magnetic field strengths: weak; moderate; and strong. If the magnetic field strength is weak, the amount that the spectral frequencies will be shifted and split apart will be very small. The shifting away from the original spectral frequency will still stimulate the shifted frequencies. This is because they will be so close to the original spectral frequency that they will still be well within its resonance curve. As for the splitting, it is so small, that it is even less than the hyperfine splitting that normally occurs. This means that in a weak magnetic field, there will be only very slight splitting of spectral frequencies, translating into very low splitting frequencies in the lower regions of the radio spectrum and down into the very low frequency region. For example, the Zeeman splitting frequency for the hydrogen atom, which is caused by the earth's magnetic field, is around 30 KHz. Larger atoms have even lower frequencies in the lower kilohertz and even hertz regions of the electromagnetic spectrum.

Without a magnetic field, an atom can be stimulated by using direct resonance with a spectral frequency or by using its fine or hyperfine splitting frequencies in the infrared through microwave, or microwave through radio regions, respectively. By merely adding a very weak magnetic field, the atom can be stimulated with an even lower radio or very low frequency matching the Zeeman splitting frequency. Thus, by simply using a weak magnetic field, a spectral catalyst range can be extended even lower into the radio frequency range. The weak magnetic field from the Earth causes Zeeman splitting in atoms in the hertz and kilohertz ranges. This means that all atoms, including those in biological organisms, are sensitive to hertz and kilohertz EM frequencies, by virtue of being subjected to the Earth's magnetic field.

At the other end of magnetic field strength, is the very strong magnetic field. In this case, the splitting apart and shifting of the spectral frequencies will be very wide. With this wide shifting of frequencies, the difference between the split frequencies will be much larger than the difference between the hyperfine splitting frequencies. This translates to Zeeman effect splitting frequencies at higher frequencies than the hyperfine splitting frequencies. This splitting occurs somewhere around the microwave region. Although the addition of a strong magnetic field does not extend the reach in the electromagnetic spectrum at one extreme or the other, as a weak magnetic field does, it still does provide an option of several more potential spectral catalyst frequencies that can be used in the microwave region.

The moderate magnetic field strength case is more complicated. The shifting and splitting caused by the Zeeman effect from a moderate magnetic field will be approximately equal to the hyperfine splitting. Although not widely discussed in the prior art, it is possible to apply a moderate magnetic field to an atom, to produce Zeeman splitting which is substantially equivalent to its' hyperfine splitting. This presents interesting possibilities. Methods for guiding atoms in chemical reactions were disclosed earlier herein by stimulating atoms with hyperfine splitting frequencies. The Zeeman effect provides a way to achieve similar effects without introducing any spectral frequencies at all. For example, by introducing a moderate magnetic field, resonance may be set-up within the atom itself, that stimulates and/or energizes and/or stabilizes the atom.

The moderate magnetic field causes low frequency Zeeman splitting that matches and hence energizes the low frequency hyperfine splitting frequency in the atom. However, the low hyperfine splitting frequencies actually correspond to the heterodyned difference between two vibrational or fine structure frequencies. When the hyperfine splitting frequency is stimulated, the two electronic frequencies will eventually be stimulated. This in turn causes the atom to be, for example, stimulated. Thus, the Zeeman effect permits a spectral energy catalyst stimulation of an atom by exposing that atom to a precise strength of a magnetic field, and the use of spectral EM frequencies is not required (i.e., so long as frequencies match, energies will transfer). The possibilities are quite interesting because an inert cell reaction system may suddenly spring to life upon the application of the proper moderate strength magnetic field.

Figure 65A:
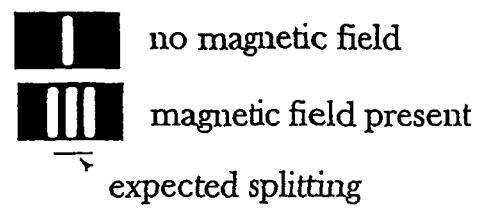
FIG. 65a is a pictorial which shows a normal Zeeman effect and FIG. 65b is a pictorial which shows an anomolous Zeeman effect.
Figure 65B:
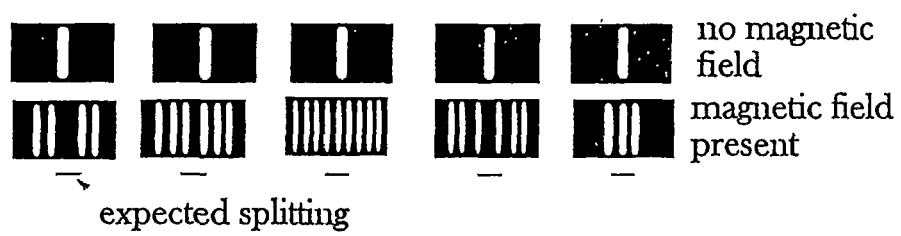

There is also a difference between the "normal" Zeeman effect and the "anomalous" Zeeman effect. With the "normal" Zeeman effect, a spectral frequency is split by a magnetic field into three frequencies, with expected even spacing between them (see FIG. 65a which shows the "normal" Zeeman effects and FIG. 65b which shows the "anomalous" Zeeman effects). One of the new split frequencies is above the original frequency, and the other new split frequency is below the original frequency. Both new frequencies are split the same distance away from the original frequency. Thus, the difference between the upper and original and the lower and original frequencies is about the same. This means that in terms of heterodyne differences, there are at most, two new heterodyned differences with the normal Zeeman effect. The first heterodyne or splitting difference is the difference between one of the new split frequencies and the original frequency. The other splitting difference is between the upper and lower new split frequencies. It is, of course, twice the frequency difference between either of the upper or lower frequencies and the original frequency.

Figure 66:
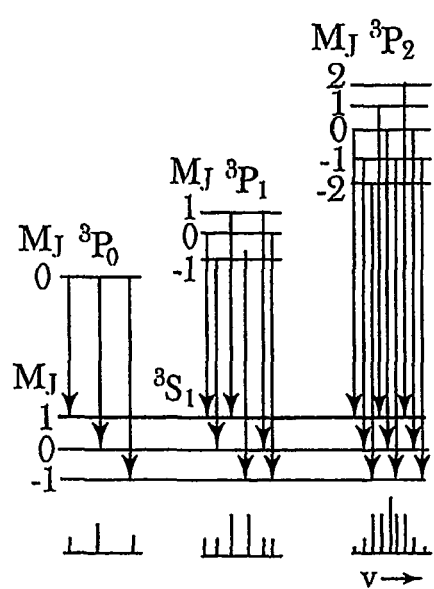
FIG. 66 shows anomalous Zeeman effect for zinc $^3P→^3S$.

In many instances the Zeeman splitting produced by a magnetic field results in more than three frequencies, or in splitting that is spaced differently than expected. This is called the "anomalous" Zeeman effect (see FIGS. 65 and 66; wherein FIG. 66 shows an anomalous Zeeman effect for zinc 3p→3s.

Figure 67A:
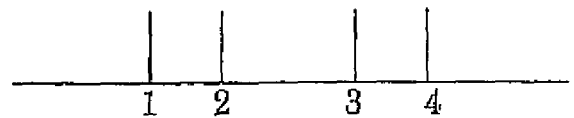
FIG. 67a shows a graphic representation of four Zeeman splitting frequencies and FIG. 67b shows a graphic representation of four new heterodyned differences.
Figure 67B:
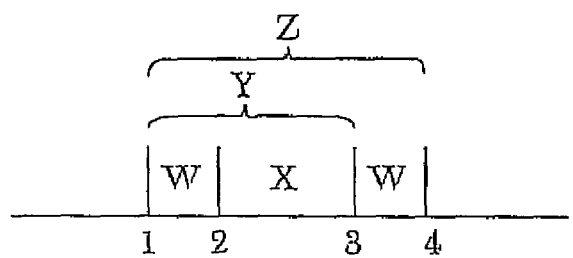

If there are still just three frequencies, and the Zeeman effect is anomalous because the spacing is different than expected, the situation is similar to the normal effect. However, there are at most, two new splitting frequencies that can be used. If, however, the effect is anomalous because more than three frequencies are produced, then there will be a much more richly varied situation. Assume an easy case where there are four Zeeman splitting frequencies (see FIG. 67*a* and FIG. 67*b*). FIG. 67*a* shows four Zeeman splitting frequencies and FIG. 67*b* shows four new heterodyned differences.

In this example of anomalous Zeeman splitting, there are a total of four frequencies, where once existed only one frequency. For simplicity's sake, the new Zeeman frequencies will be labeled 1, 2, 3, and 4. Frequencies 3 and 4 are also split apart by the same difference "w". Thus, "w" is a heterodyned splitting frequency. Frequencies 2 and 3 are also split apart by a different amount "x". So far there are two heterodyned splitting frequencies, as in the normal Zeeman effect.

However, frequencies 1 and 3 are split apart by a third amount "y", where "y" is the sum of "w" and "x". And, frequencies 2 and 4 are also split apart by the same third amount "y". Finally, frequencies 1 and 4 are split even farther apart by an amount "z". Once again, "z" is a summation amount from adding "w+x+w". Thus, the result is four heterodyned frequencies: w, x, y, and z in the anomalous Zeeman effect.

If there were six frequencies present from the anomalous Zeeman effect, there would be even more heterodyned differences. Thus, the anomalous Zeeman effect results in far greater flexibility in the choice of frequencies when compared to the normal Zeeman effect. In the normal Zeeman effect the original frequency is split into three evenly spaced frequencies, with a total of just two heterodyned frequencies. In the anomalous Zeeman effect the original frequency is split into four or more unevenly spaced frequencies, with at least four or more heterodyned frequencies.

Similar Zeeman effects can occur in molecules. Molecules come in three basic varieties: ferromagnetic; paramagnetic; and diamagnetic. Ferromagnetic molecules are typical magnets. The materials typically hold a strong magnetic field and are composed of magnetic elements such as iron, cobalt, and nickel.

Paramagnetic molecules hold only a weak magnetic field. If a paramagnetic material is put into an external magnetic field, the magnetic moment of the molecules of the material are lined up in the same direction as the external magnetic field. Now, the magnetic moment of the molecules is the direction in which the molecules own magnetic field is weighted. Specifically, the magnetic moment of a molecule will tip to whichever side of the molecule is more heavily weighted in terms of its own magnetic field. Thus, paramagnetic molecules will typically tip in the same direction as an externally applied magnetic field. Because paramagnetic materials line up with an external magnetic field, they are also weakly attracted to sources of magnetic fields.

Common paramagnetic elements include oxygen, aluminum, sodium, magnesium, calcium and potassium. Stable molecules such as oxygen ($O_2$) and nitric oxide (NO) are also paramagnetic. Molecular oxygen makes up approximately 20% of our planet's atmosphere. Both molecules play important roles in biologic organisms. In addition, unstable molecules, more commonly known as free radicals, chemical reaction intermediates or plasmas, are also paramagnetic. Paramagnetic ions include hydrogen, manganese, chromium, iron, cobalt, and nickel. Many paramagnetic substances occur in biological organisms. For instance the blood flowing in our veins is an ionic solution containing red blood cells. The red blood cells contain hemoglobin, which in turn contains ionized iron. The hemoglobin, and hence the red blood cells, are paramagnetic. In addition, hydrogen ions can be found in a multitude of organic compounds and reactions. For instance, the hydrochloric acid in a stomach contains hydrogen ions. Adenosine triphosphate (ATP), the energy system of nearly all biological organisms, requires hydrogen and manganese ions to function properly. Thus, the very existence of life itself depends on paramagnetic materials.

Diamagnetic molecules, on the other hand, are repelled by a magnetic field, and line up what little magnetic moments they have away from the direction of an external magnetic field. Diamagnetic substances do not typically hold a magnetic field. Examples of diamagnetic elements include hydrogen, helium, neon, argon, carbon, nitrogen, phosphorus, chlorine, copper, zinc, silver, gold, lead, and mercury. Diamagnetic molecules include water, most gases, organic compounds, and salts such as sodium chloride. Salts are really just crystals of diamagnetic ions. Diamagnetic ions include lithium, sodium, potassium, rubidium, caesium, fluorine, chlorine, bromine, iodine, ammonium, and sulphate. Ionic crystals usually dissolve easily in water, and as such the ionic water solution is also diamagnetic. Biologic organisms are filled with diamagnetic materials, because they are carbon-based life forms. In addition, the blood flowing in our veins is an ionic solution containing blood cells. The ionic solution (i.e., blood plasma) is made of water molecules, sodium ions, potassium ions, chlorine ions, and organic protein compounds. Hence, our blood is a diamagnetic solution carrying paramagnetic blood cells.

With regard to the Zeeman effect, first consider the case of paramagnetic molecules. As with atoms, the effects can be categorized on the basis of magnetic field strength. If the external magnetic field applied to a paramagnetic molecule is weak, the Zeeman effect will produce splitting into equally spaced levels. In most cases, the amount of splitting will be directly proportional to the strength of the magnetic field, a "first-order" effect. A general rule of thumb is that a field of one (1) oersted (i.e., slightly larger than the earth's magnetic field) will produce Zeeman splittings of approximately 1.4 MHz in paramagnetic molecules. Weaker magnetic fields will produce narrower splittings, at lower frequencies. Stronger magnetic fields will produce wider splittings, at higher frequencies. In these first order Zeeman effects, there is usually only splitting, with no shifting of the original or center frequency, as was present with Zeeman effects on atoms.

In many paramagnetic molecules there are also second-order effects where the Zeeman splitting is proportional to the square of the magnetic field strength. In these cases, the splitting is much smaller and of much lower frequencies. In addition to splitting, the original or center frequencies shift as they do in atoms, proportional to the magnetic field strength.

Figure 68A:
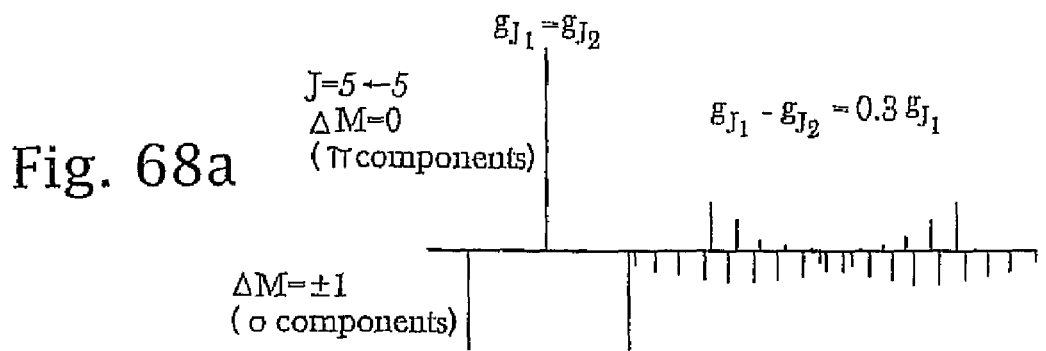
FIGS. 68a and 68b show graphs of typical Zeeman splitting patterns for two different transitions in a paramagnetic molecule.
Figure 68B:
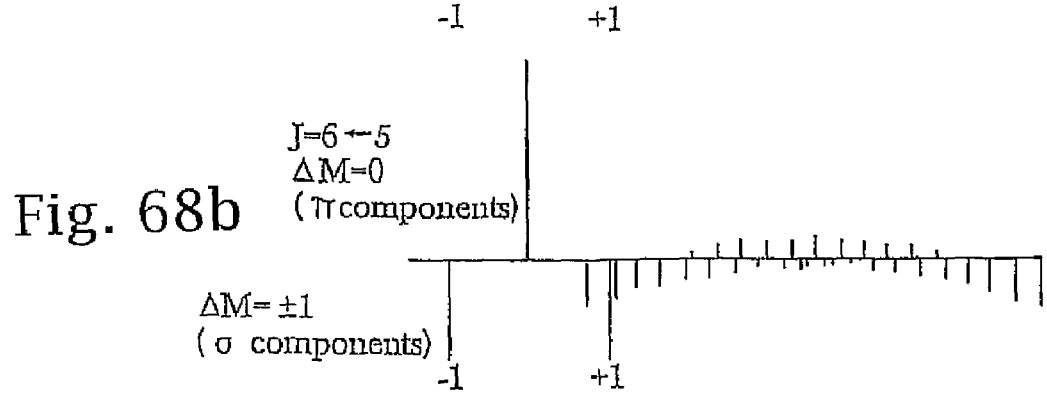

Sometimes the direction of the magnetic field in relation to the orientation of the molecule makes a difference. For instance, π frequencies are associated with a magnetic field parallel to an exciting electromagnetic field, while a frequencies are found when it is perpendicular. Both π and σ frequencies are present with a circularly polarized electromagnetic field. Typical Zeeman splitting patterns for a paramagnetic molecule in two different transitions are shown in FIGS. 68*a* and 68*b*. The π frequencies are seen when ΔM=0, and are above the long horizontal line. The σ frequencies are seen when ΔM=±1, and are below the long horizontal line. If a paramagnetic molecule was placed in a weak magnetic field, circularly polarized light would excite both sets of frequencies in the molecule. Thus, it is possible to control which set of frequencies are excited in a molecule by controlling its orientation with respect to the magnetic field.

When the magnetic field strength is intermediate, the interaction between the paramagnetic molecule's magnetic moments and the externally applied magnetic field produces Zeeman effects equivalent to other frequencies and energies in the molecule. For instance, the Zeeman spitting may be near a rotational frequency and disturb the end-over-end rotational motion of the molecule. The Zeeman splitting and energy may be particular or large enough to uncouple the molecule's spin from its molecular axis.

If the magnetic field is very strong, the nuclear magnetic moment spin will uncouple from the molecular angular momentum. In this case, the Zeeman effects overwhelm the hyperfine structure, and are of much higher energies at much higher frequencies. In spectra of molecules exposed to strong magnetic fields, hyperfine splitting appears as a small perturbation of the Zeeman splitting.

Next, consider Zeeman effects in so called "ordinary molecules" or diamagnetic molecules. Most molecules are of the diamagnetic variety, hence the designation "ordinary". This includes, of course, most organic molecules found in biologic organisms. Diamagnetic molecules have rotational magnetic moments from rotation of the positively charged nucleus, and this magnetic moment of the nucleus is only about $\frac{1}{1000}$ of that from the paramagnetic molecules. This means that the energy from Zeeman splitting in diamagnetic molecules is much smaller than the energy from Zeeman splitting in paramagnetic molecules. The equation for the Zeeman energy in diamagnetic molecules is:

$$Hz = -(g_j J = g_1 I) \cdot \beta H_o$$

where J is the molecular rotational angular momentum, I is the nuclear-spin angular momentum, $g_j$ is the rotational g factor, and $g_1$ is the nuclear-spin g factor. This Zeeman energy is much less, and of much lower frequency, than the paramagnetic Zeeman energy. In terms of frequency, it falls in the hertz and kilohertz regions of the electromagnetic spectrum.

Finally, consider the implications of Zeeman splitting for catalyst and chemical reactions and for spectral chemistry. A weak magnetic field will produce hertz and kilohertz Zeeman splitting in atoms and second order effects in paramagnetic molecules. Virtually any kind of magnetic field will produce hertz and kilohertz Zeeman splitting in diamagnetic molecules. All these atoms and molecules will then become sensitive to radio and very low frequency (VLF) electromagnetic waves. The atoms and molecules will absorb the radio or VLF energy and become stimulated to a greater or lesser degree. This could be used to add spectral energy to, for instance, a particular molecule or intermediate in a chemical cell reaction system. For instance, for hydrogen and oxygen gases turning into water over a platinum catalyst, the hydrogen atom radical is important for maintaining the reaction. In the earth's weak magnetic field, Zeeman splitting for hydrogen is around 30 KHz. Thus, the hydrogen atoms in the cell reaction system, could be energized by applying to them a Zeeman splitting frequency for hydrogen (e.g., 30 KHz). Energizing the hydrogen atoms in the cell reaction system will duplicate the mechanisms of action of platinum, and catalyze the reaction. If the reaction was moved into outer space, away from the earth's weak magnetic field, hydrogen would no longer have a 30 KHz Zeeman splitting frequency, and the 30 KHz would no longer as effectively catalyze the reaction.

The vast majority of materials on this planet, by virtue of existing within the earth's weak magnetic field, will exhibit Zeeman splitting in the hertz and kilohertz regions. This applies to biologics and organics as well as inorganic or inanimate materials. Humans are composed of a wide variety of atoms, diamagnetic molecules, and second order effect paramagnetic molecules. These atoms and molecules all exist in the earth's weak magnetic field. These atoms and molecules in humans all have Zeeman splitting in the hertz and kilohertz regions, because they are in the earth's magnetic field. Biochemical and biocatalytic processes in humans are thus sensitive to hertz and kilohertz electromagnetic radiation, by virtue of the fact that they are in the earth's weak magnetic field. As long as humans continue to exist on this planet, they will be subject to spectral energy catalyst effects from hertz and kilohertz EM waves because of the Zeeman effect from the planet's magnetic field. This has significant implications for low frequency communications, as well as chemical and biochemical reactions, diagnostics, and treatment of diseases.

A strong magnetic field will produce splitting greater than the hyperfine frequencies, in the microwave and infrared regions of the EM spectrum in atoms and paramagnetic molecules. In the hydrogen/oxygen reaction, a strong field could be added to the cell reaction system and transmit MHz and/or GHz frequencies into the reaction to energize the hydroxy radical and hydrogen reaction intermediates. If physical platinum was used to catalyze the reaction, the application of a particular magnetic field strength could result in both the platinum and the reaction intermediate spectra having frequencies that were split and shifted in such a way that even more frequencies matched than without the magnetic field. In this way, Zeeman splitting can be used to improve the effectiveness of a physical catalyst, by copying its mechanism of action (i.e., more frequencies could be caused to match and thus more energy could transfer).

A moderate magnetic field will produce Zeeman splitting in atoms and paramagnetic molecules at frequencies on par with the hyperfine and rotational splitting frequencies. This means that a cell reaction system can be energized without even adding electromagnetic energy. Similarly, by placing the cell reaction system in a moderate magnetic field that produces Zeeman splitting equal to the hyperfine or rotational splitting, increased reaction would occur. For instance, by using a magnetic field that causes hyperfine or rotational splitting in hydrogen and oxygen gas, that matches the Zeeman splitting in hydrogen atom or hydroxy radicals, the hydrogen or hydroxy intermediate would be energized and would proceed through the reaction cascade to produce water. By using the appropriately tuned moderate magnetic field, the magnetic field could be used to turn the reactants into catalysts for their own reaction, without the addition of physical catalyst platinum or the spectral catalyst of platinum. Although the magnetic field would simply be copying the mechanism of action of platinum, the reaction would have the appearance of being catalyzed solely by an applied magnetic field.

Finally, consider the direction of the magnetic field in relation to the orientation of the molecule. When the magnetic field is parallel to an exciting electromagnetic field, π frequencies are produced. When the magnetic field is perpendicular to an exciting electromagnetic field, σ frequencies are found. Assume that there is an industrial chemical cell reaction system that uses the same (or similar) starting reactants, but the goal is to be able to produce different products at will. By using magnetic fields combined with spectral energy or physical catalysts, the reaction can be guided to one set of products or another. For the first set of products, the electromagnetic excitation is oriented parallel to the magnetic field, producing one set of $\pi$ frequencies, which leads to a first set of products. To achieve a different product, the direction of the magnetic field is changed so that it is perpendicular to the exciting electromagnetic field. This produces a different set of $\sigma$ frequencies, and a different reaction pathway is energized, thus producing a different set of products. Thus, according to the present invention, magnetic field effects, Zeeman splitting, splitting and spectral energy catalysts can be used to fine-tune the specificity of many cell reaction systems.

In summary, by understanding the underlying spectral mechanism to chemical reactions, magnetic fields can be used as yet another tool to catalyze and modify those chemical reactions by modifying the spectral characteristics of at least one participant and/or at least one component in the cell reaction system.

Reaction Vessel and Conditioning Reaction Vessel Size, Shape and Composition

An important consideration in the use of spectral chemistry is the reaction vessel size, shape and composition. The reaction vessel size and shape can affect the vessel's NOF to various wave energies (e.g., EM, acoustic, electrical current, etc). This in turn may affect cell reaction system dynamics. For instance, a particularly small bench-top reaction vessel may have an EM NOF of 1,420 MHz related to a 25 cm dimension. When a reaction with an atomic hydrogen intermediate is performed in the small bench-top reaction the reaction proceeds quickly, due in part to the fact that the reactor vessel and the hydrogen hyperfine splitting frequencies match (1,420 MHz). This allows the reaction vessel and hydrogen intermediates to resonate, thus transferring energy to the intermediate and promoting the reaction pathway.

When the reaction is scaled up for large industrial production, the reaction would occur in a much larger reaction vessel with an EM NOF of, for example, 100 MHz. Because the reaction vessel is no longer resonating with the hydrogen intermediate, the reaction proceeds at a slower rate. This deficiency in the larger reaction vessel can be compensated for, by, for example, supplementing the reaction with 1,420 MHz radiation, thereby restoring the faster reaction rate.

Likewise, reaction vessel (or conditioning reaction vessel) composition may play a similar role in cell reaction system dynamics. For example, a stainless steel bench-top reaction vessel may produce vibrational frequencies which resonate with vibrational frequencies of a reactant, thus, for example, promoting disassociation of a reactant into reactive intermediates. When the reaction is scaled up for industrial production, it may be placed into, for example, a ceramic-lined metal reactor vessel. The new reaction vessel typically will not produce the reactant vibrational frequency, and the reaction will proceed at a slower rate. Once again, this deficiency in the new reaction vessel, caused by its different composition, can be compensated for either by returning the reaction to a stainless steel vessel, or by supplementing, for example, the vibrational frequency of the reactant into the ceramic-lined vessel; and/or conditioning the reaction vessel with a suitable conditioning energy prior to some or all of the other components of the reaction system being introduced into the reaction vessel.

It should now be understood that all the aspects of spectral chemistry previously discussed (resonance, targeting, poisons, promoters, supporters, electric and magnetic-fields both endogenous and exogenous to cell reaction system components, etc.) apply to the reaction vessel (or conditioning reaction vessel), as well as to, for example, any participant (or conditionable participant) placed inside it. The reaction vessel (or conditioning reaction vessel) may be comprised of matter (e.g., stainless steel, plastic, glass, and/or ceramic, etc.) or it may be comprised of a field or energy (e.g., magnetic bottle, light trapping, etc.) A reaction vessel (or conditioning reactor vessel), by possessing inherent properties such as frequencies, waves, and/or fields, may interact with other components in the cell reaction system and/or at least one participant. Likewise, holding vessels, conduits, etc., some of which may interact with the reaction system, but in which the reaction does not actually take place, may interact with one or more components in the cell reaction system and may potentially affect them, either positively or negatively. Accordingly, when reference is made to the reaction vessel, it should be understood that all portions associated therewith may also be involved in desirable reactions.

EXAMPLES

The invention will be more clearly perceived and better understood from the following specific examples.

Example 1

Replacing a Physical Catalyst with a Spectral Catalyst in a Gas Phase Reaction $2H_2+O_2$>>>>platinum catalyst >>>>$2H_2O$ Water can be produced by the method of exposing $H_2$ and $O_2$ to a physical platinum (Pt) catalyst but there is always the possibility of producing a potentially dangerous explosive risk. This experiment replaced the physical platinum catalyst with a spectral catalyst comprising the spectral pattern of the physical platinum catalyst, which resonates with and transfers energy to the hydrogen and hydroxy intermediates.

To demonstrate that oxygen and hydrogen can combine to form water utilizing a spectral catalyst, electrolysis of water was performed to provide stoichiometric amounts of oxygen and hydrogen starting gases. A triple neck flask was fitted with two (2) rubber stoppers on the outside necks, each fitted with platinum electrodes encased in glass for a four (4) inch length. The flask was filled with distilled water and a pinch of salt so that only the glass-encased portion of the electrode was exposed to air, and the unencased portion of the electrode was completely under water. The central neck was connected via a rubber stopper to vacuum tubing, which led to a Drierite column to remove any water from the produced gases.

After vacuum removal of all gases in the system (to about 700 mm Hg), electrolysis was conducted using a 12 V power source attached to the two electrodes. Electrolysis was commenced with the subsequent production of hydrogen and oxygen gases in stoichiometric amounts. The gases passed through the Drierite column, through vacuum tubing connected to positive and negative pressure gauges and into a sealed 1,000 ml, round quartz flask. A strip of filter paper, which contained dried cobalt, had been placed in the bottom of the sealed flask. Initially the cobalt paper was blue, indicating the absence of water in the flask. A similar cobalt test strip exposed to the ambient air was also blue.

The traditional physical platinum catalyst was replaced by spectral catalyst platinum electronic frequencies (with their attendant fine and hyperfine frequencies) from a Fisher Scientific Hollow Cathode Platinum Lamp which was positioned approximately one inch (about 2 cm) from the flask. This allowed the oxygen and hydrogen gases in the round quartz flask to be irradiated with emissions from the spectral catalyst. A Cathodeon Hollow Cathode Lamp Supply C610 was used to power the Pt lamp at 80% maximum current (12 mAmps). The reaction flask was cooled using dry ice in a Styrofoam container positioned directly beneath the round quartz flask, offsetting any effects of heat from the Pt lamp. The Pt lamp was turned on and within two days of irradiation, a noticeable pink color was evident on the cobalt paper strip indicating the presence of water in the round quartz flask. The cobalt test strip exposed to ambient air in the lab remained blue. Over the next four to five days, the pink colored area on the cobalt strip became brighter and larger. Upon discontinuation of the Pt emission, $H_2O$ diffused out of the cobalt strip and was taken up by the Drierite column. Over the next four to five days, the pink coloration of the cobalt strip in the quartz flask faded. The cobalt strip exposed to the ambient air remained blue.

In this Example, targeted spectral energies were used to affect chemical reactions in a gas phase.

Example 2

Replacing a Physical Catalyst with a Spectrl Catalyst in a Liquid Phase Reaction $H_2O_2$>>>>platinum catalyst >>>>$H_2O+O_2$ The decomposition of hydrogen peroxide is an extremely slow reaction in the absence of catalysts. Accordingly, an experiment was performed which showed that the physical catalyst, finely divided platinum, could be replaced with the spectral catalyst having the spectral pattern of platinum. Hydrogen peroxide, 3%, filled two (2) nippled quartz tubes. (the nippled quartz tubes consisted of a lower portion about 17 mm internal diameter and about 150 mm in length, narrowing over about a 10 mm length to an upper capillary portion being about 2.0 mm internal diameter and about 140 mm in length and were made from PhotoVac Laser quartz tubing). Both quartz tubes were inverted in 50 ml beaker reservoirs filled with (3%) hydrogen peroxide to about 40 ml and were shielded from incident light (cardboard cylinders covered with aluminum foil). One of the light shielded tubes was used as a control. The other shielded tube was exposed to a Fisher Scientific Hollow Cathode Lamp for platinum (Pt) using a Cathodeon Hollow Cathode Lamp Supply C610, at 80% maximum current (12 mA). The experiment was performed several times with an exposure time ranging from about 24 to about 96 hours. The shielded tubes were monitored for increases in temperature (there was none) to assure that any reaction was not due to thermal effects. In a typical experiment the nippled tubes were prepared with hydrogen peroxide (3%) as described above herein. Both tubes were shielded from light, and the Pt tube was exposed to platinum spectral emissions, as described above, for about 24 hours. Gas production in the control tube A measured about four (4) mm in length in the capillary (i.e., about 12.5 $mm^3$), while gas in the Pt (tube B) measured about 50 mm (i.e., about 157 $mm^3$). The platinum spectral catalyst thus increased the reaction rate about 12.5 times.

The tubes were then switched and tube A was exposed to the platinum spectral catalyst, for about 24 hours, while tube B served as the control. Gas production in the control (tube B) measured about 2 mm in length in the capillary (i.e., about 6 $mm^3$) while gas in the Pt tube (tube A) measured about 36 mm (i.e., about 113 $mm^3$), yielding about a 19 fold difference in reaction rate.

As a negative control, to confirm that any lamp would not cause the same result, the experiment was repeated with a sodium lamp at 6 mA (80% of the maximum current). Na in a traditional reaction would be a reactant with water releasing hydrogen gas, not a catalyst of hydrogen peroxide breakdown. The control tube measured gas to be about 4 mm in length (i.e., about 12 $mm^3$) in the capillary portion, while the Na tube gas measured to be about 1 mm in length (i.e., about 3 $mm^3$). This indicated that while spectral emissions can substitute for catalysts, they cannot yet substitute for reactants. Also, it indicated that the simple effect of using a hollow cathode tube emitting heat and energy into the hydrogen peroxide was not the cause of the gas bubble formation, but instead, the spectral pattern of Pt replacing the physical catalyst caused the reaction.

In this Example, targeted spectral energies were used to affect a chemical reaction in a liquid phase and subsequent transformation to a gas phase.

Example 3

Replacing a Physical Catalyst with a Spectral Catalyst in a Solid Phase Reaction It is well known that certain microorganisms have a toxic reaction to silver (Ag). The silver electronic spectrum consists of essentially two ultraviolet frequencies that fall between UV-A and UV-B. It is now understood through this invention, that the high intensity spectral frequencies produced in the silver electronic spectrum are ultraviolet frequencies that inhibit bacterial growth (by creation of free radicals and by causing bacterial DNA damage). These UV frequencies are essentially harmless to mammalian cells. Thus, it was theorized that the known medicinal and anti-microbial uses of silver are due to a spectral catalyst effect. In this regard, an experiment was conducted which showed that the spectral catalyst emitting the spectrum of silver demonstrated a toxic or inhibitory effect on microorganisms.

Bacterial cultures were placed onto standard growth medium in two petri dishes (one control and one Ag) using standard plating techniques covering the entire dish. Each dish was placed at the bottom of a light shielding cylindrical chamber. A light shielding foil-covered, cardboard disc with a patterned slit was placed over each culture plate. A Fisher Scientific Hollow Cathode Lamp for Silver (Ag) was inserted through the top of the Ag exposure chamber so that only the spectral emission pattern from the silver lamp was irradiating the bacteria on the Ag culture plate (i.e., through the patterned slit). A Cathodeon Hollow Cathode Lamp Supply C610 was used to power the Ag lamp at about 80% maximum current (3.6 mA). The control plate was not exposed to emissions of an Ag lamp, and ambient light was blocked. Both control and Ag plates were maintained at room temperature (e.g., about 70-74° F.) during the silver spectral emission exposure time, which ranged from about 12-24 hours in the various experiments. Afterwards, both plates were incubated using standard techniques (37° C., aerobic Form a Scientific Model 3157, Water-Jacketed Incubator) for about 24 hours.

The following bacteria (obtained from the Microbiology Laboratory at People's Hospital in Mansfield, Ohio, US), were studied for effects of the Ag lamp spectral emissions:
1. *E. coli;*
2. *Strep. pneumoniae;*
3. *Staph. aureus*; and
4. *Salmonella typhi.*

This group included both Gram$^+$ and Gram$^-$ species, as well as cocci and rods.

Results were as follows:
1. Controls—all controls showed full growth covering the culture plates;
2. The Ag plates
    areas unexposed to the Ag spectral emission pattern showed full growth.
    areas exposed to the Ag spectral emission pattern showed:
        a. *E. coli*—no growth;
        b. *Strep. pneumoniae*—no growth;
        c. *Staph. aureus*—no growth; and
        d. *Salmonella tyhli*—inhibited growth.

In this Example, targeted spectral energies were used to catalyze chemical reactions in in biological organisms. These reactions inhibited growth of the biological organisms.

Example 4

Replacing a Physical Catalyst with a Spectral Catalyst, and Comparing Results to Physical Catalyst Results in a Biologic Preparation To further demonstrate that certain susceptible organisms which have a toxic reaction to silver would have a similar reaction to the spectral catalyst emitting the spectrum of silver, cultures were obtained from the American Type Culture Collection (ATCC) which included *Escherichia coli* #25922, and *Klebsiella pneumonia*, subsp *Pneumoniae*, # 13883. Control and Ag plate cultures were performed as described above. After incubation, plates were examined using a binocular microscope. The *E. coli* exhibited moderate resistance to the bactericidal effects of the spectral silver emission, while the *Klebsiella* exhibited moderate sensitivity. All controls exhibited full growth.

Accordingly, an experiment was performed which demonstrated a similar result using the physical silver catalyst as was obtained with the Ag spectral catalyst. Sterile test discs were soaked in an 80 ppm, colloidal silver solution. The same two (2) organisms were again plated, as described above. Colloidal silver test discs were placed on each Ag plate, while the control plates had none. The plates were incubated as described above and examined under the binocular microscope. The colloidal silver *E. coli* exhibited moderate resistance to the bactericidal effects of the physical colloidal silver, while the *Klebsiella* again exhibited moderate sensitivity. All controls exhibited full growth.

Example 5

Augmenting a Physical Catalyst with a Spectral Catalyst

To demonstrate that oxygen and hydrogen can combine to form water utilizing a spectral catalyst to augment a physical catalyst, electrolysis of water was performed to provide the necessary oxygen and hydrogen starting gases, as in Example 1.

Two quartz flasks (A and B) were connected separately after the Drierite column, each with its own set of vacuum and pressure gauges. Platinum powder (about 31 mg) was placed in each flask. The flasks were filled with electrolytically produced stoichiometric amounts of $H_2$ and $O_2$ to 120 mm Hg. The flasks were separated by a stopcock from the electrolysis system and from each other. The pressure in each flask was recorded over time as the reaction proceeded over the physical platinum catalyst. The reaction combines three (3) moles of gases, (i.e., two (2) moles $H_2$ and one (1) mole $O_2$), to produce two (2) moles $H_2O$. This decrease in molarity, and hence progress of the reaction, can be monitored by a decrease in pressure "P" which is proportional, via the ideal gas law, (PV=nRT), to molarity "n". A baseline rate of reaction was thus obtained. Additionally, the test was repeated filling each flask with $H_2$ and $O_2$ to 220 mm Hg. Catalysis of the reaction by only the physical catalyst yielded two baseline reaction curves which were in good agreement between flasks A and B, and for both the 110 mm and 220 mm Hg tests.

Next, the traditional physical platinum catalyst in flask A was augmented with spectral catalyst platinum emissions from two (2) parallel Fisher Scientific Hollow Cathode Platinum Lamps, as in Example 1, which were positioned approximately two (2) cm from flask A. The test was repeated as described above, separating the two (2) flasks from each other and monitoring the rate of the reaction via the pressure decrease in each. Flask B served as a control flask. In flask A, the oxygen and hydrogen gases, as well as the physical platinum catalyst, were directly irradiated with emissions from the Pt lamp spectral catalyst.

Rate of reaction in the control flask B, was in good agreement with previous baseline rates. Rate of reaction in flask "A", wherein physical platinum catalyst was augmented with the platinum spectral pattern, exhibited an overall mean increase of 60%, with a maximal increase of 70% over the baseline and flask B.

In this Example, targeted spectral energies were used to change the chemical reaction properties of a solid catalyst in a gas phase (heterogeneous) reaction system.

Example 6

Replacing a Physical Catalyst with a Fine Structure Heterodyned Frequency and Replacing a Physical Catalyst with a Fine Structure Frequency the Alpha Rotation-Vibration Constant Water was electrolyzed to produce stoichiometric amounts of hydrogen and oxygen gases as described above herein. Additionally, a dry ice cooled stainless steel coil was placed immediately after the Drierite column. After vacuum removal of all gases in the system, electrolysis was accomplished using a 12 V power source attached to the two electrodes, resulting in a production of hydrogen and oxygen gases. After passing through the Drierite column, the hydrogen and oxygen gases passed through vacuum tubing connected to positive and negative pressure gauges, through the dry ice cooled stainless steel coil and then to a 1,000 ml round, quartz flask. A strip of filter paper impregnated with dry (blue) cobalt was in the bottom of the quartz flask, as an indicator of the presence or absence of water.

The entire system was vacuum evacuated to a pressure of about 700 mm Hg below atmospheric pressure. Electrolysis was performed, producing hydrogen and oxygen gases in stoichiometric amounts, to result in a pressure of about 220 mm Hg above atmospheric pressure. The center of the quartz flask, now containing hydrogen and oxygen gases, was irradiated for approximately 12 hours with continuous microwave electromagnetic radiation emitted from a Hewlett Packard microwave spectroscopy system which included an HP 83350B Sweep Oscillator, an HP 8510B Network Analyzer and an HP 8513A Reflection Transmission Test Set. The frequency used was 21.4 GHz, which corresponds to a fine splitting constant, the alpha rotation-vibration constant, of the hydroxy intermediate, and is thus a harmonic resonant heterodyne for the hydroxy radical. The cobalt strip changed strongly in color to pink which indicated the presence of water in the quartz flask, whose creation was catalyzed by a harmonic resonant heterodyne frequency for the hydroxy radical.

In this Example, targeted spectral energies were used to control a gas phase chemical reaction.

Example 7

Replacing a Physical Catalyst with a Hyperfine Splitting Frequency

An experimental dark room was prepared, in which there is no ambient light, and which can be totally darkened. A shielded, ground room (Ace Shielded Room, Ace, Philadelphia, Pa., US, Model A6H3-16; 8 feet wide, 17 feet long, and 8 feet high (about 2. meters×5.2 meters×2.4 meters) copper mesh) was installed inside the dark room.

Hydrogen peroxide (3%) was placed in nippled quartz tubes, which were then inverted in beakers filled with (3%) hydrogen peroxide, as described in greater detail herein. The tubes were allowed to rest for about 18 hours in the dark room, covered with non-metallic light blocking hoods (so that the room could be entered without exposing the tubes to light). Baseline measurements of gases in the nippled tubes were then performed.

Three nippled RF tubes were placed on a wooden grid table in the shielded room, in the center of grids 4, 54, and 127; corresponding to distances of about 107 cm, 187 cm, and 312 cm respectively, from a frequency-emitting antenna (copper tubing 15 mm diameter, 4.7 m octagonal circumference, with the center frequency at approximately 6.5 MHz. A 25 watt, 17 MHz signal was sent to the antenna. This frequency corresponds to a hyperfine splitting frequency of the hydrogen atom, which is a transient in the dissociation of hydrogen peroxide. The antenna was pulsed continuously by a BK Precision RF Signal Generator Model 2005A, and amplified by an Amplifier Research amplifier, Model 25A-100. A control tube was placed on a wooden cart immediately adjacent to the shielded room, in the dark room. All tubes were covered with non-metallic light blocking hoods.

After about 18 hours, gas production from dissociation of hydrogen peroxide and resultant oxygen formation in the nippled tubes was measured. The RF tube closest to the antenna produced 11 mm length gas in the capillary (34 $mm^3$), the tube intermediate to the antenna produced a 5 mm length (10 $mm^3$) gas, and the RF tube farthest from the antenna produced no gas. The control tube produced 1 mm gas. Thus, it can be concluded that the RF hyperfine splitting frequency for hydrogen increased the reaction rate approximately five (5) to ten (10) times.

In this Example, targeted spectral energy was used to control a chemical reaction in a liquid phase, resulting in a transformation to a gas phase.

Example 8

Replacing a Physical Catalyst with a Magnetic Field

Hydrogen peroxide (15%) was placed in nippled quartz tubes, which were then inverted in beakers filled with (15%) hydrogen peroxide, as described above. The tubes were allowed to rest for about four (4) hours on a wooden table in a shielded cage, in a dark room. Baseline measurements of gases in the nippled tubes were then performed.

Remaining in the shielded cage, in the dark room, two (2) control tubes were left on a wooden table as controls. Two (2) magnetic field tubes were placed on the center platform of an ETS Helmholtz single axis coil, Model 6402, 1.06 gauss/Ampere, pulsed at about 83 Hz by a BK Precision 20 MHz Sweep/Function Generator, Model 4040. The voltage output of the function generator was adjusted to produce an alternating magnetic field of about 19.5 milliGauss on the center platform of the Helmholtz Coil, as measured by a Holaday Model HI-3627, three (3) axis ELF magnetic field meter and probe. Hydrogen atoms, which are a transient in the dissociation of hydrogen peroxide, exhibit nuclear magnetic resonance via Zeeman splitting at this applied frequency and applied magnetic field strength. Thus, frequency of the alternating magnetic field was resonant with the hydrogen transients.

After about 18 hours, gas production from dissociation of hydrogen peroxide and resultant oxygen formation in the nippled tubes was measured. The control tubes averaged about 180 mm gas formation (540 $mm^3$) while the tubes exposed to the alternating magnetic field produced about 810 mm gas (2,430 $mm^3$), resulting in an increase in the reaction rate of approximately four (4) times.

Example 9

Negatively Catalyzing a Reaction with an Electric Field

Hydrogen peroxide (15%) was placed in four (4) nippled quartz tubes which were inverted in hydrogen peroxide (15%) filled beakers, as described in greater detail above herein. The tubes were placed on a wooden table, in a shielded room, in a dark room. After four (4) hours, baseline measurements were taken of the gas in the capillary portion of the tubes.

An Amplifier Research self-contained electromagnetic mode cell ("TEM") Model TC1510A had been placed in the dark, shielded room. A sine wave signal of about 133 MHz was provided to the TEM cell by a BK Precision RP Signal Generator, Model 2005A, and an Amplifier Research amplifier, Model 25A100. Output levels on the signal generator and amplifier wave adjusted to produce an electric field (E-field) of about five (5) V/m in the center of the TEM cell, as measured with a Holaday Industries electric field probe, Model HI-4433GRE, placed in the center of the lower chamber.

Two of the hydrogen peroxide filled tubes were placed in the center of the upper chamber of the TEM cell, about 35 cm from the wall of the shielded room. The other two (2) tubes served as controls and were placed on a wooden table, also about 35 cm from the same wall of the shielded, dark room, and removed from the immediate vicinity of the TEM cell, so that there was no ambient electric field, as confirmed by E-field probe measurements.

The 133 MHz alternating sine wave signal delivered to the TEM cell was well above the typical line width frequency at room temperature (e.g., about 100 KHz) and was theorized to be resonant with an n=20 Rydberg state of the hydrogen atom as derived from $$\Delta E = cE^{3/4}$$

where E is the change in energy in $cm^{-1}$, c is 7.51+/−0.02 for the hydrogen state n=20 and E is the electric field intensity in $(Kv/cm)^2$.

After about five (5) hours of exposure to the electric field, the mean gas production in the tubes subjected to the E-field was about 17.5 mm, while mean gas production in the control tubes was about 58 mm.

While not wishing to be bound by any particular theory or explanation, it is believed that the alternating electric field resonated with an upper energy level in the hydrogen atoms, producing a negative Stark effect, and thereby negatively catalyzing the reaction.

Example 10

Augmentation of a Physical Catalyst by Irradiating Reactants/Transients with a Spectral Catalyst Hydrogen and oxygen gases were produced in stoichiometric amounts by electrolysis, as previously described in greater detail above herein. A stainless steel coil cooled in dry ice was placed immediately after the Drierite column. Positive and negative pressure gauges were connected after the coil, and then a 1,000 ml round quartz flask was sequentially connected with a second set of pressure gauges.

At the beginning of each experimental run, the entire system was vacuum evacuated to a pressure of about minus 650 mm Hg. The system was sealed for about 15 minutes to confirm the maintenance of the generated vacuum and integrity of the connections. Electrolysis of water to produce hydrogen and oxygen gases was performed, as described previously.

Initially, about 10 mg of finely divided platinum was placed into the round quartz flask. Reactant gases were allowed to react over the platinum and the reaction rate was monitored by increasing the rate of pressure drop over time, as previously described. The starting pressure was approximately in the mid-90's mm Hg positive pressure, and the ending pressure was approximately in the low 30's over the amount of time that measurements were taken. Two (2) control runs were performed, with reaction rates of about 0.47 mm Hg/minute and about 0.48 mm Hg/minute.

For the third run, a single platinum lamp was applied, as previously described, except that the operating current was reduced to about eight (8) mA and the lamp was positioned through the center of the flask to irradiate only the reactant/transient gases, and not the physical platinum catalyst. The reaction rate was determined, as described above, and was found to be about 0.63 mm Hg/minute, an increase of 34%.

Example 11

Apparent Poisoning of a Reaction by the Spectral Pattern of a Physical Poison

The conversion of hydrogen and oxygen gases to water, over a stepped platinum physical catalyst, is known to be poisoned by gold. Addition of gold to this platinum catalyzed reaction reduces reaction rates by about 95%. The gold blocks only about one sixth of the platinum binding sites, which according to prior art, would need to be blocked to poison the physical catalyst to this degree. Thus, it was theorized that a spectral interaction of the physical gold with the physical platinum and/or reaction system could also be responsible for the poisoning effects of gold on the reaction. It was further theorized that addition of the gold spectral pattern to the reaction catalyzed by physical platinum could also poison the reaction.

Hydrogen and oxygen gases were produced by electrolysis, as described above in greater detail. Finely directed platinum, about 15 mg, was added to the round quartz flask. Starting pressures were about in the 90's mm Hg positive pressure, and ending pressures were about in the 20's mm Hg over the amount of time that measurements were taken. Reaction rates were determined as previously described. The first control run revealed a reaction rate of about 0.81 mm Hg/minute.

In the second run, a Fisher Hollow Cathode Gold lamp was applied, as previously described, at an operating frequency of about eight (8) mA, (80% maximum current), through about the center of the round flask. The reaction rate increased to about 0.87 mm Hg/minute.

A third run was then performed on the same reaction flask and physical platinum that had been in the flask exposed to the gold spectral pattern. The reaction rate decreased to about 0.75 mm Hg/minute.

In this Example, targeted spectral energies were used to control an environmental reaction condition (poison) and change the chemical reaction properties of a physical catalyst in a heterogeneous catalyst reaction system.

Example 12

Increase in Measured pH in a NaCl Water Solution Due to a Sodium Spectral Pattern This Example demonstrates the effects of conditioning a conditionable participant (distilled water) with a conditioning energy (sodium lamp) by dissolving crystalline sodium chloride (NaCl) into the water and monitoring pH changes.

a) Equipment and Materials

Figure 70:
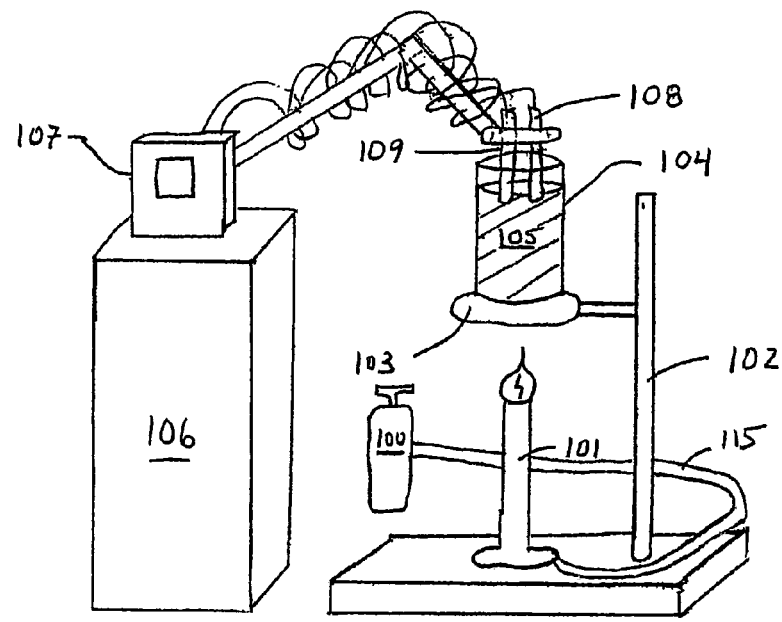
Figure 71:
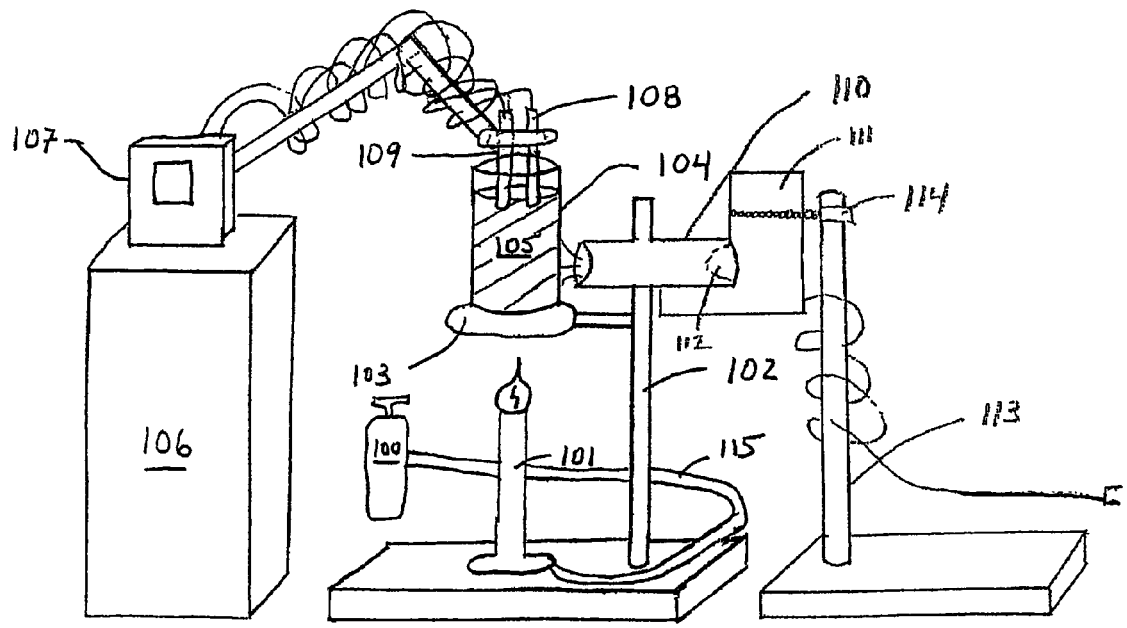
FIG. 71 shows a schematic of the experimental set-up which corresponds to a Bunsen burner heating a solution of sodium chloride and water on a hot plate, and a sodium lamp emitting an electromagnetic spectral pattern into the side of a beaker, which is discussed in Example 12b.
Figure 72:
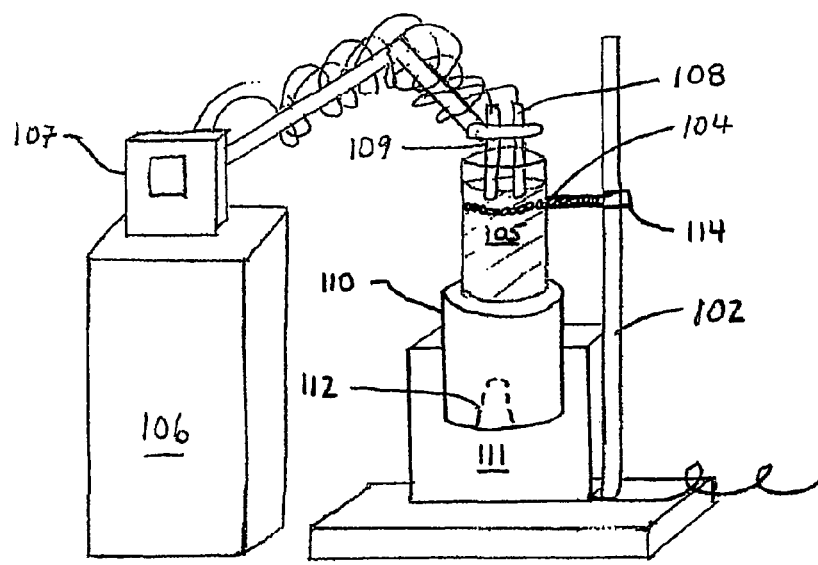
FIG. 72 shows a schematic of the experimental set-up which corresponds to a sodium lamp heating a solution of sodium chloride and water from the bottom of a beaker, which is discussed in Example 12c.
Figure 73:
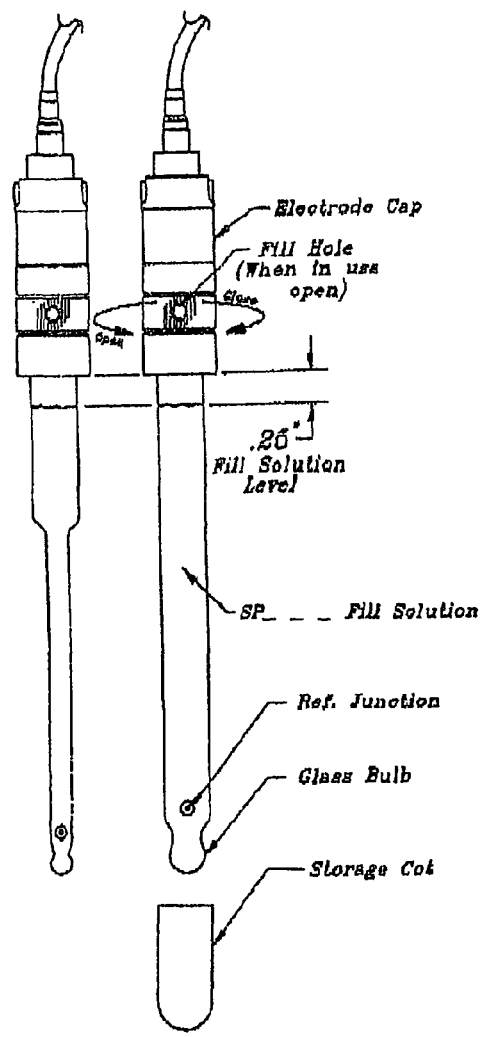
FIG. 73 shows a schematic of the pH electrode 109 used with the Accumet AR20 meter 107.

The following reference numerals refer to those items shown schematically in FIGS. 70, 71 and 72, which correspond to Examples 12a, 12b and 12c, respectively. FIG. 73 shows the pH electrode 109 in greater detail. Like reference numerals have been used whenever possible.

100—Bernzomatic propane fuel.
101—Humboldt Bunsen burner.
102—Ring stand.
103—Cast iron hot plate from Fisher Scientific.
104—1000 ml Pyrex™ cylindrical beaker.
105—A solution of water, or of sodium chloride and water.
Sodium Chloride, Fisher Chemicals, Lot No. 025149, packaged in gray plastic 3 Kg bottles. The sodium chloride, in crystalline form, is characterized as follows:
Sodium Chloride; Certified A.C.S.
Certificate of Lot Analysis
  Barium (Ba) (about 0.001%)—P.T.
  Bromide (Br)—0.01%
  Calcium (Ca)—0.0007%
  Chlorate and Nitrate (as $NO_3$)—0.0006%
  Heavy Metals (as Pb)—0.4 ppm
  Insoluble Matter—0.001%
  Iodide (I)—0.0004%
  Iron (Fe)—0.4 ppm
  Magnesium (Mg)—0.0003%
  Nitrogen Compounds (as N)—0.0003%
  pH of 5% solution at 25° C.-6.8
  Phosphate ($PO_3$)—1 ppm
  Potassium (K)—0.001%
  Sulfate ($SO_4$)—0.003%
Distilled Water—American Fare, contained in one (1) gallon translucent, colorless, plastic jugs, processed by distillation, microfiltration and ozonation. Source, Greeneville Municipal Water supply, Greeneville, Tenn. Stored in cardboard boxes in a dark, shielded room prior to use in the experiments described in Examples 12a, 12b and 12c.

106—Support structure for pH meter.

107—An AR20 "pH/mV/° C./Conductivity" meter from Accumet Research (Fisher Catalog No. 13-636-AR20 2000/2001 Catalog).

108—Temperature probe for pH meter.

109—pH Electrode for AR20 pH meter (Fisher 2000-2001 Catalog #13-620-285); and shown in greater detail in FIG. 73.

110—Aluminum foil tube made from kitchen grade aluminum foil, medium duty.

111—Stonco 70 watt high-pressure sodium security wall fixture (TLW Series Twilighter Wallprism model) fitted with a parabolic aluminum reflector which directs the light from the housing.

112—One or more sodium lamps, Stonco 70 Watt high-pressure sodium security wall light, fitted with a parabolic aluminum reflector directing the light away from the housing. The sodium bulb was a Type S62 lamp, 120V, 60 Hz, 1.5A made in Hungary by Jemanamjjasond. One or more sodium lamps was/were mounted at various angles, and location(s) as specified in each experiment. Unless stated differently in the Example, the lamp was located at about 15 inches (about 38 cm) from the beakers or dishes to maintain substantially consistent intensities.

113—Ring stand.

114—Chain clamp.

Experimental Procedure

Example 12a

FIG. 70 is a schematic of the experimental apparatus used to generate baseline measured pH information at about 55° C. as a function of time. In this Example 12a, the Bunsen burner 101 was supplied with propane fuel from the fuel source 100 via a flexible rubber tube 115. The flame from the Bunsen burner 101 was caused to be incident upon a cast iron hot plate 103 which was attached to a ring stand 102. A 1000 ml Pyrex™ cylindrical beaker 104 was placed on top of the cast iron hot plate 103. The beaker 104 contained approximately 800 ml of distilled water obtained from American Pare. An AR20 pH/mV/° C./Conductivity meter 107 from Accumet Research communicated with the 800 ml of distilled water and later with the solution 105 through a temperature probe 108 and a pH electrode 109. More details of the pH electrode can be seen in FIG. 73. The pH meter was elevated to a convenient height by the use of a support structure 106.

The pH of the distilled water in the beaker 104 was first measured at room temperature and then heated to about 55° C. in about 15-20 minutes by use of the Bunsen burner heating the hot plate 103 and the hot plate 103 radiating its conditioning energy to the beaker 104 containing the distilled water. The water temperature was monitored by the Accumet meter 107. Once a temperature of about 55° C. was obtained, about 50 grams of sodium chloride (certified A. C. S. and as discussed above herein), were added to the 800 ml of distilled water in the beaker 104 to form the solution 105. The sodium chloride was stirred into the 800 ml of distilled water by use of glass stirring rod and complete dissolution of the sodium chloride occurred within about 30-45 seconds. The temperature of the solution 105 was reduced by approximately ½ to 1° C., but was quickly brought back to about 55° C. by the Bunsen burner 101 and cast iron hot plate 103 in a matter of a few seconds. The electrodes 108 and 109 were temporarily removed from the solution 105 to permit the stirring, mixing and dissolution of the sodium chloride into the distilled water. However, the electrodes 108 and 109 were immediately reinserted into the solution 105 upon completion of the stirring.

Figure 74Q:
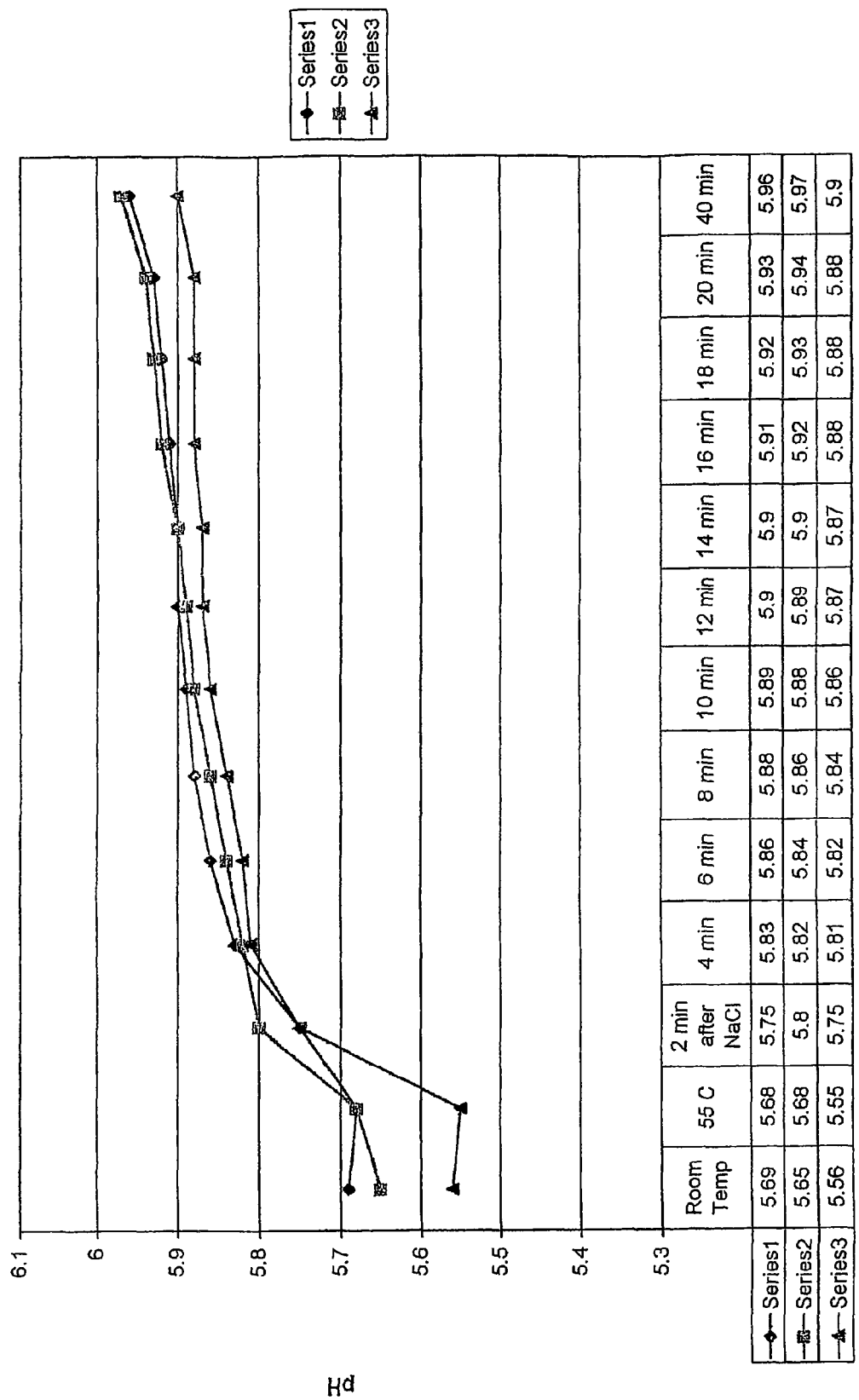

FIG. 74a shows the results of three (3) separate experiments corresponding to the experimental apparatus of FIG. 70. The plotted data show the change in measured pH of the solution 105 as a function of time at a temperature of about 55° C. In particular, the pH of the distilled water alone was first measured at room temperature and then measured at about 55° C., and thereafter the pH of the solution 105 was measured about every two minutes after the addition and dissolution of sodium chloride. The time measurements were all at intervals of about two minutes with a final measurement after about 40 minutes.

The AR20 meter 107, which used the pH electrode 109 (the electrode being shown in more detail in FIG. 73), were together calibrated by using two different buffer solutions. The first buffer solution had a pH of 4.00+/−0.01 at 25° C., and was a solution of potassium bipthalate. A second buffer solution had a pH of 7.00+/−0.01 at 25° C., and was a solution of potassium phosphate monobasic-sodium hydroxide. Both solutions were 0.05 Molar, both were certified and both were obtained from Fisher Chemicals. The use of these buffer solutions was intended to insure accuracy of the readings from the pH electrode.

All experimental conditions described in the Example occurred in the presence of standard fluorescent lighting. The fluorescent lamps were Sylvania Cool White Deluxe Fluorescent Lamps, 75 watts and were each eight (8) feet (about 2.4 meters) long. The lamps were suspended in pairs approximately 3.5 meters above the laboratory counter on which the experimental set-up was located. There were six (6) pairs of lamps present in a room which measured approximately 25 feet by 40 feet (about 7.6 meters×12.1 meters).

Example 12b

Figure 77:
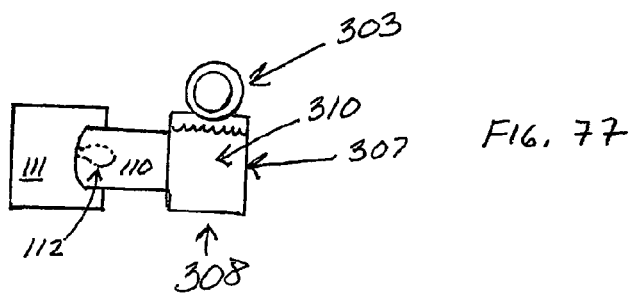
FIG. 77 shows a schematic of a sodium light used in Example 14.

FIG. 77 is a schematic of the experimental apparatus used to generate measured pH information at about 55° C. as a function of time. In this Example 12b, the Bunsen burner 101 was supplied with propane fuel from the fuel source 100 via a flexible rubber tube 115. The flame from the Bunsen burner 101 was caused to be incident upon a cast iron hot plate 103 which was attached to a ring stand 102. A 1000 ml Pyrex™ cylindrical beaker 104 was placed on top of the cast iron hot plate 103. The beaker 104 contained approximately 800 ml of distilled water obtained from American Fare. An AR20 pH/mV/° C./Conductivity meter 107 from Accumet Research communicated with the 800 ml of distilled water and later with the solution 105 through a temperature probe 108 and a pH electrode 109. More details of the pH electrode can be seen in FIG. 773. The pH meter was elevated to a convenient height by the use of a support structure 106.

The pH of the distilled water in the beaker 104 was first measured at room temperature and then heated to about 55° C. in about 15-20 minutes by use of the Bunsen burner heating the hot plate 103. The water temperature was monitored by the Accumet meter 107. Once a temperature of about 55° C. was obtained, about 50 grams of sodium chloride (certified A. C. S. and discussed above herein), were added to the 800 ml of distilled water in the beaker 104 to form the solution 105. The sodium chloride was stirred into the 800 ml of distilled water by use of glass stirring rod and complete dissolution of the sodium chloride occurred within about 30-45 seconds. The temperature of the solution 105 was reduced by approximately ½ to 1° C., but was quickly brought back to about 55° C. by the Bunsen burner 101 and cast iron hot plate 103 in a matter of a few seconds. The electrodes 108 and 109 were temporarily removed from the solution 105 to permit the stirring, mixing and dissolution of the sodium chloride into the distilled water. However, the electrodes 108 and 109 were immediately reinserted upon completion of the stirring.

A ring stand 113 was positioned adjacent to the ring stand 102 such that a high pressure sodium light 112 contained within a housing 111, and surrounded by an aluminum foil tube 110 permitted light emitted from the bulb 112 to be transmitted through the aluminum foil tube 110 and become incident upon a side of the beaker 104. The ring stand 113 was positioned such that the end of the aluminum tube 110 adjacent to the side of the beaker 104 was about ½ inch to ¾ inch away from the side of the beaker 104. The tube 110 measured about eight (8) inches long and was about 3½ inches in diameter. The top end of the sodium light bulb 112 was about five (5) inches from the end of the tube 110. In this Example 12b, the sodium light bulb 112 was actuated at about the same time that the electrodes 108 and 109 were reinserted into the solution 105 which is after the sodium chloride had been mixed into and dissolved in the distilled water. The light fixture 111 was fixed to the ring stand 113 by use of a chain clamp 114.

Figure 74B:
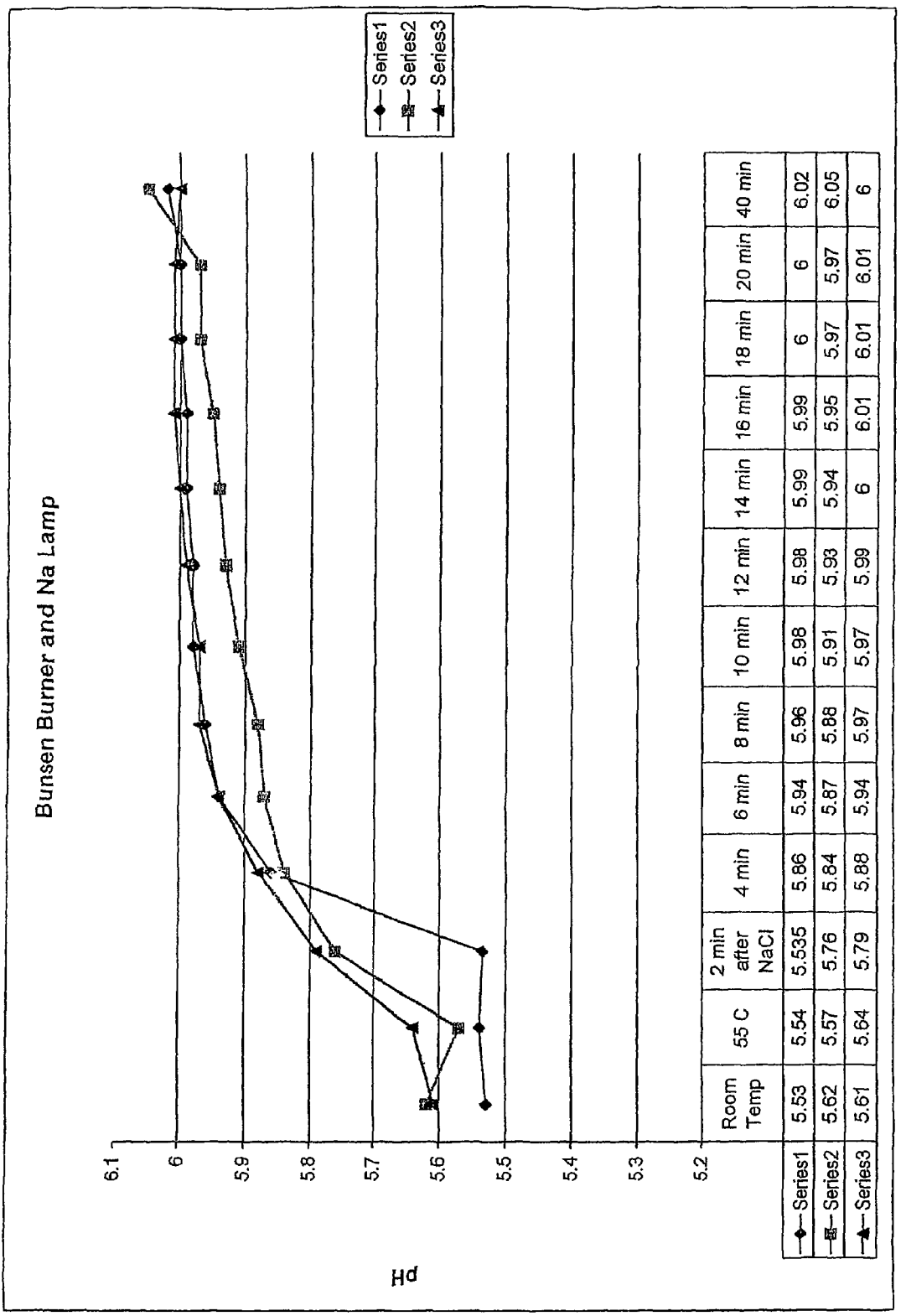
FIG. 74b is a graph of the experimental data which shows pH as a function of time and corresponds to the experimental set-up of Example 12b.

FIG. 74b shows the results of three (3) separate experiments corresponding to the experimental apparatus of FIG. 71. The plotted data show the change in measured pH of the solution 105 as a function of time at a temperature of about 55° C. In particular, the pH of the distilled water alone was first measured at room temperature and then measured at about 55° C., and thereafter measured about every two minutes after the addition and dissolution of sodium chloride and the activation of the high pressure sodium light 112. The time measurements were all at intervals of about two minutes.

The AR20 meter 107, which used the pH electrode 109 (the electrode being shown in more detail in FIG. 73) were together calibrated by using two different buffer solutions. The first buffer solution had a pH of 4.00+/−0.01 at about 25° C., and was a solution of potassium bipthalate. A second buffer solution had a pH of 7.00+/−0.01 at about 25° C., and was a solution of potassium phosphate monobasic-sodium hydroxide. Both solutions were 0.05 Molar, both were certified and both were obtained from Fisher Chemicals. The use of these buffer solutions was intended to insure accuracy of the pH readings from the pH electrode.

All experimental conditions described in the Example occurred in the presence of standard fluorescent lighting. The fluorescent lamps were Sylvania Cool White Deluxe Fluorescent Lamps, 75 watts and were each about eight (8) feet (about 2.4 meters) long. The lamps were suspended in pairs approximately 3.5 meters above the laboratory counter on which the experimental set-up was located. There were six (6) pairs of lamps present in a room which measured approximately 25 feet by 40 feet (about 7.6 meters×12.1 meters).

Example 12c

FIG. 72 is a schematic of the experimental apparatus used to generate measured pH information where the temperature of the distilled water in the beaker 104, and later in the solution 105, in the beaker 104 was heated exclusively by use of a high pressure sodium bulb 112 contained in a fixture 111.

This Example 12c differs from the previous Examples 12a and 12b in that no Bunsen burner was provided for heating. In this regard, the only heat that was generated from the energy emitted by the combination of the high pressure sodium bulb 112, and the fixture 111. In particular, the energy was transmitted to the bottom of the beaker 104 initially containing the distilled water, and later to the solution 105, through the use of the aluminum foil tube 110. Specifically, the ring stand 102 supported the beaker 104 by the use of the chain clamp 114. The beaker 104 was initially lowered into the aluminum foil tube 110 such that approximately 150-200 ml of the distilled water contained in the beaker 104 was physically located inside of the aluminum foil tube 110. The tube 110 measured about seven (7) inches long and was about four (4) inches in diameter. The top end of the sodium light bulb 112 was about four (4) inches from the end of the tube 110. Once the distilled water temperature achieved about 55° C. after about 1¼-1½ hours, the sodium chloride was added, as discussed above. The chain clamp 114 was then raised vertically slightly upon the ring stand 102 so that the bottom of the beaker 104 was now positioned slightly outside of the aluminum foil tube 110 (as shown in FIG. 72). Experience caused the precise final location of the bottom of the beaker 104 to be about ½ inch-¾ inch above the end of the aluminum foil tube 110. The primary difference between this Example 12c and the previous two Examples 12a and 12b is that the only energy provided to the distilled water and the solution 105 came from the combination of the sodium bulb 112 and the fixture 111.

Figure 74C:
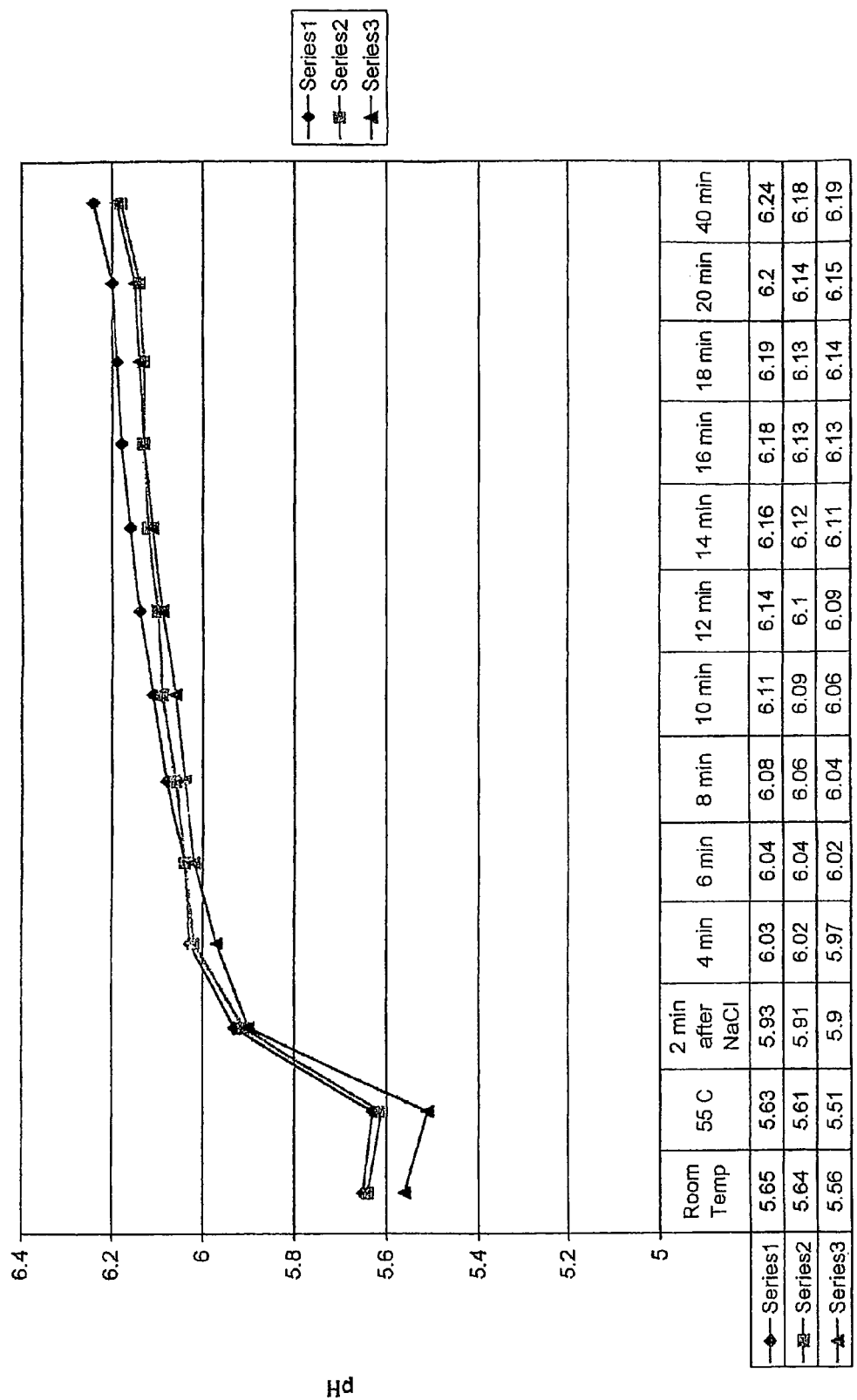
FIG. 74c is a graph of the experimental data which shows pH as a function of time and corresponds to the experimental set-up of Example 12c.

FIG. 74c shows the results of three (3) separate experiments corresponding to the experimental apparatus of FIG. 72. The plotted data show the change in measured pH of the solution 105 as a function of time at a temperature of about 55° C. In particular, the pH of the distilled water alone was first measured at room temperature and then measured at about 55° C., and thereafter the pH of the solution 105 was measured about every two minutes after the addition and dissolution of sodium chloride. The time measurements were all at intervals of about two minutes.

The AR20 meter 107, which used the pH electrode 109 (the electrode being shown in more detail in FIG. 73) were together calibrated by using two different buffer solutions. The first buffer solution had a pH of 4.00+/−0.01 at about 25° C., and was a solution of potassium bipthalate. A second buffer solution had a pH of 7.00+/−0.01 at about 25° C., and was a solution of potassium phosphate monobasic-sodium hydroxide. Both solutions were 0.05 Molar, both were certified and both were obtained from Fisher Chemicals. The use of these buffer solutions was intended to insure accuracy of the pH readings from the pH electrode.

All experimental conditions described in the Example occurred in the presence of standard fluorescent lighting. The fluorescent lamps were Sylvania Cool White Deluxe Fluorescent Lamps, 75 watts and were each about eight (8) feet (about 2.4 meters) long. The lamps were suspended in pairs approximately 3.5 meters above the laboratory counter on which the experimental set-up was located. There were six (6) of lamps present in a room which measured approximately 25 feet by 40 feet (about 7.6 meters×12.1 meters).

Example 12d

FIG. 71 is a schematic of the experimental apparatus used to generate measured pH information at about 55° C. as a function of time. In this Example 12d, a ring stand 113 was positioned adjacent to the ring stand 102 such that a high pressure sodium light 112 contained within a housing 111, and surrounded by an aluminum foil tube 110 permitted light emitted from the bulb 112 to be transmitted through the aluminum foil tube 110 and become incident upon a side of the beaker 104. The ring stand 113 was positioned such that the end of the aluminum tube 110 adjacent to the side of the beaker 104 was about ½ inch to ¾ inch (about 2.0 cm to about 2.5 cm) away from the side of the beaker 104. The tube 110 measured about eight (8) inches (about 2.4 meters) long and was about 3½ inches (about 8.5 cm) in diameter. The top end of the sodium light bulb 112 was about five (5) inches (about 12.5 cm) from the end of the tube 110. In this Example 12d, the sodium light bulb 112 was actuated about 40 minutes before heating the water with the Bunsen burner and irradiated the solution continuously throughout the pH measurements. The light fixture 111 was fixed to the ring stand 113 by use of a chain clamp 114.

The Bunsen burner 101 was supplied with propane fuel from the fuel source 100 via a flexible rubber tube 115. The flame from the Bunsen burner 101 was caused to be incident upon a cast iron hot plate 103 which was attached to a ring stand 102. A 1000 ml Pyrex™ cylindrical beaker 104 was placed on top of the cast iron hot plate 103. The beaker 104 contained approximately 800 ml of distilled water obtained from American Fare. An AR20 pH/mV/° C./Conductivity meter 107 from Accumet Research communicated with the 800 ml of distilled water and later with the solution 105 through a temperature probe 108 and a pH electrode 109. More details of the pH electrode can be seen in FIG. 73. The pH meter was elevated to a convenient height by the use of a support structure 106.

The pH of the distilled water in the beaker 104 was first measured at room temperature before actuating the sodium lamp. After the 40 minute Na lamp conditioning, the water was then heated to about 55° C. in about 15-20 minutes by use of the Bunsen burner heating the hot plate 103. The water temperature was monitored by the Accumet meter 107. Once a temperature of about 55° C. was obtained, about 50 grams of sodium chloride (certified A. C. S. and discussed above herein), were added to the 800 ml of distilled water in the beaker 104 to form the solution 105. The sodium chloride was stirred into the 800 ml of distilled water by use of glass stirring rod and complete dissolution of the sodium chloride occurred within about 30-45 seconds. The temperature of the solution 105 was reduced by approximately ½ to 1° C., but was quickly brought back to about 55° C. by the Bunsen burner 101 and cast iron hot plate 103 in a matter of a few seconds. The electrodes 108 and 109 were temporarily removed from the solution 105 to permit the stirring, mixing and dissolution of the sodium chloride into the distilled water. However, the electrodes 108 and 109 were immediately reinserted upon completion of the stirring.

Figure 74D:
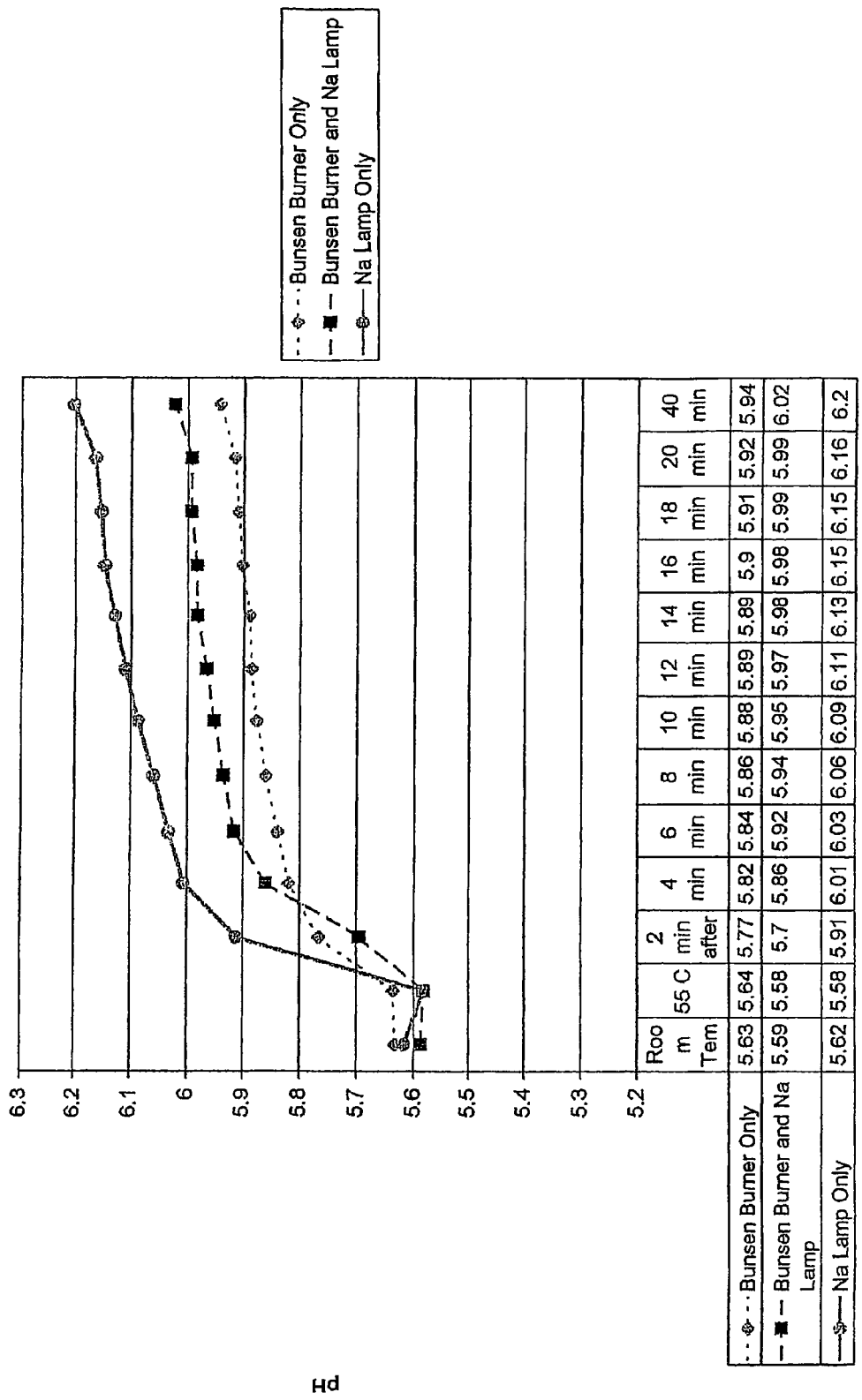
FIG. 74d is a graph which shows the averages of the three (3) different experimental conditions of experiments 12a, 12b and 12c, all superimposed on a single plot.
Figure 74E:
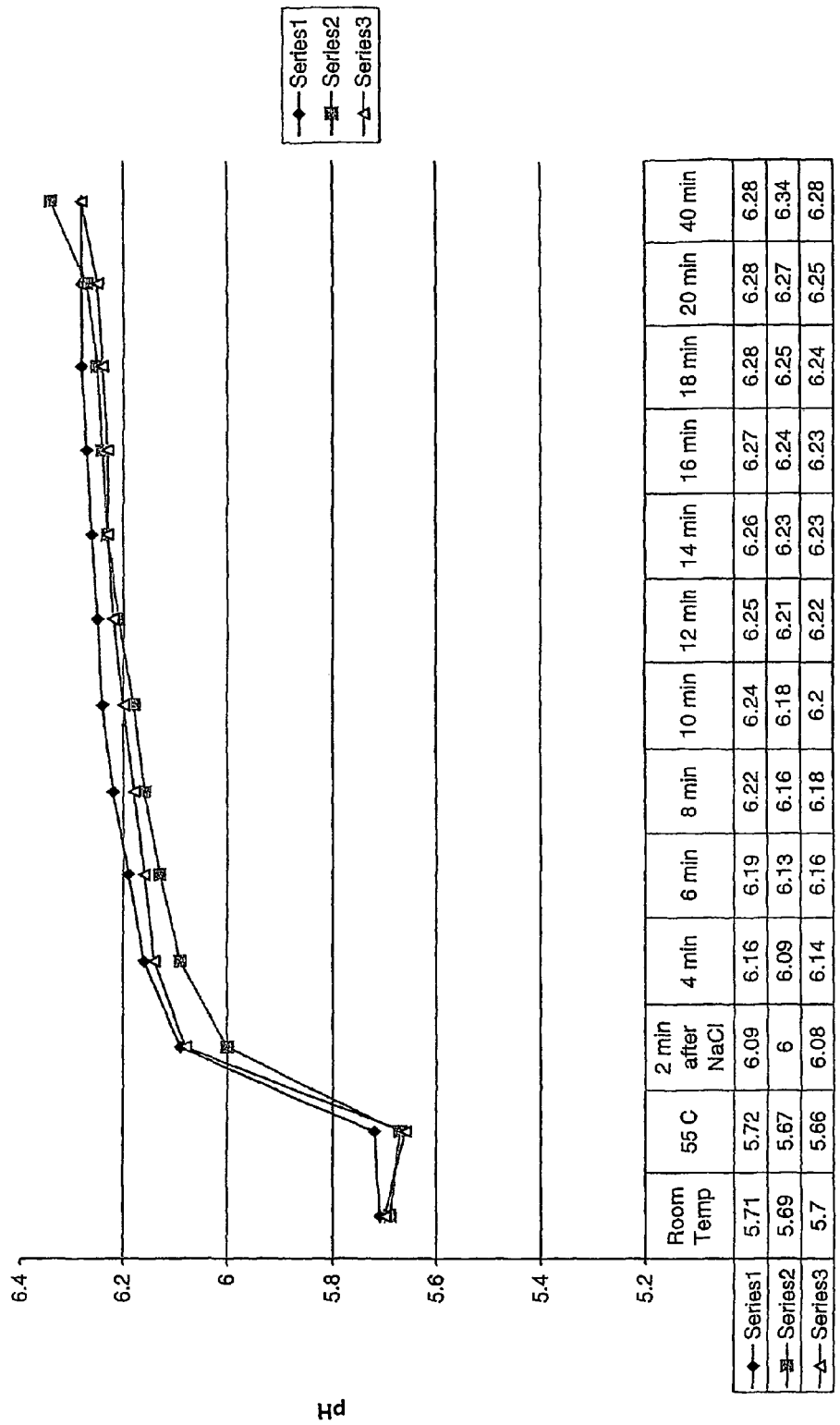
FIG. 74e is a graph of the experimental data which shows pH as a function of time and corresponds to the experimental set-up of Example 12d.

FIG. 74e shows the results of three (3) separate experiments corresponding to the experimental apparatus of FIG. 71. The plotted data show the change in measured pH of the solution 105 as a function of time at a temperature of about 55° C. In particular, the pH of the distilled water alone was first measured at room temperature and then measured at about 55° C., and thereafter measured about every two minutes after the addition and dissolution of sodium chloride and the activation of the high pressure sodium light 112. The time measurements were all at intervals of about two minutes.

The AR20 meter 107, which used the pH electrode 109 (the electrode being shown in more detail in FIG. 73) were together calibrated by using two different buffer solutions. The first buffer solution had a pH of 4.00+/−0.01 at about 25° C., and was a solution of potassium bipthalate. A second buffer solution had a pH of 7.00+/−0.01 at about 25° C., and was a solution of potassium phosphate monobasic-sodium hydroxide. Both solutions were 0.05 Molar, both were certified and both were obtained from Fisher Chemicals. The use of these buffer solutions was intended to insure accuracy of the pH readings from the pH electrode.

All experimental conditions described in the Example occurred in the presence of standard fluorescent lighting. The fluorescent lamps were Sylvania Cool White Deluxe Fluorescent Lamps, 75 watts and were each about eight (8) feet (about 2.4 meters) long. The lamps were suspended in pairs approximately 3.5 feet above the laboratory counter on which the experimental set-up was located. There were six (6) pairs of lamps present in a room which measured approximately 25 feet by 40 feet (about 2.6 meters×12.1 meters).

Example 12e

FIG. 71 is a schematic of the experimental apparatus used to generate measured pH information at about 55° C. as a function of time. In this Example 12e, a ring stand 113 was positioned adjacent to the ring stand 102 such that a high pressure sodium light 112 contained within a housing 111, and surrounded by an aluminum foil tube 110 permitted light emitted from the bulb 112 to be transmitted through the aluminum foil tube 110 and become incident upon a side of the beaker 104. The ring stand 113 was positioned such that the end of the aluminum tube 110 adjacent to the side of the beaker 104 was about ½ inch to ¾ inch (about 2.0 cm to about 2.5 cm) away from the side of the beaker 104. The tube 110 measured about eight (8) inches (about 2.4 cm) long and was about 3½ inches (about 8.5 cm) in diameter. The top end of the sodium light bulb 112 was about five (5) inches (about 12.5 cm) from the end of the tube 110. In this Example 12e, the sodium light bulb 112 was actuated about 40 minutes and then terminated, before heating the water with the Bunsen burner. The light fixture 111 was fixed to the ring stand 113 by use of a chain clamp 114.

The Bunsen burner 101 was supplied with propane fuel from the fuel source 100 via a flexible rubber tube 115. The flame from the Bunsen burner 101 was caused to be incident upon a cast iron hot plate 103 which was attached to a ring stand 102. A 1000 ml Pyrex™ cylindrical beaker 104 was placed on top of the cast iron hot plate 103. The beaker 104 contained approximately 800 ml of distilled water obtained from American Fare. An AR20 pH/mV/° C./Conductivity meter 107 from Accumet Research communicated with the 800 ml of distilled water and later with the solution 105 through a temperature probe 108 and a pH electrode 109. More details of the pH electrode can be seen in FIG. 73. The pH meter was elevated to a convenient height by the use of a support structure 106.

The pH of the distilled water in the beaker 104 was first measured at room temperature, before actuating the sodium lamp conditioning. After the 40 minutes of sodium lamp conditioning of the water, the water was then heated to about 55° C. in about 15-20 minutes by use of the Bunsen burner heating the hot plate 103. The water temperature was monitored by the Accumet meter 107. Once a temperature of about 55° C. was obtained, about 50 grams of sodium chloride (certified A. C. S. and discussed above herein), were added to the 800 ml of distilled water in the beaker 104 to form the solution 105. The sodium chloride was stirred into the 800 ml of distilled water by use of glass stirring rod and complete dissolution of the sodium chloride occurred within about 30-45 seconds. The temperature of the solution 105 was reduced by approximately ½ to 1° C., but was quickly brought back to about 55° C. by the Bunsen burner 101 and cast iron hot plate 103 in a matter of a few seconds. The electrodes 108 and 109 were temporarily removed from the solution 105 to permit the stirring, mixing and dissolution of the sodium chloride into the distilled water. However, the electrodes 108 and 109 were immediately reinserted upon completion of the stirring.

Figure 74F:
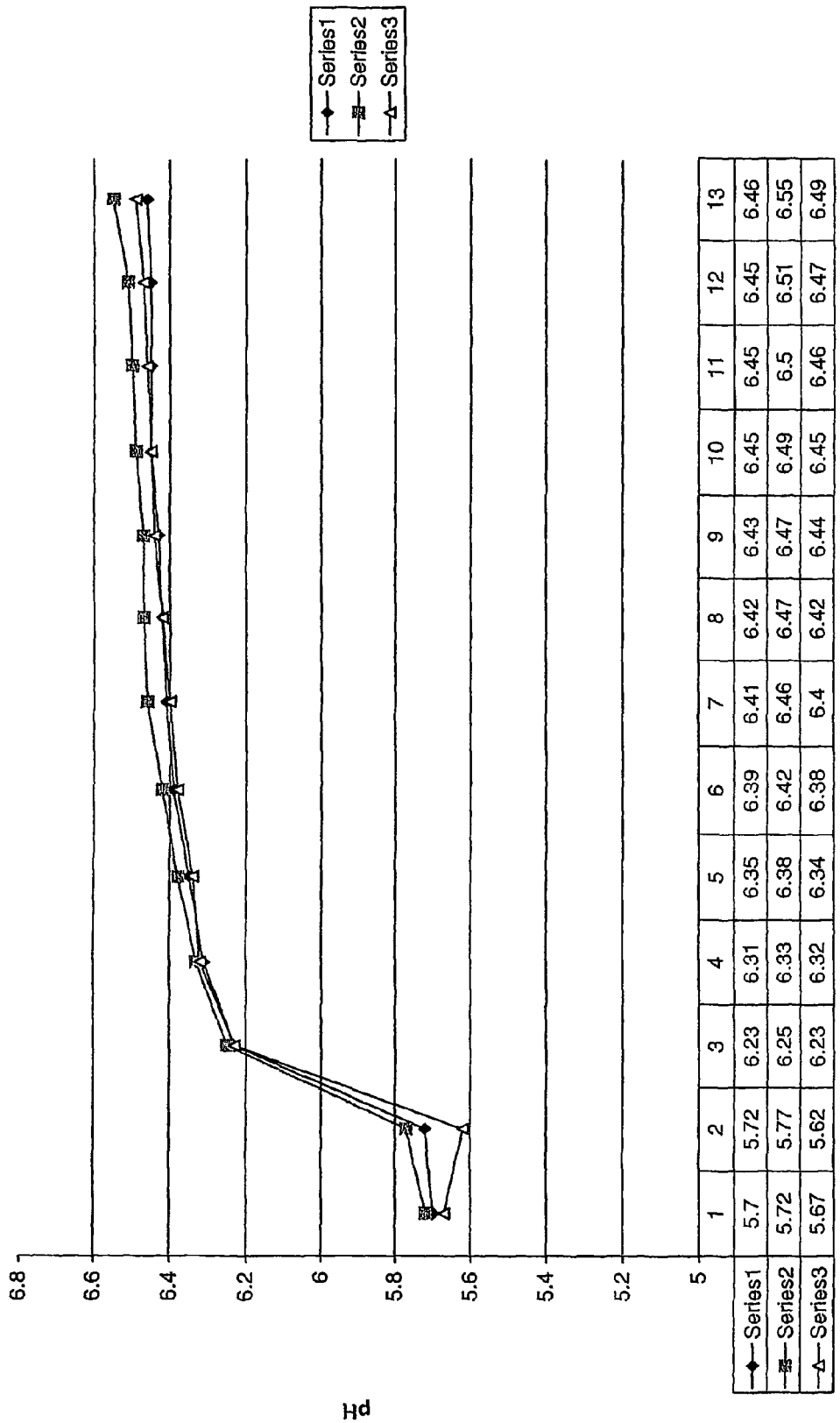
FIG. 74f is a graph of the experimental data which shows pH as a function of time and corresponds to the experimental set-up of Example 12e.

FIG. 74f shows the results of three (3) separate experiments corresponding to the experimental apparatus of FIG. 71. The plotted data show the change in measured pH of the solution 105 as a function of time at a temperature of about 55° C. In particular, the pH of the distilled water alone was first measured at room temperature and then measured at about 55° C., and thereafter measured about every two minutes after the addition and dissolution of sodium chloride and the activation of the high pressure sodium light 112. The time measurements were all at intervals of about two minutes.

Figure 74G:
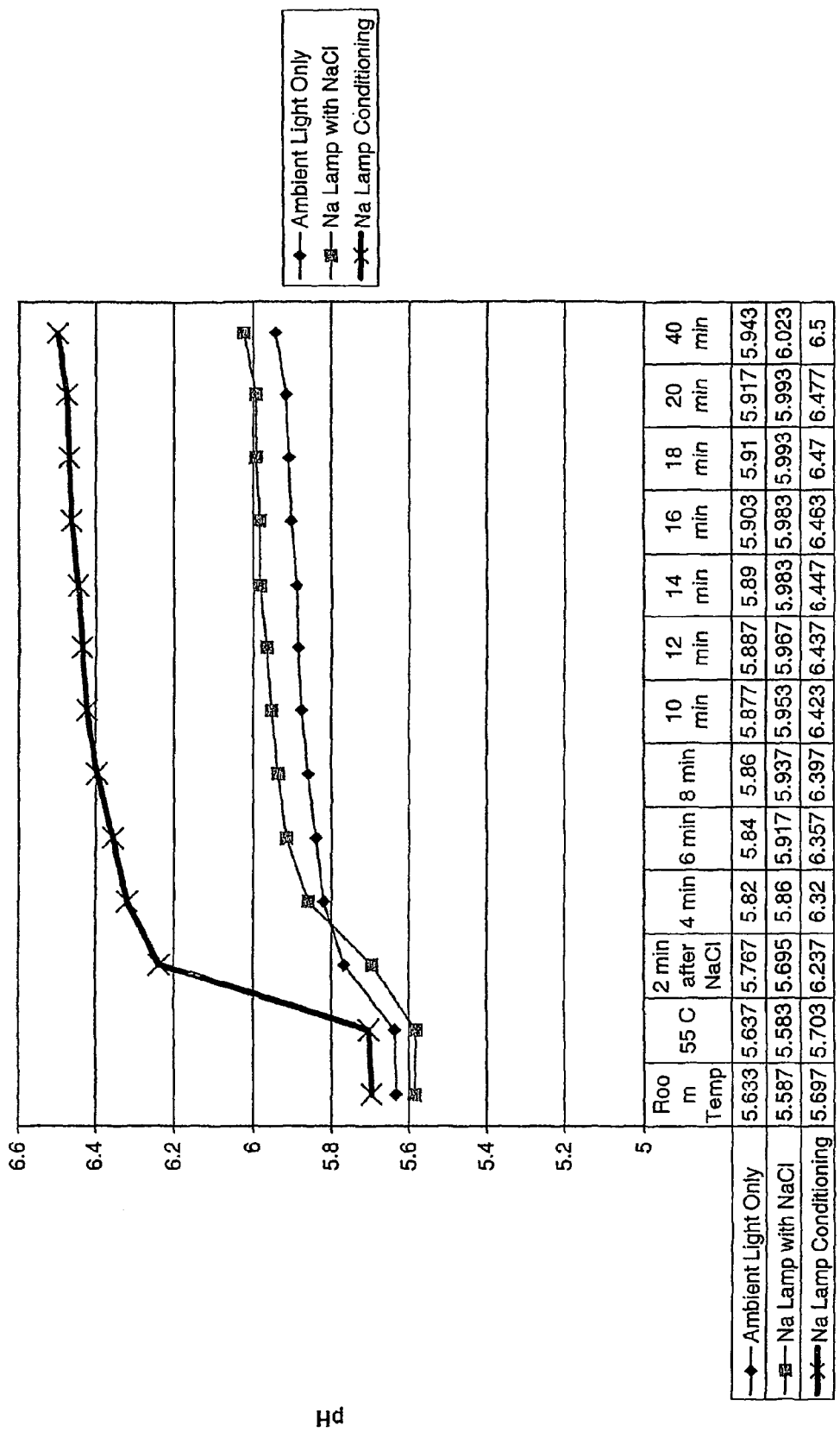
FIG. 74g is a graph which shows the averages of the three (3) different experimental conditions of experiments 12a, 12b and 12e, all superimposed on a single plot.

FIG. 74*g* shows the averages calculated from the data from each of the three (3) series of experiments from each of Examples 12a, 12b and 12e.

The AR20 meter 107, which used the pH electrode 109 (the electrode being shown in more detail in FIG. 73) were together calibrated by using two different buffer solutions. The first buffer solution had a pH of 4.00+/−0.01 at about 25° C., and was a solution of potassium bipthalate. A second buffer solution had a pH of about 7.00+/−0.01 at about 25° C., and was a solution of potassium phosphate monobasic-sodium hydroxide. Both solutions were 0.05 Molar, both were certified and both were obtained from Fisher Chemicals. The use of these buffer solutions was intended to insure accuracy of the pH readings from the pH electrode.

All experimental conditions described in the Example occurred in the presence of standard fluorescent lighting. The fluorescent lamps were Sylvania Cool White Deluxe Fluorescent Lamps, 75 watts and were each about eight (8) feet (about 2.4 meters) long. The lamps were suspended in pairs approximately 3.5 meters above the laboratory counter on which the experimental set-up was located. There were six (6) pairs of lamps present in a room which measured approximately 25 feet by 40 feet (about 7.6 meters×12.1 meters).

Example 12f

FIG. 71 is a schematic of the experimental apparatus used to generate measured pH information at about 55° C. as a function of time. In this Example 12f, a ring stand 113 was positioned adjacent to the ring stand 102 such that a high pressure sodium light 112 contained within a housing 111, and surrounded by an aluminum foil tube 110 permitted light emitted from the bulb 112 to be transmitted through the aluminum foil tube 110 and become incident upon a side of the beaker 104. The ring stand 113 was positioned such that the end of the aluminum tube 110 adjacent to the side of the beaker 104 was about ½ inch to ¾ inch (about 1 cm to about 1.5 cm) away from the side of the beaker 104. The tube 110 measured about eight (8) inches long (about 20 cm) and was about 3½ inches (about 8.5 cm) in diameter. The top end of the sodium light bulb 112 was about five (5) inches (about 12.5 cm) from the end of the tube 110. In this Example 12f, the sodium light bulb 112 was actuated about 40 minutes, terminated, and pH was measured. The light fixture 111 was fixed to the ring stand 113 by use of a chain clamp 114.

The Bunsen burner 101 was supplied with propane fuel from the fuel source 100 via a flexible rubber tube 115. The flame from the Bunsen burner 101 was caused to be incident upon a cast iron hot plate 103 which was attached to a ring stand 102. A 1000 ml Pyrex™ cylindrical beaker 104 was placed on top of the cast iron hot plate 103. The beaker 104 contained approximately 800 ml of distilled water obtained from American Fare. An AR20 pH/mV/° C./Conductivity meter 107 from Accumet Research communicated with the 800 ml of distilled water and later with the solution 105 through a temperature probe 108 and a pH electrode 109. More details of the pH electrode can be seen in FIG. 73 The pH meter was elevated to a convenient height by the use of a support structure 106.

The pH of the distilled water in the beaker 104 was first measured at room temperature, before actuating the sodium lamp conditioning. After the 40 minutes sodium lamp conditioning of the water, the following time intervals elapsed before heating the water to 55° C. with the Bunsen burner: 1) 0 minutes; 2) 20 minutes; 3) 40 minutes; 4) 60 minutes; and 5) 120 minutes. The water was then heated to about 55° C. in about 5 minutes by use of the Bunsen burner heating the hot plate 103. The water temperature was monitored by the Accumet meter 107. Once a temperature of about 55° C. was obtained, about 50 grams of sodium chloride (certified A. C. S. and discussed above herein), were added to the 800 ml of distilled water in the beaker 104 to form the solution 105. The sodium chloride was stirred into the 800 ml of distilled water by use of glass stirring rod and complete dissolution of the sodium chloride occurred within about 30-45 seconds. The temperature of the solution 105 was reduced by approximately ½ to 1° C., but was quickly brought back to about 55° C. by the Bunsen burner 101 and cast iron hot plate 103 in a matter of a few seconds. The electrodes 108 and 109 were temporarily removed from the solution 105 to permit the stirring, mixing and dissolution of the sodium chloride into the distilled water. However, the electrodes 108 and 109 were immediately reinserted upon completion of the stirring.

Figure 74H:
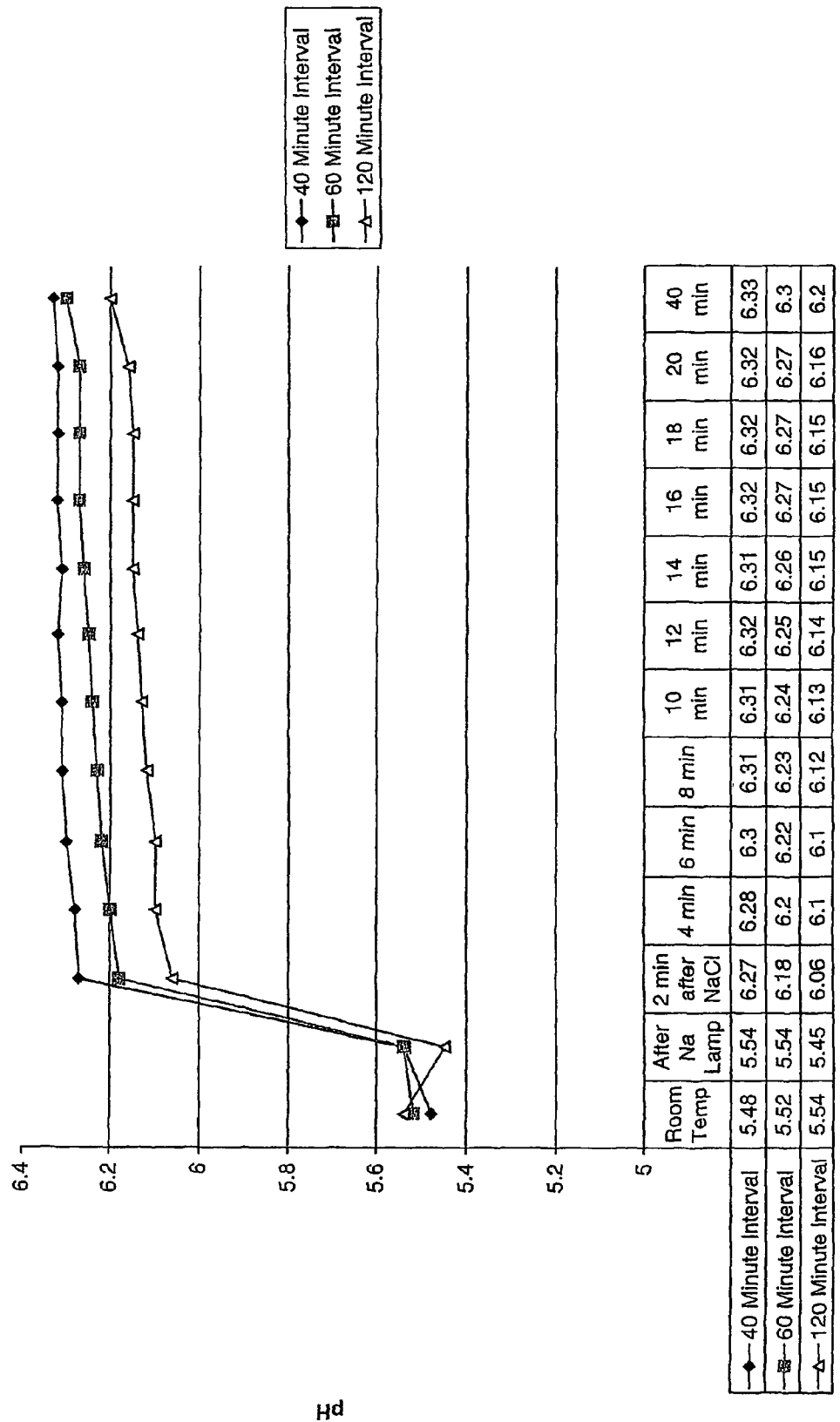
FIG. 74h is a graph which shows the results of three (3) separate experiments (#'s 3, 4 and 5) and represent decay curves generated by the experimental apparatus shown in FIG. 71.

FIG. 74*h* shows the results of three (3) separate experiments (#'s 3, 4, and 5) corresponding to the experimental apparatus of FIG. 71, representing decay curves for the Na lamp conditioning effect in water. The plotted data show the change in measured pH of the solution 105 as a function of time at a temperature of about 55° C. In particular, the pH of the distilled water alone was first measured at room temperature and then measured when the sodium lamp was terminated, and thereafter measured about every two minutes after the addition and dissolution of sodium chloride. The time measurements were all at intervals of about two (2) minutes for 20 minutes, with a final measurement at about 40 minutes.

Figure 74I:
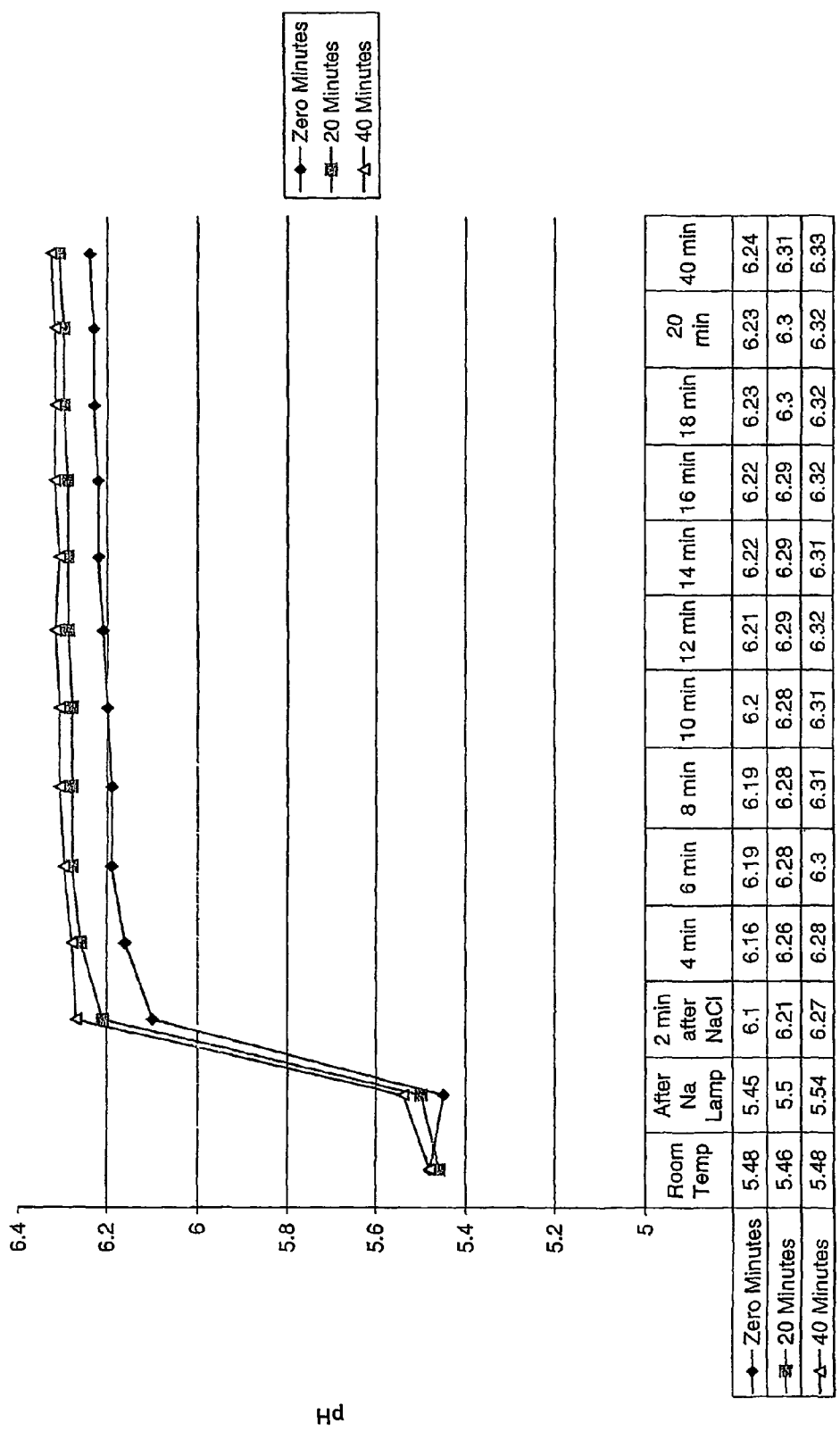
FIG. 74i is a graph which shows the results of three (3) separate experiments (#'s 1, 2 and 3) and represent activation curves generated by the experimental apparatus shown in FIG. 71.

FIG. 74*i* shows the results of three (3) separate experiments (#'s 1,2 and 3) corresponding to the experimental apparatus of FIG. 71, representing activation curves for the Na lamp conditioning effect in water.

The AR20 meter 107, which used the pH electrode 109 (the electrode being shown in more detail in FIG. 73) were together calibrated by using two different buffer solutions. The first buffer solution had a pH of 4.00+/−0.01 at about 25° C., and was a solution of potassium bipthalate. A second buffer solution had a pH of 7.00+/−0.01 at about 25° C., and was a solution of potassium phosphate monobasic-sodium hydroxide. Both solutions were 0.05 Molar, both were certified and both were obtained from Fisher Chemicals. The use of these buffer solutions was intended to insure accuracy of the pH readings from the pH electrode.

All experimental conditions described in the Example occurred in the presence of standard fluorescent lighting. The fluorescent lamps were Sylvania Cool White Deluxe Fluorescent Lamps, 75 watts and were each about eight (8) feet (about 2.4 meters) long. The lamps were suspended in pairs approximately 3.5 meters above the laboratory counter on which the experimental set-up was located. There were six (6) pairs of lamps present in a room which measured approximately 25 feet by 40 feet (about 2.6 meters×12.1 meters).

Discussion of Examples 12a, 12b, 12c, 12d, 12e and 12f

FIG. 74*d* shows the averages calculated from the data from each of the three (3) series of experiments from each of Examples 12a, 12b and 12c. The data show that the Bunsen burner—only heating corresponding to Example 12a and FIG. 70 had the smallest overall measured rise in pH after a period of time of approximately 4-6 minutes. The data generated from Example 12b, and corresponding to FIG. 71, showed an intermediate rise in measured pH with time after about 4-6 minutes. In Example 12b, the sodium spectral pattern was added only at the point when the solution 105 had attained a temperature of about 55° C.

The greatest overall increase in measured pH from a time of about 240 minutes was shown in the data corresponding to Example 12c, which corresponds to the experimental apparatus shown in FIG. 7. In this Example 12c, the distilled water in the beaker 104, was exposed to the sodium spectral pattern emitted from the sodium light bulb 112 for the longest amount of time (e.g., energy was provided to the distilled water and the solution 105 exclusively through the combination of the sodium light bulb 112 and the fixture 111) which was about 1¼-1½ hours to heat the water to about 55° C. and then for an additional 40 minutes while the pH measurements were made.

Accordingly, the data shown in FIG. 74d clearly show the effect of a sodium spectral pattern upon the measured pH of the sodium chloride/water solution 105, as measured by an AR20 meter from Accumet Research used in combination with a pH electrode 109 (as shown in more detail in FIG. 73).

FIG. 74g shows the averages calculated from the data from each of the three (3) series of experiments from each of Examples 12a, 12b and 12e. The data show that the Bunsen burner-only heating corresponding to Example 12a and FIG. 70 had the smallest overall measured rise in pH after a period of time of approximately 4-6 minutes. The data generated from Example 12b, and corresponding to FIG. 71, showed an intermediate rise in measured pH with time after about 4-6 minutes. In Example 12e, the water was conditioned by the sodium spectral pattern, after which it was heated to 55° C. and the NaCl was added and dissolved.

The greatest overall increase in measured pH from a time of about 2-40 minutes was shown in the data corresponding to Example 12e, which corresponds to the experimental apparatus shown in FIG. 71. In this Example 12e, the distilled water in the beaker 104, was exposed to the conditioning sodium spectral pattern emitted from the sodium light bulb 112 for about forty (40) minutes (e.g., conditioning energy was provided to the distilled water 105 exclusively with the sodium light bulb 112 for about 40 minutes).

Accordingly, the data shown in FIG. 74g clearly show the pH effect of a conditioning sodium spectral pattern upon distilled water, which is later used to make a sodium chloride/water solution 105, as measured by an AR20 meter from Accumet Research used in combination with a pH electrode 109 (as shown in more detail in FIG. 73).

FIG. 74h shows the experimental data from each of the three (3) experiments from Example 12f3, 12f4, and 12f5. The data (12f5) show that the 120 minute interval between conditioning of the distilled water and dissolution of the NaCl salt had the smallest overall measured rise in pH after a period of time of approximately 40 minutes. The data generated from Example 12f4, after about a 60 minute interval between conditioning of the distilled water and dissolution of the NaCl salt, showed an intermediate rise in measured pH with time after about 40 minutes. In Example 12f3, the water was conditioned by the sodium spectral pattern, and the interval between conditioning and dissolution of the NaCl salt was only about 40 minutes. Example 12f3 showed the greatest rise in pH.

Accordingly, the data shown in FIG. 74h clearly show a time-related decay effect of a conditioning sodium spectral pattern upon distilled water, which is later used to make a sodium chloride/water solution 105, as measured by an AR20 meter from Accumet Research used in combination with a pH electrode 109 (as shown in more detail in FIG. 73). The conditioning effects of a sodium spectral pattern upon distilled water remained in the water for a period of time approximately equal to the conditioning time. After an interval of 1.5 times the conditioning time, the conditioning effects of a sodium spectral pattern upon distilled water were beginning to decline. Finally, after an interval of 3.0 times the conditioning time, the conditioning effects of a sodium spectral pattern upon distilled water declined still further.

FIG. 74i shows the experimental data from each of the three (3) experiments from Example 12f1 12f2, and 121f3. The data (12f2 and 12f3) shows that the 20 and 40 minute intervals between conditioning of the distilled water and dissolution of the NaCl salt had the greatest overall measured rise in pH after a period of time of approximately 40 minutes. The data generated from Example 12f1, after a zero (0) minute interval between conditioning of the distilled water, and heating of the water and dissolution of the NaCl salt, showed a lower rise in measured pH with time after about 40 minutes.

Accordingly, the data shown in FIG. 74i clearly show a time-related activation effect of a conditioning sodium spectral pattern upon distilled water, which is later used to make a sodium chloride/water solution 105, as measured by an AR20 meter from Accumet Research used in combination with a pH electrode 109 (as shown in more detail in FIG. 73). The conditioning effects of a sodium spectral pattern upon distilled water reach their peak in the water after a period of time approximately equal to about 0.5-1.0 times the conditioning time.

In this Example, targeted spectral energies and environmental reaction conditions were used to affect phase change in solid and material properties of a liquid.

Example 12g

Chances in pH Due to Effects of Na Lamp Conditioned NaCl on pH

Sodium chloride (about 50 grams) was spread into a thin layer under a sodium lamp in an otherwise dark room overnight. The next day the salt was used in a pH experiment.

Figure 74J:
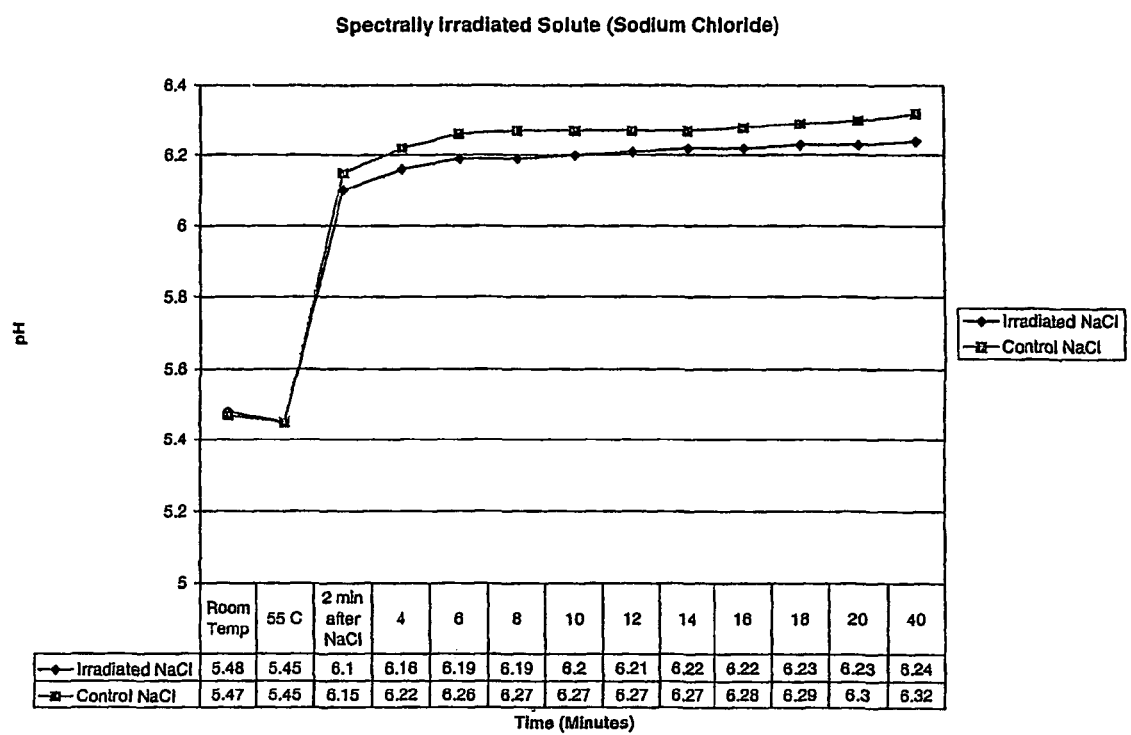
FIG. 74j is a graph which shows pH as a function of time for two sets of experiments where sodium chloride solid was conditioned prior to being dissolved in water.

Overhead fluorescent lighting was present continuously throughout both experiments. Water (about 800 ml) was placed in a 1000 ml beaker and the pH was measured. The water was next heated to about 55° C. and pH was measured again. The water temperature was maintained at about 55° C. for the remainder of the experiment. NaCl (about 50 grams) was added and stirred with a glass stir rod. Ten additional pH measurements were taken about pH was measured about 40 minutes after addition of the NaCl. FIG. 74j shows pH as a function of time for two sets of experiments where sodium chloride solid was conditioned prior to being dissolved in water.

One series of pH tests was performed on a solution made with the regular salt (which had not been conditioned), and one series of tests was performed on the solution made with the conditioned salt.

Results: The pH increased more when the salt had been conditioned with its own Na spectral energy pattern. This same effect was seen in other similar experiments. When significantly larger amounts of salt in a much thicker layer were irradiated with the same intensity, this effect was not nearly so pronounced, or was not seen at all.

In this Example, targeted spectral energies were used to change the material properties of a solid upon subsequent phase change into a liquid solution.

Example 13

Conductivity

For the following Example 13, the below-listed Equipment, materials and experimental procedures were utilized.
a) Equipment and Materials
Accumet Research AR20 ph/Conductivity Meter, calibrated with reference solutions prior to all experiments.
Traceable Conductivity Calibration Standard—Catalog #09-328-3
MicroMHOS/cm—1,004.
Microseimens/cm—1,004.
OmhS/cm—99.
PPM D. S.—669.
Accuracy @ 25° C. (+/−1.25%).
Size—16 oz (473 ml).
Analysis #—2713.
Conductivity probe # 13-620-155 with thermocouple.
Humbolt Bunsen burner with Bernozomatic propane fuel. Ring stand and Fisher cast iron ring and heating plate.
One or more sodium lamps, Stonco 70 Watt high-pressure sodium security wall light, fitted with a parabolic aluminum reflector directing the light away from the housing. The sodium bulb was a Type S62 lamp, 120V, 60 Hz, 1.5A made in Hungary by Jemanamjasond. One or more sodium lamps was/were mounted at various angles, and location(s) as specified in each experiment. Unless stated differently in the Example, the lamp was located at about 15 inches (about 38 cm) from the beakers or dishes to maintain substantially consistent intensities.
Sterile water—Bio Whittaker, contained in one liter clear, plastic bottles, processed by ultrafiltration, reverse osmosis, deionization, and distillation.

Example 13

Conductivity of Sodium Chloride Aqueous Solution

Procedures similar to those discussed in detail in Example 12 were followed with the following specific differences.

Water (about 800 ml) was placed in a 1000 ml beaker and room temperature measurements were obtained for conductivity (S/cm), dissolved solids (ppm), and resistance (kOhms), after allowing about 10 minutes for the probe to equilibrate to the water. The water was then heated to about 56.1° C., and measurements were repeated. Sodium chloride (about 0.01 gram) was added and stirred with a glass stir rod for about 30 seconds. Measurements of conductivity were obtained about every 2 minutes for about 20 minutes, and a final measurement was taken at about 40 minutes. Dissolved solids and resistance measurements were also obtained at about 4 minutes, at about 14 minutes, and at about 20 minutes after adding the salt.

The experimental apparatuses used to obtain data are shown in FIGS. 70 and 71. A conditioning probe was substituted for the pH probe of Example 12.

Four sets of parameters were evaluated, with three tests within each set:
1. Bunsen burner heating only (apparatus corresponding to FIG. 70);
2. Sodium lamp irradiation of water about 40 minutes before adding the salt (apparatus corresponding to FIG. 71);
3. Sodium lamp irradiation of water about 40 minutes after adding the salt (apparatus corresponding to FIG. 71);
4. Sodium lamp irradiation of water about 40 minutes before and after adding the salt (apparatus corresponding to FIG. 71).

Results: Conductivity appears to be increased with sodium lamp irradiation after addition of the sodium chloride.

FIG. 75*a* is a graph of the experimental data which shows conductivity as a function of time for three separate sets of Bunsen burner-only data.

FIG. 75*b* is a graph of the experimental data which shows conductivity as a function of temperature (two separate data points only) for Bunsen burner-only data.

FIG. 75*c* is a graph of the experimental data which shows conductivity as a function of time for three separate sets of Bunsen burner-only data, the plot beginning with the data point generated two minutes after sodium chloride was added to the water.

Figure 75D:
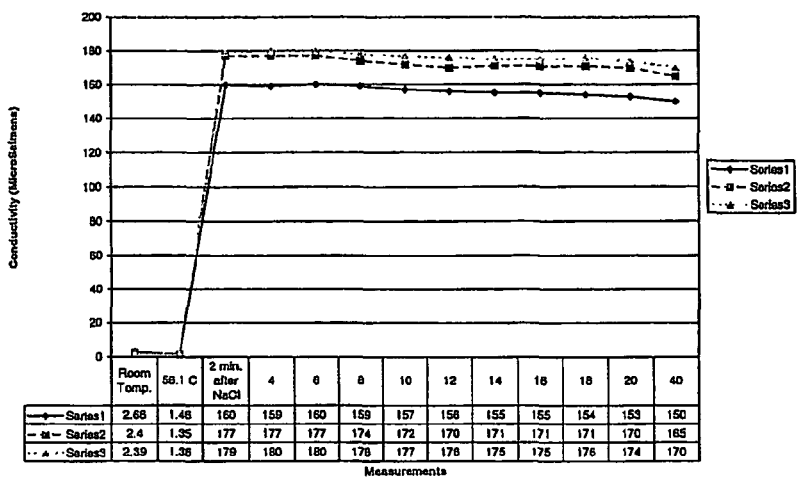
FIG. 75d is a graph of the experimental data which shows conductivity as a function of time for three separate sets of data corresponding to the water being conditioned by the sodium lamp for about 40 minutes before the sodium chloride was dissolved therein.

FIG. 75*d* is a graph of the experimental data which shows conductivity as a function of time for three separate sets of data corresponding to the water being conditioned by the sodium lamp for about 40 minutes before the sodium chloride was dissolved therein.

Figure 75E:
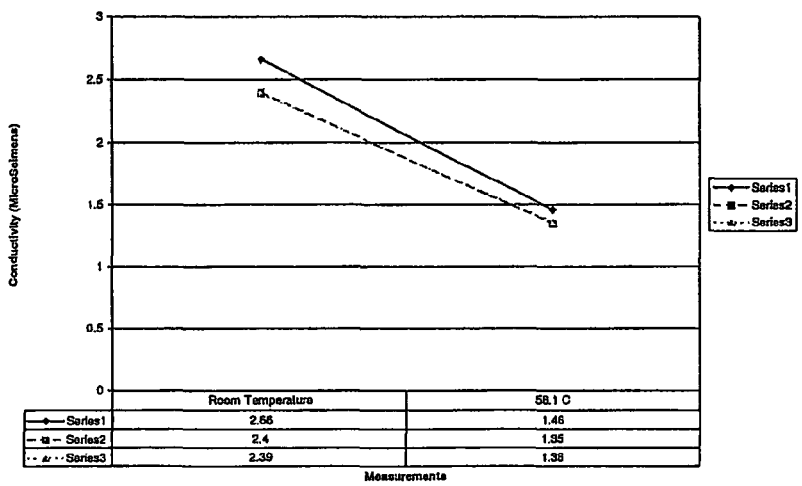
FIG. 75e is a graph of the experimental data which shows conductivity as a function of temperature (two separate data points only), corresponding to the water being conditioned by the sodium lamp for about 40 minutes before the sodium chloride was dissolved therein.

FIG. 75*e* is a graph of the experimental data which shows conductivity as a function of temperature (two separate data points only), corresponding to the water being conditioned by the sodium lamp for about 40 minutes before the sodium chloride was dissolved therein.

Figure 75F:
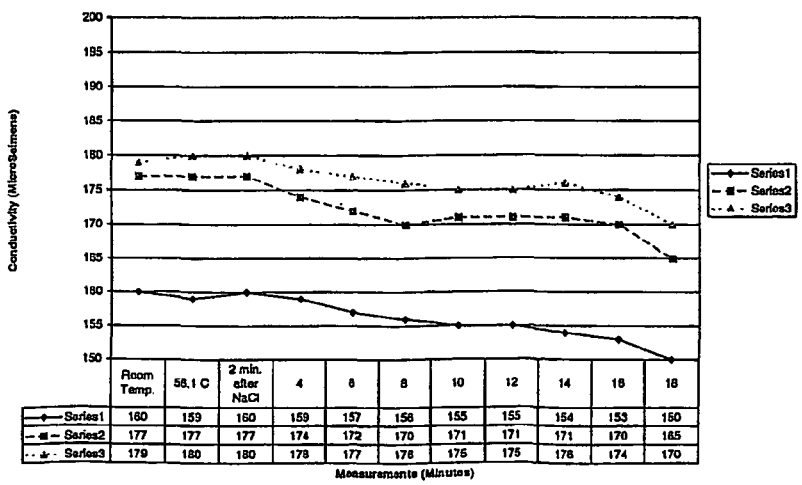
FIG. 75f is a graph of the experimental data which shows conductivity as a function of time for three separate sets of data corresponding to the water being conditioned by the sodium lamp for about 40 minutes before the sodium chloride was dissolved therein.

FIG. 75*f* is a graph of the experimental data which shows conductivity as a function of time for three separate sets of data corresponding to the water being conditioned by the sodium lamp for about 40 minutes before the sodium chloride was dissolved therein.

Figure 75G:
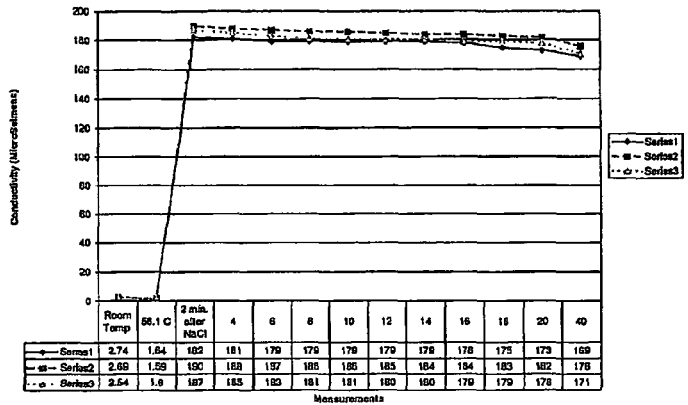
FIG. 75g is a graph of the experimental data which shows conductivity as a function of time for three separate sets of data corresponding to the solution of sodium chloride and water being irradiated with a spectral energy pattern of a sodium lamp beginning when the sodium chloride was added to the water.

FIG. 75*g* is a graph of the experimental data which shows conductivity as a function of time for three separate sets of data corresponding to the solution of sodium chloride and water being irradiated with a spectral energy pattern of a sodium lamp beginning when the sodium chloride was added to the water.

Figure 75H:
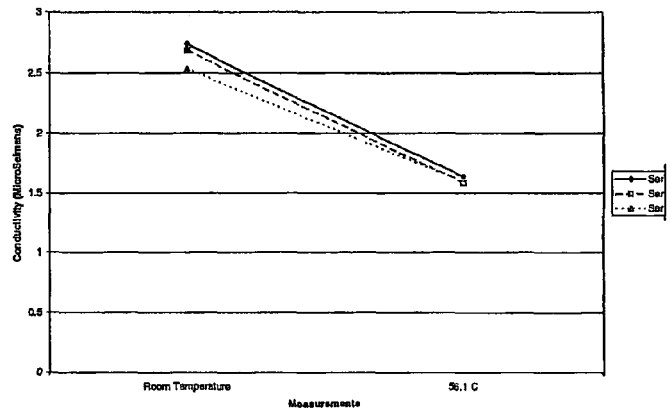
FIG. 75h is a graph of the experimental data which shows conductivity as a function of temperature (two separate data points only) corresponding to the solution of sodium chloride and water being irradiated with a spectral energy pattern of a sodium lamp beginning when the sodium chloride was added to the water.

FIG. 75*h* is a graph of the experimental data which shows conductivity as a function of temperature (two separate data points only) corresponding to the solution of sodium chloride and water being irradiated with a spectral energy pattern of a sodium lamp beginning when the sodium chloride was added to the water.

Figure 75I:
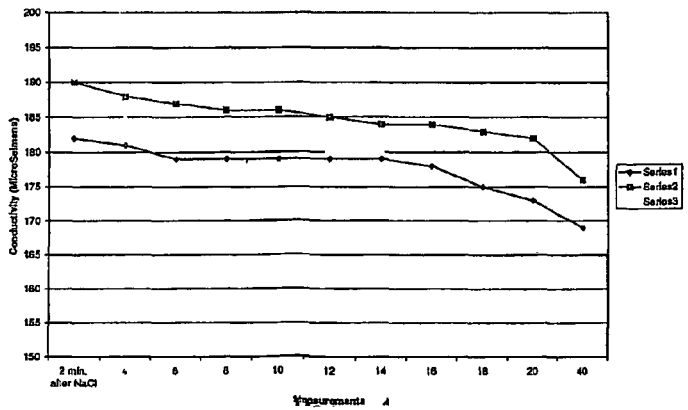
FIG. 75i is a graph of the experimental data which shows conductivity as a function of time for three separate sets of data corresponding to the solution of sodium chloride and water being irradiated with a spectral energy pattern of a sodium lamp beginning when the sodium chloride was added to the water.

FIG. 75*i* is a graph of the experimental data which shows conductivity as a function of time for three separate sets of data corresponding to the solution of sodium chloride and water being irradiated with a spectral energy pattern of a sodium lamp beginning when the sodium chloride was added to the water.

Figure 75J:
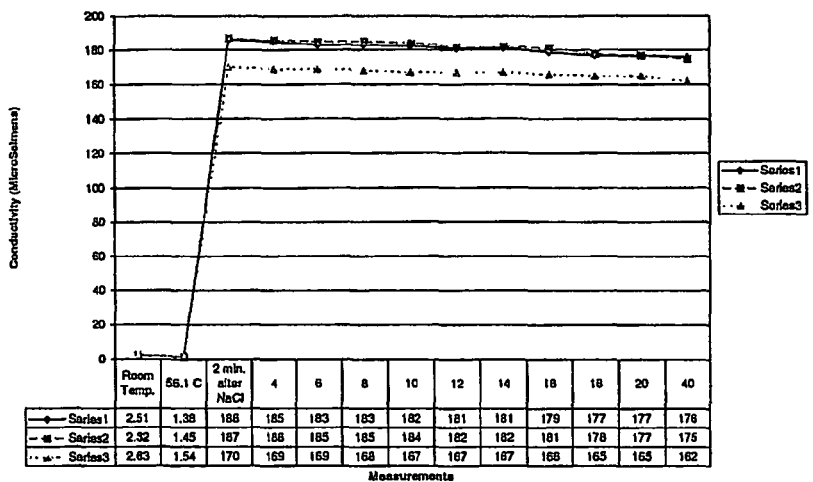
FIG. 75j is a graph of the experimental data which shows conductivity as a function of time for three separate sets of data corresponding to the water being conditioned by the sodium lamp spectral conditioning pattern for about 40 minutes before the sodium chloride was added to the water; and continually irradiating the water with the sodium light spectral pattern while sodium chloride is added thereto and remaining on while all conductivity measurements were taken.

FIG. 75*j* is a graph of the experimental data which shows conductivity as a function of time for three separate sets of data corresponding to the water being conditioned by the sodium lamp spectral conditioning pattern for about 40 minutes before the sodium chloride was added to the water; and continually irradiating the water with the sodium light spectral pattern while sodium chloride is added thereto and remaining on while all conductivity measurements were taken.

Figure 75K:
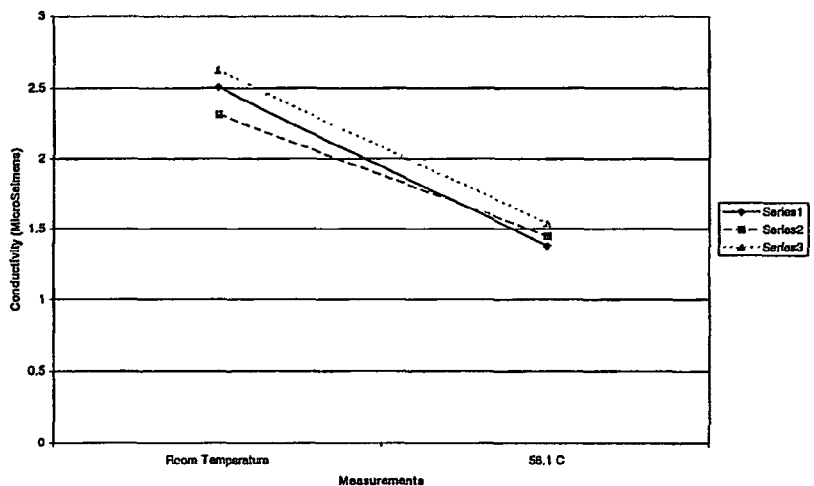
FIG. 75k is a graph of the experimental data which shows conductivity as a function of temperature (two separate data points only) for three sets of data, corresponding to the water being conditioned by the sodium lamp spectral conditioning pattern for about 40 minutes before the sodium chloride was dissolved; and continually irradiating the water with the sodium light spectral pattern while sodium chloride is added thereto and remaining on while all conductivity measurements were taken.

FIG. 75*k* is a graph of the experimental data which shows conductivity as a function of temperature (two separate data points only) for three sets of data, corresponding to the water being conditioned by the sodium lamp spectral conditioning pattern for about 40 minutes before the sodium chloride was dissolved; and continually irradiating the water with the sodium light spectral pattern while sodium chloride is added thereto and remaining on while all conductivity measurements were taken.

Figure 75L:
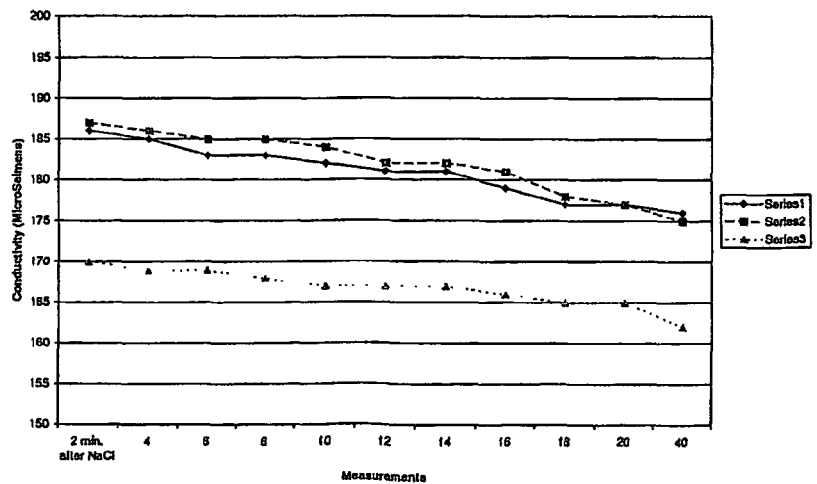
FIG. 75l is a graph of the experimental data which shows conductivity as a function of time for three separate sets of data corresponding to the water being conditioned by the sodium lamp spectral conditioning pattern for about 40 minutes before the sodium chloride was dissolved; and continually irradiating the water with the sodium light spectral pattern while sodium chloride is added thereto and remaining on while all conductivity measurements were taken.

FIG. 75*l* is a graph of the experimental data which shows conductivity as a function of time for three separate sets of data corresponding to the water being conditioned by the sodium lamp spectral conditioning pattern for about 40 minutes before the sodium chloride was dissolved; and continually irradiating the water with the sodium light spectral pattern while sodium chloride is added thereto and remaining on while all conductivity measurements were taken.

Figure 75M:
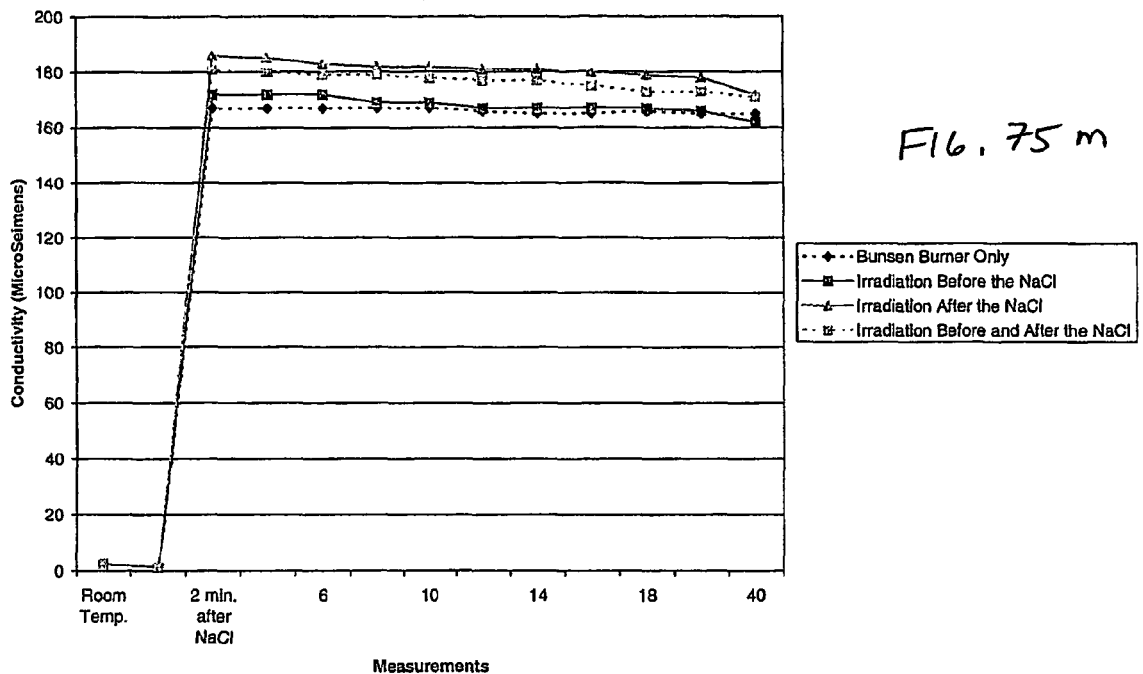
FIG. 75m is a graph of the experimental data which superimposes averages from the data in FIGS. 75a, 75d, 75g and 75j.

FIG. 75*m* is a graph of the experimental data which superimposes averages from the data in FIGS. 75*a*, 75*d*, 75*g* and 75*j*.

Figure 75N:
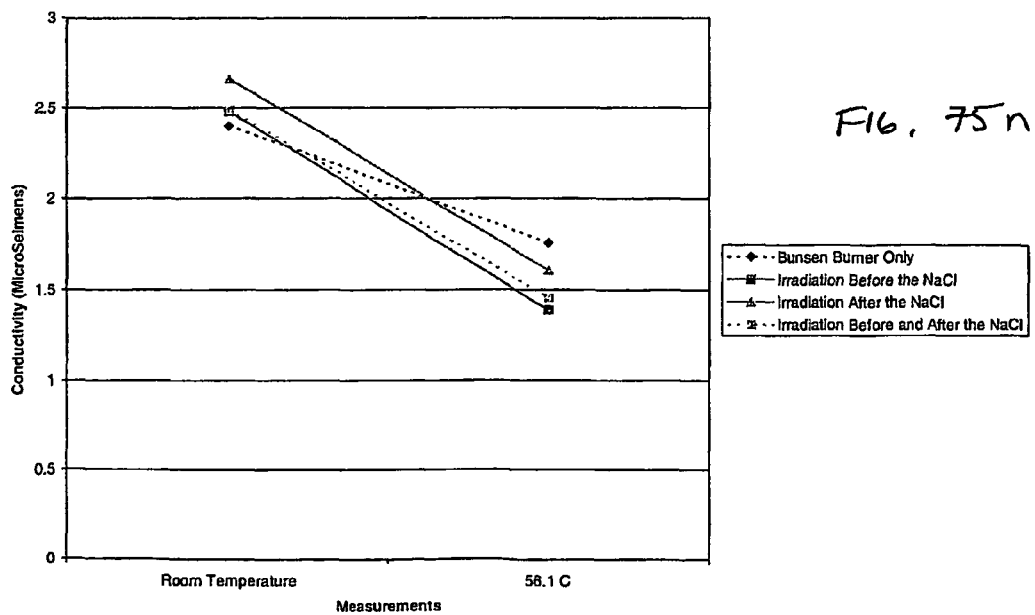
FIG. 75n is a graph of the experimental data which superimposes averages from the data in FIGS. 75b, 75e, 75h and 75k.

FIG. 75*n* is a graph of the experimental data which superimposes averages from the data in FIGS. 75*b*, 75*e*, 75*h* and 75*k*.

Figure 75O:
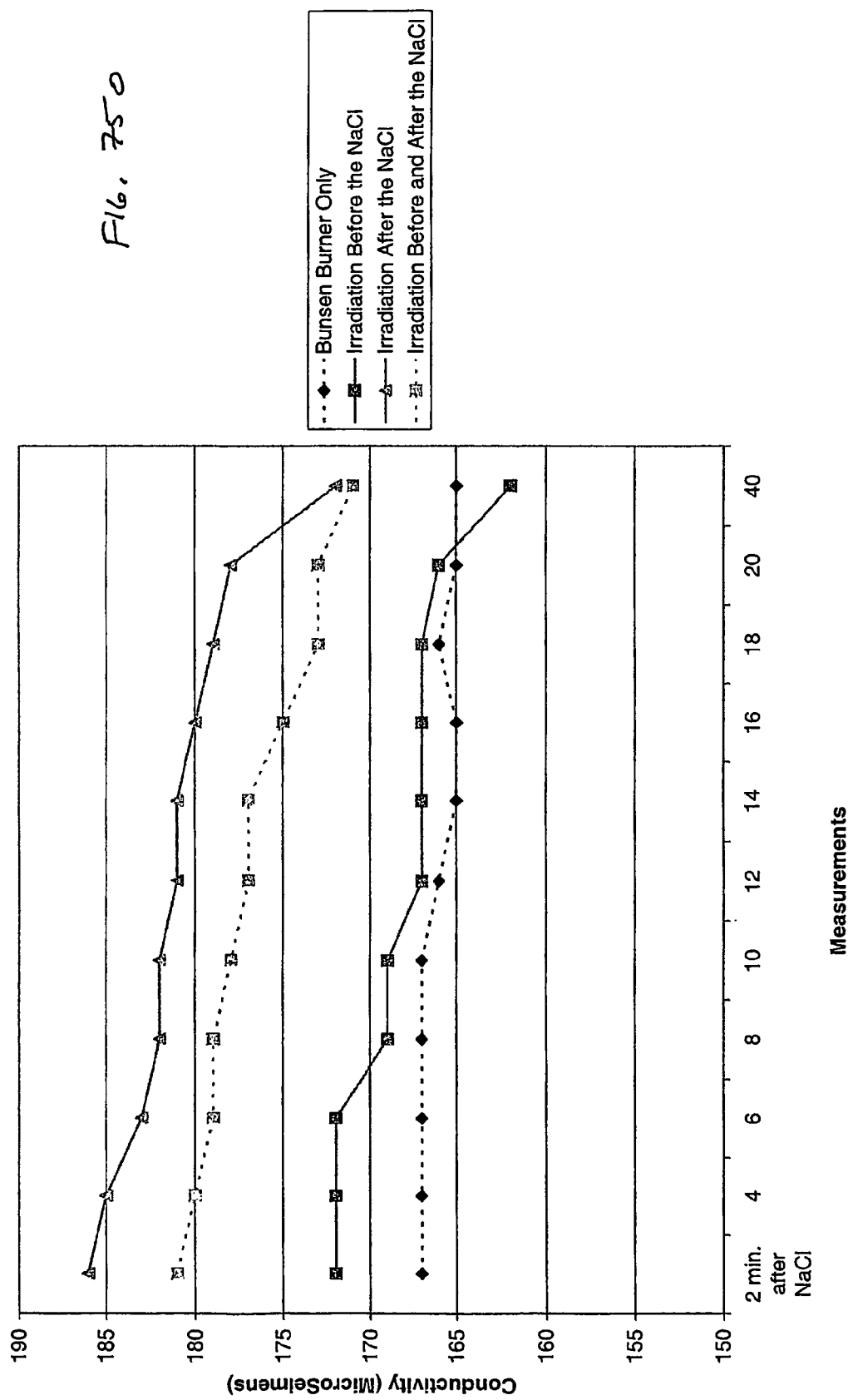
FIG. 75o is a graph of the experimental data which superimposes averages from the data in FIGS. 75c, 75f, 75i and 75j.

FIG. 75*o* is a graph of the experimental data which superimposes averages from the data in FIGS. 75*c*, 75*f*, 75*i* and 75*j*.

In this Example, targeted spectral patterns and/or targeted spectral conditioning patterns were used to change the material properties of a solvent and/or solvent/solute system.

Example 14

Batteries

Figure 76:
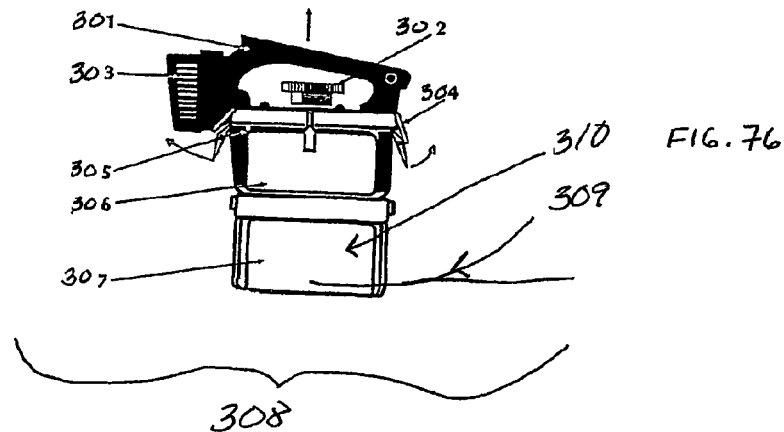
FIG. 76 shows a schematic of a flashlight battery assembly used in Example 14.

For the following Examples 14a and 14b the following Equipment, materials and experimental procedures were utilized.
a) Equipment and Materials
 Sterile water—Bio Whittaker, contained in one liter clear, plastic bottles, processed by ultrafiltration, reverse osmosis, deionization, and distillation.
 Sodium Chloride, Fisher Chemicals, Lot No. 025149, packaged in gray plastic 3 Kg bottles. The sodium chloride, in crystalline form, is characterized as follows:
 Sodium Chloride: Certified A.C.S.
 Certificate of Lot Analysis
  Barium (13a) (about 0.001%)—P.T.
  Bromide (Br)—0.01%
  Calcium (Ca)—0.0007%
  Chlorate and Nitrate (as $NO_3$)—0.0006%
  Heavy Metals (as Pb)—0.4 ppm
  Insoluble Matter—0.001%
  Iodide (I)—0.0004%
  Iron (Fe)—0.4 ppm
  Magnesium (Mg)—0.0003%
  Nitrogen Compounds (as N)—0.0003%
  pH of 5% solution at 25° C.-6.8
  Phosphate ($PO_3$)—1 ppm
  Potassium (K)—0.001%
  Sulfate ($SO_4$)—0.003%
 Battery anodes by Sovietski; #150400; Magnesium and aluminum
 Battery/flashlight assembly:Aqueous sodium chloride (NaCl) electrolyte powered flashlight by Sovietski; #150400; double cathode/anode configuration
 Sodium (Na) Lamp, Stonco 70 Watt High Pressure sodium security wall light fitted with a parabolic aluminum reflector directing the light away from the housing, oriented horizontally.
 Receptacle, clear plastic box 7.5×5.75×3.75 inches
 American Fare distilled water, in one gallon semi-opaque colorless plastic jugs, processed by distillation, microfiltration and ozonation. Source: Greenville Municipal water supply, Greenville, Tenn. Stored in shielded, darkened room, in cardboard boxes.
 Grounded, dark enclosure: 6 ft.×3 ft×1½ ft metal cabinets. (24 gauge metal); flat black paint inside
 Load box Ammeter/Voltmeter (Fuel Cell Store) Heliocentris #DBGR29126811 with 10 ohm load
 FisherBrand Dual Channel Thermometer with Offset
 2000 ml Pyrex beaker Example 14a Enhanced Sodium Chloride Battery Current with Sodium Spectral Irradiation FIG. 76 shows an aqueous NaCl battery/flashlight assembly 308. Two assemblies 308 were placed side-by-side in a grounded, dark enclosure. Electrolyte 310 was distilled water (about 1700 ml) and NaCl (about 97 g) mixed at the same time at room temperature in 2000 ml Pyrex beakers. Thermometer wires 309 were placed on the bottom center of the electrolyte receptacles 307. FIG. 77 shows Sodium lamp 112 in a housing 111 with an aluminum foil cylinder 110 that was positioned to the outside of each electrolyte receptacle 307 allowing delivery of sodium spectral irradiation through the outside of the receptacle 307, into the electrolyte solution 310, and onto the outside of the anode plate 306.

The electrolyte receptacles 307 were filled with electrolyte 310, the anode/cathode assembly 301 was lowered into the electrolyte 310, and the flashlights 303 of each assembly 308 were turned on throughout the experiment. Initial measurements of current (mAmps) and temperature were performed and then measured again every 40 minutes.

The sodium lamp was cycled as follows:
1. Off first 40 minutes;
2. On second 40 minutes;
3. Off third 40 minutes;
4. On fourth 40 minutes.

Figure 78:
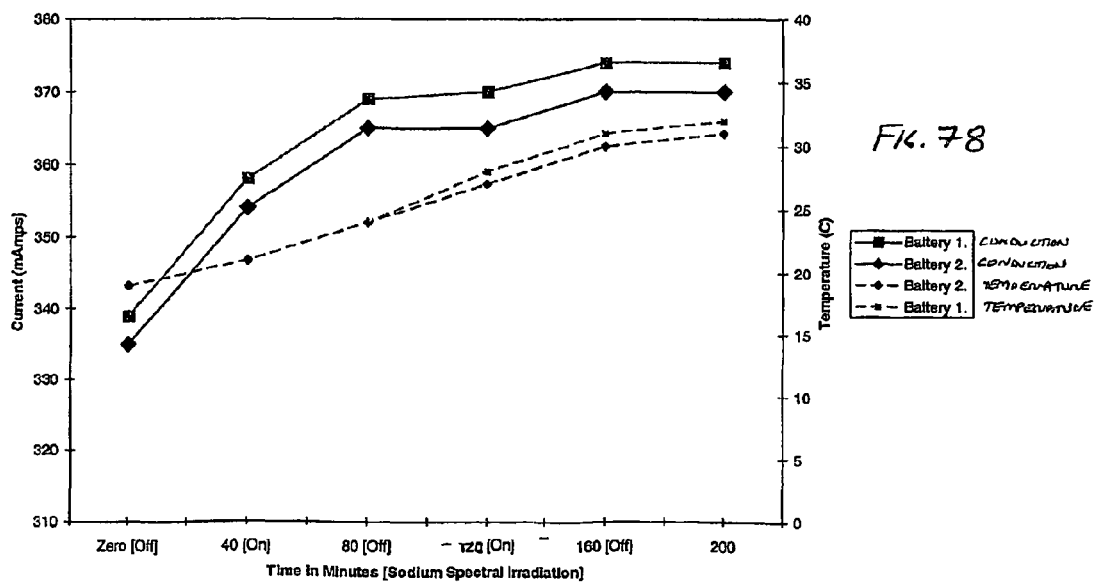

Results: As shown in FIG. 78, the standard initial current increase occurred with the sodium lamp turned off. The current increase continued with the sodium lamp turned on during the second 40 minutes. When the sodium lamp was turned off at 80 minutes however, the current stopped increasing and stayed essentially the same to 120 minutes. When the sodium lamp was turned on again at 120 minutes, the current again increased. Finally, when the sodium lamp was turned the current remained the same.

These current characteristics were not related to temperature. Although the temperature increased between 80 and 120 minutes and between 160 and 200 minutes, when the sodium lamp was off, the current did not increase, suggesting that current increase was not due to an increase in temperature.

Example 14b

Enhanced Sodium Chloride Battery Current With Sodium Spectral Irradiation

FIG. 76 shows an aqueous NaCl battery/flashlight assembly 308. Two assemblies 308 were placed side-by-side in a grounded, dark enclosure. Electrolyte 310 was distilled water (about 1700 ml) and NaCl (about 97 g) mixed at the same time at room temperature in 2000 ml Pyrex beakers. FIG. 77 shows Sodium lamp 112 in a housing 111 with an aluminum foil cylinder 110 that was positioned to the outside of each electrolyte receptacle 307 allowing delivery of sodium spectral irradiation through the outside of the receptacle 307, into the electrolyte solution 310, and onto the outside of the anode plate 306.

The electrolyte receptacles 307 were filled with electrolyte 310, the anode/cathode assembly 301 was lowered into the electrolyte 310, and the flashlights 303 of each assembly 308 were turned on throughout the experiment. Initial measurements of current (mAmps) and temperature were performed and then measured again every 10 minutes.

T sodium lamp was cycled as follows:
1. Off 0 40 minutes;
2. Off 40-70 minutes;
2. On 70-110 minutes;
3. Off 110-150 minutes;
4. On 150-190 minutes.

Figure 79:
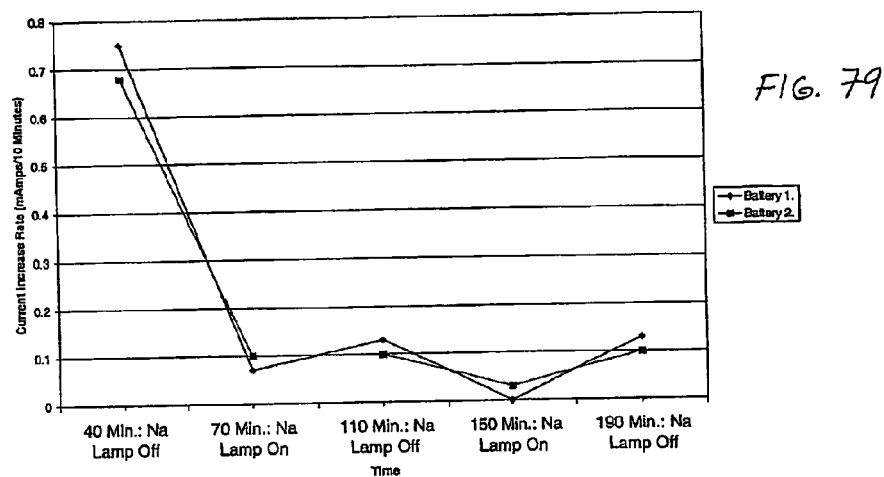
FIG. 79 shows a graph of the change in current as a function of time.

Results: As shown in FIG. 79, the standard initial current increase occurred with the sodium lamp turned off. Rate of rise of current had slowed by 40 minutes. The current increased faster with the sodium lamp turned on between 70 and 110 minutes. When the sodium lamp was turned off at from 110-150 minutes, the rate of current increase went down. When the sodium lamp was turned on again at 150 minutes, the rate of current increase went up again.

In these examples, the spectral energy pattern of sodium was used to increase current in an electrolyte.

Example 15

Corrosion

Corrosion of Steel Razor Blades in Aqueous Solutions

For the following Examples 15a and 15b, the following Equipment, materials and experimental procedures were utilized.
a) Equipment and Materials
Sterile water, BioWhittaker, contained in one liter clear, plastic bottles, processed by ultrafiltration, reverse osmosis, deionization, and distillation
Stanley Utility blades 11-921, 1095 Carbon steel
Sodium Lamp, Stonco 70 Watt high-pressure sodium security wall light, fitted with a parabolic aluminum reflector directing light away from the housing. The sodium bulb Type S62 lamp, 120 V, 60 Hz, 1.5 A made in Hungary by Jemanamjjasond.

EXAMPLE 15a

Figure 80:
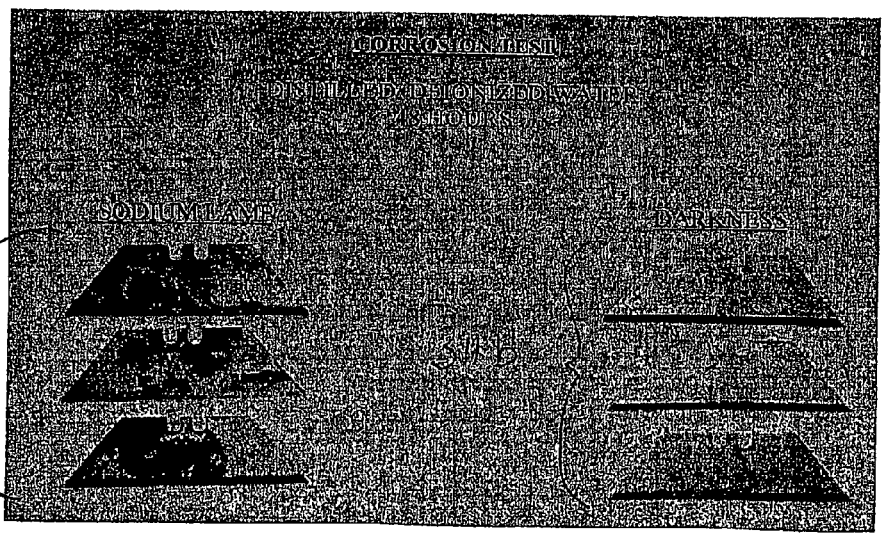
FIG. 80 shows the corrosion/non-corrosion on steel razor blades according to Example 15.
Figure 81:
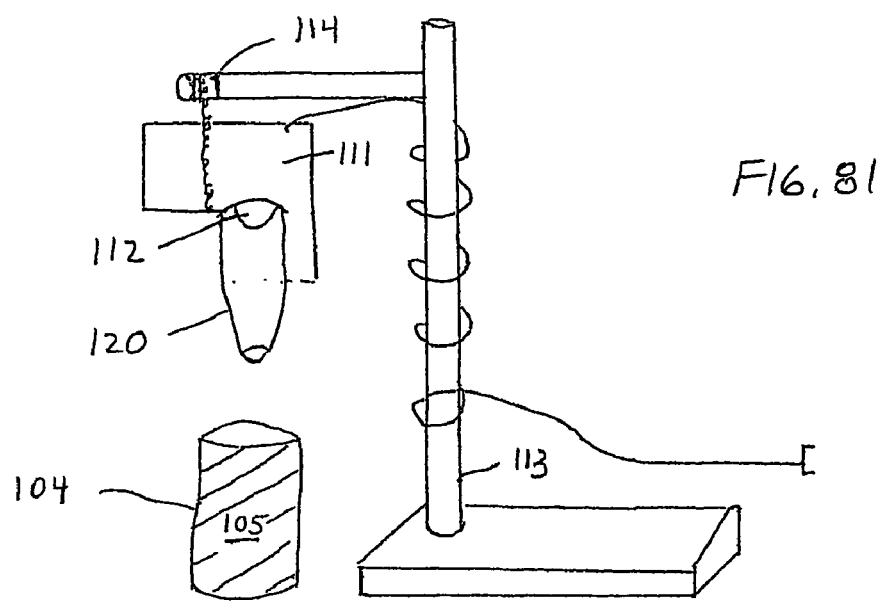
FIG. 81 shows a schematic of the apparatus used in Example 15.

Ten steel razor blades 311 were placed in a beaker 104 in distilled deionized water 105 for about 48 hours. Five razor blades 311b were kept in the dark, and five razor blades 311a were exposed only to the sodium electronic spectrum, which is resonant with water vibrational overtones. FIG. 81 shows the experimental apparatus used in this experiment. FIG. 80 shows the differences in amounts of corrosion between blades 311a and 311b.

Results: Razor blades kept in the dark had virtually no corrosion. Razor blades exposed to sodium electronic/water vibrational overtones displayed corrosion on more than 90% of the surface.

Example 15b

Twelve razor blades 311 were placed in beakers 104, in sodium chloride solution 105 (25 g/100 ml). Six razor blades (311b) were kept in total darkness and six razor blades (311a) were exposed only to the sodium electronic/water vibrational overtones from a sodium lamp. FIG. 81 shows the experimental apparatus used in this experiment.

Results: Razor blades kept in the dark (not shown) had mild corrosion over 20-25% of their surfaces. Razor blades exposed to sodium electronic/water vibrational overtones exhibited moderate corrosion (not shown) over 70-75% of their surfaces.

In these experiments, targeted spectral energies were used to change the chemical and material properties of solutions, resulting in altered electrochemical reaction rates and corrosion of solids.

What is claimed is:

1. A method for augmenting a physical catalyst in a polymer electrolyte membrane fuel cell reaction system with its own catalytic spectral pattern comprising the steps of:
   determining an electromagnetic spectral pattern of the physical catalyst;
   duplicating at least one frequency of the spectral pattern of the physical catalyst by causing at least one energy emitter source to form the catalytic spectral pattern; and
   applying energy from the energy emitter source to at least a portion of the polymer electrolyte membrane fuel cell reaction system at a sufficient intensity and for a sufficient duration to catalyze formation of at least one reaction product in a desired portion of the polymer electrolyte membrane fuel cell reaction system, wherein said energy emitter source applies at least one of an electric field, a magnetic field, and an acoustic field.

2. The method of claim 1, wherein said polymer electrolyte membrane fuel cell comprises platinum as said physical catalyst.

3. The method of claim 2, wherein said platinum physical catalyst is present in at least one electrode of said polymer electrolyte membrane fuel cell.

4. The method of claim 3, wherein said catalytic spectral pattern is directed toward said platinum physical catalyst.

5. The method of claim 4, wherein said acoustic field comprises a transducer.

6. The method of claim 5, wherein said acoustic field is directed toward said platinum physical catalyst.

7. The method of claim 5, further comprising an anode and a cathode and wherein said catalytic spectral pattern is directed toward each of said anode and said cathode in said polymer electrolyte membrane fuel cell.

8. The method of claim 3, wherein hydrogen gas is supplied as a fuel to said at least one electrode in said polymer electrolyte membrane fuel cell.

9. The method of claim 1, wherein said at least one frequency being applied is applied by said magnetic field.

10. The method of claim 1, wherein said at least one frequency being applied is applied by said electric field.

11. The method of claim 1, wherein said at least one frequency being applied is applied by said acoustic field.

12. The method of claim 1, wherein said polymer electrolyte membrane fuel cell comprises at least two electrodes and a platinum physical catalyst is present in said at least two electrodes.

13. A method for augmenting a platinum physical catalyst in a polymer electrolyte membrane fuel cell reaction system with its own catalytic spectral pattern comprising the steps of:
   determining an electromagnetic spectral pattern of the platinum physical catalyst;
   duplicating at least one frequency of the spectral pattern of the platinum physical catalyst by causing at least one energy emitter source to form the catalytic spectral pattern; and applying energy from the energy emitter source to at least a portion of the polymer electrolyte membrane fuel cell reaction system at a sufficient intensity and for a sufficient duration to catalyze formation of at least one reaction product in a desired portion of the polymer electrolyte membrane fuel cell reaction system, wherein said energy emitter source applies at least one of a magnetic field and an acoustic field.

14. The method of claim 2, wherein said polymer electrolyte membrane fuel cell comprises at least two electrodes and said platinum physical catalyst in said polymer electrolyte membrane fuel cell reaction system is present in said at least two electrodes.

15. The method of claim 2, wherein said at least one frequency being applied is applied by said acoustic field.

16. A method for augmenting a physical catalyst in a polymer electrolyte membrane fuel cell reaction system with its own catalytic spectral pattern comprising the steps of:
 determining an electromagnetic spectral pattern of the physical catalyst;
 duplicating at least one frequency of the spectral pattern of the physical catalyst by causing at least one energy emitter source to form the catalytic spectral pattern; and
 applying energy from the energy emitter source to at least a portion of the polymer electrolyte membrane fuel cell reaction system pattern at a sufficient intensity and for a sufficient duration to catalyze formation of at least one reaction product in a desired portion of the polymer electrolyte membrane fuel cell reaction system, wherein said energy emitter source applies by an electric field.

* * * * *

UNITED STATES PATENT AND TRADEMARK OFFICE
CERTIFICATE OF CORRECTION

PATENT NO. : 8,048,274 B2 Page 1 of 1
APPLICATION NO. : 10/507659
DATED : November 1, 2011
INVENTOR(S) : Juliana H. J. Brooks et al.

It is certified that error appears in the above-identified patent and that said Letters Patent is hereby corrected as shown below:

Column 161, lines 10-14 (i.e., Claim 14) should read as follows:

"14. The method of claim 13, wherein said polymer electrolyte membrane fuel cell comprises at least two electrodes and said platinum physical catalyst in said polymer electrolyte membrane fuel cell reaction system is present in said at least two electrodes."

Column 161, lines 15-16 (i.e., Claim 15) should read as follows:

"15. The method of claim 13, wherein said at least one frequency being applied is applied by said acoustic field."

Signed and Sealed this
Twentieth Day of December, 2011

David J. Kappos
*Director of the United States Patent and Trademark Office*